United States Patent
Reuillon et al.

(10) Patent No.: US 10,344,017 B2
(45) Date of Patent: Jul. 9, 2019

(54) PYRROLCARBOXAMIDE DERIVATIVES FOR THE INHIBITION OF ERK5

(71) Applicant: CANCER RESEARCH TECHNOLOGY LIMITED, London (GB)

(72) Inventors: Tristan Reuillon, Brighton (GB); Duncan Miller, Newcastle upon Tyne (GB); Stephanie Myers, Wolverhampton (GB); Lauren Molyneux, Newcastle upon Tyne (GB); Celine Cano, Newcastle upon Tyne (GB); Ian Hardcastle, Hexham (GB); Roger Griffin, London (GB); Laurent Rigoreau, Cambridge (GB); Bernard Golding, Newcastle upon Tyne (GB); Martin Noble, Newcastle upon Tyne (GB)

(*) Notice: Subject to any disclaimer, the term of this patent is extended or adjusted under 35 U.S.C. 154(b) by 0 days.

(21) Appl. No.: 15/512,661

(22) PCT Filed: Sep. 18, 2015

(86) PCT No.: PCT/GB2015/052707
§ 371 (c)(1),
(2) Date: Mar. 20, 2017

(87) PCT Pub. No.: WO2016/042341
PCT Pub. Date: Mar. 24, 2016

(65) Prior Publication Data
US 2018/0170911 A1    Jun. 21, 2018

(30) Foreign Application Priority Data
Sep. 18, 2014 (GB) .................................. 1416513.8

(51) Int. Cl.
| | |
|---|---|
| A61P 35/00 | (2006.01) |
| C07D 401/12 | (2006.01) |
| C07D 401/14 | (2006.01) |
| C07D 403/12 | (2006.01) |
| C07D 403/14 | (2006.01) |
| C07D 405/14 | (2006.01) |
| C07D 413/12 | (2006.01) |
| C07D 413/14 | (2006.01) |

(52) U.S. Cl.
CPC ............ *C07D 403/12* (2013.01); *A61P 35/00* (2018.01); *C07D 401/12* (2013.01); *C07D 401/14* (2013.01); *C07D 403/14* (2013.01); *C07D 405/14* (2013.01); *C07D 413/12* (2013.01); *C07D 413/14* (2013.01)

(58) Field of Classification Search
None
See application file for complete search history.

(56) References Cited

U.S. PATENT DOCUMENTS 7,034,049 B1 * 4/2006 Pevarello ............. A61K 31/415
514/404

FOREIGN PATENT DOCUMENTS

| WO | 01/12189 A1 | 2/2001 |
| WO | 2011/025838 A1 | 3/2011 |

OTHER PUBLICATIONS

Down et al, Bioorganic & Medicinal Chemistry Letters, 20, pp. 3936-3040 (Year: 2010).*
Lo et al, Tetrahedron Letters, 49(51), 7337-7340 (Year: 2008).*
International Search Report and Written Opinion issued in PCT/GB2015/052707, dated Oct. 26, 2015.

* cited by examiner

*Primary Examiner* — Zinna Northington Davis
(74) *Attorney, Agent, or Firm* — Heslin Rothenberg Farley & Mesiti PC

(57) ABSTRACT

The invention provides compounds of formula (I)

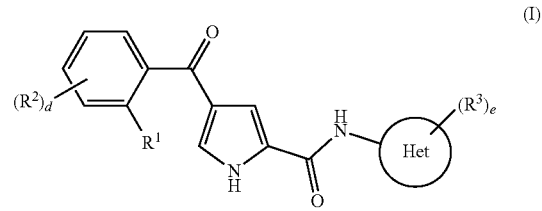

or a tautomer, stereoisomer, N-oxide, pharmaceutically acceptable salt or solvate thereof. The compounds are useful for the prophylaxis or treatment of a disease state or condition mediated by ERK5, in particular cancers.

20 Claims, No Drawings

PYRROLCARBOXAMIDE DERIVATIVES FOR THE INHIBITION OF ERK5

CROSS REFERENCE TO RELATED APPLICATIONS

This application is a national stage filing under section 371 of International Application No. PCT/GB2015/052707, filed on Sep. 18, 2015, and published on Mar. 24, 2016 as WO 2016/042341, which claims priority to Great Britain Application No. 1416513.8, filed on Sep. 18, 2014. The entire contents of each of said applications are hereby incorporated herein by reference.

FIELD OF THE INVENTION

The invention relates to new pyrroles, to pharmaceutical compositions comprising said compounds and to the use of said compounds in the treatment of diseases, e.g. cancer.

BACKGROUND OF THE INVENTION

Clinical correlative, molecular genetic and pharmacological data show certain tumours are dependent on ERK5 signalling, and that ERK5 inhibition may therefore result in antitumour activity.

Clinical Correlative Data

ERK5 is an independent prognostic biomarker in prostate cancer. Cytoplasmic ERK5 staining correlates with Gleason sum score, bony metastasis and locally advanced disease. Furthermore, nuclear ERK5 localisation is associated with poor outcome and recurrence in castrate-resistant prostate cancer. Thus strong nuclear ERK5 localisation is an independent prognostic factor ($p=<0.0001$). In matched tumour samples ($n=26$), taken before and after the development of resistance to anti-androgen therapy, ERK5 nuclear expression is associated with relapse ($p=0.008$). A similar study in breast cancer (84 cases) shows that ERK5 is over-expressed in 20% of patients and that, as in prostate cancer, expression is an independent prognostic biomarker for reduced disease-free survival. In liver cancer ERK5 over-expression has been observed in 11 of 43 samples, associated with modest gene amplification in a subset of patients, and in oral cancer elevated phospho-ERK5, but not phospho-ERK1, is associated with lymph node metastasis.

Pharmacological Studies

Critical pre-clinical data that suggest the viability of ERK5 as a small molecule drug target come from recent studies with the prototype inhibitor XMD8-92. The compound was shown to have modest anti-proliferative activity in tumour cell lines and endothelial cells, via effects on ERK5-mediated promyelocytic leukaemia protein phosphorylation and p21. More importantly, XMD8-92 was well tolerated in mice, inhibited tumour ERK5 and produced pronounced retardation of both human and murine tumour growth, i.e. complete and immediate cessation of tumour growth on commencement of treatment, with no toxicity. Furthermore, in a matrigel plug assay for bFGF-induced angiogenesis, XMD8-92 completely abrogated blood vessel formation, consistent with the role of ERK5 signalling in endothelial cell biology.

Molecular Genetic Studies

An increasing body of mechanistic data indicates that ERK5 plays at least three key roles in tumour biology, i.e. in cell proliferation and survival, in invasion and metastasis, and in angiogenesis.

Proliferation and Survival

The first role of ERK5 in tumour biology relates to mitogenic and survival signalling in tumour cells where ERK5 is downstream of cell surface tyrosine kinase receptors; the epidermal growth factor/HER receptor family being most frequently implicated. Dominant-negative ERK5 constructs are growth inhibitory in a number of cell lines, although not in every case, and when implanted into immune-deprived mice ERK5 over-expressing human prostate cancer cells result in more aggressive tumour growth when compared to non-transfected cells. Importantly, ERK5 is a downstream kinase and hence ERK5 inhibitors will not be subject to the limitations of growth factor receptor-targeted therapies, such as receptor tyrosine kinase inhibitors or receptor blocking antibodies, where RAS and RAF mutations abrogate activity; ERK5 inhibitors may retain activity in the face of RAS/RAF mutations.

With regard to survival signalling, ERK5 over-expression protects cells from, and dominant negative ERK5 sensitises cells to, apoptosis induced by physical, cytokine and therapeutic drug stimuli; however, as with many targeted drugs, the effect of ERK5 on tumour cell proliferation and survival is cell type specific.

Invasion and Metastasis

Compelling and unequivocal data demonstrates that ERK5 signalling promotes cell migration and invasion, a property that is consistent with the clinical relationship between tumour ERK5 over-expression and the presence of metastatic disease. For example, an orthotopic model of prostate cancer, demonstrates that ERK5 promotes the formation of metastases. Similarly, in breast cancer cells ERK5 knockdown reduces hepatocyte growth factor-stimulated migration, and in an in vivo orthotopic breast cancer model ERK5 knockdown results in a marked reduction in lymph node metastasis. Lastly in osteosarcoma, where ERK5 can be over-expressed, ERK5 knockdown results in a pronounced inhibition of invasion, associated with reduced MMP9 expression.

Angiogenesis

ERK5 inhibitors may also inhibit tumour angiogenesis. A substantial body of data based initially on constitutive and conditional knockout mouse models show that ERK5 is required for endothelial cell survival, in particular maintenance of vascular integrity and endothelial cell migration. Both constitutive MEK5, the obligate kinase required for ERK5 activation, and ERK5 knockout mouse embryos die at day 10.5 from tissue failure that includes impaired cardiac development. Importantly, in conditional ERK5 knockout mice ERK5 ablation in adults disrupts vascular integrity and results in death from multiple organ haemorrhage, consistent with a key role for ERK5 in endothelial cell biology. Further studies unequivocally link ERK5 signalling to tumour angiogenesis in two in vivo mouse tumour models, and hence treatment with an ERK5 inhibitor is expected to have profound therapeutic effects on tumour vasculature in solid cancers.

Therefore there is a need for the development of selective ERK5 inhibitors for the treatment of diseases.

SUMMARY OF THE INVENTION

In one aspect, the invention provides a compound of formula (I):

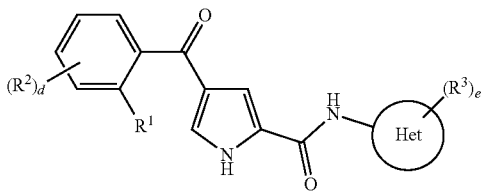

(I)

or a tautomer, stereoisomer, N-oxide, pharmaceutically acceptable salt or solvate thereof, wherein:

$R^1$ is halo;

Het is a monocyclic or bicyclic heterocyclic ring containing from 3 to 12 ring members which contains one or more (e.g. 1, 2 or 3) heteroatoms independently selected from nitrogen, oxygen or sulfur;

d is 0, 1, 2 or 3;

$R^2$ is independently selected from -Q-$R^a$, —Y-carbocyclyl and —Y-heterocyclyl wherein the carbocyclyl and heterocyclyl groups contain 3 to 12 ring members and said carbocyclyl and heterocyclyl groups may be optionally substituted by one or more (e.g. 1, 2 or 3) $R^c$; and wherein Y is independently selected from a bond, —C(=O)—$(CR^xR^y)_s$—, —$(CR^xR^y)_s$—C(=O)—, —C(=O)O—, —$(CR^xR^y)_n$—, —$NR^x$—$(CR^xR^y)_s$—, —$(CR^xR^y)_s$—$NR^x$—, —$CONR^x$—, —$NR^xCO$—, —$SO_2NR^x$—, —$NR^xSO_2$—, —$NR^xC(=O)NR^y$—, —$NR^xCSNR^y$—, —O—$(CR^xR^y)_s$—, —$(CR^xR^y)_s$—O—, —S—, —SO— and —$(CR^xR^y)_s$—$SO_2$—;

e is 0, 1, 2 or 3;

$R^3$ is independently selected from -Q-$R^b$, —Z-carbocyclyl and —Z-heterocyclyl wherein the carbocyclyl group contains 4 to 12 ring members, the heterocyclyl group contains 3 to 12 ring members and said carbocyclyl and heterocyclyl groups may be optionally substituted by one or more (e.g. 1, 2 or 3) $R^c$; and wherein Z is independently selected from a bond, —C(=O)—$(CR^xR^y)_s$—, —$(CR^xR^y)_s$—C(=O)—, —C(=O)O—, —$(CR^xR^y)_n$—, —$NR^x$—$(CR^xR^y)_s$—, —$(CR^xR^y)_s$—$NR^x$—, —CONH—, —NHCO—, —$SO_2NR^x$—, —$NR^xSO_2$—, —$NR^xC(=O)NR^y$—, —$NR^xCSNR^y$—, —O—$(CR^xR^y)_s$—, —$(CR^xR^y)_s$—O—, —S—, —SO— and —$(CR^xR^y)_s$—$SO_2$—;

$R^a$ is independently selected from halogen, $C_{1-6}$ alkyl, $C_{2-6}$ alkenyl, $C_{2-6}$ alkynyl, —$(CH_2)_s$—$C_{3-8}$ cycloalkyl, —$(CH_2)_s$—$C_{3-8}$ cycloalkenyl, —$(CH_2)_s$-phenyl, —$(CH_2)_s$-(4-7 membered saturated heterocyclyl), —$(CR^xR^y)_s$—O—$R^z$, —O—$(CR^xR^y)_n$—$OR^z$, halo$C_{1-6}$ alkyl, halo$C_{1-6}$ alkoxy, $C_{1-6}$ alkanol, nitro, $Si(R^x)_4$, —$(CH_2)_s$—CN, —$(CH_2)_s$—$S(O)_q$—$R^x$, —C(=O)$R^x$, —$(CR^xR^y)_s$—C(=O)OR, —$(CR^xR^y)_s$—O—C(=O)—$R^z$, —$(CR^xR^y)_s$—C(=O)$NR^xR^y$, —$(CH_2)_s$—$NR^xC(=O)R^y$, —$(CH_2)_s$—OC(=O)$NR^xR^y$, —$(CH_2)_s$—$NR^xC(=O)OR^y$, —$(CH_2)_s$—$NR^xR^y$, —$NR^x$—$(CH_2)_s$—$R^z$, —$(CH_2)_s$—O—C(=O)—$C_{1-4}$alkyl-$NR^xR^y$, —$(CH_2)_s$—$NR^x$—$(CH_2)_n$—O—C(=O)—$R^z$, —$(CH_2)_s$—$NR^x$—$(CH_2)_s$—$SO_2$—$R^y$, —$(CH_2)_s$—NH—$SO_2$—$NR^xR^y$, —$(CH_2)_s$—$SO_2NR^xR^y$ groups and —P(=O)$(R^x)_2$, wherein the $C_{1-6}$ alkyl, $C_{2-6}$ alkenyl, $C_{2-6}$ alkynyl, $C_{3-8}$ cycloalkyl, $C_{3-8}$ cycloalkenyl, phenyl and heterocyclyl groups may be optionally substituted by one or more (e.g. 1, 2 or 3) $R^x$;

$R^b$ and $R^c$ are independently selected from halogen, $C_{1-6}$ alkyl, $C_{2-6}$ alkenyl, $C_{2-6}$ alkynyl, —$(CH_2)_s$—$C_{4-8}$ cycloalkyl, —$(CH_2)_n$-cyclopropyl, —$(CH_2)_s$—$C_{3-8}$ cycloalkenyl, —$(CH_2)_s$-phenyl, —$(CH_2)_s$—(4-7 membered saturated heterocyclyl), —$(CR^xR^y)_s$—O—$R^z$, —O—$(CR^xR^y)_n$—$OR^z$, halo$C_{1-6}$ alkyl, halo$C_{1-6}$ alkoxy, $C_{1-6}$ alkanol, =O, =S, nitro, $Si(R^x)_4$, —$(CH_2)_s$—CN, —$(CH_2)_s$—$S(O)_q$—$R^x$, —C(=O)$R^x$, —$(CR^xR^y)_s$—C(=O)$OR^z$, —$(CR^xR^y)_s$—O—C(=O)—$R^z$, —$(CR^xR^y)_s$—C(=O)$NR^xR^y$, —$(CH_2)_s$—$NHC(=O)R^y$, —$(CH_2)_s$—OC(=O)$NR^xR^y$, —$(CH_2)_s$—$NR^xC(=O)OR^y$, —$(CH_2)_s$—$NR^xR^y$, —$NR^x$—$(CH_2)_s$—$R^z$, —$(CH_2)_s$—O—C(=O)—$C_{1-4}$alkyl-$NR^xR^y$, —$(CH_2)_s$—$NR^x$—$(CH_2)_n$—O—C(=O)—$R^z$, —$(CH_2)_s$—$NR^x$—$(CH_2)_s$—$SO_2$—$R^y$, —$(CH_2)_s$—NH—$SO_2$—$NR^xR^y$, —$(CH_2)_s$—$SO_2NR^xR^y$ groups and —P(=O)$(R^x)_2$, wherein the $C_{1-6}$ alkyl, $C_{2-6}$ alkenyl, $C_{2-6}$ alkynyl, $C_{3-8}$ cycloalkyl, $C_{3-8}$ cycloalkenyl, phenyl and heterocyclyl groups may be optionally substituted by one or more (e.g. 1, 2 or 3) $R^x$;

Q is independently selected from $NR^x$ and a bond;

$R^x$, $R^y$ and $R^z$ are independently selected from halogen, hydrogen, $C_{1-6}$ alkyl, $C_{2-6}$ alkenyl, $C_{2-6}$ alkynyl, —$(CH_2)_s$—$C_{3-8}$ cycloalkyl, —$(CH_2)_s$—$C_{3-8}$ cycloalkenyl, —$(CH_2)_n$-phenyl, —$(CH_2)_s$-(4-7 membered saturated heterocyclyl), $C_{1-6}$ alkanol optionally substituted with one or more (e.g. 1, 2 or 3) halo, —C(=O)$OC_{1-6}$ alkyl, hydroxy, $C_{1-6}$ alkoxy, halo$C_{1-6}$ alkyl, —$(CH_2)_n$—O—$C_{1-6}$alkyl, —C(=O)—$(CH_2)_n$—$C_{1-6}$ alkoxy, —C(=O)—$C_{1-6}$alkyl, —$(CH_2)_s$—CN, $C_{1-6}$ alkyl-$N(H)_{2-q}(C_{1-6}$alkyl$)_q$, —$N(H)_{2-q}(C_{1-6}$alkyl$)_q$, —C(=O)—$N(H)_{2-q}(C_{1-6}$alkyl$)_q$, —$(CH_2)_s$—NH—$SO_2$—$N(H)_{2-q}(C_{1-6}$alkyl$)_q$, —$(CH_2)_s$—$N(C_{1-4}$alkyl)-$SO_2$—$N(H)_{2-q}(C_{1-6}$alkyl$)_q$ and —$(CH_2)_s$—O—C(=O)—$C_{1-4}$alkyl-$N(H)_{2-q}(C_{1-6}$alkyl$)_q$, and when attached to nitrogen, carbon, silicon or phosphorus atom $R^x$ and $R^y$ may join to form a 3-7 membered ring optionally containing one or two additional heteroatoms selected from nitrogen, oxygen or sulfur;

s is independently selected from 0, 1, 2, 3 and 4;

n is independently selected from 1, 2, 3 and 4; and q is independently selected from 0, 1 and 2.

In further aspects of the invention there is provided a compound of formula (I) for use in the prophylaxis or treatment of a disease or condition as described herein, methods for the prophylaxis or treatment of a disease or condition as described herein comprising administering to a patient a compound of formula (I), pharmaceutical compositions comprising a compound of formula (I) and processes for the synthesis of a compound of formula (I).

Definitions

Unless the context indicates otherwise, references to formula (I) in all sections of this document (including the uses, methods and other aspects of the invention) include references to all other sub-formula, sub-groups, embodiments and examples as defined herein.

"Potency" is a measure of drug activity expressed in terms of the amount required to produce an effect of given intensity. A highly potent drug evokes a larger response at low concentrations. Potency is proportional to affinity and efficacy. Affinity is the ability of the drug to bind to a receptor. Efficacy is the relationship between receptor occupancy and the ability to initiate a response at the molecular, cellular, tissue or system level.

The term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo)activity and (de)activation of the protein kinase(s) (including (de)activation) for example by mutation(s). The terms "modulated", "modulating" and "modulate" are to be interpreted accordingly.

The term "mediated", as used e.g. in conjunction with the kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

The term "treatment" as used herein in the context of treating a condition i.e. state, disorder or disease, pertains generally to treatment and therapy, whether for a human or an animal (e.g. in veterinary applications), in which some desired therapeutic effect is achieved, for example, the inhibition of the progress of the condition, and includes a reduction in the rate of progress, a halt in the rate of progress, amelioration of the condition, diminishment or alleviation of at least one symptom associated or caused by the condition being treated and cure of the condition. For example, treatment can be diminishment of one or several symptoms of a disorder or complete eradication of a disorder.

The term "prophylaxis" (i.e. use of a compound as prophylactic measure) as used herein in the context of treating a condition i.e. state, disorder or disease, pertains generally to the prophylaxis or prevention, whether for a human or an animal (e.g. in veterinary applications), in which some desired preventative effect is achieved, for example, in preventing occurrence of a disease or guarding from a disease. Prophylaxis includes complete and total blocking of all symptoms of a disorder for an indefinite period of time, the mere slowing of the onset of one or several symptoms of the disease, or making the disease less likely to occur.

References to the prophylaxis or treatment of a disease state or condition such as cancer include within their scope alleviating or reducing the incidence e.g. of cancer.

The term 'optionally substituted' as used herein refers to a group which may be unsubstituted or substituted by a substituent as herein defined.

The prefix "$C_{x-y}$" (where x and y are integers) as used herein refers to the number of carbon atoms in a given group. Thus, a $C_{1-6}$ alkyl group contains from 1 to 6 carbon atoms, a $C_{3-6}$ cycloalkyl group contains from 3 to 6 carbon atoms, a $C_{1-4}$ alkoxy group contains from 1 to 4 carbon atoms, and so on.

The term 'halo' or 'halogen' as used herein refers to fluorine, chlorine, bromine or iodine.

The term '$C_{1-4}$alkyl' as used herein as a group or part of a group refers to a linear or branched saturated hydrocarbon group containing from 1 to 4 carbon atoms respectively. Examples of such groups include methyl, ethyl, n-propyl, isopropyl, n-butyl, isobutyl, sec-butyl, tert butyl and the like.

The term '$C_{1-4}$alkoxy' as used herein as a group or part of a group refers to an —O—$C_{1-4}$alkyl group wherein $C_{1-4}$alkyl is as defined herein. Examples of such groups include methoxy, ethoxy, propoxy, butoxy, and the like.

The term '$C_{3-6}$cycloalkyl' as used herein refers to a saturated monocyclic hydrocarbon ring of 3 to 6 carbon atoms. Examples of such groups include cyclopropyl, cyclobutyl, cyclopentyl or cyclohexyl and the like.

The term 'hydroxy$C_{1-4}$alkyl' as used herein as a group or part of a group refers to a $C_{1-4}$alkyl group as defined herein wherein one or more (e.g. 1, 2 or 3) than one hydrogen atom is replaced with a hydroxyl group. The term 'hydroxy$C_{1-4}$alkyl' therefore includes monohydroxy$C_{1-4}$ alkyl, and also polyhydroxy$C_{1-4}$ alkyl. There may be one, two, three or more hydrogen atoms replaced with a hydroxyl group, so the hydroxy$C_{1-4}$alkyl may have one, two, three or more hydroxyl groups. Examples of such groups include hydroxymethyl, hydroxyethyl, hydroxypropyl and the like.

The term 'halo$C_{1-4}$alkyl' as used herein as a group or part of a group refers to a $C_{1-4}$alkyl group as defined herein wherein one or more (e.g. 1, 2 or 3) than one hydrogen atom is replaced with a halogen. The term 'halo$C_{1-4}$alkyl' therefore include monohalo$C_{1-4}$alkyl and also polyhalo$C_{1-4}$alkyl. There may be one, two, three or more hydrogen atoms replaced with a halogen, so the halo$C_{1-4}$alkyl may have one, two, three or more halogens. Examples of such groups include fluoroethyl, fluoromethyl, trifluoromethyl or trifluoroethyl and the like.

The term 'halo$C_{1-4}$alkoxy' as used herein as a group or part of a group refers to a —O—$C_{1-4}$alkyl group as defined herein wherein one or more (e.g. 1, 2 or 3) than one hydrogen atom is replaced with a halogen. The terms 'halo$C_{1-4}$alkoxy' therefore include monohalo$C_{1-4}$alkoxy, and also polyhalo$C_{1-4}$alkoxy. There may be one, two, three or more hydrogen atoms replaced with a halogen, so the halo$C_{1-4}$alkoxy may have one, two, three or more halogens. Examples of such groups include fluoroethyloxy, difluoromethoxy or trifluoromethoxy and the like.

The term "heterocyclyl group having from 4 to 6 ring members" as used herein shall, unless the context indicates otherwise, include both aromatic and non-aromatic ring systems. Thus, for example, the term "heterocyclyl group" include within their scope aromatic, non-aromatic, unsaturated, partially saturated and fully saturated heterocyclyl ring systems. The reference to 4 to 6 ring members include 4, 5, or 6 atoms in the ring, more typically 5 or 6 ring members. Where reference is made herein to a heterocyclyl group, the heterocyclyl ring can, unless the context indicates otherwise, be optionally substituted i.e. unsubstituted or substituted, by one or more (e.g. 1, 2, 3, or 4 in particular one or two) substituents as defined herein.

The heterocyclyl group can be, for example, a five membered or six membered monocyclic ring. Each ring may contain up to five heteroatoms typically selected from nitrogen, sulfur and oxygen. Typically the heterocyclyl ring will contain up to 4 heteroatoms, more typically up to 3 heteroatoms, more usually up to 2, for example a single heteroatom. In one embodiment, the heterocyclyl ring will contain one or two heteroatoms selected from N, O, S and oxidised forms of N or S. In one embodiment, the heterocyclyl ring contains at least one ring nitrogen atom. The nitrogen atoms in the heterocyclyl rings can be basic, as in the case of an imidazole or pyridine, or essentially non-basic as in the case of an indole or pyrrole nitrogen. In general the number of basic nitrogen atoms present in the heterocyclyl group, including any amino group substituents of the ring, will be less than five.

The heterocyclyl groups can be attached via a carbon atom or a heteroatom (e.g. nitrogen). Equally the heterocyclyl groups can be substituted on a carbon atom or on a heteroatom (e.g. nitrogen).

Examples of five membered aromatic heterocyclyl groups include but are not limited to pyrrolyl, furanyl, thienyl, imidazolyl, furazanyl, oxazolyl, oxadiazolyl, oxatriazolyl, isoxazolyl, thiazolyl, thiadiazolyl, isothiazolyl, pyrazolyl, triazolyl and tetrazolyl groups.

Examples of six membered aromatic heterocyclic groups include but are not limited to pyridinyl, pyrazinyl, pyridazinyl, pyrimidinyl and triazinyl.

A nitrogen-containing aromatic heterocyclic ring must contain at least one ring nitrogen atom. The nitrogen-containing heteroaryl ring can be N-linked or C-linked. Each ring may, in addition, contain up to about four other heteroatoms typically selected from nitrogen, sulfur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing aromatic heterocyclic groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl) and tetrazolyl.

The term "non-aromatic" embraces, unless the context indicates otherwise, unsaturated ring systems without aromatic character, partially saturated and fully saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated heterocyclyl groups include piperidinyl, morpholinyl, and thiomorpholinyl. Partially saturated heterocyclyl groups include pyrazolinyl, for example pyrazolin-2-yl and pyrazolin-3-yl.

Examples of non-aromatic heterocyclyl groups are groups having from 4 to 6 ring members. Such groups typically have from 1 to 4 heteroatom ring members (more usually 1, 2, or 3 heteroatom ring members), usually selected from nitrogen, oxygen and sulfur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulfones (e.g. as in sulfolane and sulfolene), cyclic sulfoxides, cyclic sulfonamides and combinations thereof (e.g. thiomorpholine).

Particular examples include morpholinyl, piperidinyl (e.g. piperidin-1-yl, piperidin-2-yl, piperidin-3-yl and piperidin-4-yl), piperidinonyl, pyrrolidinyl (e.g. pyrrolidin-1-yl, pyrrolidin-2-yl and pyrrolidin-3-yl), pyrrolidonyl, azetidinyl, pyranyl (2H-pyran or 4H-pyran), dihydrothienyl, dihydropyranyl, dihydrofuranyl, dihydrothiazolyl, tetrahydrofuranyl, tetrahydrothienyl, dioxanyl, tetrahydropyranyl (e.g. tetrahydropyran-4-yl), imidazolinyl, imidazolidinonyl, oxazolinyl, thiazolinyl, pyrazolin-2-yl, pyrazolidinyl, piperazinonyl, piperazinyl, and N-alkyl piperazines such as N-methyl piperazinyl. In general, typical non-aromatic heterocyclyl groups include saturated groups such as piperidinyl, pyrrolidinyl, azetidinyl, morpholinyl, piperazinyl and N-alkyl piperazines such as N-methyl piperazinyl.

In a nitrogen-containing non-aromatic heterocyclyl ring the ring must contain at least one ring nitrogen atom. The nitrogen-containing heterocyclyl ring can be N-linked or C-linked. The heterocylic groups can contain, for example, cyclic amine moieties (e.g. as in pyrrolidinyl), cyclic amides (such as a pyrrolidinonyl, piperidinonyl or caprolactamyl), cyclic sulfonamides (such as an isothiazolidinyl 1,1-dioxide, [1,2]thiazinanyl 1,1-dioxide or [1,2]thiazepanyl 1,1-dioxide) and combinations thereof.

Particular examples of nitrogen-containing non-aromatic heterocyclyl groups include aziridinyl, morpholinyl, thiomorpholinyl, piperidinyl (e.g. piperidin-1-yl, piperidiny-2-1, piperidin-3-yl and piperidin-4-yl), pyrrolidinyl; (e.g. pyrrolidin-1-yl, pyrrolidin-2-yl and pyrrolidin-3-yl), pyrrolidonyl, dihydrothiazolyl, imidazolinyl, imidazolidinonyl, oxazolinyl, thiazolinyl, 6H-1,2,5-thiadiazinyl, pyrazolin-2-yl, pyrazolin-3-yl, pyrazolidinyl, piperazinyl, and N-alkyl piperazines such as N-methyl piperazinyl.

The heterocyclyl group can each be unsubstituted or substituted by one or more (e.g. 1, 2 or 3) substituent groups. For example, heterocyclyl or carbocyclyl groups can be unsubstituted or substituted by 1, 2, 3 or 4 substituents and typically it is unsubstituted or has 1, 2 or 3 substituents as defined herein.

A combination of substituents is permissible only if such as combination results in a stable or chemically feasible compound (i.e. one that is not substantially altered when kept at 40° C. or less for at least a week).

The various functional groups and substituents making up the compounds of the invention are typically chosen such that the molecular weight of the compound of the invention does not exceed 1000. More usually, the molecular weight of the compound will be less than 750, for example less than 700, or less than 650, or less than 600, or less than 550. More typically, the molecular weight is less than 525 and, for example, is 500 or less.

DETAILED DESCRIPTION OF THE INVENTION

The invention provides a compound of formula (I):

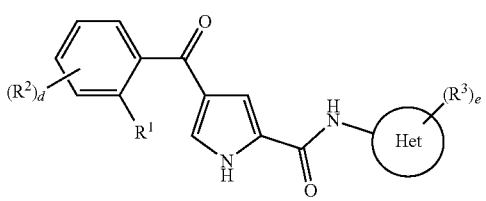

(I)

or a tautomer, stereoisomer, N-oxide, pharmaceutically acceptable salt or solvate thereof wherein $R^2$, d, Halo, Het, $R^3$ and e are as defined herein.

Het

In one embodiment, Het is a monocyclic heterocyclic ring. The monocyclic heterocyclic ring may contain 3 to 8 (e.g. 3, 4, 5, 6, 7 or 8) ring members or 3 to 6 (e.g. 5 or 6) ring members.

In one embodiment, Het is a bicyclic heterocyclic ring. The bicyclic heterocyclic ring may contain 10 to 12 (e.g. 10, 11 or 12) ring members.

In one embodiment, Het is an aromatic heterocyclic ring. In another embodiment, Het is a non-aromatic heterocyclic ring.

In one embodiment Het is a monocyclic or bicyclic heterocyclic ring containing from 3 to 12 ring members which contains one or more (e.g. 1, 2 or 3) nitrogen atom and optionally one or more (e.g. 1, 2 or 3) heteroatoms independently selected from oxygen and sulfur.

In one embodiment, Het is a monocyclic heterocyclic ring containing from 3 to 12 (e.g. 3 to 8 or 5 or 6) ring members which contains one or two nitrogen atoms and optionally one heteroatom selected from oxygen and sulphur.

In one embodiment Het is a nitrogen-containing non-aromatic ring which is aziridinyl, morpholinyl, thiomorpholinyl, piperidinyl (e.g. piperidin-1-yl, piperidiny-2-1, piperidin-3-yl and piperidin-4-yl), pyrrolidinyl; (e.g. pyrrolidin-1-yl, pyrrolidin-2-yl and pyrrolidin-3-yl), dihydrothiazolyl, imidazolinyl, imidazolidinonyl, oxazolinyl, thiazolinyl, 6H-1,2,5-thiadiazinyl, pyrazolin-2-yl, pyrazolin-3-yl, pyrazolidinyl or piperazinyl.

In one embodiment Het is a nitrogen-containing aromatic ring which is pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl) or tetrazolyl.

In one embodiment, Het is a monocyclic heterocyclic ring containing 5 or 6 ring members which contains one or two nitrogen atoms and optionally one heteroatom selected from oxygen and sulphur.

In one embodiment, Het is a monocyclic aromatic heterocyclic ring containing 5 or 6 ring members which contains one or two nitrogen atoms and no other heteroatoms, for example Het is pyridyl, pyrrolyl, imidazolyl, pyrazinyl, pyrimidinyl, pyridazinyl, triazinyl or tetrazolyl.

In one embodiment, Het is a monocyclic non-aromatic heterocyclic ring containing 5 or 6 ring members which contains one or two nitrogen atoms and no other heteroatoms, for example Het is aziridinyl, piperidinyl (e.g. piperidin-1-yl, piperidiny-2-1, piperidin-3-yl and piperidin-4-yl), pyrrolidinyl; (e.g. pyrrolidin-1-yl, pyrrolidin-2-yl and pyrrolidin-3-yl), pyrrolidonyl, imidazolinyl, pyrazolin-2-yl, pyrazolin-3-yl, pyrazolidinyl or piperazinyl.

In all these embodiments Het is optionally substituted by one, two or three $R^3$ groups. In one embodiment Het is unsubstituted (i.e. e is 0). In one embodiment Het is substituted by one, two or three $R^3$ groups (i.e. e is 1, 2 or 3). In one embodiment $R^3$ is a $C_{1-6}$ alkyl group e.g. methyl and thus the Het-$R^3$ group can be N-alkyl piperazine such as N-methyl piperazinyl. In one embodiment $R^3$ is =O and thus the Het-$R^3$ group can imidazolidinonyl or pyrrolidonyl.

In one embodiment, Het is pyridyl. In particular, Het may be 3-pyridyl and the compound of formula (I) is a compound of formula (Ia):

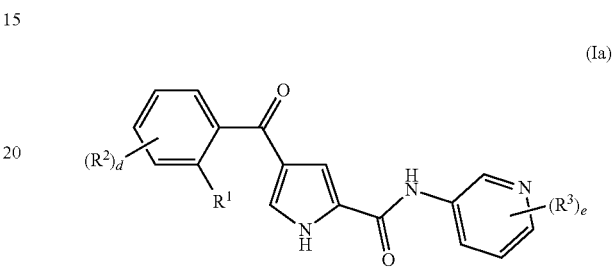

(Ia)

wherein $R^1$, $R^2$, $R^3$, d and e are as defined herein.

In one embodiment, Het is pyridyl. In particular, Het may be 4-pyridyl and the compound of formula (I) is a compound of formula (Ia'):

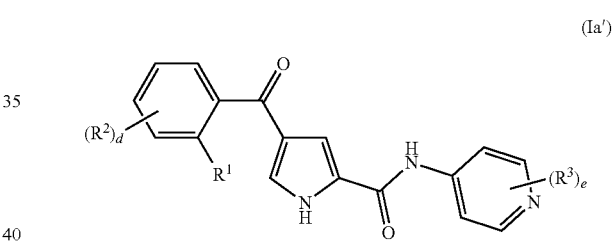

(Ia')

wherein $R^1$, $R^2$, $R^3$, d and e are as defined herein.

In one embodiment, Het is pyrazolyl. In particular, Het may be 4-pyrazolyl and the compound of formula (I) is a compound of formula (Ib):

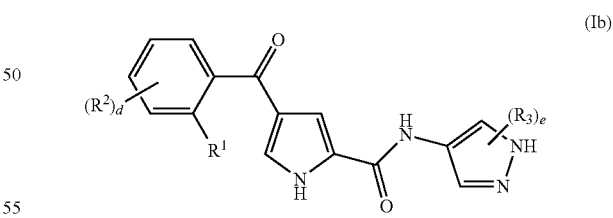

(Ib)

wherein $R^1$, $R^2$, $R^3$, d and e are as defined herein.

In one embodiment, the compound is an N-oxide, in particular an N-oxide formed on a nitrogen atom on the Het ring for example an pyridine N-oxide.

$R^1$

In one embodiment, $R^1$ is F, Cl, or Br, for example F or Cl (e.g. F).

d d is 0, 1, 2 or 3. In other words, the phenyl group of the benzoyl may, in addition to $R^1$, have 0, 1, 2 or 3 substituents $R^2$.

In one embodiment d is 1 or 2. In another embodiment d is 2.

In one embodiment, d is 1 and the substituent $R^2$ is at the 6-position of the phenyl ring of the benzoyl group.

In one embodiment, d is 2 and the two substituents $R^2$ are the 3- and 6-positions of the phenyl ring of the benzoyl group.

When d is 2 or 3 (i.e. the benzoyl group is substituted with more than one $R^2$) the substituents $R^2$ may be the same or different (i.e. are independently selected from the definitions of $R^2$).

$R^2$

In one embodiment, $R^2$ is -Q-$R^a$, wherein $R^a$ is independently selected from the group consisting of halogen, $C_{1-6}$ alkyl, $C_{2-6}$ alkenyl, $C_{2-6}$ alkynyl, —$(CH_2)_s$—$C_{3-8}$ cycloalkyl, —$(CH_2)_s$—$C_{3-8}$ cycloalkenyl, —$(CH_2)_s$-phenyl, —$(CH_2)_s$-(4-7 membered saturated heterocyclyl), —$(CR^xR^y)_s$—O—$R^z$, —O—$(CR^xR^y)_n$—$OR^z$, halo$C_{1-6}$ alkyl, halo$C_{1-6}$ alkoxy, $C_{1-6}$ alkanol, nitro, $Si(R^x)_4$, —$(CH_2)_s$—CN, —$(CH_2)_s$—S(O)$_q$—$R^x$, —C(=O)$R^x$, —$(CR^xR^y)_s$—C(=O)$OR^z$, —$(CR^xR^y)_s$—O—C(=O)—$R^z$, —$(CR^xR^y)_s$—C(=O)$NR^xR^y$, —$(CH_2)_s$—$NR^xC(=O)R^y$, —$(CH_2)_s$—OC(=O)$NR^xR^y$, —$(CH_2)_s$—$NR^xC(=O)OR^y$, —$(CH_2)_s$—$NR^xR^y$, —$NR^x$—$(CH_2)_s$—$R^z$, —$(CH_2)_s$—O—C(=O)—$C_{1-4}$alkyl-$NR^xR^y$, —$(CH_2)_s$—$NR^x$—$(CH_2)_n$—O—C(=O)—$R^z$, —$(CH_2)_s$—$NR^x$—$(CH_2)_s$—$SO_2$—$R^y$, —$(CH_2)_s$—NH—$SO_2$—$NR^xR^y$, —$(CH_2)_s$—$SO_2NR^xR^y$ groups and —P(=O)($R^x$)$_2$, wherein the $C_{1-6}$ alkyl, $C_{2-6}$ alkenyl, $C_{2-6}$ alkynyl, $C_{3-8}$ cycloalkyl, $C_{3-8}$ cycloalkenyl, phenyl and heterocyclyl groups may be optionally substituted by one or more $R^x$ (e.g. 1, 2 or 3); and $R^x$, $R^y$ and $R^z$ are independently selected from the group consisting of halogen, hydrogen, $C_{1-6}$ alkyl, $C_{2-6}$ alkenyl, $C_{2-6}$ alkynyl, —$(CH_2)_s$—$C_{3-8}$ cycloalkyl, —$(CH_2)_s$—$C_{3-8}$ cycloalkenyl, —$(CH_2)_n$-phenyl, —$(CH_2)_s$-(4-7 membered saturated heterocyclyl), $C_{1-6}$ alkanol optionally substituted with one or more (e.g. 1, 2 or 3) halo, —C(=O)$OC_{1-6}$ alkyl, hydroxy, $C_{1-6}$ alkoxy and halo$C_{1-6}$ alkyl.

In one embodiment, Q is a bond, and therefore $R^2$ is $R^a$. In one embodiment wherein Q is a bond, $R^2$ is independently selected from halogen, $C_{1-6}$ alkyl, $C_{2-6}$ alkenyl, $C_{2-6}$ alkynyl, hydroxyl, $C_{1-6}$ alkoxy, halo$C_{1-6}$ alkyl, halo$C_{1-6}$ alkoxy and $C_{1-6}$ alkanol.

In one embodiment wherein Q is a bond, $R^2$ is independently selected from halogen, $C_{1-6}$ alkyl, $C_{1-6}$ alkoxy and halo$C_{1-6}$ alkyl. In another embodiment wherein Q is a bond, $R^2$ is independently selected from halogen, $C_{1-3}$ alkyl, $C_{1-3}$ alkoxy and halo$C_{1-3}$alkyl.

In one embodiment wherein Q is a bond, $R^2$ is independently selected from halogen, for example F or Cl, and —$OCH_3$.

In one embodiment, the substituent $R^2$ is at the 2, 3 and/or 6-position of the phenyl ring.

In one embodiment, d is 2 and the compound of formula (I) is a compound of formula (Ic):

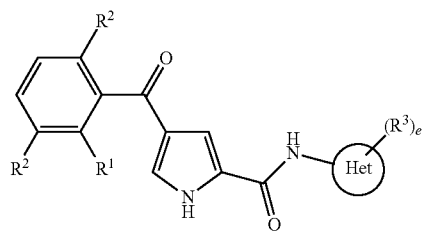

(Ic)

wherein $R^1$, $R^2$, $R^3$ and e are as defined herein.

In one embodiment of the compound of formula (Ic), $R^2$ is independently selected from halogen, $C_{1-6}$ alkyl, $C_{2-6}$ alkenyl, $C_{2-6}$ alkynyl, hydroxyl, $C_{1-6}$ alkoxy, halo$C_{1-6}$ alkyl, halo$C_{1-6}$ alkoxy and $C_{1-6}$ alkanol, for example halogen, $C_{1-3}$ alkyl, $C_{1-3}$ alkoxy and halo$C_{1-3}$alkyl (e.g. halogen, for example F or Cl, and —$OCH_3$).

In one embodiment, the compound of formula (I) is a compound of formula (Id):

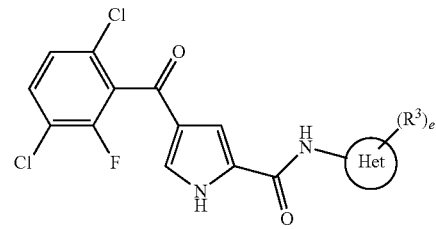

(Id)

wherein $R^3$ and e are as defined herein.

In one embodiment, the compound of formula (I) is a compound of formula (Ie):

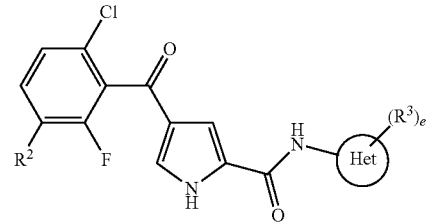

(Ie)

wherein $R^2$ is $C_{1-6}$ alkyl, $C_{2-6}$ alkenyl, $C_{2-6}$ alkynyl, or —Z-heterocyclyl wherein the heterocyclyl group contains 3 to 12 ring members and may be optionally substituted by one or more (e.g. 1, 2 or 3) $R^c$;
wherein Z is a bond, —$(CR^xR^y)_n$—, —$NR^x$—$(CR^xR^y)_s$—, —$(CR^xR^y)_s$—$NR^x$—, —O—$(CR^xR^y)_s$—, or —$(CR^xR^y)_s$—O—;
$R^c$ is independently selected from $C_{1-6}$ alkyl, $C_{2-6}$ alkenyl, $C_{2-6}$ alkynyl, hydroxyl, $C_{1-6}$ alkoxy, halo$C_{1-6}$ alkyl, and halo$C_{1-6}$ alkoxy;
$R^x$ and $R^y$ are $C_{1-6}$ alkyl, $C_{2-6}$ alkenyl, $C_{2-6}$ alkynyl, hydroxyl, $C_{1-6}$ alkoxy, halo$C_{1-6}$ alkyl, or halo$C_{1-6}$ alkoxy.

In one embodiment of the compound of formula (Ie), $R^3$ is —Z-heterocyclyl wherein the heterocyclyl group is pyridinyl (e.g. 3-pyridinyl) or piperidnyl (e.g. 4-piperidnyl), and may be substituted by one or more (e.g. 1, 2 or 3, for example 0 or 1) $R^c$;
and Z is a bond, —$(CH_2)_n$—, —$NR^x$—$(CH_2)_s$—, —$(CH_2)_s$—$NR^x$—, —O—$(CH_2)_s$—, and —$(CH_2)_s$—O—;
$R^c$ is independently selected from $C_{1-6}$ alkyl, $C_{2-6}$ alkenyl, $C_{2-6}$ alkynyl, hydroxyl, $C_{1-6}$ alkoxy, halo$C_{1-6}$ alkyl, and halo$C_{1-6}$ alkoxy;
$R^x$ is $C_{1-6}$ alkyl, $C_{2-6}$ alkenyl, $C_{2-6}$ alkynyl, hydroxyl, $C_{1-6}$ alkoxy, halo$C_{1-6}$ alkyl, or halo$C_{1-6}$ alkoxy.

In one embodiment, $R^2$ is independently selected from —Y-heterocyclyl wherein said heterocyclyl groups may be optionally substituted by one or more (e.g. 1, 2 or 3) $R^c$. In one embodiment, $R^2$ is independently selected from —Y-heterocyclyl wherein the heterocyclyl group contain 4 to 6 ring members, in particular 5 to 6 ring members and wherein said heterocyclyl groups may be optionally substituted by one or more (e.g. 1, 2 or 3) $R^c$. In one embodiment, $R^2$ is independently selected from —Y-(saturated heterocyclyl with 4 to 6 ring members) wherein said heterocyclyl groups may be optionally substituted by one or more (e.g. 1, 2 or 3) $R^c$ e.g. $R^2$ is morpholinyl or piperazinyl. In one embodiment Y is a bond.

In one embodiment, $R^2$ is independently selected from —Y-carbocyclyl wherein said carbocyclyl groups may be optionally substituted by one or more (e.g. 1, 2 or 3) $R^c$. In one embodiment, $R^2$ is independently selected from —Y-carbocyclyl wherein the carbocyclyl group contain 3 to 6 ring members, in particular 3 to 5 ring members and wherein said carbocyclyl groups may be optionally substituted by one or more (e.g. 1, 2 or 3) $R^c$. In one embodiment, $R^2$ is independently selected from —Y-(saturated carbocyclyl with 3 to 6 ring members) wherein said heterocyclyl groups may be optionally substituted by one or more (e.g. 1, 2 or 3) $R^c$ e.g. $R^2$ is cyclopropyl. In one embodiment Y is a bond.

In one embodiment, $R^2$ is independently selected from $C_{1-4}$ alkoxy, —$(CH_2)_s$—OH, and a four to six membered saturated heterocycle including one or more nitrogen atom e.g. morpholinyl or piperazinyl.

In one embodiment, $R^2$ is methoxy, ethoxy, methoxyethoxy, methanesulphonylethoxy, —O-oxetanyl, —O-tetrahydrofuranyl or —O-tetrahydropyranyl.

In one embodiment, $R^2$ is —O-piperidinyl, —O—(N-methylpiperidinyl), —O—CHF2, —O—CF3, —O— azetidinyl, —O—(N-methyazetidinyl), —O-dimethylethylamine.

In one embodiment, $R^2$ is independently selected from —$(CR^xR^y)_s$—O—$R^z$ and $C_{1-6}$ alkanol.

In one embodiment, d is 1 and the compound of formula (I) is a compound of formula (If):

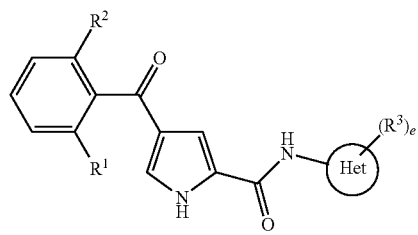

(If)

wherein $R^1$, $R^2$, $R^3$ and e are as defined herein.

In one embodiment of the compound of formula (If), $R^2$ is independently selected from halogen, $C_{1-6}$ alkyl, $C_{2-6}$ alkenyl, $C_{2-6}$ alkynyl, hydroxyl, $C_{1-6}$ alkoxy, halo$C_{1-6}$ alkyl, halo$C_{1-6}$ alkoxy, and $C_{1-6}$ alkanol, for example halogen, $C_{1-3}$ alkyl, $C_{1-3}$ alkoxy, and halo$C_{1-3}$alkyl (halogen, for example F or Cl, and —$OCH_3$).

In one embodiment, the compound of formula (I) is a compound of formula (Ig):

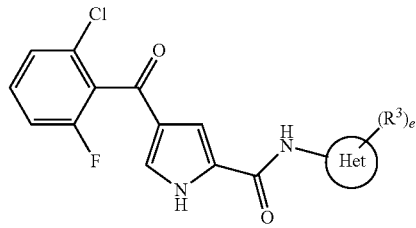

(Ig)

wherein $R^3$ and e are as defined herein.

Y

In one embodiment, Y is independently selected from a bond, —C(=O)—$(CR^xR^y)_s$—, —$(CR^xR^y)_s$—C(=O)—, —C(=O)O—, —$(CR^xR^y)_n$—, —$NR^x$—$(CR^xR^y)_s$—, —$(CR^xR^y)_s$—$NR^x$—, —$CONR^x$—, —$NR^xCO$—, —$SO_2NR^x$—, —O—$(CR^xR^y)_s$—, and —$(CR^xR^y)_s$—O—.

In one embodiment, Y is a bond.

e e is 0, 1, 2 or 3. In other words, the Het group may have 0, 1, 2 or 3 substituents $R^3$.

In one embodiment e is 1 or 2. In another embodiment e is 1.

When e is 2 or 3 (i.e. the Het group is substituted with more than one $R^3$) the substituents $R^3$ may be the same or different (i.e. are independently selected from the definition of $R^3$).

$R^3$

In one embodiment, $R^3$ is independently selected from -Q-$R^b$, —Z-carbocyclyl and —Z-heterocyclyl. wherein the carbocyclyl group contains 4 to 12 ring members, the heterocyclyl group contains 3 to 12 ring members and said carbocyclyl and heterocyclyl groups may be optionally substituted by one or more (e.g. 1, 2 or 3) $R^c$; and wherein Z is independently a bond, —$(CR^xR^y)_n$—, —$NR^x$—$(CR^xR^y)_s$—, —$(CR^xR^y)_s$—$NR^x$—, —O—$(CR^xR^y)_s$—, —$(CR^xR^y)_s$—O—;

wherein $R^b$ is independently selected from the group consisting of halogen, $C_{1-6}$ alkyl, $C_{2-6}$ alkenyl, $C_{2-6}$ alkynyl, —$(CH_2)_s$—$C_{4-8}$ cycloalkyl, —$(CH_2)_n$-cyclopropyl, —$(CH_2)_s$—$C_{3-8}$ cycloalkenyl, —$(CH_2)_s$-phenyl, —$(CH_2)_s$-(4-7 membered saturated heterocyclyl), —$(CR^xR^y)_s$—O—$R^z$, —O—$(CR^xR^y)_n$—$OR^z$, halo$C_{1-6}$ alkyl, halo$C_{1-6}$ alkoxy, $C_{1-6}$ alkanol, —C(=O)$R^x$, —$(CR^xR^y)_s$—C(=O)$OR^z$, —$(CR^xR^y)_s$—O—C(=O)—$R^z$, —$(CR^xR^y)_s$—C(=O)$NR^xR^y$, —$(CH_2)_s$—NHC(=O)$R^y$, —$(CH_2)_s$—OC(=O)$NR^xR^y$, —$(CH_2)_s$—$NR^xC$(=O)$OR^y$, —$(CH_2)_s$—$NR^xR^y$, —$NR^x$—$(CH_2)_s$—$R^z$, —$(CH_2)_s$—O—C(=O)—$C_{1-4}$alkyl-$NR^xR^y$, —$(CH_2)_s$—$NR^x$—$(CH_2)_n$—O—C(=O)—$R^z$, —$(CH_2)_s$—$NR^x$—$(CH_2)_s$—$SO_2$—$R^y$, —$(CH_2)_s$—NH—$SO_2$—$NR^xR^y$, —$(CH_2)_s$—$SO_2NR^xR^y$ groups and —P(=O)($R^x$)$_2$, wherein the $C_{1-6}$ alkyl, $C_{2-6}$ alkenyl, $C_{2-6}$ alkynyl, $C_{3-8}$ cycloalkyl, $C_{3-8}$ cycloalkenyl, phenyl and heterocyclyl groups may be optionally substituted by one or more (e.g. 1, 2 or 3) $R^x$; and $R^x$, $R^y$ and $R^z$ are independently selected from the group consisting of halogen, hydrogen, $C_{1-6}$ alkyl, $C_{2-6}$ alkenyl, $C_{2-6}$ alkynyl, —$(CH_2)_s$—$C_{3-8}$ cycloalkyl, —$(CH_2)_s$—$C_{3-8}$ cycloalkenyl, —$(CH_2)_n$-phenyl, —$(CH_2)_s$-(4-7 membered saturated heterocyclyl), $C_{1-6}$ alkanol optionally substituted with one or more (e.g. 1, 2 or 3) halo, —C(=O)O$C_{1-6}$ alkyl, hydroxy, $C_{1-6}$ alkoxy and halo$C_{1-6}$ alkyl.

In one embodiment, Q is a bond, and therefore $R^3$ is $R^b$. In one embodiment wherein Q is a bond, $R^3$ is independently selected from halogen, $C_{1-6}$ alkyl, $C_{2-6}$ alkenyl, $C_{2-6}$ alkynyl, hydroxyl, $C_{1-6}$ alkoxy, halo$C_{1-6}$ alkyl, halo$C_{1-6}$ alkoxy and $C_{1-6}$ alkanol.

In one embodiment wherein Q is a bond, $R^3$ is independently selected from halogen, $C_{1-6}$ alkyl, $C_{2-6}$ alkenyl, $C_{2-6}$ alkynyl, hydroxyl, $C_{1-6}$ alkoxy, halo$C_{1-6}$ alkyl, halo$C_{1-6}$ alkoxy, $C_{1-6}$ alkanol, —Z-carbocyclyl and —Z-heterocyclyl, wherein the carbocyclyl group contains 4 to 12 ring members, the heterocyclyl group contains 3 to 12 ring members and said carbocyclyl and heterocyclyl groups may be optionally substituted by one or more (e.g. 1, 2 or 3) $R^c$; wherein Z is independently selected from a bond, $-(CR^xR^y)_n-$, $-NR^x-(CR^xR^y)_s-$, $-(CR^xR^y)_s-NR^x-$, $-O-(CR^xR^y)_s-$, and $-(CR^xR^y)_s-O-$;

$R^b$ is independently selected from halogen, $C_{1-6}$ alkyl, $C_{2-6}$ alkenyl, $C_{2-6}$ alkynyl, hydroxyl, $C_{1-6}$ alkoxy, halo$C_{1-6}$ alkyl, and halo$C_{1-6}$ alkoxy; and $R^x$, $R^y$ and $R^z$ are independently selected from the group consisting of halogen, hydrogen, $C_{1-6}$ alkyl, $C_{2-6}$ alkenyl, $C_{2-6}$ alkynyl, $-(CH_2)_s-C_{3-8}$ cycloalkyl, $-(CH_2)_s-C_{3-8}$ cycloalkenyl, $-(CH_2)_n$-phenyl, $-(CH_2)_s$-(4-7 membered saturated heterocyclyl), $C_{1-6}$ alkanol optionally substituted with one or more (e.g. 1, 2 or 3) halo, $-C(=O)OC_{1-6}$ alkyl, hydroxy, $C_{1-6}$ alkoxy and halo$C_{1-6}$ alkyl.

In one embodiment wherein Q is a bond, $R^3$ is independently selected from $C_{1-6}$ alkyl, $C_{2-6}$ alkenyl, $C_{2-6}$ alkynyl, and —Z-heterocyclyl wherein the heterocyclyl group contains 3 to 6 ring members and may be optionally substituted by one or more (e.g. 1, 2 or 3) $R^c$;
wherein Z is independently selected from a bond, $-(CR^xR^y)_n-$, $-NR^x-(CR^xR^y)_s-$, $-(CR^xR^y)_s-NR^x-$, $-O-(CR^xR^y)_s-$, and $-(CR^xR^y)_s-O-$;

$R^b$ is independently selected from $C_{1-6}$ alkyl, $C_{2-6}$ alkenyl, $C_{2-6}$ alkynyl, hydroxyl, $C_{1-6}$ alkoxy, halo$C_{1-6}$ alkyl, and halo$C_{1-6}$ alkoxy; and $R^x$, $R^y$ and $R^z$ are independently selected from $C_{1-6}$ alkyl, $C_{2-6}$ alkenyl, $C_{2-6}$ alkynyl, hydroxyl, $C_{1-6}$ alkoxy, halo$C_{1-6}$ alkyl, and halo$C_{1-6}$ alkoxy.

In one embodiment wherein Q is a bond, $R^3$ is independently selected from $C_{1-6}$ alkyl, $C_{2-6}$ alkenyl, $C_{2-6}$ alkynyl, and —Z-heterocyclyl wherein the heterocyclyl group contains 5 or 6 ring members and contains one or more (e.g. 1, 2 or 3) nitrogen atom and optionally one or more (e.g. 1, 2 or 3) heteroatoms independently selected from oxygen and sulphur, and the heterocyclyl group may be optionally substituted by one or more (e.g. 1, 2 or 3) $R^c$;
wherein Z is independently selected from a bond, $-(CH_2)_n-$, $-NR^x-(CH_2)_s-$, $-(CH_2)_s-NR^x-$, $-O-(CH_2)_s-$, and $-(CH_2)_s-O-$;

$R^c$ is independently selected from $C_{1-6}$ alkyl, $C_{2-6}$ alkenyl, $C_{2-6}$ alkynyl, hydroxyl, $C_{1-6}$ alkoxy, halo$C_{1-6}$ alkyl, and halo$C_{1-6}$ alkoxy; and $R^x$, $R^y$ and $R^z$ are independently selected from $C_{1-6}$ alkyl, $C_{2-6}$ alkenyl, $C_{2-6}$ alkynyl, hydroxyl, $C_{1-6}$ alkoxy, halo$C_{1-6}$ alkyl, and halo$C_{1-6}$ alkoxy.

In one embodiment, $R^3$ is independently selected from —Z-heterocyclyl wherein the heterocyclyl group an aromatic group e.g. pyridinyl (e.g. 3-pyridinyl) or a saturated group e.g. piperidnyl (e.g. 4-piperidnyl), and may be substituted by one or more (e.g. 1, 2 or 3, for example 0 or 1) $R^c$;
wherein Z is independently selected from a bond, $-(CH_2)_n-$, $-NR^x-(CH_2)_s-$, $-(CH_2)_s-NR^x-$, $-O-(CH_2)_s-$, and $-(CH_2)_s-O-$;

$R^c$ is independently selected from $C_{1-6}$ alkyl, $C_{2-6}$ alkenyl, $C_{2-6}$ alkynyl, hydroxyl, $C_{1-6}$ alkoxy, halo$C_{1-6}$ alkyl, and halo$C_{1-6}$ alkoxy; and $R^x$, $R^y$ and $R^z$ are independently selected from $C_{1-6}$ alkyl, $C_{2-6}$ alkenyl, $C_{2-6}$ alkynyl, hydroxyl, $C_{1-6}$ alkoxy, halo$C_{1-6}$ alkyl, and halo$C_{1-6}$ alkoxy.

In one embodiment, $R^3$ is independently selected from —Z-heterocyclyl wherein the heterocyclyl group is a saturated group e.g. piperidnyl (e.g. 4-piperidnyl), and may be substituted by one or more (e.g. 1, 2 or 3, for example 0 or 1) $R^c$;
wherein Z is independently selected from a bond, $-(CH_2)_s-$, $-NH-(CH_2)_s-$ or $-O-(CH_2)_s-$, $R^c$ is independently selected from $C_{1-6}$ alkyl, $C_{2-6}$ alkynyl, hydroxyl, $C_{1-6}$ alkoxy, halo$C_{1-6}$ alkyl, and halo$C_{1-6}$ alkoxy;

$R^x$, $R^y$ and $R^z$ are independently selected from $C_{1-6}$ alkyl, $C_{2-6}$ alkenyl, $C_{2-6}$ alkynyl, hydroxyl, $C_{1-6}$ alkoxy, halo$C_{1-6}$ alkyl, and halo$C_{1-6}$ alkoxy; and s is 0 or 1.

In one embodiment $R^3$ is independently selected from -tetrahydropyranyl, -oxetanyl, -tetrahydrofuranyl, $-CH_2CH_2-SO_2CH_3$, $-OCH_2CH_2-SO_2CH_3$, $-CH_2N(CH_3)_2$, $-CH_2N(CH_3)CH_2CH_2OCH_3$, $-O$-oxetanyl, $-OCH_2CH_2OCH_3$, $-OCH_2CH_2OH$, $-CH_2$-(hydroxypiperidinyl), $-CH_2N(CH_2CH_2OCH_3)_2$ and $-NH$-piperidinyl.

In one embodiment $R^3$ is $-(CH_2)_s-NR^xR^y$. In one embodiment when attached to nitrogen, $R^x$ and $R^y$ may join to form a 3-7 membered ring optionally containing one or two additional heteroatoms selected from nitrogen, oxygen or sulphur.

In one embodiment, the compound of formula (I) is a compound of formula (Ih):

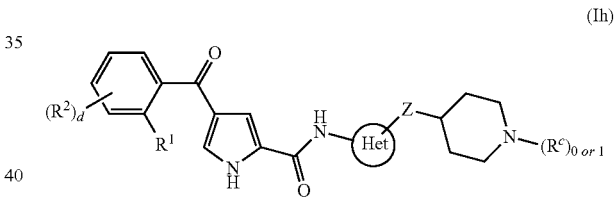

(Ih)

wherein Z is a bond, $-(CH_2)_s-$, $-NH-(CH_2)_s-$ or $-O-(CH_2)_s-$, and wherein s is 0, 1, or 2.

In one embodiment $R^c$ is absent i.e. is hydrogen. In one embodiment, $R^c$ is $C_{1-3}$ alkyl, $C_{1-3}$ haloalkyl (e.g. $C_{1-3}$fluoroalkyl) or $C(=O)C_{1-3}$ haloalkyl (e.g. $C(=O)C_{1-3}$ fluoroalkyl). In one embodiment $R^c$ is $C_{1-3}$ alkyl.

In one embodiment Z is $-NH-$, $-CH_2-$ or $-O-$ e.g. $-CH_2-$ or $-O-$.

Z

In one embodiment Z is a bond, $-(CR^xR^y)_n-$, $-NR^x-(CR^xR^y)_s-$, $-(CR^xR^y)_s-NR^x-$, $-O-(CR^xR^y)_s-$, and $-(CR^xR^y)_s-O-$.

In one embodiment Z is $-NH-$, $-CH_2-$ or $-O-$ e.g. $-CH_2-$ or $-O-$.

s

In one embodiment, s is independently selected from 0, 1 and 2. In one embodiment, s is independently selected from 0 or 1 e.g. 1.

n

In one embodiment, n is independently selected from 1, 2 and 3. In one embodiment, n is independently selected from 1 and 2 e.g. 1.

q

In one embodiment, q is independently selected from 1 and 2 e.g. 2.

Subformulae

In one embodiment, the compound of formula (I) is a compound of formula (II):

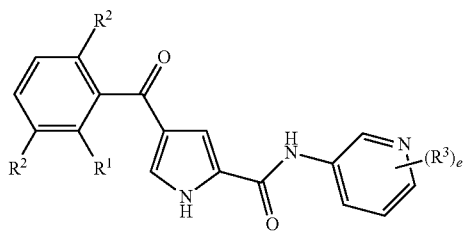

(II)

wherein $R^1$, $R^2$, $R^3$ and e are as defined herein.

In one embodiment of the compound of formula (II), $R^2$ is independently selected from halogen, $C_{1-6}$ alkyl, $C_{2-6}$ alkenyl, $C_{2-6}$ alkynyl, hydroxyl, $C_{1-6}$ alkoxy, halo$C_{1-6}$ alkyl, halo$C_{1-6}$ alkoxy, and $C_{1-6}$ alkanol, for example halogen, $C_{1-3}$ alkyl, $C_{1-3}$ alkoxy, and halo$C_{1-3}$alkyl (e.g. halogen, for example F or Cl, and —OCH$_3$).

In one embodiment, the compound of formula (II) is a compound of formula (IIa):

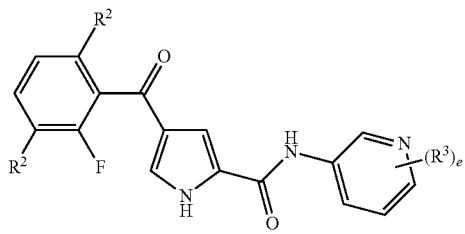

(IIa)

wherein $R^2$, $R^3$ and e are as defined herein.

In one embodiment of the compound of formula (IIa), $R^2$ is independently selected from halogen, $C_{1-3}$ alkyl and $C_{1-3}$ alkoxy e.g. F, Cl, and —OCH$_3$.

In one embodiment, the compound of formula (IIa) is a compound of formula (IIb):

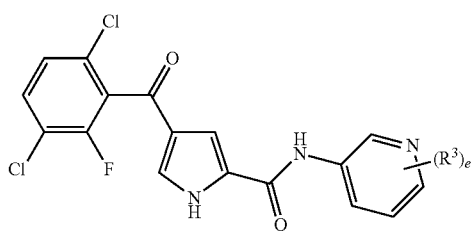

(IIb)

wherein $R^3$ and e are as defined herein.

In one embodiment, the compound of formula (IIa) is a compound of formula (IIb'):

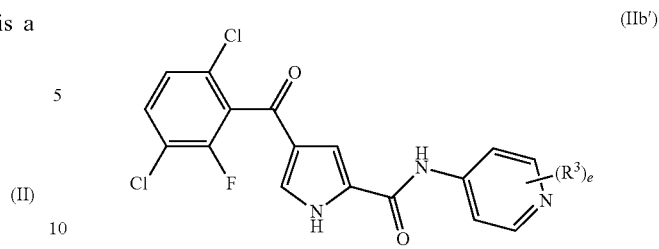

(IIb')

wherein $R^3$ and e are as defined herein.

In one embodiment of the compound of formula (IIb') $R^3$ is piperazine.

In one embodiment, the compound of formula (IIb) is a compound of formula (IIc):

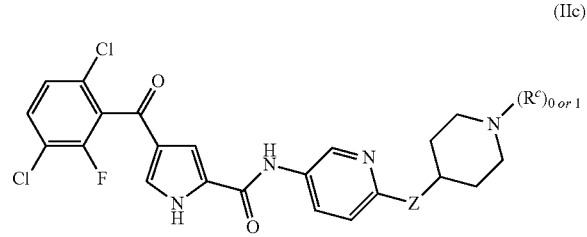

(IIc)

wherein Z is a bond, —(CH$_2$)$_s$—, —NH—(CH$_2$)$_s$— or —O—(CH$_2$)$_s$—, wherein s is 0, 1, 2 or 3, and $R^c$ is H or $C_{1-3}$ alkyl. In one embodiment Z is CH$_2$ or —O— and $R^c$ is H or Me.

In one embodiment, the compound of formula (I) is a compound of formula (III):

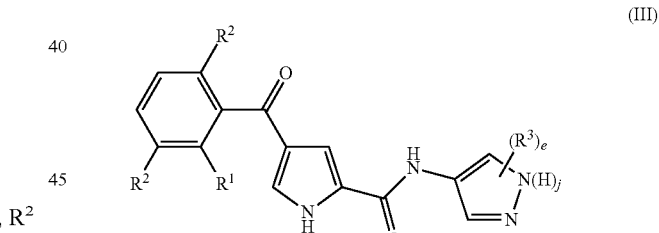

(III)

wherein $R^1$, $R^2$, $R^3$ and e are as defined herein and j is 0 or 1.

One of the $R^3$ substituents may be attached to the nitrogen atom, and therefore in this embodiment j is 0 because the N-substituent is $R^3$. Alternatively, none of the $R^3$ substituents may be attached to the nitrogen atom, and therefore in this embodiment j is 1 because the N-substituent is H.

In one embodiment of the compound of formula (III), $R^3$ is independently selected from halogen, $C_{1-6}$ alkyl, hydroxyl, $C_{1-6}$ alkoxy, halo$C_{1-6}$ alkyl, halo$C_{1-6}$ alkoxy, $C_{1-6}$ alkanol and a heterocyclyl group which contains 3 or 7 ring members and one or more (e.g. 1, 2 or 3) heteroatoms independently selected from nitrogen, oxygen and sulphur, wherein the alkyl group may be optionally substituted by hydroxy or SO$_2$C$_{1-3}$alkyl, and wherein the heterocyclyl group may be optionally substituted by one or more (e.g. 1, 2 or 3) $R^c$ wherein $R^c$ is $C_{1-6}$ alkyl, hydroxyl, $C_{1-6}$ alkoxy, halo$C_{1-6}$ alkyl, or halo$C_{1-6}$ alkoxy e.g. $R^c$ is $C_{1-6}$ alkyl.

In one embodiment, the compound of formula (III) is a compound of formula (IIIa):

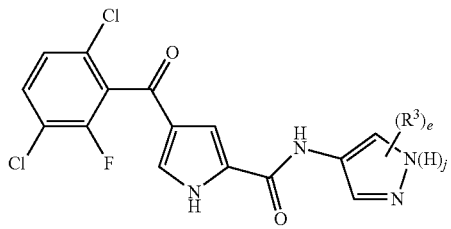

(IIIa)

wherein R³, e and j are as defined herein.

In one embodiment of the compound of formula (IIIa), R³ is independently selected from halogen, C$_{1-6}$ alkyl, hydroxyl, C$_{1-6}$ alkoxy, haloC$_{1-6}$ alkyl, haloC$_{1-6}$ alkoxy, C$_{1-6}$ alkanol or a heterocyclyl group which contains 3 or 7 ring members and one or more (e.g. 1, 2 or 3) heteroatoms independently selected from nitrogen, oxygen and sulphur, wherein the alkyl group may be optionally substituted by hydroxy or —SO$_2$C$_{1-3}$alkyl, and wherein the heterocyclyl group may be optionally substituted by one or more (e.g. 1, 2 or 3) R$^c$ wherein R$^c$ is selected from C$_{1-6}$ alkyl, hydroxyl, C$_{1-6}$ alkoxy, haloC$_{1-6}$ alkyl, and haloC$_{1-6}$ alkoxy e.g. R$^c$ is C$_{1-6}$ alkyl.

In one embodiment, the compound of formula (IIIa) is a compound of formula (IIIb):

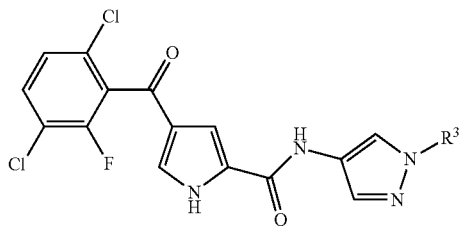

(IIIb)

wherein R³ is as defined herein.

In one embodiment of the compound of formula (IIIb), R³ is C$_{1-3}$ alkyl or a heterocyclyl group which contains 3 or 7 ring members and one or more (e.g. 1, 2 or 3) heteroatoms independently selected from nitrogen, oxygen and sulphur, wherein the alkyl group may be optionally substituted by hydroxy or SO$_2$C$_{1-3}$alkyl, and wherein the heterocyclyl group may be optionally substituted by one or more (e.g. 1, 2 or 3) R$^c$ wherein R$^c$ is C$_{1-6}$ alkyl, C$_{2-6}$ alkenyl, C$_{2-6}$ alkynyl, hydroxyl, C$_{1-6}$ alkoxy, haloC$_{1-6}$ alkyl, or haloC$_{1-6}$ alkoxy e.g. R$^c$ is C$_{1-6}$ alkyl.

In one embodiment of the compound of formula (IIIb), R³ is C$_{1-3}$ alkyl or a heterocyclyl group which contains 5 or 6 ring members and contains one or more (e.g. 1, 2 or 3) nitrogen atom and optionally one or more (e.g. 1, 2 or 3) heteroatoms independently selected from oxygen and sulphur, and the heterocyclyl group may be optionally substituted by one or more (e.g. 1, 2 or 3) R$^c$ wherein R$^c$ is C$_{1-6}$ alkyl, C$_{2-6}$ alkenyl, C$_{2-6}$ alkynyl, hydroxyl, C$_{1-6}$ alkoxy, haloC$_{1-6}$ alkyl, or haloC$_{1-6}$ alkoxy e.g. R$^c$ is C$_{1-6}$ alkyl.

In one embodiment of the compound of formula (IIIb), R³ is —(CH$_2$)$_s$—OH, —(CH$_2$)$_s$—SO$_2$Me, or a four to six membered saturated heterocycle including one or more oxygen atom e.g. oxetane, tetrahydrofuran or tetrahydropyran.

In one embodiment of the compound of formula (IIIb), R³ is C$_{1-3}$ alkyl, for example methyl.

In one embodiment, the compound of formula (I) is a compound of formula (IV):

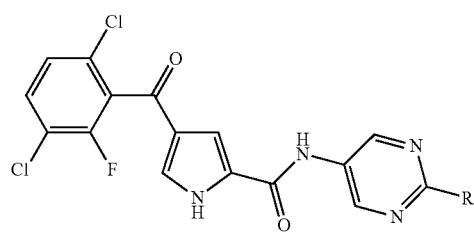

(IV)

wherein R³ is as defined herein.

In one embodiment the compound of formula (IV) is a compound of formula (IVa):

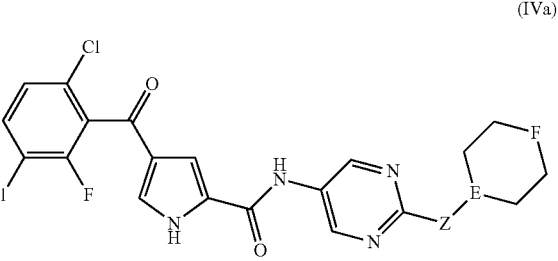

(IVa)

wherein Z is a bond, —(CH$_2$)$_s$—, —NH—(CH$_2$)$_s$— or —O—(CH$_2$)$_s$—, wherein s is 0, 1, 2 or 3, E is N or CH, and F is O or NR$^c$ where R$^c$ is H or C$_{1-3}$ alkyl. In one embodiment Z is CH$_2$ or —O— and R$^c$ is H or Me.

In one embodiment the invention provides a compound of formula (I)

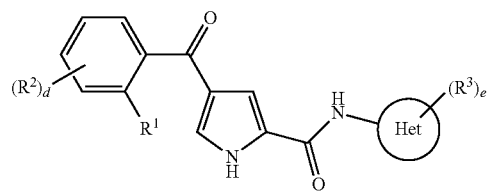

(I)

or a tautomer, stereoisomer, N-oxide, pharmaceutically acceptable salt or solvate thereof, wherein:
R¹ is F, Cl or Br;
Het is selected from pyridinyl (e.g. 3-pyridinyl, 4-pyridinyl), pyrazolyl (e.g. 3-pyrazolyl), pyrimidinyl (e.g. 3-pyrimidinyl, 2-pyrimidinyl), piperidinyl (e.g. 4-piperidinyl), pyridazine (e.g. 3-pyridazine), isoxazole (e.g. 5-isoxazole), tetrahydropyran (e.g. 4-tetrahydropyran), indazole (e.g. 7-indazole), piperazine (e.g. 1-piperazine) and pyrrolidinyl (e.g. 3-pyrrolidinyl),
d is 0, 1 or 2;
R² is independently selected from F, Cl, Br, —OCH$_3$, CH$_3$, Et, —CH═CH$_2$, —CF$_3$, —C(CH$_3$)═CH$_2$, —CCH, —OH, —OEt, —OCH$_2$CH$_2$OCH$_3$, —O-tetrahydrofuranyl, —CHO, —COOH, —O—CH$_2$—CH$_2$—SO$_2$—CH$_3$, —O-tetrahydropyranyl, —O-oxetanyl, —O—CH(CH$_2$OH)

(CH₂Cl), —O—CH(CH₂Cl)(CH₂Cl), —CH₂—NHCH₃ and cyclopropyl;

e is 0, 1 or 2;

R³ is independently selected from C$_{1-3}$ alkyl optionally substituted by hydroxyl or halo, hydroxy, C$_{1-3}$ alkoxy, F, Cl, =O, —C(=O)OtBu, —NH—CH₂CH₂—N(CH₃)₂, —NH—CH₂CH₂—NEt₂, —NH—CH₂CH₂—SO₂CH₃, —NH—CH₂CH₂—, —NH—CH₂CH₂-pyrrolidinyl, —NH—CH₂CH₂-morpholinyl, —NH—CH₂CH₂-piperidinyl, —NCH₃—(N—CH₃-piperidinyl), —(NCH₃-piperidinyl), —O-piperidinyl, —O—(N—CH₃-piperidinyl), —CH₂-piperidinyl, —CH₂—(N—CH₃-piperidinyl), —CH₂-piperazinyl, —CH₂—(N—CH₃-piperazinyl), —CH₂-morpholinyl, -pyrrolidinyl, —CH₂-pyridinyl, -piperazinyl, —CH₂CH₂—OCH₃, —CH₂CH₂—NEt₂, —CH₂—(N—CH₃-imidazolyl), piperidinyl, azetidinyl, —NH—(N—CH₃-piperidinyl), —(N-haloalkyl-piperidinyl), —(N—CH₃-piperazinyl), —NHNCH₃, —N(CH₃)₂, —(N-cyclopropylpiperazinyl), —(NBoc-piperazinyl), morpholinyl, -piperidinyl-OAc, —NH—(N-cyclopropyl-piperidinyl), —NH—(N-trifluoroacetyl-piperidinyl), —NH—(N-pyrimidinyl-piperidinyl), —NH—(N—SO₂CH₃-piperidinyl), —NH—(N-acetyl-piperidinyl), —NH—(N-ethyl-piperidinyl), —NH—(N-iPr-piperidiny)l, —NH—(N-Boc-piperidinyl), tetrahydropyranyl, oxetanyl, tetrahydrofuranyl, —CH₂CH₂—SO₂CH₃, —OCH₂CH₂—SO₂CH₃, —CH₂N(CH₃)₂, —CH₂N(CH₃)CH₂CH₂OCH₃, —O-oxetanyl, —OCH₂CH₂OCH₃, —OCH₂CH₂OH, —CH₂-(hydroxypiperidinyl), —CH₂N(CH₂CH₂OCH₃)₂ and —NH-piperidinyl.

In one embodiment the invention provides a compound of formula (I)

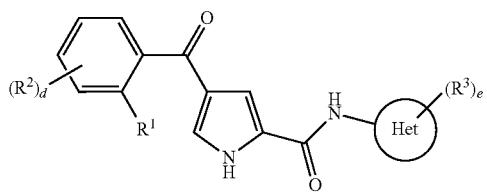

(I)

or a tautomer, stereoisomer or a tautomer, stereoisomer, N-oxide, pharmaceutically acceptable salt or solvate thereof, wherein:

R¹ is F or Cl;

Het is selected from pyridinyl (e.g. 3-pyridinyl), pyrazolyl (e.g. 4-pyrazolyl), pyrimidinyl (e.g. 3-pyrimidinyl), and pyrrolidinyl (e.g. 3-pyrrolidinyl), d is 0 or 1;

R² is independently selected from Cl, —OMe, —OEt, —OCH₂CH₂OCH₃, —O-tetrahydrofuranyl, —CHO, —COOH, —O-tetrahydropyranyl, —O-oxetanyl, —O—CH(CH₂OH)(CH₂Cl), —O—CH(CH₂Cl)(CH₂Cl), and CH₂—NHCH₃;

e is 0 or 1;

R³ is independently selected from C$_{1-3}$ alkyl optionally substituted by hydroxyl, —NH—CH₂CH₂—NEt₂, —NH—CH₂CH₂-pyrrolidinyl, —NH—CH₂CH₂-piperidinyl, —CH₂-piperidinyl, —CH₂—(N—CH₃-piperidinyl), —CH₂-piperazinyl, —CH₂—(N—CH₃-piperazinyl), —CH₂-morpholinyl, azetidinyl, tetrahydropyranyl, oxetanyl, tetrahydrofuranyl, —CH₂CH₂—SO₂CH₃, —OCH₂CH₂—SO₂CH₃, —CH₂N(CH₃)₂, —CH₂N(CH₃)CH₂CH₂OCH₃, —O-oxetanyl, —OCH₂CH₂OCH₃, —OCH₂CH₂OH, —CH₂-(hydroxypiperidinyl), —CH₂N(CH₂CH₂OCH₃)₂, and —NH-piperidinyl.

In one embodiment, the invention provides a compound of formula (I) which is one of the Examples 1-234 or is selected from the Examples 1-234 or a tautomer, stereoisomer, N-oxide, pharmaceutically acceptable salt or solvate thereof.

In one embodiment, the invention provides a compound of formula (I) which is one of the Examples 235-284 or is selected from the Examples 235-284 or a tautomer, stereoisomer, N-oxide, pharmaceutically acceptable salt or solvate thereof.

In one embodiment, the invention provides a compound of formula (I) which is one of the Examples 285-287 or is selected from the Examples 285-287 or a tautomer, stereoisomer, N-oxide, pharmaceutically acceptable salt or solvate thereof.

In one embodiment, the invention provides a compound of formula (I) which is one of the Examples 1-287 or is selected from the Examples 1-287 or a tautomer, stereoisomer, N-oxide, pharmaceutically acceptable salt or solvate thereof.

In one embodiment, the invention provides a compound of formula (I) which is selected from the following compounds or is one of the following compounds, or a tautomer, stereoisomer, N-oxide, pharmaceutically acceptable salt or solvate thereof:

4-(3,6-Dichloro-2-fluorobenzoyl)-N-(1-(piperidin-4-ylmethyl)-1H-pyrazol-4-yl)-1H-pyrrole-2-carboxamide;

4-(3,6-Dichloro-2-fluorobenzoyl)-N-(6-(piperidin-4-ylmethyl)pyridin-3-yl)-1H-pyrrole-2-carboxamide;

4-(3,6-Dichloro-2-fluorobenzoyl)-N-(6-((1-methylpiperidin-4-yl)methyl)pyridin-3-yl)-1H-pyrrole-2-carboxamide;

4-(3,6-Dichloro-2-fluorobenzoyl)-N-(6-((1-methylpiperidin-4-yl)oxy)pyridin-3-yl)-1H-pyrrole-2-carboxamide;

4-(3,6-Dichloro-2-fluorobenzoyl)-N-(1-(piperidin-4-yl)-1H-pyrazol-4-yl)-1H-pyrrole-2-carboxamide;

4-(3,6-Dichloro-2-fluorobenzoyl)-N-(1-methyl-1H-pyrazol-4-yl)-1H-pyrrole-2-carboxamide; and 4-(3,6-Dichloro-2-fluorobenzoyl)-N-(pyridin-3-yl)-1H-pyrrole-2-carboxamide.

In one embodiment, the invention provides a compound which is 4-(3,6-Dichloro-2-fluorobenzoyl)-N-(1-methyl-1H-pyrazol-4-yl)-1H-pyrrole-2-carboxamide, or a tautomer, stereoisomer, N-oxide, pharmaceutically acceptable salt or solvate thereof.

For the avoidance of doubt, it is to be understood that each general and specific embodiment and example for one substituent may be combined with each general and specific embodiment and example for one or more, typically all, other substituents as defined herein and that all such embodiments are embraced by this application.

Salts, Solvates, Tautomers, Isomers, N-Oxides, Esters, Prodrugs and Isotopes

A reference to a compound of the formula (I), sub-groups thereof (e.g. formulae (Ia), (Ia'), (Ib), (Ic), (Id), (Ie), (If), (Ig), (Ih), (II), (IIa), (IIb), (IIb'), (IIc), (III), (IIIa), (IIIb) and (IV)) and any example also includes ionic forms, salts, solvates, isomers (including geometric and stereochemical isomers), tautomers, N-oxides, esters, prodrugs, isotopes and protected forms thereof, for example, as discussed below; typically, the salts or tautomers or isomers or N-oxides or solvates thereof; and more typically, the salts or tautomers or N-oxides or solvates thereof, even more typically the salts or tautomers or solvates thereof.

Salts

Many compounds of the formula (I) can exist in the form of salts, for example acid addition salts or, in certain cases salts of organic and inorganic bases such as carboxylate, sulfonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphorsulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

If the compound is anionic, or has a functional group which may be anionic (e.g., —COOH may be —COO⁻), then a salt may be formed with an organic or inorganic base, generating a suitable cation. Examples of suitable inorganic cations include, but are not limited to, alkali metal ions such as Li⁺, Na⁺ and K⁺, alkaline earth metal cations such as Ca²⁺ and Mg²⁺, and other cations such as Al³⁺ or Zn⁺. Examples of suitable organic cations include, but are not limited to, ammonium ion (i.e., NH₄⁺) and substituted ammonium ions (e.g., NH₃R⁺, NH₂R₂⁺, NHR₃⁺, NR₄⁺). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salt forms, which may be useful, for example, in the purification or separation of the compounds of the invention, also form part of the invention.

In one embodiment of the invention, there is provided a pharmaceutical composition comprising a solution (e.g. an aqueous solution) containing a compound of the formula (I) and sub-groups and examples thereof as described herein in the form of a salt in a concentration of greater than 10 mg/ml, typically greater than 15 mg/ml and typically greater than 20 mg/ml.

N-Oxides

Compounds of the formula (I) containing an amine function may also form N-oxides. A reference herein to a compound of the formula (I) that contains an amine function also includes the N-oxide.

Where a compound contains several amine functions one, or more than one, nitrogen atom may be oxidised to form an N-oxide. Particular examples of N-oxides are the N-oxides of a tertiary amine or a nitrogen atom of a nitrogen-containing heterocyclic group.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4ᵗʰ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

In one embodiment of the invention, the compound is an N-oxide, from on a nitrogen atom on the Het ring, for example a pyridine N-oxide as in Examples 118, 127 and 128.

Geometric Isomers and Tautomers

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, certain heteroaryl rings can exist in the two tautomeric forms such as A and B shown below. For simplicity, a formula may illustrate one form but the formula is to be taken as embracing both tautomeric forms.

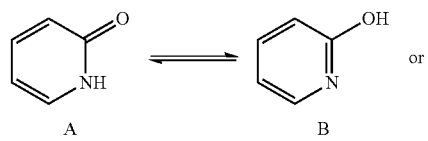

or

-continued

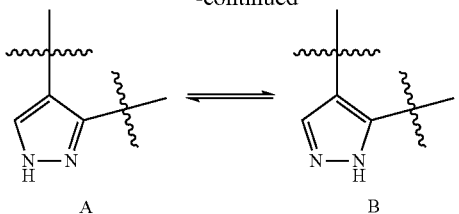

Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

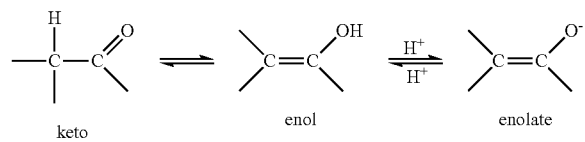

Stereoisomers

Unless otherwise mentioned or indicated, the chemical designation of compounds denotes the mixture of all possible stereochemically isomeric forms.

Stereocentres are illustrated in the usual fashion, using 'hashed' or 'wedged' lines. e.g.

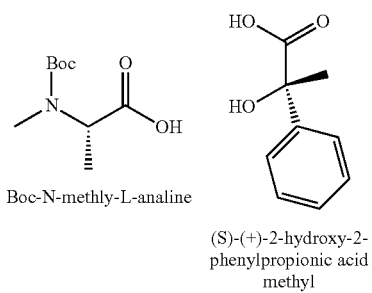

Boc-N-methly-L-analine (S)-(+)-2-hydroxy-2-phenylpropionic acid methyl

Where a compound is described as a mixture of two diastereoisomers/epimers, the configuration of the stereocentre is not specified and is represented by straight lines.

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry by Jerry March*, 4th Edition, John Wiley & Sons, New York, 1992, pages 109-114, and see also Cahn, Ingold & Prelog, *Angew. Chem. Int. Ed. Engl.,* 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic acid, separating the diastereoisomers by preferential crystallisation, and then dissociating the salts to give the individual enantiomer of the free base.

Additionally enantiomeric separation can be achieved by covalently linking a enantiomerically pure chiral auxiliary onto the compound and then performing diastereoisomer separation using conventional methods such as chromatography. This is then followed by cleavage of the aforementioned covalent linkage to generate the appropriate enantiomerically pure product.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds of formula (I) which are stereochemically pure. When a compound of formula (I) is for instance specified as R, this means that the compound is substantially free of the S isomer. If a compound of formula (I) is for instance specified as E, this means that the compound is substantially free of the Z isomer. The terms cis, trans, R, S, E and Z are well known to a person skilled in the art.

Isotopic Variations

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2H$ (D) and $^3H$ (T), carbon, such as $^{11}C$, $^{13}C$ and $^{14}C$, chlorine, such as $^{36}Cl$, fluorine, such as $^{18}F$, iodine, such as $^{123}I$, $^{125}I$ and $^{131}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be used in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Esters

Esters such as carboxylic acid esters, acyloxy esters and phosphate esters of the compounds of formula (I) bearing a carboxylic acid group or a hydroxyl group are also embraced by Formula (I). Examples of esters are compounds containing the group —C(═O)OR, wherein R is an ester substituent, for example, a $C_{1-7}$ alkyl group, a $C_{3-12}$ heterocyclyl group, or a $C_{5-12}$ aryl group, typically a $C_{1-6}$ alkyl group. Particular examples of ester groups include, but are not limited to, —C(═O)OCH$_3$, —C(═O)OCH$_2$CH$_3$, —C(═O)OC(CH$_3$)$_3$, and —C(═O)OPh. Examples of acyloxy (reverse ester) groups are represented by —OC(═O)R, wherein R is an acyloxy substituent, for example, a $C_{1-6}$ alkyl group, a $C_{3-12}$ heterocyclyl group, or a $C_{5-12}$ aryl group, typically a $C_{1-6}$ alkyl group. Particular examples of acyloxy groups include, but are not limited to, —OC(═O)CH$_3$ (acetoxy), —OC(═O)CH$_2$CH$_3$, —OC(═O)C(CH$_3$)$_3$, —OC(═O)Ph, and —OC(═O)CH$_2$Ph. Examples of phosphate esters are those derived from phosphoric acid.

In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group.

Solvates and Crystalline Forms

Also encompassed by formula (I) are any polymorphic forms of the compounds, and solvates such as hydrates, alcoholates and the like.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS.

Alternatively the skilled person can deliberately form a solvate using crystallisation conditions that include an amount of the solvent required for the particular solvate. Thereafter the standard methods described herein, can be used to establish whether solvates had formed.

Furthermore, the compounds of the present invention may have one or more polymorph or amorphous crystalline forms and as such are intended to be included in the scope of the invention.

Complexes

Formula (I) also includes within its scope complexes (e.g. inclusion complexes or clathrates with compounds such as cyclodextrins, or complexes with metals) of the compounds. Inclusion complexes, clathrates and metal complexes can be formed by means of methods well known to the skilled person.

Prodruqs

Also encompassed by formula (I) are any pro-drugs of the compounds of the formula (I). By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(═O) OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required.

Examples of such metabolically labile esters include those of the formula —C(═O)OR wherein R is:
$C_{1-7}$alkyl (e.g., -Me, -Et, -nPr, -iPr, -nBu, -sBu, -iBu, -tBu);
$C_{1-7}$aminoalkyl (e.g., aminoethyl; 2-(N,N-diethylamino) ethyl; 2-(4-morpholino)ethyl); and acyloxy-$C_{1-7}$alkyl (e.g., acyloxymethyl; acyloxyethyl; pivaloyloxymethyl; acetoxymethyl; 1-acetoxyethyl; 1-(1-methoxy-1-methyl) ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT), and ligand-directed enzyme pro-drug therapy (LIDEPT), etc.). For example, the prodrug may be a sugar derivative or other glycoside conjugate, or may be an amino acid ester derivative. In one embodiment formula (I) does not include pro-drugs of the compounds of the formula (I) within its scope.

Methods for the Preparation of Compounds of Formula (I)

In this section, as in all other sections of this application unless the context indicates otherwise, references to formula (I) also include all other subformula e.g. formulae (Ia), (Ia'), (Ib), (Ic), (Id), (Ie), (If), (Ig), (Ih), (II), (IIa), (IIb), (IIb'), (IIc), (III), (IIIa), (IIIb) and (IV) and examples thereof as defined herein, unless the context indicates otherwise.

Compounds of the formula (I) can be prepared in accordance with synthetic methods well known to the skilled person.

According to a further aspect of the invention there is provided a process for preparing a compound of formula (I), or a tautomer, stereoisomer, N-oxide, pharmaceutically acceptable salt, or solvate thereof which comprises:
(a) reacting a compound of formula (A) with a compound of formula (B):

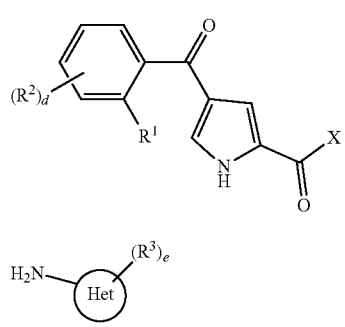

(A)

(B)

where $R^1$, $R^2$, d, $R^3$, e, and Het are as defined herein, and X is a leaving group and/or
(b) interconversion of a compound of formula (I) or protected derivative thereof to a further compound of formula (I) or protected derivative thereof; and/or
(c) deprotection of a protected derivative of a compound of formula (I); and/or
(d) providing a compound of formula (I) and forming a pharmaceutically acceptable salt of the compound.

In one embodiment, the compound (A) is a carboxylic acid (i.e. X is hydroxyl), and the reaction between acid (A) and amine (B) is typically carried out in the presence of a reagent of the type commonly used in the formation of peptide linkages. Examples of such reagents include 1,3-dicyclohexylcarbodiimide (DCC) (Sheehan et al, *J. Amer. Chem Soc.* 1955, 77, 1067), 1-ethyl-3-(3'-dimethylaminopropyl)-carbodiimide (referred to herein either as EDC or EDAC but also known in the art as EDCI and WSCDI) (Sheehan et al, *J. Org. Chem.*, 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al, *Tetrahedron Letters*, 1990, 31, 205). Carbodiimide-based coupling agents are advantageously used in combination with 1-hydroxy-7-azabenzotriazole (HOAt) (L. A. Carpino, *J. Amer. Chem. Soc.*, 1993, 115, 4397) or 1-hydroxybenzotriazole (HOBt) (Konig et al, *Chem. Ber.*, 103, 708, 2024-2034). Typical coupling reagents include EDC (EDAC) and DCC in combination with HOAt or HOBt.

The coupling reaction is typically carried out in a non-aqueous, non-protic solvent such as acetonitrile, dioxan, dimethylsulphoxide, dichloromethane, dimethylformamide or N-methylpyrrolidine, or in an aqueous solvent optionally together with one or more miscible cosolvents. The reaction can be carried out at room temperature or, where the reactants are less reactive (for example in the case of electron-poor anilines bearing electron withdrawing groups such as sulphonamide groups) at an appropriately elevated temperature. The reaction may be carried out in the presence of a non-interfering base, for example a tertiary amine such as triethylamine or N,N-diisopropylethylamine.

As an alternative, the compound of formula (A) is a reactive derivative of the carboxylic acid, e.g. an anhydride (X is —(C═O)OR) or acid chloride (X is Cl). Reaction with a reactive derivative such an anhydride is typically accomplished by stirring the amine and anhydride at room temperature in the presence of a base such as pyridine.

The compounds of formula (A) can be prepared by Friedel-Crafts acylation of commercially available methyl 1H-pyrrole-2-carboxylate with the relevant benzoyl acid chloride. Selectivity for the 4-position is achieved using $AlCl_3$ as the Lewis acid.

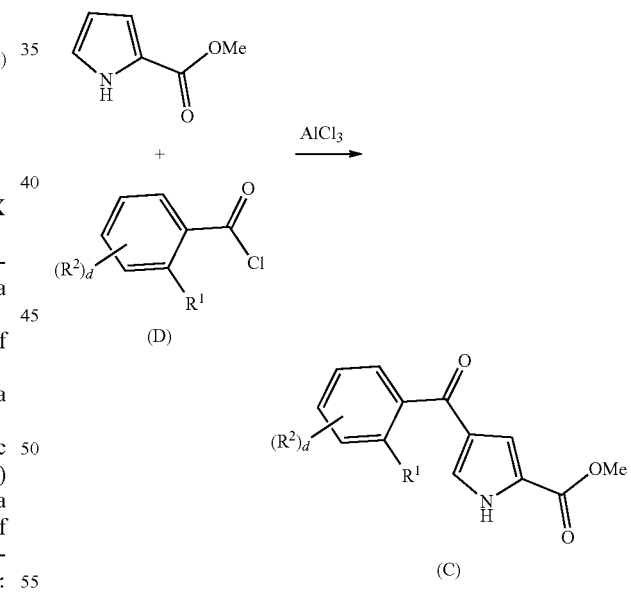

If necessary, benzoyl acid chlorides were synthesised from the corresponding carboxylic acid, for example using $SOCl_2$/DMF in THF.

Hydrolysis of the methyl ester (C) to give acid (A) may be achieved using conventional methods of ester hydrolysis, for example using lithium hydroxide.

In one embodiment of the invention, Het is a 4-piperidinyl group. These compounds can be prepared by coupling the appropriate acid with 1-Boc-4-aminopyridine, and then derivatizing the piperidine:

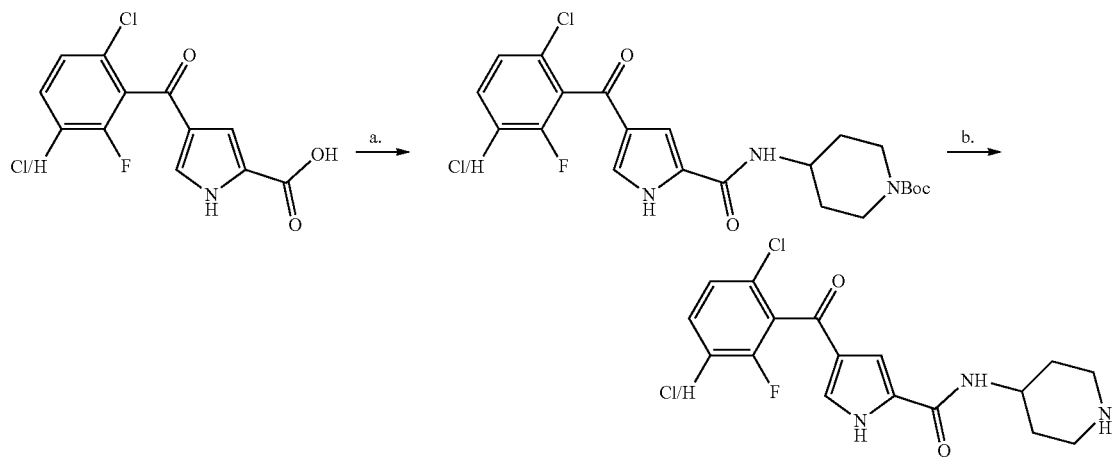

Reagents and conditions a). i). CDI (2 eq.), THF, 70° C., 3 h; ii). 1-Boc-4-aminopiperidine (2.2 eq), 50° C., 3 h, (X = H, 75%; X = Cl, 79%); b). Et$_3$SiH, TFA/CH$_2$Cl$_2$, r.t., 2 h, (X = H, 99%; X = Cl, 75%).

X = H or Cl

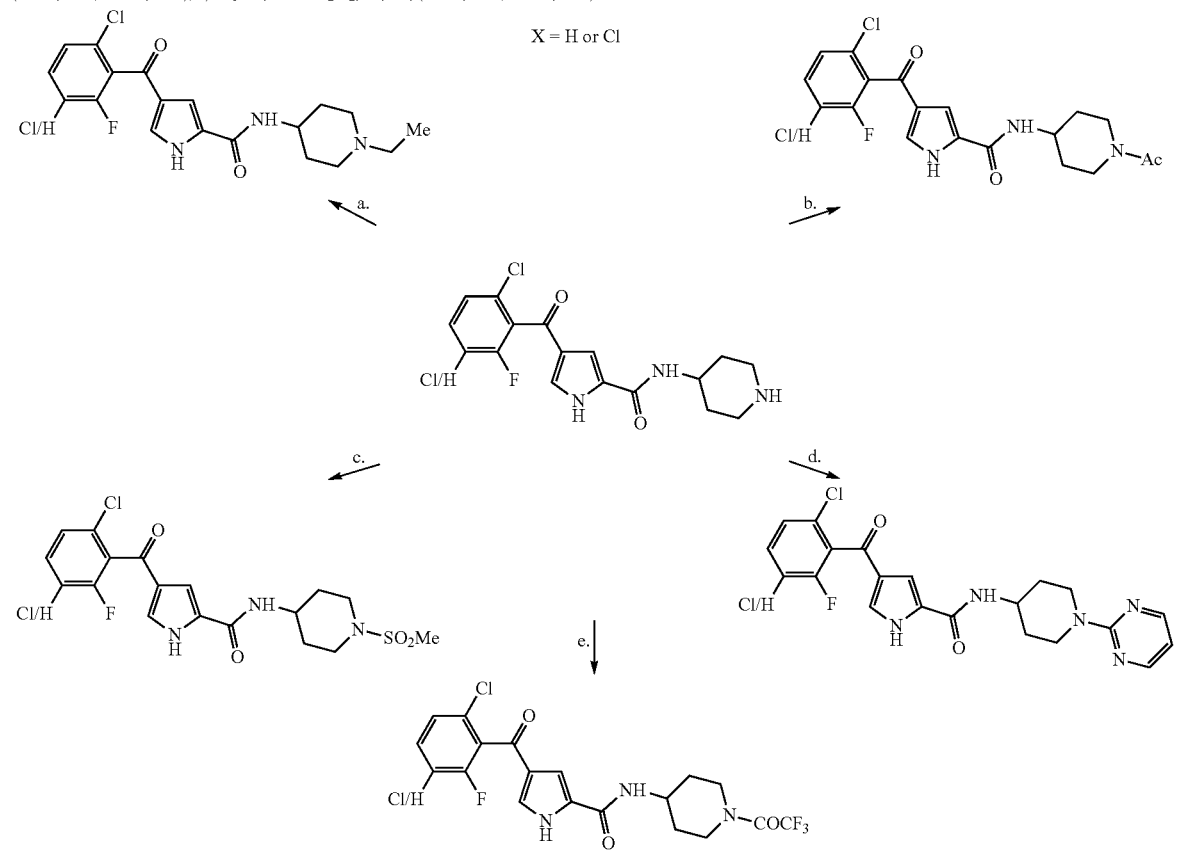

Reagents and conditions
a. i). MeCHO (2 eq.), AcOH (2 eq.), MgSO$_4$, MeOH, r.t., 1 h; ii). NaCNBH$_3$ (1.5 eq.), r.t., 18 h, (X = H, 16%);
b. AcCl (1.1 eq.), Et$_3$N (1.2 eq), CH$_2$Cl$_2$, r.t., 1 h, (X = H, 48%; X = Cl, 52%);
c. MeSO$_2$Cl (1.5 eq.), Et$_3$N (1.5 eq.), CH$_2$Cl$_2$, r.t., 1 h, (X = H, 27%; X = Cl, 35%);
d. 2-chloropyrimidine (1 eq.), iPr$_2$EtNH (1.2 eq.), MeCN, MW, 150° C., 1.5 h, X = H, 23%);
e. (CF$_3$CO)$_2$O (4.5 eq), Et$_3$N (1.2 eq.), CH$_2$Cl$_2$/dioxane, r.t., 3 h, (X = Cl, 41%).

The required intermediates are either commercially available, known in the literature, prepared by methods analogous to those in the literature or prepared by methods analogous to those described in the example experimental procedures below. Other compounds may be prepared by functional group interconversion of the groups using methods well known in the art.

A wide range of well known functional group interconversions are known by a person skilled in the art for converting a precursor compound to a compound of formula I and are described in *Advanced Organic Chemistry* by Jerry March, 4$^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

If appropriate, the reactions previously described below are followed or preceded by one or more reactions known to the skilled of the art and are performed in an appropriate order to achieve the requisite substitutions defined above to afford other compounds of formula (I). Non-limiting examples of such reactions whose conditions can be found in the literature include:

protection of reactive functions,
deprotection of reactive functions,
halogenation,
dehalogenation,
dealkylation,
alkylation or arylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of ester groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
N-oxidation,
salification.

In a further embodiment the invention provides a novel intermediate.

Protecting Groups

In many of the reactions described herein, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(=O)R), for example, as: a t-butyl ether; a tetrahydropyranyl (THP) ether; a benzyl, benzhydryl (diphenylmethyl), or trityl (triphenylmethyl) ether; a trimethylsilyl or t-butyldimethylsilyl ether; or an acetyl ester (—OC(=O)CH$_3$).

An aldehyde or ketone group may be protected, for example, as an acetal (R—CH(OR)$_2$) or ketal (R$_2$C(OR)$_2$), respectively, in which the carbonyl group (>C=O) is treated with, for example, a primary alcohol. The aldehyde or ketone group is readily regenerated by hydrolysis using a large excess of water in the presence of acid.

An amine group may be protected, for example, as an amide (—NRCO—R) or a carbamate (—NRCO—OR), for example, as: a methyl amide (—NHCO—CH$_3$); a benzyl carbamate (—NHCO—OCH$_2$C$_6$H$_5$, —NH-Cbz or NH—Z); as a t-butyl carbamate (—NHCO—OC(CH$_3$)$_3$, —NH-Boc); a 2-biphenyl-2-propyl carbamate (—NHCO—OC(CH$_3$)$_2$C$_6$H$_4$C$_6$H$_5$, —NH-Bpoc), as a 9-fluorenylmethyl carbamate (—NH-Fmoc), as a 6-nitroveratryl carbamate (—NH-Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulfonyl)ethyl carbamate (—NH-Psec).

Other protecting groups for amines, such as cyclic amines and heterocyclic N—H groups, include toluenesulfonyl (tosyl) and methanesulfonyl (mesyl) groups, benzyl groups such as a para-methoxybenzyl (PMB) group and tetrahydropyranyl (THP) groups.

A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$alkyl ester; or a C$_{5-20}$ aryl-C$_{1-7}$ alkyl ester (e.g., a benzyl ester; a nitrobenzyl ester; para-methoxybenzyl ester. A thiol group may be protected, for example, as a thioether (—SR), for example, as: a benzyl thioether; an acetamidomethyl ether (—S—CH$_2$NHC(=O)CH$_3$).

Isolation and Purification of the Compounds of the Invention

The compounds of the invention can be isolated and purified according to standard techniques well known to the person skilled in the art and examples of such methods include chromatographic techniques such as column chromatography (e.g. flash chromatography) and HPLC. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9. An example of such a system for purifying compounds via preparative LC-MS is described below in the Examples section of this application (under the heading "Mass Directed Purification LC-MS System").

Methods of recrystallisation of compounds of formula (I) and salt thereof can be carried out by methods well known to the skilled person—see for example (P. Heinrich Stahl (Editor), Camille G. Wermuth (Editor), ISBN: 3-90639-026-8, Handbook of Pharmaceutical Salts: Properties, Selection, and Use, Chapter 8, Publisher Wiley-VCH). Products obtained from an organic reaction are seldom pure when isolated directly from the reaction mixture. If the compound (or a salt thereof) is solid, it may be purified and/or crystallized by recrystallisation from a suitable solvent. A good recrystallisation solvent should dissolve a moderate quantity of the substance to be purified at elevated temperatures but only a small quantity of the substance at lower temperature. It should dissolve impurities readily at low temperatures or not at all. Finally, the solvent should be readily removed from the purified product. This usually means that it has a relatively low boiling point and a person skilled in the art will know recrystallising solvents for a particular substance, or if that information is not available, test several solvents. To get a good yield of purified material, the minimum amount of hot solvent to dissolve all the impure material is used. In practice, 3-5% more solvent than necessary is used so the solution is not saturated. If the impure compound contains an impurity which is insoluble in the solvent it may then be removed by filtration and then allowing the solution to crystallize. In addition, if the impure compound contains traces of coloured material that are not native to the compound, it may be removed by adding a small amount of decolorizing agent e.g. activating charcoal to the hot solution, filtering it and then allowing it to crystallize. Usually crystallization spontaneously occurs upon cooling the solution. If it is not, crystallization may be induced by cooling the solution below room temperature or by adding a single crystal of pure material (a seed crystal). Recrystallisation can also be carried out and/or the yield optimized by the use of an anti-solvent or co-solvent. In this case, the compound is dissolved in a suitable solvent at elevated temperature, filtered and then an additional solvent in which the required compound has low solubility is added to aid crystallization. The crystals are then typically isolated using vacuum filtration, washed and then dried, for example, in an oven or via desiccation.

Other examples of methods for purification include sublimation, which includes an heating step under vacuum for example using a cold finger, and crystallization from melt (Crystallization Technology Handbook 2nd Edition, edited by A. Mersmann, 2001).

Biological Effects

The compounds of the invention, subgroups and examples thereof, are modulators e.g. inhibitors of ERK5, and which may be useful in preventing or treating disease states or conditions described herein. In addition the compounds of the invention, and subgroups thereof, will be useful in preventing or treating diseases or condition mediated by ERK5.

Thus, for example, it is envisaged that the compounds of the invention will be useful in alleviating or reducing the incidence of cancer.

The compounds of the present invention may be useful for the treatment of the adult population. The compounds of the present invention may be useful for the treatment of the pediatric population.

More particularly, the compounds of the formula (I) and sub-groups thereof are inhibitors of ERK5. For example, compounds of the invention have affinity against ERK5.

Certain compounds are compounds that have affinity for ERK5. Certain compounds of the invention are those having $IC_{50}$ values of less than 0.1 µM.

The MAPK p38α is a close homologue of ERK5, with 48% sequence identity in the kinase domain and 56% in the active site. ERK2 is the closest homologue with 51% sequence identity in the kinase domain and 78% in the active site. Despite ERK2 having more structural identity with ERK5, it has a larger gatekeeper residue (glutamine) than ERK5 (leucine), meaning that gaining selectivity for ERK5 over ERK2 may be achieved. The gatekeeper residue in p38α is a threonine residue and, as such, is more similar in size to the leucine gatekeeper residue of ERK5. This means achieving selectivity for ERK5 over p38α is more challenging.

In addition many of the compounds of the invention exhibit selectivity for ERK5 compared to other kinases in particular p38 and ERK2, and such compounds represent one embodiment of the invention.

In one embodiment of the invention the compounds have at least 10 times greater affinity against ERK5 than for other kinases. In particular, the compounds of the invention may have 2-, 5-, 10- and 100-fold selectivity for ERK5 over MAPK p38 (e.g. p38α). MAPK p38 inhibition is associated with toxicities including liver toxicity so it is desirable to have selectivity for ERK5 over p38. The selectivity can be determined using the methods described herein. In addition the compounds of the invention exhibit reduced P450 inhibition.

ERK5 is phosphorylated by Mitogen-activated protein kinase 5, MEK5 (also known as MAP2K5, MAPKK5). MEK5 is the upstream activator of ERK5 in many epithelial cells. In one embodiment the compounds of the invention may also inhibit MEK5. In one embodiment the compounds of the invention may be dual MEK5/ERK5 inhibitors.

As a consequence of their activity against ERK5 it is anticipated that the compounds may prove useful in treating or preventing proliferative disorders such as cancers.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, bowel, colorectal, rectum and anus), liver (hepatocellular carcinoma), gall bladder and biliary system, exocrine pancreas, kidney (for example renal cell carcinoma), lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, testes, cervix, myometrium, endometrium, thyroid (for example thyroid follicular carcinoma), brain, adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

Thus, in the pharmaceutical compositions, uses or methods of this invention for treating a disease or condition comprising abnormal cell growth (i.e. uncontrolled and/or rapid cell growth), the disease or condition comprising abnormal cell growth in one embodiment is a cancer.

Metastasis or metastatic disease is the spread of a disease from one organ or part to another non-adjacent organ or part. The cancers which can be treated by the compounds of the invention include primary tumours (i.e. cancer cells at the originating site), local invasion (cancer cells which penetrate and infiltrate surrounding normal tissues in the local area), and metastatic (or secondary) tumours ie. tumours that have formed from malignant cells which have circulated through the bloodstream (haematogenous spread) or via lymphatics or across body cavities (trans-coelomic) to other sites and tissues in the body. In particular, the compounds of the invention may be useful in the treatment of metastasis and metastatic cancers.

In one embodiment the cancer is a metastatic cancer. In one embodiment the cancer is an invasive cancer.

Particular cancers include, lung, brain, ovarian, endometrial, head and neck, liver, pancreatic, prostate, thyroid, mesenchymal, lymphoma and leukemia.

In one embodiment the haematological malignancy is leukaemia. In one embodiment the leukemia is AML. In one embodiment the haematological malignancy is promyelocytic leukaemia. In one embodiment the compound is used in the treatment of metastasis, In another embodiment the haematological malignancies is lymphoma. In one embodiment the lymphoma is selected from DLBCL, Hodgkin's lymphoma, non-Hodgkin's lymphoma, and anaplastic large cell lymphoma. In one embodiment the leukemia is CLL.

Particular cancers include breast (e.g. primary tumour, metastasis-containing lymph nodes, invasive ductal carcinoma), lung (e.g. NSCLC, SCC), brain (e.g. gliomas, glioblastoma multiforme, atrocytoma, ependymoma, meningeal sarcoma), head and neck (e.g. squamous cell carcinoma), liver (e.g. cholangiocarcimona), pancreatic (e.g. pancreatic endocrine), thyroid (e.g. aneuploid papillary thyroid cancer), and mesenchymal (e.g. fibrous tumours).

In one embodiment the cancer is a cancer of the lung. In one particular embodiment the cancer is prostate or breast or oral.

Particular cancers include epithelial or squamous cell carcinomas. In one embodiment the cancer is endothelial cancer.

In one embodiment leukemia, such as acute and chronic leukaemias, acute myeloid leukaemia (AML), acute lymphocytic leukaemia (ALL) and chronic lymphocytic leukaemia (CLL).

Particular cancers include those mediated by ERK5. In one embodiment the cancer is a cancer which overexpresses ERK5, for example, lung, prostate, breast or liver.

A further aspect of the invention includes a compound of the invention for use in the prophylaxis or treatment of cancer in a patient selected from a sub-population possessing cancers which overexpress ERK5.

A further aspect of the invention includes a compound of the invention for use in the prophylaxis or treatment of cancer in a patient selected from a sub-population possessing cancers which exhibit mutated ERK5.

A further aspect of the invention includes a compound of the invention for use in the prophylaxis or treatment of cancer in a patient selected from a sub-population possessing cancers which an EGF-stimulated ERK5 pathway.

Certain cancers are resistant to treatment with particular drugs. This can be due to the type of the tumour (most common epithelial malignancies are inherently chemoresistant and prostate is relatively resistant to currently available regimens of chemotherapy or radiation therapy) or resistance can arise spontaneously as the disease progresses or as a result of treatment. In this regard, references to prostate includes prostate with resistance towards anti-androgen therapy, in particular abiratorone or enzalutamide, or castrate-resistant prostate. Similarly references to multiple myeloma includes bortezomib-insensitive multiple myeloma or refractory multiple myeloma and references to chronic myelogenous leukemia includes imitanib-insensitive chronic myelogenous leukemia and refractory chronic myelogenous leukemia.

It is further envisaged that the compounds of the invention will be particularly useful in the treatment or prevention of cancers of a type associated with or characterised by the presence of elevated levels of ERK5, or mutants of ERK5, or splice variants of ERK5 for example the cancers referred to in this context herein.

Whether a particular cancer is one which is sensitive to ERK5 inhibition, may be determined by a method as set out in the section headed "Methods of Diagnosis".

In one embodiment the invention provides a compound for use in the treatment of a disease or condition which is mediated by ERK5. In a further embodiment the invention provides a compound for use in the treatment of a disease or condition which overexpresses ERK5. In a further embodiment the invention provides a compound for use in the treatment of a disease or condition which is mediated by a mutated ERK5.

The compounds may also be useful in the treatment of tumour growth, pathogenesis, resistance to chemo- and radio-therapy by sensitising cells to chemotherapy and as an anti-metastatic agent.

Therapeutic anticancer interventions of all types necessarily increase the stresses imposed on the target tumour cells. Inhibitors of ERK5 represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

The potential role of ERK5 in angiogenesis means the compounds of the invention may have a function in the treatment of non-oncological diseases. In addition, ERK5 is also known to play a role in cell proliferation and survival and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In particular, the compounds of the invention may be useful in the treatment of ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

In addition the compounds of the invention may be useful in the treatment of atherosclerosis, vascular injury, fibrosis, and inflammation such as chronic inflammatory diseases including rheumatoid arthritis.

The affinity of the compounds of the invention as inhibitors of ERK5 can be measured using the biological and biophysical assays set forth in the examples herein and the level of affinity exhibited by a given compound can be defined in terms of the $IC_{50}$ value. Certain compounds of the present invention are compounds having an $IC_{50}$ value of less than 1 µM, or less than 0.1 µM.

In one embodiment the invention provides a compound for use in the treatment of a disease or condition which is mediated by ERK5. In a further embodiment the disease or condition which is mediated by ERK5 is a cancer which is characterised by overexpression of ERK5 and/or mutation of ERK5.

A further aspect provides the use of a compound for the manufacture of a medicament for the treatment of a disease or condition as described herein, in particular cancer.

Methods of Diagnosis

Prior to administration of a compound of the formula (I), a patient may be screened to determine whether a disease or condition from which the patient is or may be suffering is one which would be susceptible to treatment with a compound having activity against ERK5 and/or MEK5. The term 'patient' includes human and veterinary subjects.

For example, a biological sample taken from a patient may be analysed to determine whether a condition or disease, such as cancer, that the patient is or may be suffering from is one which is characterised by a genetic abnormality (e.g. contains a mutated form of a kinase as described herein) or abnormal protein expression which leads to over-activation of a kinase, to up-regulation of the levels or activity of ERK5 and/or MEK5, to sensitisation of a pathway to normal ERK5 and/or MEK5 activity or to upregulation of a biochemical pathway downstream of ERK5 and/or MEK5 activation.

Examples of such abnormalities that result in activation or sensitisation of the kinase signal, loss of, or inhibition of apoptotic pathways, up-regulation of receptors or their ligands, cytogenetic aberrations or presence of mutant variants of the receptors or ligands e.g. RTK variants. Tumours with mutations of ERK5 or up-regulation of ERK5, in particular over-expression of ERK5, or gain-of-function mutants of ERK5, may be particularly sensitive to ERK5 inhibitors. For example, overexpression and mutations of ERK5 has been identified in a range of cancers as discussed in the Background section.

The term up-regulation includes elevated expression or over-expression of protein, resulting from mechanisms including gene amplification (i.e. multiple gene copies), cytogenetic aberration and increased expression by a transcriptional or post-translational effect, and hyperactivity and activation, including activation by mutations. Thus, the patient may be subjected to a diagnostic test to detect a marker characteristic of up-regulation of ERK5. The term diagnosis includes screening. By marker we include genetic markers including, for example, the measurement of DNA composition to identify presence of mutations of ERK5 or genetic amplification. The term marker also includes markers which are characteristic of up regulation of ERK5 and/or MEK5, including protein levels, protein state, post-translational modifications and mRNA levels of the aforementioned proteins.

The diagnostic tests and screens are typically conducted on a biological sample (i.e. body tissue or body fluids) selected from tumour biopsy samples, blood samples (isolation and enrichment of shed tumour cells), cerebrospinal fluid, plasma, serum, saliva, stool biopsies, sputum, chromosome analysis, pleural fluid, peritoneal fluid, buccal smears, skin biopsy or urine.

Methods of identification and analysis of cytogenetic aberration, genetic amplification, mutations and up-regulation of proteins are known to a person skilled in the art. Screening methods could include, but are not limited to, standard methods such as DNA sequence analysis by conventional Sanger or next-generation sequencing methods, reverse-transcriptase polymerase chain reaction (RT-PCR), RNA sequencing (RNAseq), nanostring hybridisation proximity RNA nCounter assays, or in-situ hybridization such as fluorescence in situ hybridization (FISH).

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Typical probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer*, 3:3). Briefly, the protocol is as follows: double-stranded cDNA is synthesized from total RNA using a (dT)24 oligomer for priming first-strand cDNA synthesis from polyadenylated mRNA, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight to gene-specific oligonucleotide probes on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site-specific antibodies. The skilled person will recognize that all such well-known techniques for detection of upregulation of ERK5, detection of ERK5 splice variants or ERK5 mutations.

Abnormal levels of proteins such as ERK5 can be measured using standard protein assays, for example, those assays described herein. Elevated levels or overexpression could also be detected in a tissue sample, for example, a tumour tissue by measuring the protein levels with an assay such as that from Chemicon International. The protein of interest would be immunoprecipitated from the sample lysate and its levels measured.

Alternative methods for the measurement of the over expression or elevation of ERK5 including the isoforms thereof, include the measurement of microvessel density. This can for example be measured using methods described by Orre and Rogers (Int J Cancer (1999), 84(2), 101-8). Assay methods also include the use of markers.

Therefore all of these techniques could also be used to identify tumours particularly suitable for treatment with the compounds of the invention.

Therefore in a further aspect of the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against ERK5.

Another aspect of the invention includes a compound of the invention for use in the prophylaxis or treatment of cancer in a patient selected from a sub-population possessing overexpression of ERK5.

Another aspect of the invention includes a compound of the invention for use in the prophylaxis or treatment of cancer in a patient selected as possessing a cytogenetic aberration that results in overexpression of ERK5.

The methods described herein could be used to diagnose patients have a cancer possessing a mutation of ERK5 and/or MEK5.

Therefore another aspect of the invention includes a compound of the invention for use in the prophylaxis or treatment of cancer in a patient selected as possessing a mutation in ERK5.

MRI determination of blood vessel pathophysiology (e.g. using MRI gradient echo, spin echo, and contrast enhancement to measure blood volume, relative vessel size, and vascular permeability) in combination with circulating biomarkers may also be used to identify patients suitable for treatment with a compound of the invention.

Thus a further aspect of the invention is a method for the diagnosis and treatment of a disease state or condition mediated by a ERK5 and/or MEK5, which method comprises (i) screening a patient to determine whether a disease or condition from which the patient is or may be suffering is one which would be susceptible to treatment with a compound having activity against ERK5 and/or MEK5; and (ii) where it is indicated that the disease or condition from which the patient is thus susceptible, thereafter administering to the patient a compound of formula 1 and sub-groups or examples thereof as defined herein.

Pharmaceutical Formulations

While it is possible for the active compound to be administered alone, it is generally presented as a pharmaceutical composition (e.g. formulation).

Thus, the present invention further provides pharmaceutical compositions, as defined above, and methods of making a pharmaceutical composition comprising (e.g admixing) at least one compound of formula (I) (and sub-groups thereof as defined herein), together with one or more pharmaceutically acceptable excipients and optionally other therapeutic or prophylactic agents as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short-term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, cosolvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one typical embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another typical embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compound of formula (I) may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% active ingredient and from 99% (w/w) to 5% (w/w) of a pharmaceutically acceptable excipient or combination of excipients. Typically, the compositions comprise from approximately 20% (w/w) to approximately 90%,% (w/w) active ingredient and from 80% (w/w) to 10% of a pharmaceutically acceptable excipient or combination of excipients. The pharmaceutical compositions comprise from approximately 1% to approximately 95%, typically from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and cosolvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) polymers (depending on dose). The film coats of the tablet or capsule typically contain 0-10% (w/w) release-controlling (e.g. delaying) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described herein. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

The compounds of the formula (I) and sub-groups as defined herein may be useful in the prophylaxis or treatment of a range of disease states or conditions mediated by ERK5. Examples of such disease states and conditions are set out above.

The compounds are generally administered to a subject in need of such administration, for example a human or animal patient, typically a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

It may be beneficial to use a compound of the invention as a single agent or to combine the compound of the invention with another agent which acts via a different mechanism to regulate cell growth thus treating two of the characteristic features of cancer development. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

The compounds as defined herein can be administered as the sole therapeutic agent or they can be administered in combination therapy with one of more other compounds (or therapies) for treatment of a particular disease state, for example a neoplastic disease such as a cancer as hereinbefore defined. For the treatment of the above conditions, the compounds of the invention may be advantageously employed in combination with one or more other medicinal agents, more particularly, with other anti-cancer agents or adjuvants (supporting agents in the therapy) in cancer therapy. Examples of other therapeutic agents or treatments that may be administered together (whether concurrently or at different time intervals) with the compounds of the formula (I) include but are not limited to:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Chromatin targeted therapies
Radiotherapy, and,
Other therapeutic or prophylactic agents.

Particular examples of anti-cancer agents or adjuvants (or salts thereof), include but are not limited to any of the agents selected from groups (i)-(xlvi), and optionally group (xlvii), below:

(i) Platinum compounds, for example cisplatin (optionally combined with amifostine), carboplatin or oxaliplatin;
(ii) Taxane compounds, for example paclitaxel, paclitaxel protein bound particles (Abraxane™), docetaxel, cabazitaxel or larotaxel;
(iii) Topoisomerase I inhibitors, for example camptothecin compounds, for example camptothecin, irinotecan (CPT11), SN-38, or topotecan;

(iv) Topoisomerase II inhibitors, for example anti-tumour epipodophyllotoxins or podophyllotoxin derivatives for example etoposide, or teniposide;
(v) Vinca alkaloids, for example vinblastine, vincristine, liposomal vincristine (Onco-TCS), vinorelbine, vindesine, vinflunine or vinvesir;
(vi) Nucleoside derivatives, for example 5-fluorouracil (5-FU, optionally in combination with leucovorin), gemcitabine, capecitabine, tegafur, UFT, S1, cladribine, cytarabine (Ara-C, cytosine arabinoside), fludarabine, clofarabine, or nelarabine;
(vii) Antimetabolites, for example clofarabine, aminopterin, or methotrexate, azacitidine, cytarabine, floxuridine, pentostatin, thioguanine, thiopurine, 6-mercaptopurine, or hydroxyurea (hydroxycarbamide);
(viii) Alkylating agents, such as nitrogen mustards or nitrosourea, for example cyclophosphamide, chlorambucil, carmustine (BCNU), bendamustine, thiotepa, melphalan, treosulfan, lomustine (CCNU), altretamine, busulfan, dacarbazine, estramustine, fotemustine, ifosfamide (optionally in combination with mesna), pipobroman, procarbazine, streptozocin, temozolomide, uracil, mechlorethamine, methylcyclohexylchloroethylnitrosurea, or nimustine (ACNU);
(ix) Anthracyclines, anthracenediones and related drugs, for example daunorubicin, doxorubicin (optionally in combination with dexrazoxane), liposomal formulations of doxorubicin (eg. Caelyx™, Myocet™, Doxil™), idarubicin, mitoxantrone, epirubicin, amsacrine, or valrubicin;
(x) Epothilones, for example ixabepilone, patupilone, BMS-310705, KOS-862 and ZK-EPO, epothilone A, epothilone B, desoxyepothilone B (also known as epothilone D or KOS-862), aza-epothilone B (also known as BMS-247550), aulimalide, isolaulimalide, or luetherobin;
(xi) DNA methyl transferase inhibitors, for example temozolomide, azacytidine or decitabine;
(xii) Antifolates, for example methotrexate, pemetrexed disodium, or raltitrexed;
(xiii) Cytotoxic antibiotics, for example antinomycin D, bleomycin, mitomycin C, dactinomycin, carminomycin, daunomycin, levamisole, plicamycin, or mithramycin;
(xiv) Tubulin-binding agents, for example combrestatin, colchicines or nocodazole;
(xv) Signal Transduction inhibitors such as Kinase inhibitors (e.g. EGFR (epithelial growth factor receptor) inhibitors, VEGFR (vascular endothelial growth factor receptor) inhibitors, PDGFR (platelet-derived growth factor receptor) inhibitors, MTKI (multi target kinase inhibitors), Raf inhibitors, mTOR inhibitors) for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), or PLX4032 (RG7204);
(xvi) Aurora kinase inhibitors for example AT9283, barasertib (AZD1152), TAK-901, MK0457 (VX680), cenisertib (R-763), danusertib (PHA-739358), alisertib (MLN-8237), or MP-470;
(xvii) CDK inhibitors for example AT7519, roscovitine, seliciclib, alvocidib (flavopiridol), dinaciclib (SCH-727965), 7-hydroxy-staurosporine (UCN-01), JNJ-7706621, BMS-387032 (a.k.a. SNS-032), PHA533533, PD332991, ZK-304709, or AZD-5438;
(xviii) PKA/B inhibitors and PKB (akt) pathway inhibitors for example AT13148, AZ-5363, Semaphore, SF1126 and MTOR inhibitors such as rapamycin analogues, AP23841 and AP23573, calmodulin inhibitors (forkhead translocation inhibitors), API-2/TCN (triciribine), RX-0201, enzastaurin HCl (LY317615), NL-71-101, SR-13668, PX-316, or KRX-0401 (perifosine/NSC 639966);
(xix) Hsp90 inhibitors for example AT13387, herbimycin, geldanamycin (GA), 17-allylamino-17-desmethoxygeldanamycin (17-AAG) e.g. NSC-330507, Kos-953 and CNF-1010, 17-dimethylaminoethylamino-17-demethoxygeldanamycin hydrochloride (17-DMAG) e.g. NSC-707545 and Kos-1022, NVP-AUY922 (VER-52296), NVP-BEP800, CNF-2024 (BIIB-021 an oral purine), ganetespib (STA-9090), SNX-5422 (SC-102112) or IPI-504;
(xx) Monoclonal Antibodies (unconjugated or conjugated to radioisotopes, toxins or other agents), antibody derivatives and related agents, such as anti-CD, anti-VEGFR, anti-HER2 or anti-EGFR antibodies, for example rituximab (CD20), ofatumumab (CD20), ibritumomab tiuxetan (CD20), GA101 (CD20), tositumomab (CD20), epratuzumab (CD22), lintuzumab (CD33), gemtuzumab ozogamicin (CD33), alemtuzumab (CD52), galiximab (CD80), trastuzumab (HER2 antibody), pertuzumab (HER2), trastuzumab-DM1 (HER2), ertumaxomab (HER2 and CD3), cetuximab (EGFR), panitumumab (EGFR), necitumumab (EGFR), nimotuzumab (EGFR), bevacizumab (VEGF), ipilimumab (CTLA4), catumaxumab (EpCAM and CD3), abagovomab (CA125), farletuzumab (folate receptor), elotuzumab (CS1), denosumab (RANK ligand), figitumumab (IGF1R), CP751,871 (IGF1R), mapatumumab (TRAIL receptor), metMAB (met), mitumomab (GD3 ganglioside), naptumomab estafenatox (5T4), or siltuximab (IL6);
(xxi) Estrogen receptor antagonists or selective estrogen receptor modulators (SERMs) or inhibitors of estrogen synthesis, for example tamoxifen, fulvestrant, toremifene, droloxifene, faslodex, or raloxifene;
(xxii) Aromatase inhibitors and related drugs, such as exemestane, anastrozole, letrazole, testolactone aminoglutethimide, mitotane or vorozole;
(xxiii) Antiandrogens (i.e. androgen receptor antagonists) and related agents for example bicalutamide, nilutamide, flutamide, cyproterone, or ketoconazole;
(xxiv) Hormones and analogues thereof such as medroxyprogesterone, diethylstilbestrol (a.k.a. diethylstilboestrol) or octreotide;
(xxv) Steroids for example dromostanolone propionate, megestrol acetate, nandrolone (decanoate, phenpropionate), fluoxymestrone or gossypol,
(xxvi) Steroidal cytochrome P450 17alpha-hydroxylase-17,20-lyase inhibitor (CYP17), e.g. abiraterone;
(xxvii) Gonadotropin releasing hormone agonists or antagonists (GnRAs) for example abarelix, goserelin acetate, histrelin acetate, leuprolide acetate, triptorelin, buserelin, or deslorelin;
(xxviii) Glucocorticoids, for example prednisone, prednisolone, dexamethasone;
(xxix) Differentiating agents, such as retinoids, rexinoids, vitamin D or retinoic acid and retinoic acid metabolism blocking agents (RAMBA) for example accutane, alitretinoin, bexarotene, or tretinoin;
(xxx) Farnesyltransferase inhibitors for example tipifarnib;
(xxxi) Chromatin targeted therapies such as histone deacetylase (HDAC) inhibitors for example sodium butyrate, suberoylanilide hydroxamide acid (SAHA), depsipeptide (FR 901228), dacinostat (NVP-LAQ824), R306465/JNJ-16241199, JNJ-26481585, trichostatin A, vorinostat, chlamydocin, A-173, JNJ-MGCD-0103, PXD-101, or apicidin;

(xxxii) Proteasome Inhibitors for example bortezomib, carfilzomib, CEP-18770, MLN-9708, or ONX-0912;
(xxxiii) Photodynamic drugs for example porfimer sodium or temoporfin;
(xxxiv) Marine organism-derived anticancer agents such as trabectidin;
(xxxv) Radiolabelled drugs for radioimmunotherapy for example with a beta particle-emitting isotope (e.g., Iodine-131, Yittrium-90) or an alpha particle-emitting isotope (e.g., Bismuth-213 or Actinium-225) for example ibritumomab or Iodine tositumomab;
(xxxvi) Telomerase inhibitors for example telomestatin;
(xxxvii) Matrix metalloproteinase inhibitors for example batimastat, marimastat, prinostat or metastat;
(xxxviii) Recombinant interferons (such as interferon-γ and interferon α) and interleukins (e.g. interleukin 2), for example aldesleukin, denileukin diftitox, interferon alfa 2a, interferon alfa 2b, or peginterferon alfa 2b;
(xxxix) Selective immunoresponse modulators for example thalidomide, or lenalidomide;
(xl) Therapeutic Vaccines such as sipuleucel-T (Provenge) or OncoVex;
(xli) Cytokine-activating agents include Picibanil, Romurtide, Sizofiran, Virulizin, or Thymosin;
(xlii) Arsenic trioxide;
(xliii) Inhibitors of G-protein coupled receptors (GPCR) for example atrasentan;
(xliv) Enzymes such as L-asparaginase, pegaspargase, rasburicase, or pegademase;
(xlv) DNA repair inhibitors such as PARP inhibitors for example, olaparib, velaparib, iniparib, INO-1001, AG-014699, or ONO-2231;
(xlvi) Agonists of Death receptor (e.g. TNF-related apoptosis inducing ligand (TRAIL) receptor), such as mapatumumab (formerly HGS-ETR1), conatumumab (formerly AMG 655), PR095780, lexatumumab, dulanermin, CS-1008, apomab or recombinant TRAIL ligands such as recombinant Human TRAIL/Apo2 Ligand;
(xlvii) Prophylactic agents (adjuncts); i.e. agents that reduce or alleviate some of the side effects associated with chemotherapy agents, for example
anti-emetic agents,
agents that prevent or decrease the duration of chemotherapy-associated neutropenia and prevent complications that arise from reduced levels of platelets, red blood cells or white blood cells, for example interleukin-11 (e.g. oprelvekin), erythropoietin (EPO) and analogues thereof (e.g. darbepoetin alfa), colony-stimulating factor analogs such as granulocyte macrophage-colony stimulating factor (GM-CSF) (e.g. sargramostim), and granulocyte-colony stimulating factor (G-CSF) and analogues thereof (e.g. filgrastim, pegfilgrastim),
agents that inhibit bone resorption such as denosumab or bisphosphonates e.g. zoledronate, zoledronic acid, pamidronate and ibandronate,
agents that suppress inflammatory responses such as dexamethasone, prednisone, and prednisolone,
agents used to reduce blood levels of growth hormone and IGF-I (and other hormones) in patients with acromegaly or other rare hormone-producing tumours, such as synthetic forms of the hormone somatostatin e.g. octreotide acetate,
antidote to drugs that decrease levels of folic acid such as leucovorin, or folinic acid,
agents for pain e.g. opiates such as morphine, diamorphine and fentanyl,
non-steroidal anti-inflammatory drugs (NSAID) such as COX-2 inhibitors for example celecoxib, etoricoxib and lumiracoxib,
agents for mucositis e.g. palifermin,
agents for the treatment of side-effects including anorexia, cachexia, oedema or thromboembolic episodes, such as megestrol acetate.

Each of the compounds present in the combinations of the invention may be given in individually varying dose schedules and via different routes. As such, the posology of each of the two or more agents may differ: each may be administered at the same time or at different times. A person skilled in the art would know through his or her common general knowledge the dosing regimes and combination therapies to use. For example, the compound of the invention may be using in combination with one or more other agents which are administered according to their existing combination regimen. Examples of standard combination regimens are provided below.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, typically 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

Where the compound of the formula (I) is administered in combination therapy with one, two, three, four or more other therapeutic agents (typically one or two, typically one), the compounds can be administered simultaneously or sequentially. In the latter case, the two or more compounds will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the typical method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The compounds of the invention may also be administered in conjunction with non-chemotherapeutic treatments such as radiotherapy, photodynamic therapy, gene therapy; surgery and controlled diets.

The compounds of the present invention also have therapeutic applications in sensitising tumour cells for radiotherapy and chemotherapy. Hence the compounds of the present invention can be used as "radiosensitizer" and/or "chemosensitizer" or can be given in combination with another "radiosensitizer" and/or "chemosensitizer". In one embodiment the compound of the invention is for use as chemosensitizer.

The term "radiosensitizer" is defined as a molecule administered to patients in therapeutically effective amounts to increase the sensitivity of the cells to ionizing radiation and/or to promote the treatment of diseases which are treatable with ionizing radiation.

The term "chemosensitizer" is defined as a molecule administered to patients in therapeutically effective amounts to increase the sensitivity of cells to chemotherapy and/or promote the treatment of diseases which are treatable with chemotherapeutics.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

For use in combination therapy with another chemotherapeutic agent, the compound of the formula (I) and one, two, three, four or more other therapeutic agents can be, for example, formulated together in a dosage form containing two, three, four or more therapeutic agents i.e. in a unitary pharmaceutical composition containing all components. In an alternative, the individual therapeutic agents may be formulated separately and presented together in the form of a kit, optionally with instructions for their use.

In one embodiment the pharmaceutical composition comprises a compound of formula I together with a pharmaceutically acceptable carrier and optionally one or more therapeutic agent(s)

In another embodiment the invention relates to the use of a combination according to the invention in the manufacture of a pharmaceutical composition for inhibiting the growth of tumour cells.

In a further embodiment the invention relates to a product containing a compound of formula I and one or more anticancer agent, as a combined preparation for simultaneous, separate or sequential use in the treatment of patients suffering from cancer.

EXAMPLES

The invention will now be illustrated, but not limited, by reference to the specific embodiments described in the following examples. Compounds are named using an automated naming package such as AutoNom (MDL) or are as named by the chemical supplier. In the examples, the following abbreviations are used:
AcOH acetic acid
Boc tert-butyloxycarbonyl
Boc-Abu-OH (S)-2-(Boc-amino)butyric acid
BuLi butyllithium
CDI 1,1-carbonyldiimidazole
DAST Diethylaminosulfur trifluoride
DCM dichloromethane
DIPEA N-ethyl-N-(1-methylethyl)-2-propylamine
DMC dimethyl carbonate
DMF N,N-dimethylformamide
DMSO dimethyl sulfoxide
EDC 1-ethyl-3-(3'-dimethylaminopropyl)-carbodiimide hydrochloride
$Et_3N$ triethylamine
EtOAc ethyl acetate
EtOH ethanol
$Et_2O$ diethyl ether
HATU 2-(7-aza-1H-benzotriazole-1-yl)-1,1,3,3-tetramethyluronium hexafluorophosphate)
HBTU O-benzotriazole-N,N,N',N'-tetramethyl-uronium-hexafluorophosphate
HCl hydrochloric acid
HOAc acetic acid
HOAt 1-hydroxyazabenzotriazole
HOBt 1-hydroxybenzotriazole
HPLC high pressure liquid chromatography
IPA isopropyl alcohol
KHMDS potassium hexamethyldisilazide
LiHMDS lithium bis(trimethylsilyl)amide
MeCN acetonitrile
MeOH methanol
mins. minutes
MS mass spectrometry
MW microwave
$NaBH(OAc)_3$ sodium triacetoxyborohydride
NaOtBu potassium tert-butoxide
NMP N-methyl-2-pyrrolidinone
NMR nuclear magnetic resonance spectroscopy
$Pd_2(dba)_3$ tris(dibenzylideneacetone)dipalladium (o)
$Pd(OAc)_2$ palladium (2) acetate
$Pd(PPh_3)_4$ tetrakis(triphenylphosphine)palladium (0)
petrol petroleum ether fraction with boiling point range 40-60° C.
PyBrop bromo-tris-pyrrolidino-phosphonium hexafluorophosphate
RT room temperature
$SiO_2$ silica
TBTU N,N,N',N'-tetramethyl-O-(benzotriazol-1-yl)uronium tetrafluoroborate
TEA triethylamine
TFA trifluoroacetic acid
THF tetrahydrofuran
UV Ultraviolet Solvents and Reagents Chemicals were purchased from Sigma-Aldrich, Alfa Aesar and Apollo Scientific unless otherwise stated. Sure-Seal™ or Acroseal™ bottles of anhydrous solvents were purchased from Sigma-Aldrich or Acros, respectively. Deuterated solvents used for NMR were purchased from Sigma-Aldrich. Unless stated, reactions were carried out under an inert atmosphere of nitrogen.

Column Chromatography

Purification using column chromatography was achieved using a Biotage automated flash purification system with UV monitoring at 298 nm and collection at 254 nm. Biotage automated chromatography pre-packed silica cartridges were used in most cases. Where stated, the purification of some compounds was performed using Biotage C18 reversed phase silica columns, which have octadecyl (end-capped) functionalised silica or Biotage KP-NH cartridges were used for the separation of highly polar compounds, which uses primary amine bonded silica.

Where necessary, semi-preparative HPLC was carried out using one of the following machines: (i) Varian Prostar Modular HPLC system with a binary pumping system, UV detector and fraction collector and controlled by Varian Star software. (ii) Agilent 1200 HPLC system with a binary pump, autosampler, fraction collector and diode array detector and controlled by Agilent ChemStation software.

Microwave Assisted Synthesis

Where stated, reactions were carried out under microwave irradiation in sealed microwave vials, with the use of a Biotage Initiator Sixty with a robotic sample bed. Reactions were irradiated at 2.45 GHz, and were able to reach temperatures between 60 and 250° C. Heating was at a rate of 2-5 OC/sec and the pressure was able to reach 20 bar.

Analytical Techniques

All melting points were measured using a Stuart Scientific SMP3 apparatus. $^1H$ NMR spectra were obtained using a Bruker Avance III 500 spectrometer using a frequency of 500 MHz. $^{13}C$ and $^{19}F$ NMR spectra were acquired using the Bruker Avance III 500 spectrometer, operating at a frequency of 125 MHz, and 470 MHz, respectively. The abbreviations for spin multiplicity are as follows: s=singlet; d=doublet; t=triplet; q=quartet, quin=quintet, sept=septet and m=multiplet. Combinations of these abbreviations are employed to describe more complicated splitting patterns (e.g. dd=doublet of doublets) and where broadening of the peak is observed, spin multiplicity is accompanied by the prefix br=broad. $^1H$ NMR Data is recorded in DMSO-d6 as solvent unless indicated.

LC-MS were conducted using a Waters Acquity UPLC system with PDA and ELSD. When a 2 min gradient was used, the sample was eluted on Acquity UPLC BEH C18, 1.7 μm, 2.1×50 mm, with a flow rate of 0.6 mL/min using 5-95% 0.1% formic acid/MeCN. Analytical purity of compounds were determined using Waters XTerra RP18, 5 μm (4.6×150 mm) column at 1 mL/min using either 0.1% aqueous ammonia and acetonitrile or 0.1% aqueous formic acid and acetonitrile with a gradient of 5-100% over 15 min.

FTIR spectra were measured using a Bio-Rad FTS 3000MX diamond ATR apparatus. UV spectra were recorded on a Hitachi U-2800A spectrophotometer and were performed in ethanol. HRMS were provided by the ESPRC National Mass Spectrometry Service, University of Wales, Swansea.

Synthetic Methods

By following methods similar and/or analogous to general procedures below, the compounds set out in Table 1 were prepared.

The following synthetic procedures are provided for illustration of the methods used; for a given preparation or step the precursor used may not necessarily derive from the individual batch synthesised according to the step in the description given.

Where a compound is described as a mixture of two diastereoisomers/epimers, the configuration of the stereocentre is not specified and is represented by straight lines.

As understood by a person skilled in the art, compounds synthesised using the protocols as indicated may exist as a solvate e.g. hydrate, and/or contain residual solvent or minor impurities. Compounds isolated as a salt form, may be of integer stoichiometric i.e. mono- or di-salts, or of intermediate stoichiometry.

Some of the compounds below are isolated as the salt, in particular as the trifluoroacetic acid salt.

Examples 1-287

General Procedure 1: CDI Amide Coupling

Carbonyl diimidazole (CDI, 2 eq.) was added to a solution of the relevant carboxylic acid in THF (2 mL/mmol) and the mixture and heated to 70° C. for 3 h. The relevant amine (2.5 eq.) was added and the mixture was heated at 70° C. for 2 h. The mixture was partitioned between EtOAc (2×20 mL) and saturated $NaHCO_{3(aq.)}$. The organic layers were combined, washed with brine (20 mL), dried over $MgSO_4$ and the solvent removed in vacuo.

General Procedure 2: Cyanuric Fluoride Amide Coupling

Cyanuric fluoride (0.7 eq.) was added to the relevant carboxylic acid (1 eq.) and pyridine (1 eq.) in MeCN (2 mL/mmol). The relevant amine (2.5 eq.) was added and the mixture was stirred at r.t. for 18 h. The reaction was diluted with EtOAc, washed with water and 0.5 M aqueous HCl, followed by further washes with saturated aqueous $NaHCO_3$ and brine. The organic layer was dried over $MgSO_4$ and the solvent removed in vacuo.

General Procedure 3: $PCl_3$ Amide Coupling

The relevant carboxylic acid (1 eq.), the relevant amine (2.5 eq.) and $PCl_3$ (1 eq.) were combined in MeCN (4 mL/mmol) and heated under microwave irradiation to 100° C. for 30 min. The mixture was allowed to cool, 2 M $NaOH_{(aq)}$ (20 mL) was added, the mixture was stirred for 10 min, and then extracted with EtOAc (3×20 mL). The organic layers were combined, washed with brine, dried over $MgSO_4$ and the solvent removed in vacuo.

General Procedure 4: Boc Deprotection in $TFA/CH_2Cl_2$

TFA (2 mL/mmol) and $Et_3SiH$ (2.5 eq.) were added to the relevant carbamate (1 eq.) in DCM (2 mL/mmol) and the mixture was stirred at r.t. for 2 h. The solvent was removed in vacuo, the residues partitioned between EtOAc (5×30 mL) and $NaHCO_{3(aq)}$ (40 mL). The organic extracts were combined, dried over $MgSO_4$, and the solvent removed in vacuo.

General Procedure 5: Hydrogenation of Heteroaromatic Nitro Group

The relevant nitro compound (1 eq.) was dissolved in MeOH (5 mL/mmol) and hydrogenated on a Thales H-cube over 10% Pd/C on full $H_2$ mode at 40° C. for 2 h with continuous recycling of the reaction mixture. The solvent was removed in vacuo.

General Procedure 6: Amine Displacement of 4-Nitro-2-Chloropyrimidine

The relevant amine (1 eq.), 2-chloro-5-nitropyrimidine (1 eq.), and $Et_3N$ (1.1 eq.) were combined in THF (5 mL/mmol) at 0° C., and the mixture allowed to stir at r.t. for 1 h. The solvent was removed in vacuo, and the residue partitioned between EtOAc (2×30 mL) and water (20 mL). The organic layer washed with brine, dried over $MgSO_4$ and the solvent removed in vacuo.

General Procedure 7: Mitsunobu Alkylation of 4-Nitropyrazole

Diethylazodicarboxylate (1.5 eq.) was added dropwise to a mixture of 4-nitropyrazole (1 eq.), triphenylphosphine (1.73 g, 6.63 mmol, 1.5 eq.) and the substrate alcohol (1 eq.), in THF at 0° C. The mixture was stirred at 0° C. for 10 min, and then allowed to warm to r.t. and stirred at r.t. for 18 h. The mixture was partitioned between EtOAc (2×30 mL) and water (20 mL), washed with brine (20 mL), dried over $MgSO_4$ and the solvent removed in vacuo.

General Procedure 8: Eschweiler-Clarke Conversion of a Boc Protected Amine to a Methylamine Formaldehyde (37% w/v aqueous, 4 eq.) was added to the substrate carbamate (1 eq.) in formic acid (10 mL/mmol), and the mixture was heated to 100° C. for 3 h in a sealed tube. The mixture was allowed to cool, basified with 10% $K_2CO_{3(aq)}$, and extracted with EtOAc (2×20 mL). The organic extracts were combined, washed with brine, dried over $MgSO_4$, and the solvent removed in vacuo.

General Procedure 9: Amide Coupling with 2-Chloro-1-Methylpyridinium Iodide

Pyrrole acid (1 eq.), $Et_3N$ (2.5 eq.), and 2-chloro-1-methylpyridinium iodide (1.1 eq.) were combined in DCM (15 mL/mmol) and stirred at r.t. for 10 min, followed by the addition of the substrate amine (1.25 eq.) in DCM (2.5 mL/mmol). The reaction was stirred at r.t. for 18 h, the solvent evaporated, and the mixture partitioned between EtOAc (2×15 mL) and 10% aqueous $K_2CO_3$ (15 mL). The organic layers were combined, washed with brine, dried over $MgSO_4$ and the solvent removed in vacuo.

General Procedure 10: Thionyl Chloride Preparation of Acid Chloride

To a solution or a suspension of the appropriate carboxylic acid (1 mol equiv.) in THF (1 mL/mmol of carboxylic acid), cooled at 0° C., was added thionyl chloride (1.5 mol equiv.) and N,N-dimethylformamide (0.1 mol equiv.). The resulting solution was stirred at 0° C. for 30 min and allowed to warm to room temperature. Upon completion, the solvent was removed in vacuo. The crude material was used in the next step without further purification.

General Procedure 11: Acylation

To a suspension of aluminium trichloride (2.5 mol equiv.) in DCM (1 mL/mmol of aluminium trichloride), cooled at 0° C., was added the appropriate acyl chloride (2 mol equiv.) followed by methyl 1H-pyrrole-2-carboxylate (1 mol equiv.). The resulting solution was stirred at 0° C. for 30 min and allowed to warm to room temperature. After 20 h, the reaction mixture was cooled to 0° C. and quenched by cautious addition of 1 M aq. HCl (0.5 mL/mmol of aluminium trichloride). The resulting solution was stirred at room temperature for 2 h. The reaction was then diluted with water (20 mL) and extracted with DCM (3×50 mL). The pooled organic extracts were washed with sat. aq. NaHCO$_3$ and brine (50 mL, respectively), dried over MgSO$_4$ and concentrated in vacuo. The crude product was purified by column chromatography.

General Procedure 12: Lithium Hydroxide Hydrolysis

To the appropriate pyrrole ester (1 mol equiv.) in THF (8 mL/mmol of pyrrole ester) was added a 2 M aq. solution of lithium hydroxide (15 mol equiv.). The resulting mixture was heated at 67° C. for 18 h. Upon completion, the mixture was acidified to pH 3 using a 4 M aq. solution of HCl. The reaction was then diluted with water (30 mL) and extracted with EtOAc (3×50 mL). The pooled organic extracts were washed with water and brine (50 mL, respectively), dried over MgSO$_4$ and concentrated in vacuo. The crude material was used in the next step without further purification.

General Procedure 13: PCl$_3$ Amide Coupling

To the appropriate carboxylic acid (1 mol equiv.) in acetonitrile (5 mL/mmol of carboxylic acid) was added the appropriate amine (2.5 mol equiv.) and phosphorus trichloride (1 mol equiv.). The resulting mixture was heated at 150° C. for 7 min under microwave irradiation. After cooling, the mixture was quenched by addition of 2 M aq. NaOH (10 mL/mmol of carboxylic acid). The resulting heterogeneous solution was stirred at room temperature until solubilisation of all the brown residues formed during the reaction. The mixture was extracted with EtOAc (3×20 mL), the pooled organic extracts were washed with an acetate buffer pH=4.65 (20 mL) and brine (20 mL), dried over MgSO$_4$ and concentrated in vacuo. The crude product was purified by column chromatography.

General Procedure 14: Cyanuric Fluoride Amide Coupling

To the appropriate carboxylic acid (1 mol equiv.) in acetonitrile (10 mL/mmol of carboxylic acid) was added pyridine (1 mol equiv.) and cyanuric fluoride (0.4 mol equiv.). The reaction mixture was stirred at room temperature for 30 min before addition of the appropriate amine (2.5 mol equiv.). The resulting mixture was stirred at 40° C. for 24 h. Upon completion, the mixture was quenched by addition of sat. aq. NaHCO$_3$ (15 mL) and extracted with EtOAc (3×20 mL). The pooled organic extracts were washed with an acetate buffer pH=4.65 and brine (30 mL, respectively), dried over MgSO$_4$ and concentrated in vacuo. The crude product was purified by column chromatography.

General Procedure 15: Hydrogenation of Nitropyridine

The appropriate nitropyridine in MeOH (20 mL/mmol of nitropyridine) was subjected to palladium catalyzed hydrogenation using an H-Cube® reactor and a 10% Pd/C CatCart. The reaction mixture was conducted at 40° C. under a full pressure of hydrogen for 8 h.

General Procedure 16: Palladium Coupling

The appropriate chloropyridine (1 mol equiv.) in dioxane (4.9 mL/mmol of chloropyridine) was sparged with nitrogen for 15 minutes. To this solution, potassium carbonate (3 mol equiv.), the appropriate boronic acid (1.1 mol equiv.) and tetrakis(triphenylphosphine)palladium(0) (0.1 mol equiv.) were added. The resulting mixture was heated at 100° C. for 48 h. Upon completion, the heterogenous mixture was filtered through Celite and the solvent was removed in vacuo. The crude residue was dissolved in a mixture of EtOAc and water (20 mL, respectively) and extracted with EtOAc (3×25 mL). The pooled organic extracts were washed with water (30 mL) and brine (30 mL), dried over MgSO$_4$ and concentrated in vacuo. The crude product was purified by column chromatography.

General Procedure 17: Amine Displacement

To 2-chloro-5-nitropyrimidine (1 mol equiv.) in THF (5.0 mL/mmol of 2-chloro-5-nitropyrimidine), cooled at 0° C., was added triethylamine (1.1 mol equiv.) followed by the appropriate amine. The resulting solution was stirred at 0° C. for 5 min and allowed to warm to room temperature. Upon completion, the solvent was removed in vacuo. The crude residue was dissolved in EtOAc (20 mL), washed with water (20 mL) and extracted with EtOAc (3×25 mL). The pooled organic extracts were washed with brine (30 mL), dried over MgSO$_4$ and concentrated in vacuo. The crude product was purified by column chromatography.

General Procedure 18: Amide Coupling with 2-Chloro-1-Methylpyridinium Iodide

To the appropriate 1H-pyrrole-2-carboxylic acid (1 mol equiv.) in DCM (10 mL/mmol of carboxylic acid) was added triethylamine (2.5 mol equiv.), 2-chloro-1-methylpyridinium iodide (1.1 mol equiv.) and the appropriate amine (1.25 mol equiv.). The resulting solution was stirred at room temperature for 24 h. Upon completion, the solvent was removed in vacuo. The crude residue was dissolved in EtOAc (30 mL), washed with sat. aq. NaHCO$_3$ (20 mL) and extracted with EtOAc (3×20 mL). The pooled organic extracts were washed with brine (30 mL), dried over MgSO$_4$ and concentrated in vacuo. The crude product was purified by column chromatography.

General Procedure 19: Hydrogenation of Nitropyrimidine

The appropriate nitropyrimidine in 1:1 MeOH:THF mixture (20 mL/mmol of nitropyrimidine) was subjected to palladium catalyzed hydrogenation using an H-Cube® reactor and a 10% Pd/C CatCart. The reaction mixture was conducted at 40° C. under a full pressure of hydrogen for 8 h.

General Procedure 20: Formylation

To a suspension of the appropriate Boc-protected amine in formic acid (4 mL/mmol of amine) was added a solution of formaldehyde in water (37 wt. %) (4 mol equiv.). The resulting mixture was heated at 95° C. for 3 h. Upon completion, the reaction was cooled in an ice bath and quenched by addition of 2 M aq. NaOH until the pH was alkaline and then extracted with EtOAc (3×20 mL). The pooled organic extracts were washed with water and brine (40 mL, respectively), dried over MgSO$_4$ and concentrated in vacuo. The crude product was purified by column chromatography.

General Procedure 21: Boc Deprotection in TFA/DCM

To the appropriate Boc-protected amine (1 mol equiv.) in DCM (5 mL/mmol of amine) was added trifluoroacetic acid (5 mL/mmol of amine) and triethylsilane (2.5 mol equiv.). The resulting mixture was stirred at room temperature for 2 h. Upon completion, the solvent was removed in vacuo. The crude residue was dissolved in EtOAc (30 mL), washed with sat. aq. NaHCO$_3$ (20 mL) and extracted with EtOAc (3×20 mL). The pooled organic extracts were washed with brine (30 mL), dried over MgSO$_4$ and concentrated in vacuo. The crude product was purified by column chromatography.

General Procedure 22: Friedel Crafts Acylation

Aluminium chloride (2.5 equiv.) was added to DCM (2.5 mL/mmol pyrrole) at 0° C., followed by the appropriate benzoyl chloride or acid anhydride (2.0 equiv.). Methyl 2-pyrrole carboxylate (1.0 equiv.) was then added, and the resulting mixture was stirred at 0° C. for 1 h before being warmed to RT and left to stir overnight. The mixture was quenched with a 1.0 M aqueous solution of HCl until effervescence ceased, and the resulting mixture was extracted using DCM (5 mL/mmol pyrrole). The combined organic extracts were washed with a saturated aqueous solution of NaHCO$_3$, followed by water and a saturated brine solution (5 mL/mmol pyrrole respectively), before being dried over $Na_2SO_4$, and the filtrate concentrated in vacuo. The crude product was purified by medium pressure flash chromatography (MPLC).

General Procedure 23: Ester Hydrolysis

The appropriate pyrrole ester (1.0 equiv.) was dissolved in THF (8 mL/mmol pyrrole). A solution of LiOH (20 equiv.) in water (13.0 mL/mmol pyrrole) was added, and the resulting mixture was heated at 60° C. overnight. The mixture was cooled and acidified using a 1.0 M aqueous solution of HCl to pH 3-4, causing a precipitate. The solid was extracted using EtOAc (2×50 mL/mmol pyrrole), and the combined organic layers washed with water followed by brine (50 mL/mmol pyrrole respectively) before being dried over $Na_2SO_4$. The filtrate was concentrated in vacuo to afford the pure product.

General Procedure 24: Amide Coupling with CDI

The appropriate pyrrole carboxylic acid (1.0 equiv.) was dissolved in THF (5 mL/mmol pyrrole) before carbonyldiimidazole (2.0 equiv.) was added, and the reaction mixture was heated to reflux at 70° C. for 3 h. After this time, the reaction was cooled to 50° C. before the appropriate amine (2.5 equiv.) was added and the mixture heated for a further 3 h. The reaction mixture was cooled to RT and left to stir overnight. The mixture was diluted with EtOAC (50 mL/mmol pyrrole), washed with water and brine (50 mL/mmol pyrrole respectively) and extracted with EtOAc (3×30 mL/mmol pyrrole). The combined organic extracts were dried over $Na_2SO_4$, and the filtrate concentrated in vacuo. Purification was achieved using MPLC.

General Procedure 25: Amide Coupling with $PCl_3$

The appropriate carboxylic acid (1.0 equiv.) was dissolved in MeCN (5 mL/mmol pyrrole) before the relevant amine (2.5 equiv.) was added followed by phosphorus trichloride (1.0 equiv.). The mixture was heated using microwave irradiation at 150° C. for 5 min. The reaction was quenched with a few drops of $H_2O$ and the solvent removed in vacuo. The residue was re-dissolved in EtOAc (50 mL/mmol pyrrole) and washed with a saturated aqueous solution of $NaHCO_3$ (50 mL/mmol pyrrole) before being extracted with EtOAc (3×30 mL/mmol pyrrole). The combined organic extracts were dried over $Na_2SO_4$, and the filtrate concentrated in vacuo to afford the crude product, which was purified by MPLC.

General Procedure 26: Boc Deprotection

The appropriate Boc-protected piperidine (1.0 equiv.) was dissolved in DCM (6 mL/mmol pyrrole) before TFA (6 mL/mmol pyrrole) was added followed by $Et_3SiH$ (2.5 equiv.) The reaction mixture was allowed to stir at RT for 1 h before the solvent was removed in vacuo. The residue was dissolved in EtOAc (50 mL/mmol pyrrole) before being washed with saturated aqueous solution of $NaHCO_3$ (3×50 mL/mmol pyrrole) and extracted with EtOAc (3×30 mL/mmol pyrrole). The organic extracts were combined, dried over $Na_2SO_4$ and concentrated to give the pure product.

General Procedure 27: CDI Mediated Amide Coupling

A solution of carbonyldiimidazole (2.0 eq.) and the relevant carboxylic acid (1.0 eq.) in THF (5 mL/mmol) was heated to 70° C. for 3 h. The appropriate amine (2.5 eq.) was added and the mixture heated at 50° C. for 3 h then at RT for 16 h. The product was extracted with EtOAc (2×100 mL), washed with brine (100 mL) and dried over $Na_2SO_4$. Purification via column chromatography gave the desired product General Procedure 28: Acid Chloride Synthesis To a solution or suspension of the relevant carboxylic acid (1 eq.) in THF (1 mL/mmol) was added $SOCl_2$ (1.5 eq.) at 0° C., followed by DMF (cat). The resulting mixture was stirred at RT for 3 h, and then concentrated in vacuo. The crude material was used in the next step without further purification.

General Procedure 29: Friedel-Crafts Acylation

To a suspension of $AlCl_3$ (2.5 eq.) in DCM (1 mL/mmol $AlCl_3$) at 0° C. was added the relevant acid chloride (2 eq.) followed by methyl 1H-pyrrole-2-carboxylate (1 eq.). The resulting mixture was allowed to reach RT and stirred for 16 h. The reaction was quenched at 0° C. with a 1M aqueous solution of HCl (20 mL). The product was extracted with DCM (3×100 mL), washed with an aqueous saturated solution of $NaHCO_3$ (2×100 mL) and brine (100 mL). Combined organic layers were dried over $Na_2SO_4$ and concentrated in vacuo. Purification via column chromatography (silica; 0-50% EtOAc/Petrol) gave the desired product.

General Procedure 30: Ester Hydrolysis and/or Tosyl Group Hydrolysis

To a solution of the relevant ester (1 eq.) in THF (8 mL/mmol) was added a solution of LiOH monohydrate (20 eq.) in $H_2O$ (13 mL/mmol). The resulting mixture was heated at 65° C. for 16 h, cooled to RT and acidified to pH 3-4 with a 1M aqueous solution of HCl. The product was extracted with EtOAc (3×100 mL). Combined organic layers were washed with brine (200 mL), dried over $Na_2SO_4$ and concentrated in vacuo to give the desired product.

General Procedure 31: Deprotection of a Boc Protecting Group with TFA

To a solution of the relevant Boc protected amine (1 eq.) in DCM (5 mL/mmol) was added triethylsilane (2.5 eq.) where indicated, followed by TFA (2 mL/mmol). The resulting solution was stirred at RT for 1 h. The mixture was concentrated in vacuo, and triturated with diethyl ether (10 mL) to give the TFA salt. To obtain the free base, the TFA salt was triturated with an aqueous saturated solution of $NaHCO_3$ (10 mL) and the product extracted with EtOAc (2×30 mL). Combined organic layers were washed with brine (30 mL), dried over $Na_2SO_4$ and concentrated in vacuo to give the desired product.

General Procedure 32: $PCl_3$ Mediated Amide Coupling

A microwave vial was charged with the relevant carboxylic acid (1 eq.), the desired amine (2.5 eq), MeCN (2 mL/mmol) and $PCl_3$ (1 eq.). The resulting mixture was heated at 150° C. with microwave irradiation for 5 min unless otherwise stated. The mixture was quenched with an aqueous saturated solution of $NaHCO_3$ (10 mL) and diluted with $H_2O$ (30 mL). The crude product was extracted with EtOAc (3×30 mL). Combined organic layers were washed with brine (50 mL), dried over $Na_2SO_4$, and concentrated in vacuo. Purification via column chromatography gave the desired product.

General Procedure 33: Suzuki Coupling 1

A microwave vial was charged with the relevant bromoaryl species (1 eq.), $Cs_2CO_3$ (1.5 eq.) the desired boronic acid (3 eq.), dichloro [1,1'-bis(di-tert-butylphosphino)]ferrocene palladium (11) (10 mol %), and dioxane (10 mL/mmol). The resulting mixture was degassed for 20 min, and then heated at 150° C. under microwave irradiation for 1 h. The mixture was diluted with MeOH (20 mL) and passed through a Celite cartridge to remove metallic impurities. The resulting solution was concentrated in vacuo and the crude material was either engaged directly in the next step or purified by column chromatography to give the desired product.

General Procedure 34: Suzuki Coupling 2

A microwave vial was charged with the relevant bromoaryl species (1 eq.), KOAc (3 eq.), bis(pinacolato)diboron (1.5 eq.), dichloro [1,1' bis(di-tert-butylphosphino)]ferrocene palladium (11) (10 mol %) and dioxane (10 mL/mmol). The resulting mixture was degassed for 20 min, and then heated at 150° C. under microwave irradiation for 15 min. To this mixture was then added 2-bromopyridine (1.5 eq.), $Na_2CO_3$ (1.2 eq), $H_2O$ (0.2 mL), and tetrakis (triphenylphosphine)palladium (0) (10 mol %). The resulting mixture was degassed for 20 min, and then heated conventionally at 110° C. for 16 h. The mixture was diluted with MeOH (20 mL), passed through a Celite cartridge, and the resulting solution concentrated in vacuo. Purification via column chromatography (silica; 10-50% EtOAc/petrol) gave the desired product.

General Procedure 35

To the appropriate 1H-pyrrole-2-carboxylic acid (1 mol equiv.) in DCM (10 mL/mmol of carboxylic acid) were added triethylamine (2.5 mol equiv.), 2-chloro-1-methylpyridinium iodide (1.1 mol equiv.) and the appropriate amine (1.25 mol equiv.). The resulting solution was stirred at 42° C. for 24 h. Upon completion, the solvent was removed in vacuo. The crude residue was dissolved in EtOAc (30 mL), washed with saturated aq. $NaHCO_3$ (20 mL) and extracted with EtOAc (3×20 mL). The combined organic extracts were washed with brine (30 mL), dried over $MgSO_4$ and concentrated in vacuo. The crude product was purified by column chromatography.

General Procedure 36

To a suspension of the appropriate Boc-protected amine in formic acid (4 mL/mmol of amine) was added a solution of formaldehyde in water (37 wt. %) (4 mol equiv.). The resulting mixture was heated at 95° C. for 3 h. Upon completion, the reaction was cooled in an ice bath and quenched by addition of 2 M aq. NaOH until the pH was alkaline and then extracted with EtOAc (3×20 mL). The pooled organic extracts were washed with water and brine (40 mL, respectively), dried over $MgSO_4$ and concentrated in vacuo. The crude product was purified by column chromatography.

General Procedure 37

To the appropriate Boc-protected amine (1 mol equiv.) in DCM (5 mL/mmol of amine) were added trifluoroacetic acid (5 mL/mmol of amine) and triethylsilane (2.5 mol equiv.). The resulting mixture was stirred at RT for 2 h. Upon completion, the solvent was removed in vacuo. The crude residue was dissolved in EtOAc (30 mL), washed with saturated aq. $NaHCO_3$ (20 mL) and extracted with EtOAc (3×20 mL). The pooled organic extracts were washed with brine (30 mL), dried over $MgSO_4$ and concentrated in vacuo. The crude product was purified by column chromatography.

General Procedure 38

The appropriate nitro compound in MeOH:THF (1:1) (20 mL/mmol of nitropyrimidine) was subjected to palladium-catalysed hydrogenation using an H-Cube® reactor and a 10% Pd/C CatCart. The reaction was conducted at 40° C. under a full pressure of hydrogen for 8 h. Upon completion, the solvents were removed in vacuo and the crude product was purified by column chromatography if required.

General Procedure 39

To a solution of 2-chloro-5-nitropyridine (8) (1 mol equiv.) in THF (5.0 mL/mmol of 2-chloro-5-nitropyridine), cooled at 0° C., was added triethylamine (1.1 mol equiv.), followed by the appropriate amine. The resulting solution was stirred at 67 C overnight. Upon completion, the solvent was removed in vacuo. The crude residue was dissolved in EtOAc (20 mL), washed with water (20 mL) and extracted with EtOAc (3×25 mL). The combined organic extracts were washed with brine (30 mL), dried over $MgSO_4$ and concentrated in vacuo. The crude product was purified by column chromatography.

General Procedure 40

To the appropriate 3-alkyloxy-4-chloro-2-fluorobenzene (1 mol equiv.) in THF (3 mL/mmol of benzene), cooled at −78° C., was added dropwise n-butyllithium (2.4 M in hexane, 1 mol equiv.). The resulting mixture was stirred at −78° C. for 30 min. Crushed solid carbon dioxide was added in one portion and the reaction allowed to warm to RT. After 1 h, the solvent was removed in vacuo and the crude residue dissolved in 2 M aq. NaOH (20 mL). The aqueous layer was washed with EtOAc (20 mL), then acidified to pH 1-2 using a 4 M aq. solution of HCl and extracted with EtOAc (3×25 mL). The pooled organic extracts were washed with water (30 mL) and brine (30 mL), dried over $MgSO_4$ and concentrated in vacuo. The crude product was purified by column chromatography.

General Procedure 41

To the appropriate pyrrole ester (1 mol equiv.) in THF (8 mL/mmol of pyrrole ester) was added a 2 M aq. solution of lithium hydroxide (15 mol equiv.). The resulting mixture was heated at 67° C. for 18 h. Upon completion, the mixture was acidified to pH 3 using a 4 M aq. solution of HCl. The reaction was then diluted with water (30 mL) and extracted with EtOAc (3×50 mL). The pooled organic extracts were washed with water and brine (50 mL, respectively), dried over $MgSO_4$ and concentrated in vacuo. The crude material was used in the next step without further purification.

General Procedure 42

To the appropriate carboxylic acid (1 mol equiv.) in acetonitrile (5 mL/mmol of carboxylic acid) were added the appropriate amine (2.5 mol equiv.) and phosphorus trichloride (1 mol equiv.). The resulting mixture was heated at 150 C for 7 min under microwave irradiation. After cooling, the mixture was quenched by addition of 2 M aq. NaOH (10 mL/mmol of carboxylic acid). The resulting heterogeneous solution was stirred at RT until solubilisation of all the brown residues formed during the reaction. The mixture was extracted with EtOAc (3×20 mL), the pooled organic extracts were washed with an acetate buffer pH=4.65 (20 mL) and brine (20 mL), dried over $MgSO_4$ and concentrated in vacuo. The crude product was purified by column chromatography.

General Procedure 43

To 4-chloro-2-fluorophenol (86) (1 mol equiv.) in THF (5 mL/mmol of phenol), cooled at 0° C., were added triphenylphosphine (1.5 mol equiv.) and the appropriate alcohol (1.3 mol equiv.). Diethyl azodicarboxylate (1.5 mol equiv.) was then added dropwise at 0° C. The resulting orange solution was stirred at 0° C. for 30 min and allowed to warm to RT. The reaction was left stirring for 24 h. Upon completion, the mixture was diluted with EtOAc (30 mL), washed with saturated aq. $NaHCO_3$ and brine (20 mL, respectively), dried over $MgSO_4$ and concentrated in vacuo. The crude orange solid was purified by column chromatography.

General Procedure 44: Mitsunobu Alkylation of 4-Nitropyrazole

Diethylazodicarboxylate (1.5 eq.) was added dropwise to a mixture of 4-nitropyrazole (1 eq.), triphenylphosphine (1.73 g, 6.63 mmol, 1.5 eq.) and the substrate alcohol (1 eq.), in THF at 0° C. The mixture was stirred at 0° C. for 10 min, and then allowed to warm to r.t. and stirred at r.t. for 18 h. The mixture was partitioned between EtOAc (2×30 mL) and water (20 mL), washed with brine (20 mL), dried over MgSO₄ and the solvent removed in vacuo.

General Procedure 45: CDI Amide Coupling

Carbonyl diimidazole (CDI, 2 eq.) was added to a solution of the relevant carboxylic acid in THF (2 mL/mmol) and the mixture and heated to 70° C. for 3 h. The relevant amine (2.5 eq.) was added and the mixture was heated at 70° C. for 2 h. The mixture was partitioned between EtOAc (2×20 mL) and saturated NaHCO₃(aq.). The organic layers were combined, washed with brine (20 mL), dried over MgSO₄ and the solvent removed in vacuo.

Preparation of Starting Materials

Methyl 4-(2-chloro-6-fluorobenzoyl)-1H-pyrrole-2-carboxylate

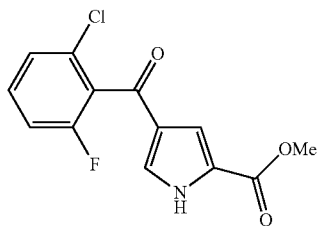 [SMILES: COC(=O)c1cc(C(=O)c2c(F)cccc2Cl)c[nH]1]

To a suspension of AlCl₃ (2.23 g, 16.8 mmol, 2.5 eq.) in DCM (17 mL) at 0° C. was added 2-chloro-6-fluorobenzoyl chloride (1.8 mL, 13.3 mmol, 2 eq.). The mixture was stirred at 0° C. for 10 minutes, and then methyl-1H-pyrrole-2-carboxylate (847 mg, 6.7 mmol, 1 eq.) was added. The mixture was stirred at r.t. for 18 h, cooled to 0° C. and aqueous HCl (1 M) added until gas evolution ceased. Rochelle's salt (sat'd aq., 50 mL) was added and the mixture stirred at r.t. for 45 min. The mixture was then extracted with DCM (3×100 mL), the organic layers combined, washed with 10% NaHCO₃$_{(aq)}$ (100 mL) and brine (100 mL), dried over MgSO₄, and solvent removed in vacuo. The residue was purified by MPLC on SiO₂ with a gradient elution from 0% to 100% EtOAc/petrol to give a white solid (1.74 g, 92%); δH NMR (500 MHz; DMSO-d₆) $\delta_H$ 3.83 (3H, s, OMe), 7.02-7.05 (1H, m, H-3), 7.42 (1H, app td, J=8.2 and 0.8 Hz, H-5'), 7.49 (1H, d, J=8.2 Hz, H-3'), 7.57 (1H, dd, J=1.7 and 3.3 Hz, H-5), 7.61 (1H, td, J=6.3 Hz and 8.2 Hz, H-4'), 12.94 (1H, br s, NH); MS (ES+) m/z 282.3 [M+H]⁺; MS (ES−) m/z 280.2 [M−H]⁻; HRMS calcd for $C_{13}H_{10}{}^{35}Cl_1F_1O_3N_1$ [M+H]⁺ 282.0328, found 282.0333.

Methyl 4-(3,6-dichloro-2-fluorobenzoyl)-1H-pyrrole-2-carboxylate

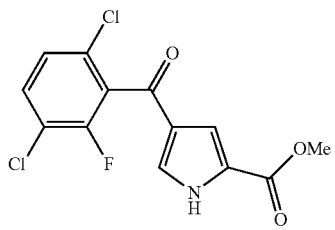 [SMILES: COC(=O)c1cc(C(=O)c2c(Cl)ccc(Cl)c2F)c[nH]1]

To a suspension of AlCl₃ (11.9 g, 89.6 mmol, 2.5 eq.) in DCM (100 mL) at 0° C. was added 3,6-dichloro-2-fluorobenzoyl chloride (16.3 mL, 71.7 mmol, 2 eq.). The mixture was stirred at 0° C. for 10 minutes, and then methyl-1H-pyrrole-2-carboxylate (4.48 g, 35.8 mmol, 1 eq.) was added. The mixture was stirred at r.t. for 18 h, cooled to 0° C. and aqueous HCl (1 M) added until gas evolution ceased. Rochelle's salt (sat'd aq., 200 mL) was added and the mixture stirred at r.t. for 45 min. The mixture was extracted with DCM (4×150 mL), the organic layers combined, dried over MgSO₄, and solvent removed in vacuo. The residue was purified by MPLC on SiO₂ with a gradient elution from 0% to 65% EtOAc/petrol to give a white solid (10.12 g, 89%); δH NMR (500 MHz; DMSO-d₆) ¹H 3.84 (3H, s, CH₃), 7.12 (1H, app t, J=1.5 Hz, H-pyrrole), 7.53 (1H, dd, J=0.9 and 8.5 Hz, H-5'), 7.71 (1H, dd, J=1.5 and 3.2 Hz, H-pyrrole), 7.80 (1H, app t, J=8.5 Hz, H-4'), 12.98 (1H, s, NH-pyrrole); MS (ES+) m/z 314.2, 316.1 [M+H]⁺.

4-(2-Chloro-6-fluorobenzoyl)-1H-pyrrole-2-carboxylic Acid

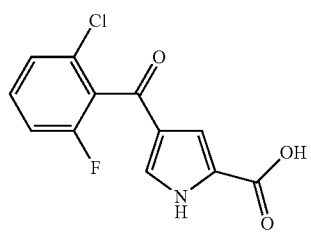 [SMILES: O=C(O)c1cc(C(=O)c2c(F)cccc2Cl)c[nH]1]

A solution of LiOH (2.9 g, 121 mmol, 20 eq.) in H₂O (80 mL) was added to 1 (1.7 g, 6.05 mmol, 1 eq.) in THF (48 mL) and heated to 65° C. for 18 h. After cooling to r.t., the mixture was acidified to pH 3 with 1 M HCl$_{(aq)}$ and extracted with EtOAc (2×150 mL). The combined organic layers were washed with water and brine, dried over MgSO₄, and solvent removed in vacuo to give a white solid (1.6 g, 99%); ¹H NMR (500 MHz; DMSO-d₆) $\delta_H$ 6.98 (1H, br s, H-pyrrole), 7.42 (td, J=8.2 and 0.6 Hz, H-5'), 7.47-7.51 (2H, m, H-3' and H-pyrrole), 7.61 (1H, td, J=6.3 and 8.2 Hz, H-4'), 12.75 (1H, br s, NH-pyrrole), 12.97 (1H, br s, CO₂H); m/z 268.3 [M+H]⁺; MS (ES−) m/z 266.2 [M−H]⁻; HRMS calcd for $C_{12}H_6{}^{35}Cl_1F_1N_1O_3$ [M+H]⁺ 266.0026, found 266.0018.

4-(3,6-Dichloro-2-fluorobenzoyl)-1H-pyrrole-2-carboxylic Acid

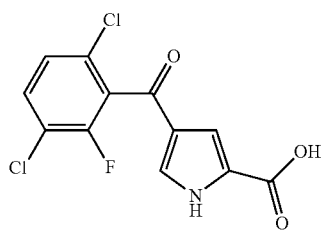 [SMILES: O=C(O)c1cc(C(=O)c2c(Cl)ccc(Cl)c2F)c[nH]1]

A solution of LiOH (26.6 g, 632 mmol, 20 eq.) in H₂O (140 mL) was added to 2 (10.0 g, 31.6 mmol, 1 eq.) in THF (180 mL) and heated to 65° C. for 48 h. After cooling to r.t., the mixture was acidified to pH 3 with 1 M HCl$_{(aq)}$ and extracted with EtOAc (2×300 mL). The combined organic layers were washed with water and brine, dried over MgSO$_4$, and solvent removed in vacuo to give a white solid; $^1$H NMR (500 MHz; DMSO-d$_6$) δ$_H$ 7.07 (1H, app t, J=1.6 Hz, H-pyrrole), 7.53 (1H, dd, J=1.1 and 8.6 Hz, H-5'), 7.71 (1H, dd, J=1.6 and 3.2 Hz, H-pyrrole), 7.80 (1H, app t, J=8.6 Hz, H-4'), 12.81 (1H, br s, NH-pyrrole), 13.00 (1H, br s, CO$_2$H).

By following methods similar and/or analogous to those described herein, the compounds set out in the Table 1 below were prepared from the corresponding starting materials.

TABLE 1

| Ex. | Structure | Name | General prep | $^1$H NMR Data | MS |
|---|---|---|---|---|---|
| 1. | 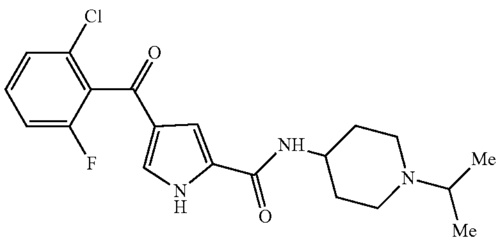 [SMILES: CC(C)N1CCC(NC(=O)c2cc(C(=O)c3c(F)cccc3Cl)c[nH]2)CC1] | 4-(2-Chloro-6-fluorobenzoyl)-N-(1-isopropyl-piperidin-4-yl)-1H-pyrrole-2-carboxamide | 1 | 0.99 (6H, d, J = 6.5 Hz, 2 × Me), 1.49 (2H, ddd, J = 3.6 Hz, 12.1 Hz, and 15.5 Hz, 2 × H-piperidine), 1.75-1.83 (2H, m, 2 × H-piperidine), 2.14-2.22 (2H, m, 2 × CH—N-piperidine), 2.72 (1H, sept, J = 6.5 Hz, CH(Me)$_2$), 2.77-2.84 (2H, m, 2 × CH—N-piperidine), 3.64-3.75 (1H, m, CO—NH—CH), 7.23 (1H, brs, H-3), 7.35 (1H, br s, H-5), 7.39-7.45 (1H, app t, J = 8.2 Hz, H-5'), 7.49 (1H, d, J = 8.2 Hz, H-3'), 7.60 (1H, td, J = 6.3 Hz, 8.2 Hz, H-4'), 8.13 (1H, d, J = 8.0 Hz, CO—NH), 12.43 (1H, br s, NH-pyrrole) | 392 |
| 2. | 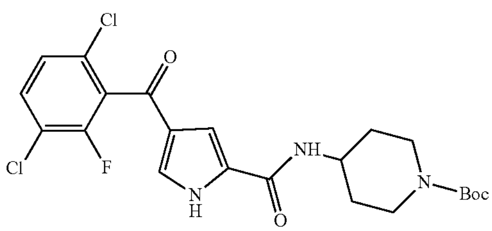 [SMILES: CC(C)(C)OC(=O)N1CCC(NC(=O)c2cc(C(=O)c3c(Cl)ccc(Cl)c3F)c[nH]2)CC1] | tert-Butyl 4-(4-(3,6-dichloro-2-fluorobenzoyl)-1H-pyrrole-2-carboxamido)piperidine-1-carboxylate | 1 | 1.33-1.47 (11H, m, C(CH$_3$)$_3$ and 2 × H-piperidine), 1.80 (2H, dd, J = 3.0 and 12.8 Hz, 2 × H-piperidine), 2.87 (2H, br s, 2 × CH—N-piperidine), 3.89-4.01 (2H, m, 2 × CH—N-piperidine and CH—NH-piperidine), 7.25 (1H, br s, H-pyrrole), 7.51 (1H, br s, H-pyrrole), 7.54 (1H, dd, J = 1.1 and 8.6 Hz, H-5'), 7.80 (1H, app t, J = 8.6 Hz, H-4'), 8.15 (1H, d, J = 8.0 Hz, CO—NH), 12.53 (1H, s, NH-pyrrole) | 482.2 |
| 3. | 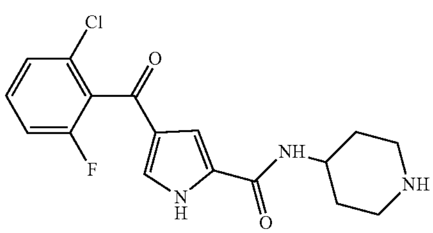 [SMILES: O=C(NC1CCNCC1)c1cc(C(=O)c2c(F)cccc2Cl)c[nH]1] | 4-(2-Chloro-6-fluorobenzoyl)-N-(piperidin-4-yl)-1H-pyrrole-2-carboxamide | 4 | 1.59-1.71 (2H, m, 2 × H-piperidine), 1.91-1.99 (2H, m, 2 × H-piperidine), 2.93-3.04 (2H, m, 2 × CH—N-piperidine), 3.25-3.34 (2H, m, 2 × CH—N-piperidine), 3.96-4.07 (1H, m, CO—NH—CH), 7.28 (1H, br s, H-3), 7.36 (1H, br s, H-5), 7.39-7.45 (1H, app t, J = 8.1 Hz, H-5'), 7.49 (1H, d, J = 8.1 Hz, H-3'), 7.60 (1H, td, J = 6.3 and 8.1 Hz, H-4'), 8.00 (1H, br s, NH), 8.30 (1H, d, J = 7.6 Hz, CO—NH), 12.47 (1H, br s, NH-pyrrole) | 352.4 |
| 4. | 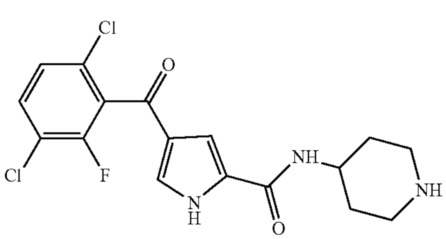 [SMILES: O=C(NC1CCNCC1)c1cc(C(=O)c2c(Cl)ccc(Cl)c2F)c[nH]1] | 4-(3,6-Dichloro-2-fluorobenzoyl)-N-(piperidin-4-yl)-1H-pyrrole-2-carboxamide | 4 | 1.39 (2H, dq, J = 3.8 and 12.0 Hz, 2 × H-piperidine), 1.74 (2H, dd, J = 2.5 and 12.0 Hz, 2 × H-piperidine), 2.51 (2H, dd, J = 2.5 and 12.0 Hz, 2 × CH-piperidine), 2.94-3.01 (2H, m, 2 × H-piperidine), 3.75-3.85 (1H, m, CH—NH—CO), 4.13 (1H, br s, NH), 7.27 (1H, br s, H-pyrrole), 7.49 (1H, br s, H-pyrrole), 7.54 (1H, dd, J = 1.2 and 8.6 Hz, H-5'), 7.80 (1H, app t, J = 8.6 Hz, H-4'), 8.12 (1H, d, J = 8.0 Hz, CO—NH) | 382.1 |

Example 5: 4-(2-Chloro-6-fluorobenzoyl)-N-(1-ethylpiperidin-4-yl)-1H-pyrrole-2-carboxamide

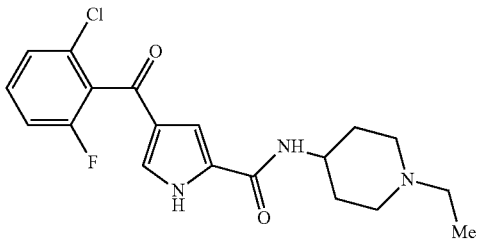 [SMILES: CCN1CCC(NC(=O)c2cc(C(=O)c3c(F)cccc3Cl)c[nH]2)CC1]

Example 3 (120 mg, 0.34 mmol, 1 eq.), acetaldehyde (39 µL, 0.69 mmol, 2 eq.), acetic acid (39 µL, 0.69 mmol, 2 eq.), and MgSO$_4$ (150 mg) were combined in MeOH (3 mL) and stirred at r.t. for 1 h. Sodium cyanoborohydride (32 mg, 0.51 mmol, 1.5 eq) was added and the mixture stirred at r.t. for 18 h. The mixture was quenched with water, basified with 10% NaHCO$_3$ (aq) and extracted with CH$_2$Cl$_2$ (2×15 mL). the organic layers were combined, dried over MgSO$_4$, and the solvent removed in vacuo. The residue was purified by MPLC on SiO$_2$ with a gradient elution from 95/5/0/5 to 86/14/1.4 CH$_2$Cl$_2$/MeOH/NH$_4$OH to give a white solid (21 mg, 16%). $^1$H NMR (500 MHz; DMSO-d$_6$) $\delta_H$ 1.02 (3H, t, J=7.1 Hz, N—CH$_2$CH$_3$), 1.52 (2H, app qd, J=11.8 and 3.3 Hz, 2×H-piperidine), 1.74-1.81 (2H, m, 2×H-piperidine), 1.90-1.97 (2H, m, 2×CH—N-piperidine), 2.34 (2H, q, J=7.1 Hz, N—CH$_2$CH$_3$), 2.85-2.92 (2H, m, 2×CH—N-piperidine), 3.67-3.77 (1H, m, CH—NH-piperidine), 7.23 (br s, H-3), 7.35 (br s, H-5), 7.39-7.44 (1H, app t, J=8.2, H-5'), 7.49 (1H, d, J=8.2 Hz, H-3'), 7.60 (1H, td, J=6.3 and 8.2 Hz, H-4'), 8.14 (1H, d, J=7.7 Hz, CO—NH), 12.43 (1H, s, NH pyrrole); MS (ES+) m/z 378.4 (75.8%) [M($^{35}$Cl)+H]$^+$, 380.4 (24.2%) [M($^{37}$Cl)+H]$^+$; HRMS calcd for C$_{19}$H$_{22}$$^{35}$Cl$_1$F$_1$N$_3$O$_2$ [M+H]$^+$ 378.1379, found 378.1388.

Example 6: N-(1-Acetylpiperidin-4-yl)-4-(2-chloro-6-fluorobenzoyl)-1H-pyrrole-2-carboxamide

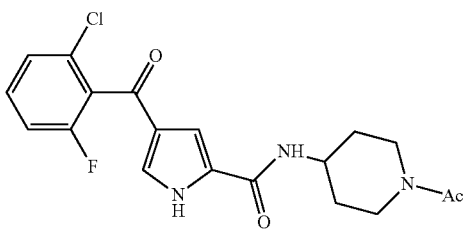 [SMILES: CC(=O)N1CCC(NC(=O)c2cc(C(=O)c3c(F)cccc3Cl)c[nH]2)CC1]

Acetyl chloride (17 µL, 0.24 mmol, 1.1 eq.) was added to Example 3 (75 mg, 0.21 mmol, 1 eq.) and Et$_3$N (36 µL, 0.26 mmol, 1.2 eq.) in DCM (2 mL) at r.t. and the mixture was stirred at r.t. for 30 min. Methanol was added and the solvent removed in vacuo. The residue was partitioned between EtOAc (2×20 mL) and H$_2$O (10 mL), washed with brine (10 mL), dried over MgSO$_4$, and the solvent removed in vacuo. The residue was purified by MPLC on SiO$_2$ with a gradient elution from 0 to 5% MeOH/DCM to give a white solid (40 mg, 48%); R$_f$ 0.2 (3% MeOH/EtOAc); m.p. 257-259° C.; λ$_{max}$(EtOH)/nm 281, 236; IR ν$_{max}$/cm$^{-1}$ 3503, 3370, 1626, 1565; $^1$H NMR (500 MHz; DMSO-d$_6$) $\delta_H$ 1.29-1.50 (2H, m, 2×CH-piperidine), 1.77-1.90 (2H, m, 2×CH-piperidine), 2.04 (3H, s, CH$_3$), 2.70 (1H, app td, J=12.5 and 2.5 Hz, CH—N-piperidine), 3.16 (1H, app td, J=12.5 and 2.5 Hz, CH—N-piperidine), 3.84 (1H, d, J=13.6 Hz, CH—N-piperidine), 3.96-4.05 (1H, m, CH—NH-piperidine), 4.35 (1H, d, J=13.6 Hz, CH—N-piperidine), 7.23 (1H, br s, H-3), 7.37 (1H, br s, H-5), 7.39-7.44 (1H, app t, J=8.2 Hz, H-5'), 7.49 (1H, d, J=8.2 Hz, H-3'), 7.60 (1H, td, J=6.3 and 8.2 Hz, H-4'), 8.19 (1H, d, J=8.1 Hz, CO—NH), 12.48 (1H, br s, NH-pyrrole); $^{19}$F NMR (470 MHz; DMSO-d$_6$) $\delta_F$ −114.42; $^{13}$C NMR (125 MHz; DMSO-d$_6$) $\delta_C$ 21.2 (Me), 31.9 (2×CH$_2$-piperidine), 44.7 (2×CH$_2$-piperidine), 46.0 (CH—NH-piperidine), 110.0 (C-pyrrole), 114.9 (d, J$_{CF}$=21.8 Hz, C-5'), 125.0 (C-pyrrole), 125.8 (J$_{CF}$=3.1 Hz, C-3'), 128.1 (d, J$_{CF}$=23.2 Hz, C-1'), 128.2 (C-pyrrole) 128.8 (CH-pyrrole), 130.4 (d, J$_{CF}$=5.9 Hz, C-2'), 131.7 (d, J$_{CF}$=9.3 Hz, C-4'), 158.5 (d, J$_{CF}$=246.9 Hz, C-6'), 159.0 (CO—NH), 168.0 (CO—N), 183.9 (CO); MS (ES+) m/z 392.4 (75.8%) [M($^{35}$Cl)+H]$^+$, 394.4 (24.2%) [M($^{37}$Cl)+H]$^+$; HRMS calcd for C$_{19}$H$_{20}$$^{35}$Cl$_1$F$_1$N$_3$O$_2$ [M+H]$^+$ 392.1172, found 392.1174.

Example 7: N-(1-Acetylpiperidin-4-yl)-4-(3,6-dichloro-2-fluorobenzoyl)-1H-pyrrole-2-carboxamide

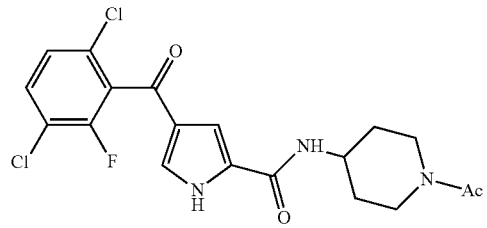 [SMILES: CC(=O)N1CCC(NC(=O)c2cc(C(=O)c3c(Cl)ccc(Cl)c3F)c[nH]2)CC1]

Example 4 (75 mg, 0.2 mmol, 1 eq), acetyl chloride (15 µL, 0.22 mmol, 1.1 eq.), and Et$_3$N (33 µL, 0.24 mmol, 1.2 eq) were combined in CH$_2$Cl$_2$ (2 mL), and stirred at r.t. for 1 h. Further Et$_3$N (0.5 eq) and methanesulfonyl chloride (0.5 eq.) were added and the mixture was stirred at r.t. for 1 h, quenched with methanol, partitioned between CH$_2$Cl$_2$ (20 mL) and HCl$_{(aq)}$ (0.5 M, 10 mL). The organic extract washed with brine (10 mL), dried over MgSO$_4$ and the solvent removed in vacuo. The residue was purified by MPLC on NH$_2$SiO$_2$ with a gradient elution from 1% to 3% MeOH:CH$_2$Cl$_2$ to give a white solid (43 mg, 52%); $^1$H NMR (500 MHz; DMSO-d$_6$) $\delta_H$ 1.30-1.50 (2H, m, 2×H-piperidine), 1.77-1.90 (2H, m, 2×H-piperidine), 2.04 (3H, s, CH$_3$), 2.71 (1H, app td, J=2.5 and 12.5 Hz, CH—N-piperidine), 3.12-3.20 (1H, m, CH—N-piperidine), 3.81-3.88 (1H, m, CH—N-piperidine), 3.96-4.06 (1H, m, CH—NH-piperidine), 4.31-4.39 (1H, m, CH—N-piperidine), 7.26 (1H, s, H-pyrrole), 7.51 (1H, s, H-pyrrole), 7.54 (1H, dd, J=1.2 and 8.6 Hz, H-5'), 7.80 (1H, app t, J=8.6 Hz, H-4'), 8.17 (1H, d, J=7.9 Hz, CO—NH), 12.54 (1H, s, NH-pyrrole); MS (ES−) m/z 424.3 (75.8%) [M($^{35,35}$Cl)+H]$^+$, 426.2 (24.2%) [M($^{35,37}$Cl)+H]$^+$; HRMS calcd for C$_{19}$H$_{19}$$^{35}$Cl$_2$F$_1$N$_3$O$_3$ [M+H]$^+$ 426.0782, found 426.0773.

Example 8: 4-(2-Chloro-6-fluorobenzoyl)-N-(1-(methylsulfonyl)piperidin-4-yl)-1H-pyrrole-2-carboxamide

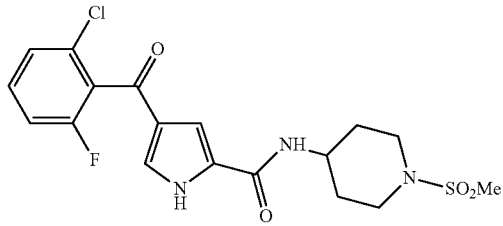 [SMILES: CS(=O)(=O)N1CCC(NC(=O)c2cc(C(=O)c3c(F)cccc3Cl)c[nH]2)CC1]

Example 3 (100 mg, 0.29 mmol), methanesulfonyl chloride (24 μL, 0.32 mmol, 1.1 eq.), and triethylamine (48 μL, 0.34 mmol, 1.2 eq.) were combined in $CH_2Cl_2$ (1 mL) and stirred at r.t. for 1 h. Further methanesulfonyl chloride (20 μL, 0.27 mmol, 0.9 eq.) was added and the mixture was stirred for a further 30 min, quenched with water (5 mL) and extracted with $CH_2Cl_2$ (2×10 mL). The organic extracts were combined, washed with 1 M $HCl_{(aq)}$ (10 mL), dried over $MgSO_4$, and the solvent removed in vacuo. The residue was purified by MPLC on $SiO_2$ with a gradient elution from 40% to 100% EtOAc/petrol to give a white solid (33 mg, 27%). $^1H$ NMR (500 MHz; DMSO-$d_6$) $\delta_H$ 1.58 (1H, app qd, J=11.7 and 4.1 Hz, 2×H-piperidine), 1.87-1.96 (2H, m, 2×H-piperidine), 2.84-2.95 (4H, m, 2×CH—N-piperidine, and $CH_3$), 3.55-3.63 (2H, m, 2×CH—N-piperidine), 3.85-3.95 (1H, m, CH—NH-piperidine), 7.23 (1H, br s, H-3), 7.38 (1H, br s, H-5), 7.42 (1H app t, J=8.2 Hz, H-5'), 7.48 (1H, d, J=8.2 Hz, H-3'), 7.60 (1H, td, J=6.5 and 8.2 Hz, H-4'), 8.25 (1H, d, J=8.2 Hz, CO—NH), 12.46 (1H, br s, NH-pyrrole); MS (ES+) m/z 428.3 (75.8%) $[M(^{35}Cl)+H]^+$, 430.4 (24.2%) $[M(^{37}Cl)+H]^+$; HRMS calcd for $C_{18}H_{20}{}^{35}Cl_1F_1N_3O_4S_1$ $[M+H]^+$ 428.0842, found 428.0849.

Example 9: 4-(3,6-Dichloro-2-fluorobenzoyl)-N-(1-(methylsulfonyl) piperidin-4-yl)-1H-pyrrole-2-carboxamide

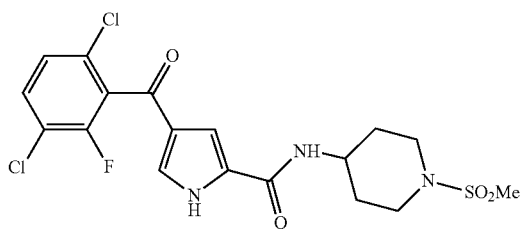 [SMILES: CS(=O)(=O)N1CCC(NC(=O)c2cc(C(=O)c3c(Cl)ccc(Cl)c3F)c[nH]2)CC1]

Example 4 (80 mg, 0.21 mmol, 1 eq.), methanesulfonyl chloride (24 μL, 0.31 mmol, 1.5 eq.), and $Et_3N$ (43 μL, 0.31 mmol, 1.5 eq) were combined in $CH_2Cl_2$ (2 mL) and stirred at r.t. for 30 min. Further $Et_3N$ (1 eq) and methanesulfonyl chloride (1 eq.) were added and the mixture was stirred at r.t. for 1 h, quenched with ethanol, and partitioned between $CH_2Cl_2$ (3×20 mL) and water (10 mL). The organic extracts were combined, washed with brine (10 mL), dried over $MgSO_4$, and the solvent removed in vacuo. The residue was purified by MPLC on $NH_2SiO_2$ with a gradient elution from 50% to 100% EtOAc:petrol to give a white solid (34 mg, 35%); $^1H$ NMR (500 MHz; DMSO-$d_6$) $\delta_H$ 1.58 (2H, app qd, J=3.5 and 12.5 Hz, 2×H-piperidine), 1.92 (2H, app dd, J=2.8 and 12.5 Hz, 2×H-piperidine), 2.88 (2H, dd, J=2.2 and 12.5 Hz, 2×CH—N-piperidine), 2.92 (3H, s, $CH_3$), 3.56-3.63 (2H, m, 2×CH—N-piperidine), 3.86-3.96 (1H, m, CH—NH-piperidine), 7.27 (1H, s, H-pyrrole), 7.52 (1H, s, H-pyrrole), 7.54 (1H, dd, J=1.1 and 8.6 Hz, H-5'), 7.81 (1H, app t, J=8.6 Hz, H-4'), 8.23 (1H, d, J=7.7 Hz, CO—NH), 12.55 (1H, s, NH-pyrrole); MS (ES-) m/z 460.2 (75.8%) $[M(^{35,35}Cl)+H]^+$, 462.2 (24.2%) $[M(^{35,37}Cl)+H]^+$; HRMS calcd for $C_{18}H_{19}{}^{35}Cl_2F_1N_3O_4S$ $[M+H]^+$ 462.0452, found 462.0448.

Example 10: 4-(2-Chloro-6-fluorobenzoyl)-N-(1-(pyrimidin-2-yl)piperidin-4-yl)-1H-pyrrole-2-carboxamide

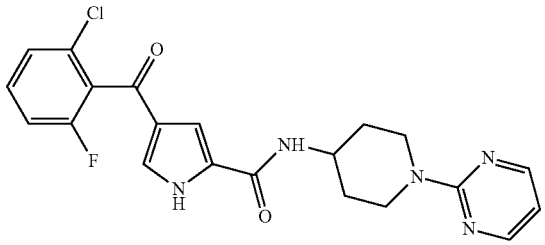 [SMILES: O=C(NC1CCN(c2ncccn2)CC1)c1cc(C(=O)c2c(F)cccc2Cl)c[nH]1]

Example 3 (70 mg, 0.20 mmol, 1 eq.), 2-chloropyrimidine (23 mg, 0.2 mmol, 1 eq.), Hunig's base (42 μL, 0.24 mmol, 1.2 eq.), and MeCN (1.5 mL) were combined and heated to 150° C. for 90 minutes under microwave irradiation. The mixture was partitioned between EtOAc (2×20 mL) and 10% aqueous citric acid (10 mL). The organic layers were washed with 10% aq. sodium carbonate, dried over $MgSO_4$ and the solvent removed in vacuo. The residue was purified by MPLC on $SiO_2$ with a gradient elution from 50% to 100% EtOAc/petrol to give a white solid (20 mg, 23%); $R_f$ 0.5 (10% MeOH/$CH_2Cl_2$); m.p. 235-238° C.; $\lambda_{max}$(EtOH)/nm 287, 245; IR $\nu_{max}$/cm$^{-1}$ 3372, 3191, 3118, 2926, 2853, 1629, 1588, 1566; $^1H$ NMR (500 MHz; DMSO-$d_6$) $\delta_H$ 1.45 (2H, qd, J=12.1 and 4.1 Hz, 2×H-piperidine), 1.84-1.90 (2H, m, 2×H-piperidine), 3.05 (2H, td, J=12.1 and 2.4 Hz, 2×H—N-piperidine), 4.05-4.15 (1H, m, CH—NH-piperidine), 4.63-4.69 (2H, m, 2×CH—N-piperidine), 6.64 (1H, t, J=4.7 Hz, H-pyrimidine), 7.20 (1H, br s, H-3), 7.35 (1H, br s, H-5), 7.40 (1H, dd, J=1.0 and 8.4 Hz, H—Ar), 7.48 (1H, d, J=8.4 Hz, H—Ar), 7.59 (1H, td, J=6.3 and 8.4 Hz, H-4'), 8.16 (1H, d, J=7.9 Hz, CONH), 8.40 (2H, d, J=4.7 Hz, 2×H-pyrimidine), 12.47 (1H, br s, NH-pyrrole); $^{19}F$ NMR (470 MHz; DMSO-$d_6$) $\delta_F$ −114.42; $^{13}C$ NMR (125 MHz; DMSO-$d_6$) $\delta_C$ 31.1 (2×CH-piperidine), 42.6 (2×CH—N-piperidine), 46.3 (CH—NH-piperidine), 109.0 (C-pyrimidine), 109.8 (CH-pyrrole), 114.9 (d, $J_{CF}$=21.8 Hz, C-5'), 125.0 (C-pyrrole), 125.8 (d, $J_{CF}$=2.8 Hz, C-3'), 128.1 (d, $J_{CF}$=23.2 Hz, C-1'), 128.3 (C-pyrrole), 128.9 (CH-pyrrole), 130.4 (d, $J_{CF}$=6.3 Hz, C-2'), 131.7 (d, $J_{CF}$=9.1 Hz, C-4'), 158.0 (2×CH-pyrimidine), 158.5 (d, $J_{CF}$=246 Hz, C-6'), 159.0 (C-pyrimidine), 161.7 (CO—NH), 183.9 (CO); MS (ES+) m/z 428.4 (75.8%) $[M(^{35}Cl)+H]^+$, 430.4 (24.2%) $[M(^{37}Cl)+H]^+$; HRMS calcd for $C_{21}H_{20}{}^{35}Cl_1F_1N_5O_2$ $[M+H]^+$ 428.1284, found 428.1290.

Example 11: 4-(3,6-Dichloro-2-fluorobenzoyl)-N-(1-(2,2,2-trifluoroacetyl)piperidin-4-yl)-1H-pyrrole-2-carboxamide

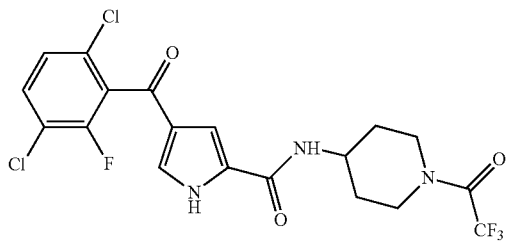 [SMILES: O=C(NC1CCN(C(=O)C(F)(F)F)CC1)c1cc(C(=O)c2c(Cl)ccc(Cl)c2F)c[nH]1]

Trifluoroacetic anhydride (28 μL, 0.3 mmol, 1.5 eq.) was added to a solution of Example 4 (76 mg, 0.2 mmol, 1 eq.), Et₃N (31 μL, 0.24 mol, 1.2 eq.) in CH₂Cl₂ (2 mL) and dioxane (2 mL) at 0° C. The mixture was stirred at r.t. for 2 h, before further trifluoroacetic anhydride (54 μL, 0.6 mmol, 3 eq) and Et₃N (52 μL, 0.6 mmol, 2 eq.) were added. After stirring for 1 h at r.t., the reaction was partitioned between EtOAc (2×20 mL) and water (10 mL), the organic layers combined, washed with brine, dried over MgSO₄ and the solvent removed in vacuo. The residue was purified by MPLC on SiO₂ with gradient elution from 25% to 80% EtOAc/petrol to give a white solid (39 mg, 41%); ¹H NMR (500 MHz; DMSO-d₆) $\delta_H$ 1.43-1.58 (2H, m, 2×H-piperidine), 1.92-2.03 (2H, m, 2×H-piperidine), 3.08-3.16 (1H, m, H-piperidine), 3.40-3.48 (1H, m, H-piperidine), 3.86-3.94 (1H, m, H-piperidine), 4.09-4.19 (1H, m, H-piperidine), 4.25-4.33 (1H, m, H-piperidine), 7.25 (1H, s, H-pyrrole), 7.50-7.57 (2H, m, H-pyrrole and H-5'), 7.81 (1H, appt, J=8.4 Hz, H-4'), 8.21 (1H, d, J=7.9 Hz, CO—NH), 12.57 (1H, s, NH-pyrrole); HRMS calcd for $C_{19}H_{19}{}^{35}C_2F_4N_4O_3$ [M+NH₄]⁺ 497.0765, found 497.0758.

By following methods similar and/or analogous to those described herein, the compounds set out in the Table 2 below were prepared from the corresponding starting materials.

TABLE 2

| Ex. | Structure | Name | General prep | 1H NMR Data | MS |
|---|---|---|---|---|---|
| 12. | 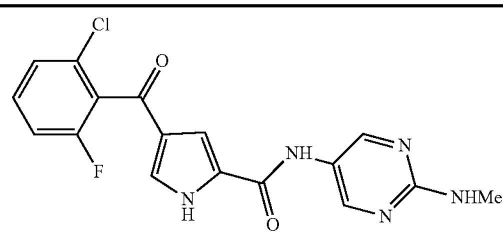 | 4-(2-Chloro-6-fluorobenzoyl)-N-(2-(methylamino)pyrimidin-5-yl)-1H-pyrrole-2-carboxamide | 2 | 2.83 (3H, d, J = 4.8 Hz, Me), 7.04 (1H, q, J = 4.8 Hz, NHMe), 7.39 (1H, s, H-pyrrole), 7.43 (1H, app t, J = 8.3 Hz, H-5'), 7.48 (1H, s, H-pyrrole), 7.50, (1H, d, J = 8.3 Hz, H-3'), 7.62 (1H, qd, J = 6.2 and 8.3 Hz, H-4'), 8.53 (2H, s, 2 × H-pyrimidine), 9.98 (1H, s, CO—NH), 12.68 (1H, s, NH-pyrrole) | 376.3 |
| 13. | 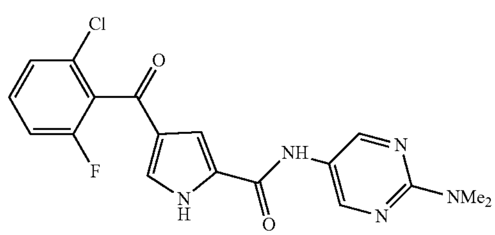 [SMILES: CN(C)c1ncc(NC(=O)c2cc(C(=O)c3c(F)cccc3Cl)c[nH]2)cn1] | 4-(2-Chloro-6-fluorobenzoyl)-N-(2-(dimethylamino)pyrimidin-5-yl)-1H-pyrrole-2-carboxamide | 2 | 3.15 (6H, s, NMe₂), 7.39 (1H, s, H-pyrrole), 7.44 (1H, app t, J = 8.4 Hz, H-5'), 7.49 (1H, s, H-pyrrole), 7.50 (1H, d, J = 8.4 Hz, H-3'), 7.62 (1H, td, J = 6.3 and 8.4 Hz, H-4'), 8.61 (2H, s, 2 × H-pyrimidine), 10.02 (1H, s, CO—NH), 12.70 (1H, s, NH) | 390.3 |
| 14. | 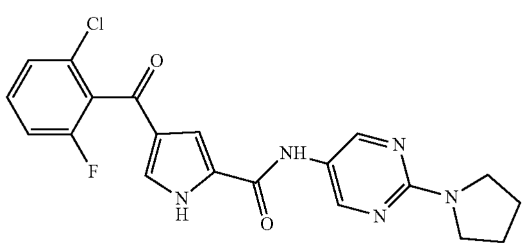 [SMILES: O=C(Nc1cnc(N2CCCC2)nc1)c1cc(C(=O)c2c(F)cccc2Cl)c[nH]1] | 4-(2-Chloro-6-fluorobenzoyl)-N-(2-(pyrrolidin-1-yl)pyrimidin-5-yl)-1H-pyrrole-2-carboxamide | 2 | 2.52-2.56 (4H, m, 2 × CH₂-pyrrolidine), 3.48-3.53 (4H, m, 2 × CH₂-N-pyrrolidine), 7.37-7.44 (2H, m, CH-pyrrole and H—Ar), 7.47-7.53 (2H, m, CH-pyrrole and H—Ar), 7.58-7.65 (1H, td, J = 6.3 and 8.2 Hz, H-4'), 8.59 (2H, s, 2 × H-pyrimidine), 10.01 (1H, br s, CO—NH), 12.69 (1H, br s, NH-pyrrole) | 416.4 |
| 15. | 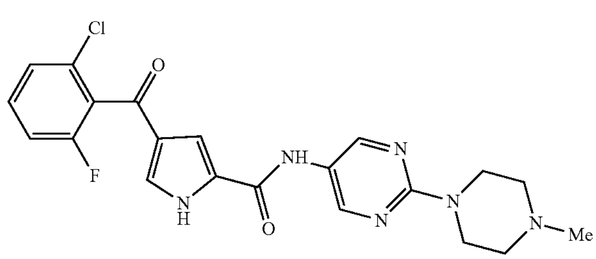 [SMILES: CN1CCN(c2ncc(NC(=O)c3cc(C(=O)c4c(F)cccc4Cl)c[nH]3)cn2)CC1] | 4-(2-Chloro-6-fluorobenzoyl)-N-(2-(4-methylpiperazin-1-yl)pyrimidin-5-yl)-1H-pyrrole-2-carboxamide | 2 | 2.24 (3H, s, NMe), 2.35-2.42 (4H, m, H-piperazine), 3.68-3.76 (4H, m, H-piperazine), 7.40 (1H, s, H-pyrrole), 7.44 (1H, app t, J = 8.2 Hz, H-5'), 7.48-7.54 (2H, m, H-pyrrole and H-3'), 7.62 (1H, td, J = 6.3 and 8.2 Hz, H-4'), 8.61 (2H, s, 2 × H-pyrimidine), 10.05 (1H, s, CO—NH), 12.69 (1H, s, NH-pyrrole) | 445.4 |

TABLE 2-continued

| Ex. | Structure | Name | General prep | 1H NMR Data | MS |
|---|---|---|---|---|---|
| 16. | 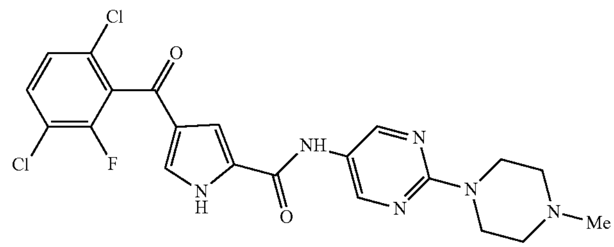 [SMILES: CN1CCN(c2ncc(NC(=O)c3cc(C(=O)c4c(Cl)ccc(Cl)c4F)c[nH]3)cn2)CC1] | 4-(3,6-Dichloro-2-fluorobenzoyl)-N-(2-(4-methyl-piperazin-1-yl)pyrimidin-5-yl)-1H-pyrrole-2-carboxamide | 2 | 2.25 (3H, s, CH₃), 2.37-2.41 (4H, m, 2 × CH₂-piperazine), 3.70-3.76 (4H, m, 2 × CH₂-piperazine), 7.44 (1H, s, H-pyrrole), 7.56 (1H, dd, J = 1.1 and 8.6 Hz, H-5'), 7.64 (1H, s, H-pyrrole), 7.82 (1H, app t, J = 8.6 Hz, H-4'), 8.64 (2H, s, 2 × H-pyrimidine), 10.07 (1H, s, CO—NH), 12.78 (1H, s, NH) | 477.3 |
| 17. | 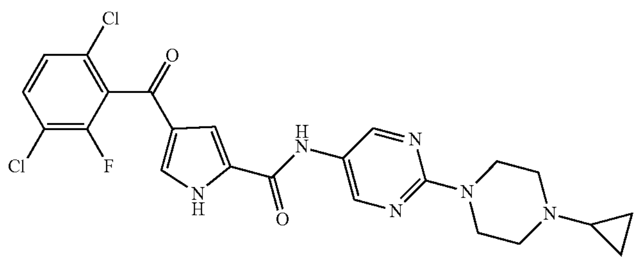 [SMILES: O=C(Nc1cnc(N2CCN(C3CC3)CC2)nc1)c1cc(C(=O)c2c(Cl)ccc(Cl)c2F)c[nH]1] | N-(2-(4-cyclopropyl-piperazin-1-yl)pyrimidin-5-yl)-4-(3,6-dichloro-2-fluorobenzoyl)-1H-pyrrole-2-carboxamide | 2 | 0.37-0.41 (2H, m, 2 × H-cyclopropyl), 0.45-0.50 (2H, m, 2 × H-cyclopropyl), 1.65-1.71 (1H, m, N—CH—cPr), 2.60-2.64 (4H, m, 2 × CH₂-piperazine), 3.68-3.72 (4H, m, 2 × CH₂-piperazine), 7.43 (1H, s, H-pyrrole), 7.56 (1H, dd, J = 1.1 and 8.5 Hz, H-5'), 7.64 (1H, s, H-pyrrole), 7.82 (1H, app t, J = 8.5 Hz, H-4'), 8.64 (2H, s, 2 × H-pyrimidine), 10.07 (CO—NH), 12.78 (NH-pyrrole) | 462. |
| 18. | 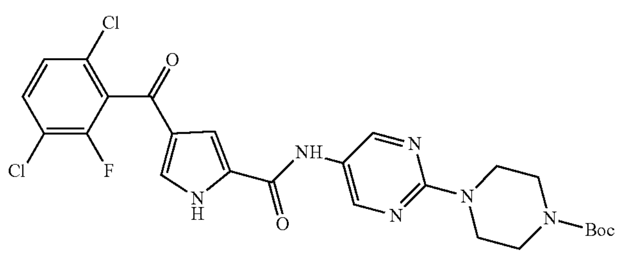 [SMILES: CC(C)(C)OC(=O)N1CCN(c2ncc(NC(=O)c3cc(C(=O)c4c(Cl)ccc(Cl)c4F)c[nH]3)cn2)CC1] | tert-Butyl 4-(5-(4-(3,6-dichloro-2-fluorobenzoyl)-1H-pyrrole-2-carbox-amido)pyr-imidin-2-yl)piperazine-1-carboxylate | 2 | 1.46 (9H, s, C(CH₃)₃, 3.40-3.47 (4H, m, 2 × CH₂-piperazine), 3.70-3.76 (4H, m, 2 × CH₂-piperazine), 7.44 (1H, s, H-pyrrole), 7.56 (1H, d, J = 8.6 Hz, H-5'), 7.82 (1H, app t, J = 8.6 Hz, H-4'), 8.67 (2H, s, 2 × H-pyrimidine), 10.10 (1H, s, CO—NH), 12.79 (1H, s, NH) | 563.1 |
| 19. | 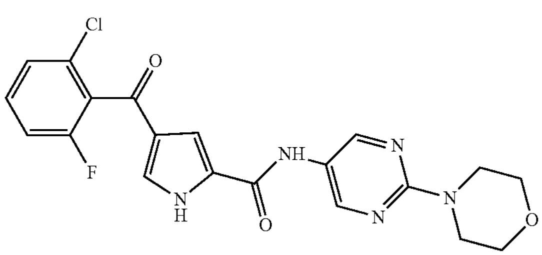 [SMILES: O=C(Nc1cnc(N2CCOCC2)nc1)c1cc(C(=O)c2c(F)cccc2Cl)c[nH]1] | 4-(2-Chloro-6-fluorobenzoyl)-N-(2-morpholino-pyrimidin-5-yl)-1H-pyrrole-2-carboxamide | 2 | 3.70 (8H, s, 4 × CH₂-morpholine), 7.41 (1H, m, H-pyrrole), 7.44 (1H, app. t, J = 8.3 Hz, H-5'), 7.48-7.52 (2H, m, H-pyrrole and H-3'), 7.62 (1H, td, J = 6.3 and 8.3 Hz, H-4'), 8.68 (2H, s, 2 × H-pyrimidine), 10.10 (CO—NH), 12.72 (NH-pyrrole) | 430.1 |
| 20. | 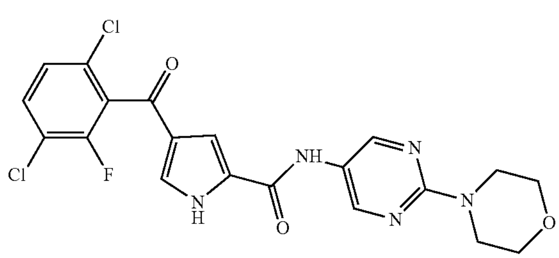 [SMILES: O=C(Nc1cnc(N2CCOCC2)nc1)c1cc(C(=O)c2c(Cl)ccc(Cl)c2F)c[nH]1] | 4-(3,6-Dichloro-2-fluorobenzoyl)-N-(2-morpholino-pyrimidin-5-yl)-1H-pyrrole-2-carboxamide | 2 | 3.70 (8H, s, 4 × CH₂-morpholine), 7.44 (1H, s, H-pyrrole), 7.56 (1H, d, J = 8.4 Hz, H-5'), 7.65 (1H, s, H-pyrrole), 7.82 (app t, J = 8.4 H, H-4'), 8.68 (2H, s, 2 × H-pyrimidine), 10.10 (1H, s, CO—NH), 12.79 (1H, s, NH) | 464.1 |

TABLE 2-continued

| Ex. | Structure | Name | General prep | 1H NMR Data | MS |
|---|---|---|---|---|---|
| 21. | 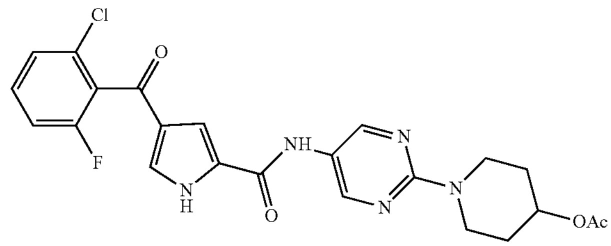 [SMILES: CC(=O)OC1CCN(c2ncc(NC(=O)c3cc(C(=O)c4c(F)cccc4Cl)c[nH]3)cn2)CC1] | 1-(5-(4-(2-Chloro-6-fluorobenzoyl)-1H-pyrrole-2-carboxamido)pyrimidin-2-yl)piperidin-4-yl acetate | 2 | $^1$H NMR (500 MHz; DMSO-d$_6$) $\delta_H$ 1.51-1.61 (2H, m, 2 × H-piperidine), 1.88-1.95 (2H, m, 2 × H-piperidine), 2.06 (3H, s, COCH$_3$), 3.45-3.53 (2H, m, 2 × H-piperidine), 4.15-4.22 (2H, m, 2 × H-piperidine), 4.92-4.99 (1H, m, CHOAc), 7.40 (1H, s, H-pyrrole), 7.44 (1H, app t, J = 8.5 Hz, H-5'), 7.48-7.53 (2H, m, H-pyrrole and H-3'), 7.62 (1H, td, J = 6.1 and 8.5 Hz, H-4'), 8.64 (2H, s, 2 × H-pyrimidine), 10.07 (1H, s, CO—NH), 12.71 (1H, s, NH-pyrrole) | 486.1 329 |
| 22. | 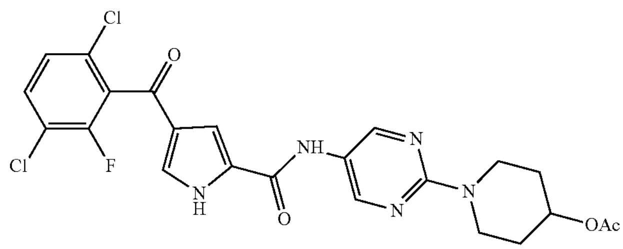 [SMILES: CC(=O)OC1CCN(c2ncc(NC(=O)c3cc(C(=O)c4c(Cl)ccc(Cl)c4F)c[nH]3)cn2)CC1] | 1-(5-(4-(3,6-Dichloro-2-fluorobenzoyl)-1H-pyrrole-2-carboxamido)pyrimidin-2-yl)piperidin-4-yl acetate | 2 | 1.50-1.61 (2H, m, 2 × H-piperidine), 1.87-1.96 (2H, m, 2 × H-piperidine), 2.06 (3H, s, COCH$_3$), 3.46-3.53 (2H, m, 2 × H-piperidine), 4.16-4.23 (2H, m, 2 × H-piperidine), 4.92-4.99 (1H, m, CHOAc), 7.44 (1H, s, H-pyrrole), 7.56 (1H, dd, J = 1.2 and 8.7 Hz, H-5'), 7.64 (1H, s, H-pyrrole), 7.82 (1H, app t, J = 8.7 Hz, H-4'), 8.65 (2H, s, 2 × H-pyrimidine), 10.07 (1H, s, CO—NH), 12.78 (1H, s, NH-pyrrole) | 518.3 |
| 23. | 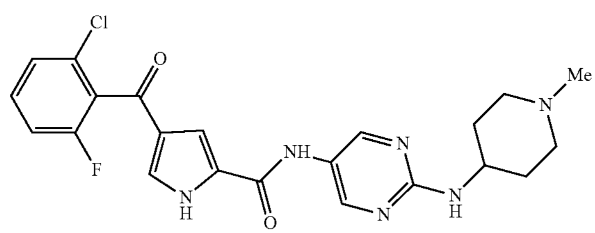 [SMILES: CN1CCC(Nc2ncc(NC(=O)c3cc(C(=O)c4c(F)cccc4Cl)c[nH]3)cn2)CC1] | 4-(2-Chloro-6-fluorobenzoyl)-N-(2-((1-methyl-piperidin-4-yl)amino)pyrimidin-5-yl)-1H-pyrrole-2-carboxamide | 2 | 1.53 (2H, qd, J = 3.1 and 11.4 Hz, 2 × H-piperidine), 1.80-1.89 (2H, m, 2 × H-piperidine), 1.98 (2H, app t, J = 11.4 Hz, 2 × H-piperidine), 2.19 (3H, s, CH$_3$), 2.73-2.82 (2H, m, 2 × H-piperidine), 3.60-3.71 (1H, m, CH—NH), 7.03 (1H, d, J = 7.9 Hz, NH-piperidine), 7.39 (1H, s, H-pyrrole), 7.43 (1H, app t, J = 8.4 Hz, H-5'), 7.48 (1H, s, H-pyrrole), 7.50 (1H, d, J = 8.4 Hz, H-3'), 7.62 (1H, td, J = 6.3 and 8.4 Hz, H-4'), 8.51 (2H, s, 2 × H-pyrimidine), 9.98 (1H, s, CO—NH), 12.68 (1H, s, NH-pyrrole) | 457.2 |
| 24. | 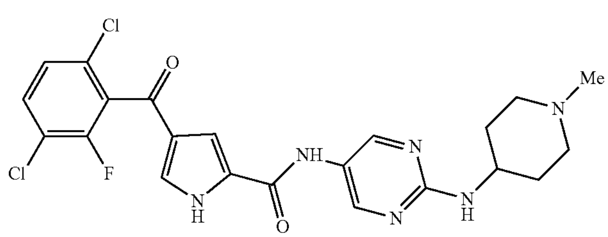 [SMILES: CN1CCC(Nc2ncc(NC(=O)c3cc(C(=O)c4c(Cl)ccc(Cl)c4F)c[nH]3)cn2)CC1] | 4-(3,6-Dichloro-2-fluorobenzoyl)-N-(2-((1-methyl-piperidin-4-yl)amino)pyrimidin-5-yl)-1H-pyrrole-2-carboxamide | 2 | 1.54 (2H, qd, J = 3.1 and 11.5 Hz, 2 × H-piperidine), 1.81-1.89 (2H, m, 2 × H-piperidine), 1.92-2.02 (2H, m, 2 × H-piperidine), 2.19 (3H, s, CH$_3$), 2.73-2.81 (2H, m, 2 × H-piperidine), 3.61-3.72 (1H, m, CH—NH-piperidine), 7.02 (1H, d, J = 7.8 Hz, NH-piperidine), 7.42 (1H, s, H-pyrrole), 7.56 (1H, d, J = 8.6 Hz, H-5'), 7.63 (1H, s, H-pyrrole), 7.82 (1H, app t, J = 8.6 Hz, H-4'), 8.51 (2H, s, 2 × H-pyrimidine), 9.98 (1H, s, CO—NH), 12.74 (1H, br s, NH-pyrrole); | 491.4, 493.4 |

TABLE 2-continued

| Ex. | Structure | Name | General prep | 1H NMR Data | MS |
|---|---|---|---|---|---|
| 25. | 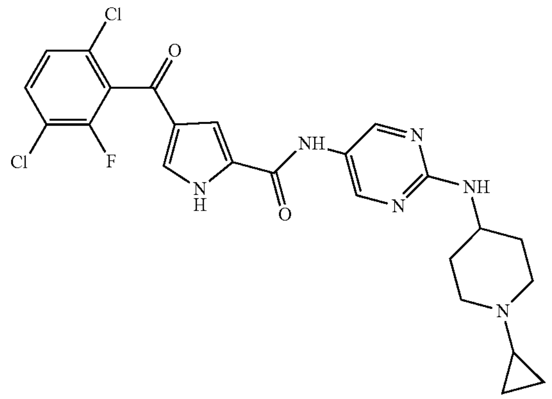 [SMILES: O=C(Nc1cnc(NC2CCN(C3CC3)CC2)nc1)c1cc(C(=O)c2c(Cl)ccc(Cl)c2F)c[nH]1] | N-(2-((1-Cyclopropyl-piperidin-4-yl)amino)pyrimidin-5-yl)-4-(3,6-dichloro-2-fluorobenzoyl)-1H-pyrrole-2-carboxamide | 2 | 0.29-0.34 (2H, m, 2 × H-cyclopropyl), 0.41-0.46 (2H, m, 2 × H-cyclopropyl), 1.45 (2H, app qd, J = 3.6 and 11.8 Hz, 2 × H-piperidine), 1.59-1.65 (1H, m, N—CH-cyclopropyl), 1.81-1.88 (2H, m, 2 × H-piperidine), 2.25 (2H, app td, J = 2.0 and 11.8 Hz, 2 × H-piperidine), 2.90-3.00 (2H, m, 2 × H-piperidine), 3.65-3.75 (1H, m, NH—CH-piperidine), 7.03 (1H, d, J = 7.9 Hz, NH), 7.42 (1H, s, H-pyrrole), 7.56 (1H, dd, J = 1.1 and 8.5 Hz, H-4'), 7.63 (1H, s, H-pyrrole), 7.82 (1H, app t, J = 8.5 Hz, H-5'), 8.51 (2H, s, 2 × H-pyrimidine) | 517.1 |
| 26. | 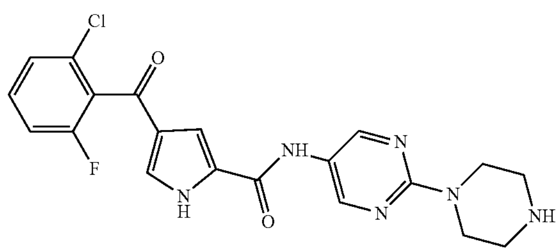 [SMILES: O=C(Nc1cnc(N2CCNCC2)nc1)c1cc(C(=O)c2c(F)cccc2Cl)c[nH]1] | 4-(2-Chloro-6-fluorobenzoyl)-N-(2-(piperazin-1-yl)pyrimidin-5-yl)-1H-pyrrole-2-carboxamide | 4 | 2.75-2.79 (4H, m, 2 × CH$_2$-piperazine), 3.64-3.68 (4H, m, 2 × CH$_2$-piperazine), 7.39 (1H, s, H-pyrrole), 7.43 (1H, app t, J = 8.4 Hz, H-5'), 7.49 (1H, s, H-pyrrole), 7.50 (1H, d, J = 8.4 Hz, H-3'), 7.62 (1H, app dt, J = 6.3 and 8.4 Hz, H-4'), 8.62 (2H, s, 2 × H-pyrimidine), 10.06 (1H, s, CO—NH); | 429.1 |
| 27. | 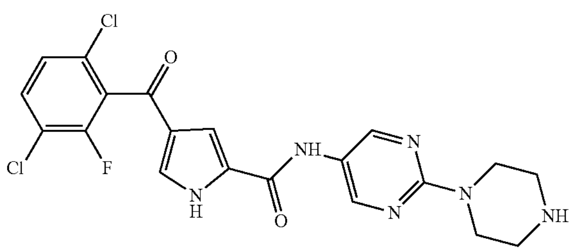 [SMILES: O=C(Nc1cnc(N2CCNCC2)nc1)c1cc(C(=O)c2c(Cl)ccc(Cl)c2F)c[nH]1] | 4-(3,6-Dichloro-2-fluorobenzoyl)-N-(2-(piperazin-1-yl)pyrimidin-5-yl)-1H-pyrrole-2-carboxamide | 4 | 2.75-2.79 (4H, m, 2 × CH$_2$-piperazine), 3.64-3.69 (4H, m, 2 × CH$_2$-piperazine), 7.42 (1H, s, H-pyrrole), 7.55 (1H, d, J = 8.6 Hz, H-5'), 7.63 (1H, s, H-pyrrole), 7.82 (1H, app t, J = 8.6 Hz, H-4'), 8.62 (2H, s, 2 × H-pyrimidine), 10.05 (1H, br s, CO—NH) | 463.1 |

Example 28: 4-(2-Chloro-6-fluorobenzoyl)-N-(2-(4-hydroxypiperidin-1-yl)pyrimidin-5-yl)-1H-pyrrole-2-carboxamide

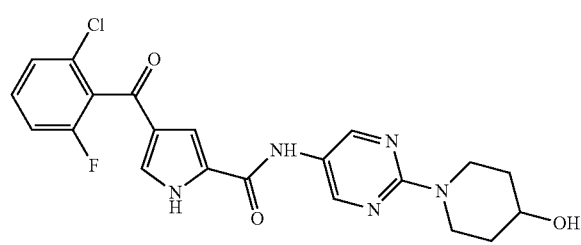 [SMILES: O=C(Nc1cnc(N2CCC(O)CC2)nc1)c1cc(C(=O)c2c(F)cccc2Cl)c[nH]1]

K$_2$CO$_3$ (37 mg, 0.27 mmol, 2 eq.) was added to a solution of Example 21 (65 mg, 0.13 mmol, 1 eq.) in a mixture of THF (2 mL), MeOH (2 mL), and H$_2$O (2 mL). The mixture was stirred at r.t for 18 h, partitioned between EtOAc (2×25 mL) and H$_2$O (20 mL), washed with brine, dried over MgSO$_4$ and the solvent removed in vacuo to give a pale yellow solid (55 mg, 93%); R$_f$ 0.3 (NH$_2$SiO$_2$, 5% MeOH/EtOAc); $^1$H NMR (500 MHz, DMSO-d$_6$) δ$_H$ 1.31-1.42 (2H, m, 2×H-piperidine), 1.76-1.84 (2H, m, 2×H-piperidine), 3.23-3.33 (2H, m, 2×H-piperidine), 3.72-3.80 (1H, m, CHOH), 4.23-4.30 (2H, m, 2×H-piperidine), 4.75 (1H, d, J=4.2 Hz, OH), 7.40 (1H, s, H-pyrrole), 7.44 (1H, app t, J=8.5 Hz, H-5'), 7.49 (1H, s, H-pyrrole), 8.23 (1H, d, J=8.5 Hz, H-3'), 7.62 (1H, td, J=6.1 and 8.5 Hz, H-4'), 8.61 (2H, s, 2×H-pyrimidine), 10.05 (1H, s, CO—NH), 12.70 (1H, s, NH-pyrrole); LCMS (ES+) m/z 444.4 (75.8%) [M($^{35,35}$Cl)+H]$^+$, 446.4 (24.2%) [M($^{35,37}$Cl)+H]$^+$; HRMS calc for C$_{21}$H$_{20}$$^{35}$Cl$_1$F$_1$N$_5$O$_3$ [M+H]$_+$ 444.1233, found 444.1225.

Example 29: 4-(3,6-Dichloro-2-fluorobenzoyl)-N-(2-(4-hydroxypiperidin-1-yl)pyrimidin-5-yl)-1H-pyrrole-2-carboxamide

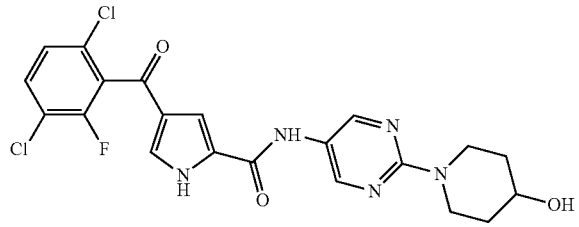 [SMILES: O=C(Nc1cnc(N2CCC(O)CC2)nc1)c1cc(C(=O)c2c(Cl)ccc(Cl)c2F)c[nH]1]

K$_2$CO$_{3(s)}$ (42 mg, 0.31 mmol, 2 eq.) was added to a solution of Example 22 (80 mg, 0.15 mmol, 1 eq.) in a mixture of THF (2 mL), MeOH (2 mL), and H$_2$O (2 mL). The mixture was stirred at r.t for 18 h, partitioned between EtOAc (2×25 mL) and H$_2$O (20 mL), washed with brine, dried over MgSO$_4$ and the solvent removed in vacuo to give a pale yellow solid (40 mg, 54%); R$_f$ 0.5 (EtOAc); m.p. 200-202° C.; λ$_{max}$(EtOH)/nm 289, 227; IR ν$_{max}$/cm$^{-1}$ 3251, 2934, 1638, 1585; $^1$H NMR (500 MHz; DMSO-d$_6$) δ$_H$ 1.31-1.41 (2H, m, 2×H-piperidine), 1.76-1.86 (2H, m, 2×H-piperidine), 3.28 (2H, ddd, J=3.2 Hz, 10.0 and 13.3 Hz, 2×CH—N piperidine), 3.72-3.80 (1H, m, CH—OH), 4.22-4.32 (2H, m, 2×CH—N piperidine), 4.75 (1H, d, J=4.3 Hz, OH), 7.43 (1H, s, H-pyrrole), 7.56 (1H, dd, J=1.3 and 8.6 Hz, H-5'), 7.64 (1H, s, CH-pyrrole), 7.83 (1H, app t, J=8.6 Hz, H-4'), 8.62 (2H, s, 2×H-pyrimidine), 10.05 (1H, s, CO—NH), 12.77 (1H, s, NH-pyrrole); $^{19}$F NMR (470 MHz; DMSO-d$_6$) δ$_F$ −116.68; $^{13}$C NMR (125 MHz; DMSO-d$_6$) δ$_C$ 33.9 (2×CH$_2$-piperidine), 41.5 (2×CH$_2$-piperidine), 66.2 (CHOH), 111.0 (CH-pyrrole), 119.3 (d, J$_{CF}$=18.1 Hz, C-3'), 123.2 (C-pyrimidine), 124.7 (C-pyrrole), 126.9 (d, J$_{CF}$=3.6 Hz, C-5'), 128.4 (C-pyrrole), 129.2 (d, J$_{CF}$=17.5 Hz, C-1'), 129.3 (C-6'), 129.9 (CH-pyrrole), 131.8 (C-4'), 151.2 (2×CH-pyrimidine), 153.8 (d, J$_{CF}$=248.4 Hz, C-2'), 158.4 (CO—NH), 158.4 (C-pyrimidine), 182.6 (CO); HRMS calc for C$_{21}$H$_{19}$$^{35}$Cl$_2$F$_1$N$_5$O$_3$ [M+H]$^+$ 478.0843, found 478.0834.

By following methods similar and/or analogous to those described herein, the compounds set out in the Table 3 below were prepared from the corresponding starting materials.

Example 32: 4-(3,6-Dichloro-2-fluorobenzoyl)-N-(6-((1-methylpiperidin-4-yl)amino)pyridin-3-yl)-1H-pyrrole-2-carboxamide

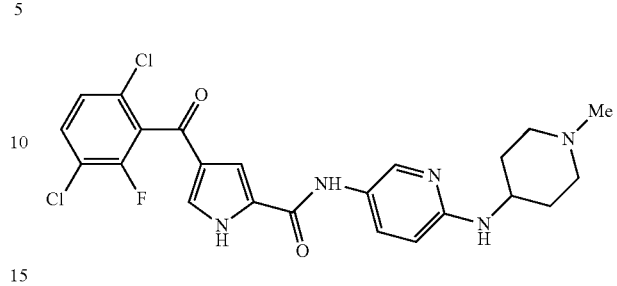

1-Methyl-4-aminopiperidine (794 μL, 6.32 mmol, 2 eq.), 2-chloro-5-nitropyridine (500 mg, 3.15 mmol, 1 eq.) and K$_2$CO$_3$ (304 μL, 2.18 mmol, 1.1 eq.) were combined in THF (10 mL) and heated to 80° C. for 3 h. The mixture was allowed to cool to r.t., partitioned between EtOAc (2×50 mL) and water (30 mL), washed with brine, dried over MgSO$_4$ and solvent removed in vacuo. The residue was purified by MPLC on SiO$_2$ with gradient elution from 50% to 100% EtOAc/petrol to give N-(1-Methylpiperidin-4-yl)-5-nitropyridin-2-amine (417 mg, 56%); $^1$H NMR (500 MHz; DMSO-d$_6$) δ$_H$ 1.46-1.58 (2H, m, 2×H-piperidine), 1.85-1.93 (2H, m, 2×H-piperidine), 1.97-2.06 (2H, m, 2×H-piperidine), 2.20 (3H, s, CH$_3$), 2.73-2.81 (2H, m, 2×H-piperidine), 3.85-3.97 (1H, m, CH-piperidine), 6.58 (1H, d, J=9.4 Hz, H-3-pyridine), 8.09 (2H, m, NH and H-4-pyridine), 8.94 (1H, d, J=2.8 Hz, H-6-pyridine); HRMS calc for C$_{11}$H$_{17}$N$_4$O$_2$ [M+H]$^+$ 237.1346, found 237.1340.

Prepared according to general procedure 5 using N-(1-Methylpiperidin-4-yl)-5-nitropyridin-2-amine (400 mg, 1.69 mmol) and MeOH (35 mL) for 18 h to give N$^2$-(1-Methylpiperidin-4-yl)pyridine-2,5-diamine (330 mg, 95%); $^1$H NMR (500 MHz; DMSO-d$_6$) δ$_H$ 1.37 (2H, qd, J=11.3 and 3.5 Hz, 2×CH-piperidine), 1.82-1.90 (2H, m, 2×CH-piperidine), 1.93-2.01 (2H, m, 2×CH-piperidine), 2.18 (CH$_3$),

TABLE 3

| Ex. | Structure | Name | General prep | 1H NMR Data | MS |
|---|---|---|---|---|---|
| 30. | 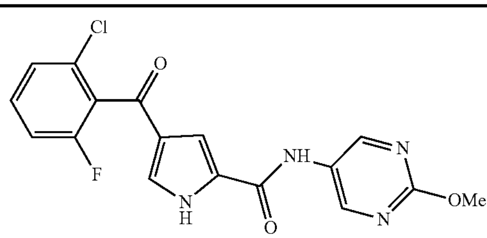 | 4-(2-Chloro-6-fluorobenzoyl)-N-(2-methoxy-pyrimidin-5-yl)-1H-pyrrole-2-carboxamide | 2 | 3.94 (3H, s, OMe), 7.41-7.48 (2H, m, H-pyrrole and H-5'), 7.51 (1H, d, J = 8.3 Hz, H-3'), 7.54 (1H, br s, H-pyrrole), 7.62 (1H, td, J = 6.3 and 8.3 Hz, H-4'), 8.90 (2H, s, 2 × CH-pyrimidine), 10.34 (1H, s, NH), 12.78 (1H, br s, NH) | 375.3 |
| 31. | 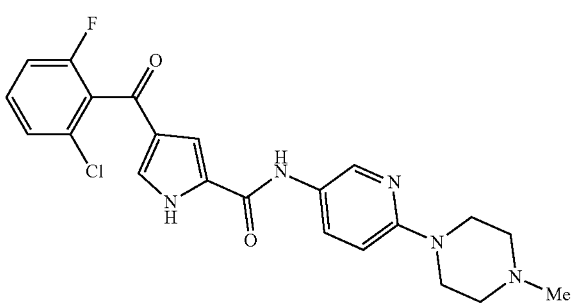 [SMILES: CN1CCN(c2ccc(NC(=O)c3cc(C(=O)c4c(F)cccc4Cl)c[nH]3)cn2)CC1] | 4-(2-Chloro-6-fluorobenzoyl)-N-(6-(4-methyl-piperazin-1-yl)pyridin-3-yl)-1H-pyrrole-2-carboxamide | 2 | 2.25 (3H, s, CH$_3$), 2.41-2.45 (4H, m, 2 × CH$_2$-piperazine), 3.44-3.49 (4H, m, 2 × CH$_2$-piperazine), 6.88 (1H, d, J = 9.0 Hz, H-3-pyridine), 7.40-7.48 (3H, m, H-3' and 2 × H-pyrrole), 7.50 (1H, d, J = 8.2 Hz, H-3'), 7.62 (1H, qd, J = 6.2 and 8.2 Hz, H-4'), 7.87 (1H, dd, J = 2.5 and 9.0 Hz, H-4-pyridine), 8.43 (1H, d, J = 2.5 Hz, H-6-pyridine), 9.99 (1H, s, CO—NH), 12.64 (1H, s, NH-pyrrole) | 442.1 432 |

2.69-2.76 (2H, m, 2×CH-piperidine), 3.42-3.52 (1H, m, CH-piperidine), 4.26 (2H, s, NH$_2$), 5.39 (1H, d, J=5.9 Hz, NH), 6.31 (1H, d, J=8.7 Hz, H-3-pyridine), 6.83 (1H, dd, J=2.7 and 8.7 Hz, H-4-pyridine), 7.46 (1H, d, J=2.7 Hz, H-6-pyridine); HRMS calc for C$_{11}$H$_{19}$N$_4$ [M+H]$^+$ 207.1604, found 207.1601.

N$^2$-(1-Methylpiperidin-4-yl)pyridine-2,5-diamine (150 mg, 0.73 mmol, 1.5 eq) was added to pyrrole acid (147 mg, 0.48 mmol, 1 eq.), pyridine (39 µL, 0.48 mmol, 1 eq) and PyBrOP (339 mg, 0.73 mmol, 1.5 eq) in MeCN (2 mL), the mixture was stirred at r.t. for 1 h and then partitioned between EtOAc (2×30 mL) and H$_2$O (20 mL). The organic layers were combined, washed with brine, dried (MgSO$_4$) and the solvent removed in vacuo. The residue was purified by MPLC on NH$_2$SiO$_2$ with gradient elution from 3% to 15% MeOH/CH$_2$Cl$_2$ to give a beige solid, which was re-purified by MPLC on SiO$_2$ with gradient elution from 93/3/0.3 to 88/12/1.2 EtOAc/MeOH/NH$_4$OH to give a white solid (45 mg, 19%); $^1$H NMR (500 MHz; DMSO-d$_6$) δ$_H$ 1.45 (2H, qd, J=11.0 and 3.8 Hz, 2×CH-piperidine), 1.86-1.93 (2H, m, 2×CH-piperidine), 1.96-2.05 (2H, m, 2×CH-piperidine), 2.19 (3H, s, CH$_3$), 2.72-2.79 (2H, m, 2×CH-piperidine), 3.59-3.69 (1H, m, CH—NH-piperidine), 6.33 (1H, d, J=7.8 Hz, NH-piperidine), 6.50 (1H, d, J=8.9 Hz, H-3-pyridine), 7.42 (1H, s, H-pyrazole), 7.55 (1H, dd, J=1.0 and 8.6 Hz, H-5'), 7.58 (1H, s, H-pyrazole), 7.63 (1H, dd, J=2.6 and 9.0 Hz, H-4-pyridine), 7.81 (1H, app t, J=8.6 Hz, H-4'), 8.23 (1H, d, J=2.6 Hz, H-6-pyridine), 9.85 (1H, s, CO—NH), 12.59 (1H, br s, NH-pyrrole); HRMS calcd for C$_{23}$H$_{23}$$^{35}$Cl$_2$F$_1$N$_5$O$_2$ [M+H]$^+$ 490.1207, found 490.1193.

By following methods similar and/or analogous to those described herein, the compounds set out in the Table 4 below were prepared from the corresponding starting materials.

Example 35: 4-(2-Chloro-6-fluorobenzoyl)-N-(2-(pyrrolidin-1-yl)pyridin-4-yl)-1H-pyrrole-2-carboxamide

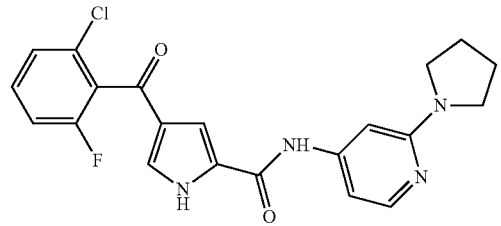

Example 33 (60 mg, 0.15 mmol, 1 eq.) and pyrrolidine (20 µL, 0.30 mmol, 2 eq.) were combined in NMP (1 mL) and heated under microwave irradiation at 250° C. for 3 h. The solvent was removed in vacuo and the residue was purified by MPLC on NH$_2$SiO$_2$ with gradient elution from 100% CH$_2$Cl$_2$ to 3% MeOH/CH$_2$Cl$_2$ to give a pale brown solid (27 mg, 42%); R$_f$ 0.5 (NH$_2$SiO$_2$, 5% MeOH/CH$_2$Cl$_2$); m.p. 198-201° C.; λ$_{max}$(EtOH)/nm 293, 252; IR ν$_{max}$/cm$^{-1}$ 3352, 2958, 2854, 1634, 1571; $^1$H NMR (500 MHz; DMSO-d$_6$) δ$_H$ 1.95-2.01 (4H, m, 2×CH$_2$ pyrrolidine), 3.36-3.42 (4H, m, 2×CH$_2$—N-pyrrolidine), 6.89 (d, 1H, J=1.5 Hz, H-3-pyridine), 7.02 (1H, dd, J=1.5 and 5.7 Hz, H-5-pyridine), 7.44 (1H, app t, J=8.4 Hz, H-5'), 7.48-7.56 (3H, m, H-3-pyrrole, H-5-pyrrole and H-3'), 7.62 (1H, td, J=6.5 and 8.4 Hz, H-4'), 7.98 (1H, d, J=5.7 Hz, H-6-pyridine), 10.09 (1H, s, CO—NH), 12.70 (1H, br s, NH-pyrrole); $^{19}$F NMR (470 MHz; DMSO-d$_6$) δ$_F$ –114.31; $^{13}$C NMR (125 MHz; DMSO-d$_6$) δ$_C$ 25.0. (2×CH$_2$-pyrrolidine), 46.3 (2×CH$_2$—N-pyrrolidine), 95.2 (C-3-pyridine), 103.0 (C-5-pyridine), 111.6 (CH-pyrrole), 115.0 (d, J$_{CF}$=21.4 Hz, C-5'), 125.3 (C-pyrrole), 125.9 (d, J$_{CF}$=2.7 Hz, C-3'), 128.3 (C-pyrrole), 129.5 (CH-pyrrole), 130.4 (d, J$_{CF}$=6.0 Hz, C-2'), 131.9 (d, J$_{CF}$=9.0 Hz, C-4'), 146.4 (C-2-pyridine), 148.4 (C-6-pyridine), 157.9

TABLE 4

| Ex. | Structure | Name | General prep | 1H NMR Data | MS |
|---|---|---|---|---|---|
| 33. | 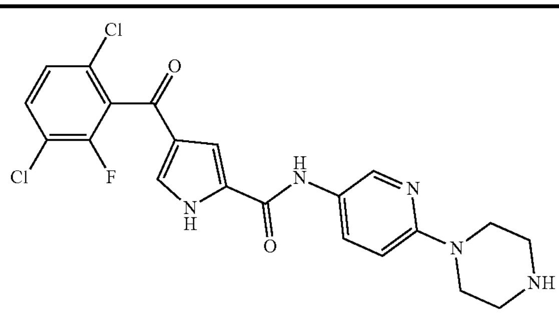 | 4-(3,6-Dichloro-2-fluorobenzoyl)-N-(6-(piperazin-1-yl)pyridin-3-yl)-1H-pyrrole-2-carboxamide | 4 | 2.78-2.84 (4H, m, 4 × H-piperazine), 3.36-3.41 (4H, m, 4 × H-piperazine), 6.85 (1H, d, J = 9.1 Hz, H-3-pyridine), 7.45 (1H, s, H-pyrrole), 7.55 (1H, dd, J = 1.2 and 8.6 Hz, H-3'), 7.61 (1H, s, H-pyrrole), 7.82 (1H, app t, J = 8.6 Hz, H-4'), 7.86 (1H, dd, J = 2.6 and 9.1 Hz, H-4-pyridine), 8.43 (1H, d, J = 2.6 Hz, H-6-pyridine), 9.98 (1H, s, CO—NH) | 462.0 884. |
| 34. | 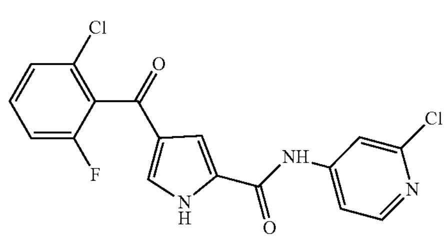 [SMILES: O=C(Nc1ccnc(Cl)c1)c1cc(C(=O)c2c(F)cccc2Cl)c[nH]1] | 4-(2-Chloro-6-fluorobenzoyl)-N-(2-chloropyridin-4-yl)-1H-pyrrole-2-carboxamide | 3 | 7.44 (1H, app t, J = 8.4 Hz, H-5'), 7.51 (1H, d, J = 8.4 Hz, C-3'), 7.57 (1H, s, H-pyrrole), 7.58 (1H, s, H-pyrrole), 7.63 (1H, td, J = 6.3 and 8.4 Hz, H-4'), 7.73 (1H, dd, J = 1.7 and 5.7 Hz, C-5-pyridine), 7.92 (1H, d, J = 1.7 Hz, C-3-pyridine), 8.33 (1H, d, J = 5.7 Hz, C-6-pyridine), 10.55 (1H, s, CO—NH), 12.85 (1H, s, NH-pyrrole) | 375.8 |

(C-4-pyridine), 158.6 (d, $J_{CF}$=246.7 Hz, C-6'), 158.8 (CO—NH), 183.9 (CO); MS (ES+) m/z 413.2 (75.8%) [M($^{35}$Cl)+H]$_+$, 415.2 (24.2%) [M($^{37}$Cl)+H]$^+$; HRMS calcd for $C_{21}H_{19}{}^{35}Cl_1F_1N_4O_2$ [M+H]$^+$ 413.1175, found 413.1167.

Example 36: 4-(2-Chloro-6-fluorobenzoyl)-N-(2-(4-methylpiperazin-1-yl)pyridin-4-yl)-1H-pyrrole-2-carboxamide

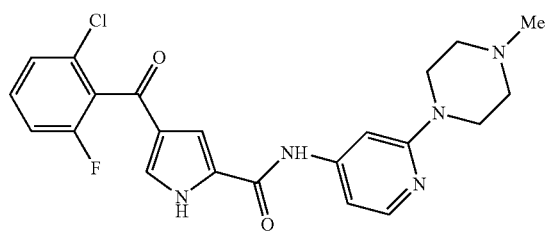 [SMILES: CN1CCN(c2cc(NC(=O)c3cc(C(=O)c4c(F)cccc4Cl)c[nH]3)ccn2)CC1]

Example 34 (60 mg, 0.16 mmol), 1-methylpiperazine (36 µL, 0.32 mmol, 2 eq.), and NMP (1 mL) were combined and heated to 250° C. under microwave irradiation for 3 h. The solvent was removed in vacuo and the residue was purified by MPLC on SiO$_2$ with a gradient elution from 99:1:0.1 to 95:5:0.5 EtOAc/MeOH/NH$_4$OH. Product containing fractions were combined, evaporated and the residue re-was purified by MPLC on NH$_2$SiO$_2$ with gradient elution from 100% CH$_2$Cl$_2$ to 5% MeOH/CH$_2$Cl$_2$ to give a pale brown solid (10 mg, 14%); R$_f$ 0.25 (NH$_2$SiO$_2$, 5% MeOH/EtOAc); m.p. 275° C. dec.; $\lambda_{max}$(EtOH)/nm 292, 250; IR $v_{max}$/cm$^{-1}$ 3245, 1655, 1621, 1573; $^1$H NMR (500 MHz; DMSO-d$_6$) $\delta_H$ 2.25 (3H, s, CH$_3$), 2.41-2.46 (4H, m, 2×CH$_2$-piperazine), 3.43-3.49 (4H, m, 2×CH$_2$-piperazine), 7.15 (1H, dd, J=1.3 and 5.5 Hz, H-5-pyridine), 7.19 (1H, s, H-pyrrole), 7.44 (1H, app t, J=8.5 Hz, H-5'), 7.48-7.58 (3H, m, H-pyrrole, H-3' and H-3-pyridine), 7.62 (1H, dt, J=6.1 and 8.5 Hz, H-4'), 8.05 (1H, d, J=5.5 Hz, H-6-pyridine), 10.11 (1H, s, CO—NH), 12.70 (1H, br s, NH-pyrrole); $^{19}$F NMR (470 MHz; DMSO-d$_6$) $\delta_F$ −114.31; $^{13}$C NMR (125 MHz; DMSO-d$_6$) $\delta_C$ 44.7 (2×CH$_2$-piperazine), 45.8 (CH$_3$), 54.3 (2×CH$_2$-piperazine), 96.1 (C-3-pyridine), 104.7 (C-5-pyridine), 111.7 (CH-pyrrole), 115.0 (d, $J_{CF}$=21.5 Hz, C-5'), 125.3 (C-pyrrole), 125.9 (d, $J_{CF}$=3.1 Hz, C-3'), 128.0 (d, $J_{CF}$=23.2 Hz, C-1'), 128.2 (C-pyrrole) 130.0 (CH-pyrrole), 130.4 (d, $J_{CF}$=5.9 Hz, C-2'), 131.9 (d, $J_{CF}$=9.1 Hz, C-4'), 147.1 (C-2-pyridine), 148.3 (C-6-pyridine), 158.6 (d, $J_{CF}$=247.0 Hz, C-6'), 158.9 (CO—NH), 160.0 (C-4-pyridine), 184.0 (CO); HRMS calc for $C_{22}H_{22}{}^{35}Cl_1F_1N_5O_2$ [M+H]$^+$ 442.1441, found 442.1430.

Example 37: 4-(3,6-Dichloro-2-fluorobenzoyl)-N-(2-(4-methylpiperazin-1-yl)pyridin-4-yl)-1H-pyrrole-2-carboxamide

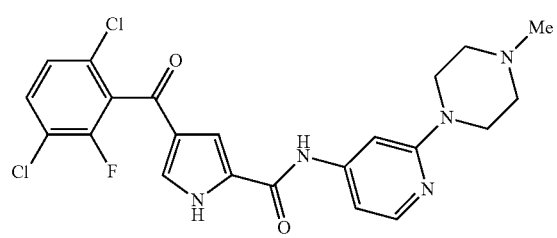 [SMILES: CN1CCN(c2cc(NC(=O)c3cc(C(=O)c4c(Cl)ccc(Cl)c4F)c[nH]3)ccn2)CC1]

4-(3,6-Dichloro-2-fluorobenzoyl)-N-(pyridin-4-yl)-1H-pyrrole-2-carboxamide was prepared according to general procedure C using 4 (500 mg, 1.65 mmol, 1 eq.), 4-aminopyridine (388 mg, 4.13 mmol, 2.5 eq), PCl$_3$ (144 µL, 1.65 mmol, 1 eq.) and MeCN (5 mL). Purification by MPLC on SiO$_2$ with a gradient elution from 2% to 10% MeOH/CH$_2$Cl$_2$ gave a white solid (360 mg, 58%); $^1$H NMR (500 MHz; DMSO-d$_6$) $\delta_H$ 7.56 (1H, dd, J=1.3 and 8.6 Hz, H-5'), 7.61 (1H, s, H-pyrrole), 7.68-7.71 (1H, m, H-pyrrole), 7.77 (1H, dd, J=1.5 and 4.8 Hz, 2×H-pyridine), 7.83 (1H, app t, J=8.6 Hz, H-4'), 8.50 (2H, dd, J=1.5 and 4.8 Hz, 2×H-pyridine), 10.39 (1H, s, CO—NH), 12.87 (1H, s, NH-pyrrole); HRMS calcd for $C_{17}H_{11}{}^{35}Cl_1F_1N_3O_2$ [M+H]$^+$ 378.0207, found 378.0210.

mCPBA (339 mg, 1.96 mmol, 1.5 eq.) was added to a suspension of 4-(3,6-Dichloro-2-fluorobenzoyl)-N-(pyridin-4-yl)-1H-pyrrole-2-carboxamide (340 mg, 0.9 mmol, 1 eq.) in MeCN (8 mL), and the mixture was stirred at r.t. for 18 h. Two drops of water were added, the solvent removed in vacuo and the residue was purified by MPLC on SiO$_2$ with a gradient elution from 4% to 15% MeOH/EtOAc gave 4-(4-(3,6-Dichloro-2-fluorobenzoyl)-1H-pyrrole-2-carboxamido)pyridine-1-oxide as a white solid (340 mg, 72%); $^1$H NMR (500 MHz; DMSO-d$_6$) $\delta_H$ 7.54-7.58 (2H, m, H-pyrrole and H-5'), 7.69 (1H, dd, J=1.3 and 3.3 Hz, H-pyrrole), 7.78-7.85 (3H, m, 2×H-pyridine and H-4'), 8.17-8.21 (2H, m, 2×H-pyridine), 10.51 (1H, s, CO—NH), 12.87 (1H, s, NH-pyrrole); HRMS calcd for $C_{17}H_{11}{}^{35}Cl_2F_1N_3O_3$ [M+H]$^+$ 394.0156, found 394.0154.

PyBrOP (154 mg, 0.33 mmol, 1.3 eq.) was added to a suspension of 4-(4-(3,6-Dichloro-2-fluorobenzoyl)-1H-pyrrole-2-carboxamido)pyridine-1-oxide (100 mg, 0.25 mmol, 1 eq.), 1-methylpiperazine (36 µL, 0.32 mmol, 1.25 eq.) and Hunig's base (165 µL, 0.95 mmol, 3.75 eq.) in DCM (1.6 mL) and the reaction was stirred at r.t for 18 h. The mixture was partitioned between EtOAc (2×30 mL) and H$_2$O (20 mL), washed with brine, dried over MgSO$_4$, and the solvent removed in vacuo. The residue was purified by MPLC on SiO$_2$ with gradient elution from 3% to 8% MeOH/DCM to give impure product (52 mg). This was further purified by HPLC to give a white solid (20 mg, 17%); $^1$H NMR (500 MHz; DMSO-d$_6$) 2.25 (CH$_3$), 2.41-2.46 (4H, m, H-piperazine), 3.44-3.50 (4H, m, H-piperazine), 7.16 (1H, dd, J=1.6 and 5.5 Hz, H-5-pyridine), 7.19 (H-3-pyridine), 7.53-7.58 (2H, m, H-pyrrole and H-5'), 7.68 (1H, s, H-pyrrole), 7.83 (1H, app t, J=8.4 Hz, H-4'), 8.05 (1H, d, J=5.7 Hz, H-6-pyridine), 10.13 (1H, s, CO—NH), 12.80 (1H, br s, NH-pyrrole); HRMS calcd for $C_{22}H_{21}{}^{35}Cl_2F_1N_5O_2$ [M+H]$^+$ 476.1051, found 476.1044.

Example 38: 4-(3,6-Dichloro-2-fluorobenzoyl)-N-(2-morpholinopyridin-4-yl)-1H-pyrrole-2-carboxamide

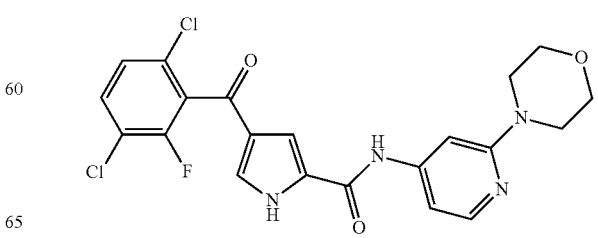

PyBrOP (154 mg, 0.33 mmol, 1.3 eq.) was added to a suspension of 4-(4-(3,6-Dichloro-2-fluorobenzoyl)-1H-pyrrole-2-carboxamido)pyridine-1-oxide (100 mg, 0.25 mmol, 1 eq.), morpholine (28 μL, 0.37 mmol, 1.25 eq.) and Hunig's base (165 μL, 0.95 mmol, 3.75 eq.) in $CH_2Cl_2$ (1.6 mL) and the reaction was stirred at r.t for 18 h. The mixture was partitioned between $CH_2Cl_2$ (2×20 mL) and 10% $K_2CO_3$ (20 mL, aqueous w/v), washed with brine, dried over $MgSO_4$, and the solvent removed in vacuo. The residue was purified by MPLC on C18 reverse phase $SiO_2$ with gradient elution from 60:40:0.4 $MeOH/H_2O/HCO_2H$ to 99.9:0.1 $MeOH/HCO_2H$. Product containing fractions were re-purified by MPLC on $NH_2SiO_2$ with gradient elution from $CH_2Cl_2$ to 4% $MeOH/CH_2Cl_2$ to give a white solid (16 mg, 14%); $^1H$ NMR (500 MHz; DMSO-$d_6$) 3.41-3.45 (4H, m, H-morpholine), 3.72-3.77 (4H, m, H-morpholine), 7.18-7.22 (2H, m, H-3 pyridine and H-5-pyridine), 7.54-7.59 (2H, m, H-pyrrole and H-5'), 7.68 (1H, br s, H-pyrrole), 7.83 (1H, app t, J=8.4 Hz, H-4'), 8.06-8.09 (1H, m, H-6-pyridine), 10.16 (1H, s, CO—NH), 12.79 (1H, br s, NH-pyrrole).

By following methods similar and/or analogous to those described herein, the compounds set out in the Table 5 below were prepared from the corresponding starting materials.

clear oil (304 mg, 84%); $^1H$ NMR (500 MHz; DMSO-$d_6$) $\delta_H$ 1.24 (2H, qd, J=3.6 and 12.5 Hz, 2×H-piperidine), 1.42-1.50 (2H, m, 2×H-piperidine), 1.77-1.89 (3H, m, 3×H-piperidine), 2.16 (3H, s, $CH_3$), 2.72-2.80 (2H, m, 2×H-piperidine), 4.11 (2H, d, J=7.3 Hz, pyrazole-$CH_2$-piperidine), 8.30 (1H, s, H-pyrazole), 8.93 (1H, s, H-pyrazole); HRMS calc for $C_{10}H_{17}N_4O_2$ $[M+H]^+$ 225.1346, found 225.1341.

1-((1-Methylpiperidin-4-yl)methyl)-1H-pyrazol-4-amine was prepared according to general procedure E using methyl-4-((4-nitro-1H-pyrazol-1-yl)methyl)piperidine (190 mg, 0.85 mmol) and MeOH (20 mL) for 2 h to give a pale brown oil (150 mg, 91%); $^1H$ NMR (500 MHz; DMSO-$d_6$) $\delta_H$ 1.18 (2H, qd, J=12.5 and 3.7 Hz, 2×H-piperidine), 1.39-1.47 (2H, m, 2×H-piperidine), 1.61-1.72 (1H, m, H-piperidine), 1.74-1.84 (2H, m, 2×H-piperidine), 2.15 (3H, s, $CH_3$), 2.70-2.78 (2H, m, 2×H-piperidine), 3.80 (2H, d, J=7.3 Hz, N—$CH_2$—CH), 6.91 (1H, s, H-pyrazole), 7.02 (1H, s, H-pyrazole)

1-((1-Methylpiperidin-4-yl)methyl)-1H-pyrazol-4-amine (140 mg, 0.43 mmol, 1.5 eq) was added to 4-(3,6-Dichloro-2-fluorobenzoyl)-1H-pyrrole-2-carboxylic acid (87 mg, 0.29 mmol, 1 eq.), pyridine (23 μL, 0.29 mmol, 1 eq) and PyBrOP

TABLE 5

| Ex. | Structure | Name | General prep | 1H NMR Data | MS |
|---|---|---|---|---|---|
| 39. | 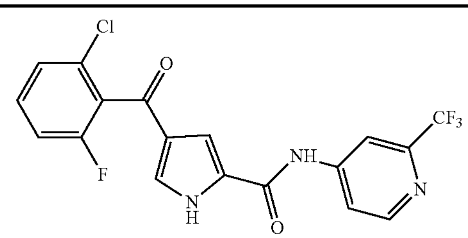 | 4-(2-Chloro-6-fluorobenzoyl)-N-(2-(trifluoromethyl)pyridin-4-yl)-1H-pyrrole-2-carboxamide | 3 | 7.42 (1H, app t, J = 8.2 Hz, H-5'), 7.49 (1H, d, J = 8.2 Hz, H-3'), 7.56 (1H, s, H-pyrrole), 7.57 (1H, s, H-pyrrole), 7.60 (1H, td, J = 6.0 and 8.2 Hz, H-4'), 8.03 (1H, dd, J = 1.9 and 5.6 Hz, H-5-pyridine), 8.23 (1H, d, J = 1.9 Hz, H-3-pyridine), 8.65 (1H, d, J = 5.6 Hz, H-6-pyridine), 10.67 (CO—NH), 12.85 (NH-pyrrole) | 412.2 |
| 40. | 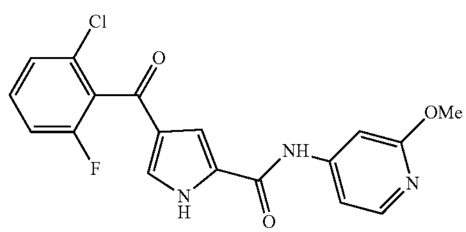 [SMILES: COc1cc(NC(=O)c2cc(C(=O)c3c(F)cccc3Cl)c[nH]2)ccn1] | 4-(2-Chloro-6-fluorobenzoyl)-N-(2-methoxypyridin-4-yl)-1H-pyrrole-2-carboxamide | 2 | 3.86 (3H, s, $CH_3$), 7.31 (1H, s, H-pyrrole), 7.32 (1H, d, J = 1.6 Hz, H-3-pyridine), 7.44 (1H, app t, J = 8.5 Hz, H-5'), 7.49-7.57 (3H, m, H-pyrrole, H-3' and H-5-pyridine), 7.62 (1H, app dt, J = 6.3 and 8.5 Hz, H-4'), 8.09 (1H, d, J = 5.7 Hz, H-6-pyridine), 10.33 (CO—NH), 12.97 (NH-pyrrole) | 372.2 |

Example 41: 4-(3,6-Dichloro-2-fluorobenzoyl)-N-(1-((1-methylpiperidin-4-yl)methyl)-1H-pyrazol-4-yl)-1H-pyrrole-2-carboxamide

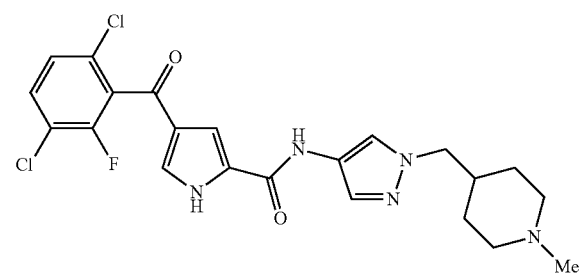 [SMILES: CN1CCC(Cn2cc(NC(=O)c3cc(C(=O)c4c(Cl)ccc(Cl)c4F)c[nH]3)cn2)CC1]

Methyl-4-((4-nitro-1H-pyrazol-1-yl)methyl)piperidine was prepared according to general procedure 8 to give a (200 mg, 0.43 mmol, 1.5 eq) in MeCN (2 mL), the mixture was stirred at r.t. for 1 h and then partitioned between EtOAc (2×30 mL) and $H_2O$ (20 mL). The organic layers were combined, washed with brine, dried ($MgSO_4$) and the solvent removed in vacuo. Purification by MPLC on $NH_2SiO_2$ with gradient elution from 1% to 4% $MeOH/CH_2Cl_2$ gave a beige solid (53 mg, 39%); $^1H$ NMR (500 MHz; DMSO-$d_6$) $\delta_H$ 1.23 (2H, qd, J=3.0 and 12.5 Hz, 2×H-piperidine), 1.41-1.51 (2H, m, 2×H-piperidine), 1.70-1.85 (3H, m, 3×H-piperidine), 2.15 ($CH_3$), 2.72-2.80 (2H, m, 2×H-piperidine), 4.00 (2H, d, J=7.3 Hz, N—$CH_2$—CH), 7.35 (1H, s, H-pyrrole), 7.53-7.61 (3H, m, H-4', H-pyrrole and H-pyrazole), 7.82 (1H, app t, J=8.4 Hz, H-3'), 7.97 (1H, s, H-pyrazole), 10.28 (1H, s, CO—NH), 12.52 (1H, br s, NH-pyrrole); HRMS calc for $C_{22}H_{23}{}^{35}Cl_2F_1N_5O_2$ $[M+H]^+$ 478.1207, found 478.1195.

Example 42: 4-(3,6-Dichloro-2-fluorobenzoyl)-N-(1-(1-(2,2,2-trifluoroethyl)piperidin-4-yl)-1H-pyrazol-4-yl)-1H-pyrrole-2-carboxamide

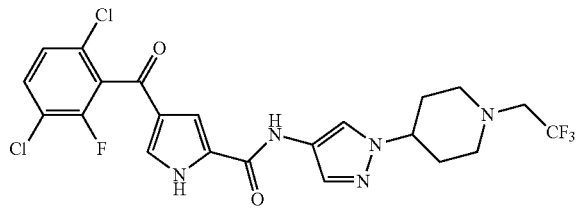 [SMILES: O=C(Nc1cnn(C2CCN(CC(F)(F)F)CC2)c1)c1cc(C(=O)c2c(Cl)ccc(Cl)c2F)c[nH]1]

Prepared according to general procedure 9 using 4-(3,6-dichloro-2-fluorobenzoyl)-1H-pyrrole-2-carboxylic acid (100 mg, 0.33 mmol, 1 eq.), Et$_3$N (115 μL, 0.83 mmol, 2.5 eq.), and 2-chloromethylpyridinium iodide (93 mg, 0.36 mmol, 1.1 eq.) in DCM (4 mL) followed by the addition of 91 (102 mg, 0.41 mmol, 1.25 eq.) with stirring at r.t. for 18 h. The residue was purified by MPLC on SiO$_2$ with gradient elution from 20% to 45% EtOAc/petrol to give a white solid (60 mg, 34%); $^1$H NMR (500 MHz; DMSO-d$_6$) δ$_H$ 1.90-2.03 (4H, m, H-piperidine), 2.53-2.61 (2H, m, H-piperidine), 3.01-3.08 (2H, m, H-piperidine), 3.27 (2H, q, J$_{HF}$=10.2 Hz, CH$_2$CF$_3$), 4.15-4.24 (1H, m, H-piperidine), 7.36 (1H, s, H-pyrrole), 7.56 (1H, dd, J=1.1 and 8.6 Hz, H-5'), 7.58-7.62 (2H, m, H-pyrrole and H-pyrazole), 7.82 (1H, app t, J=8.6 Hz, H-4'), 8.02 (1H, s, H-pyrazole), 10.29 (1H, s, CO—NH), 12.67 (1H, br s, NH-pyrrole).

By following methods similar and/or analogous to those described herein, the compounds set out in the Table 6 below were prepared from the corresponding starting materials.

TABLE 6

| Ex. | Structure | Name | General prep | 1H NMR Data | MS |
|---|---|---|---|---|---|
| 43. | 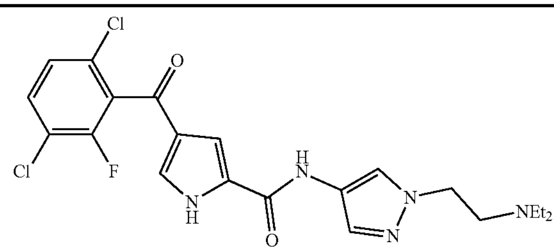 | 4-(3,6-Dichloro-2-fluorobenzoyl)-N-(1-(2-(diethylamino)ethyl)-1H-pyrazol-4-yl)-1H-pyrrole-2-carboxamide | 9 | 0.95 (6H, t, J = 7.1 Hz, N—CH$_2$—CH$_3$), 2.51 (4H, q, J = 7.1 Hz, N—CH$_2$—CH$_3$), 2.78 (2H, t, J = 6.5 Hz, CH$_2$—NEt$_2$), 4.14 (2H, t, J = 6.5 Hz, CH$_2$—CH$_2$—NEt$_2$), 7.35 (1H, s, H-pyrrole), 7.54-7.57 (2H, m, H-pyrazole and H-5'), 7.59 (1H, s, H-pyrrole), 7.82 (1H, app t, J = 8.4 Hz, H-4'), 8.03 (1H, s, H-pyrazole), 10.26 (1H, s, CO—NH), 12.66 (NH-pyrrole) | 466.1 201 |
| 44. | 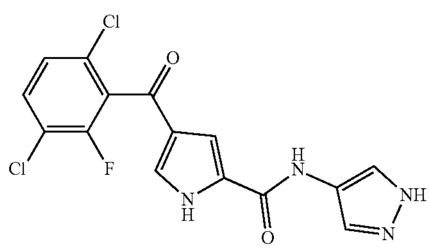 [SMILES: O=C(Nc1cn[nH]c1)c1cc(C(=O)c2c(Cl)ccc(Cl)c2F)c[nH]1] | 4-(3,6-Dichloro-2-fluorobenzoyl)-N-(1H-pyrazol-4-yl)-1H-pyrrole-2-carboxamide | 2 | 7.36 (1H, s, H-pyrrole), 7.56 (1H, dd, J = 1.1 & 8.5 Hz, H-5'), 7.60 (1H, s, H-pyrrole), 7.57 (1H, s, H-pyrazole), 7.82 (1H, app t, J = 8.5 Hz, H-4'), 7.97 (1H, s, H-pyrazole), 10.29 (1H, s, CO—NH), 12.60-12.73 (2H, m, NH-pyrrole and NH-pyrazole) | 367.0 158 |
| 45. | 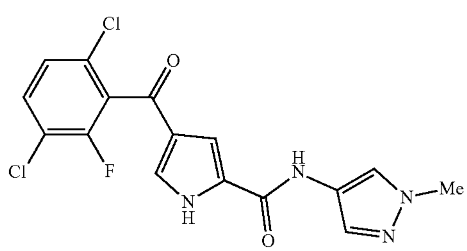 [SMILES: Cn1cc(NC(=O)c2cc(C(=O)c3c(Cl)ccc(Cl)c3F)c[nH]2)cn1] | 4-(3,6-Dichloro-2-fluorobenzoyl)-N-(1-methyl-1H-pyrazol-4-yl)-1H-pyrrole-2-carboxamide | 2 | 3.85 (3H, s, CH$_3$), 7.36 (1H, s, H-pyrrole), 7.54 (1H, s, H-pyrazole), 7.56 (1H, dd, J = 1.2 & 8.5 Hz, H-5'), 7.59 (1H, s, H-pyrrole), 7.82 (1H, app t, J = 8.5 Hz, H-4'), 7.98 (1H, s, H-pyrazole), 10.28 (1H, s, CO—NH), 12.68 (NH-pyrrole); | 381.0 318. |
| 46. | 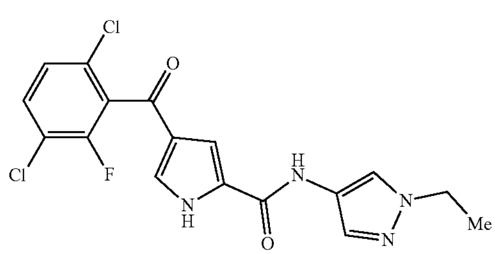 [SMILES: CCn1cc(NC(=O)c2cc(C(=O)c3c(Cl)ccc(Cl)c3F)c[nH]2)cn1] | 4-(3,6-Dichloro-2-fluorobenzoyl)-N-(1-ethyl-1H-pyrazol-4-yl)-1H-pyrrole-2-carboxamide | 9 | 1.39 (3H, t, J = 7.3 Hz, CH$_3$), 4.15 (2H, q, J = 7.3 Hz, CH$_2$), 7.35 (1H, s, H-pyrrole), 7.53-7.58 (2H, m, H-5' and H-pyrazole), 7.59 (1H, s, H-pyrrole), 7.82 (1H, app t, J = 8.4 Hz, H-4'), 8.00 (1H, s, H-pyrazole), 10.27 (1H, s, CO—NH), 12.66 (1H, s, NH-pyrrole) | |

TABLE 6-continued

| Ex. | Structure | Name | General prep | 1H NMR Data | MS |
|---|---|---|---|---|---|
| 47. | 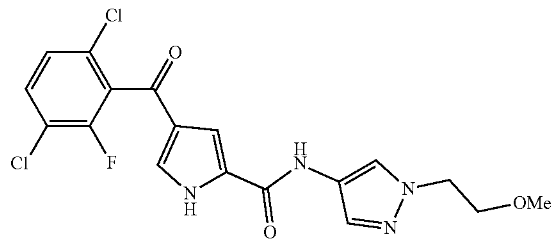 [SMILES: COCCn1cc(NC(=O)c2cc(C(=O)c3c(Cl)ccc(Cl)c3F)c[nH]2)cn1] | 4-(3,6-Dichloro-2-fluorobenzoyl)-N-(1-(2-methoxyethyl)-1H-pyrazol-4-yl)-1H-pyrrole-2-carboxamide | 9 | 3.27 (3H, s, CH$_3$), 3.70 (2H, t, J = 5.3 Hz, CH$_2$—N), 4.27 (2H, t, J = 5.3 Hz, CH$_2$—O), 7.35 (1H, s, H-pyrrole), 7.56 70 (1H, dd, J = 1.2 and 8.5 Hz, H-5'), 7.58 (1H, s, H-pyrazole), 7.60 (1H, s, H-pyrrole), 7.82 (1H, app t, J = 8.5 Hz, H-4'), 8.00 (1H, s, H-pyrazole), 10.28 (1H, s, CO—NH), 12.67 (1H, s, NH-pyrrole) | (120 |
| 48. | 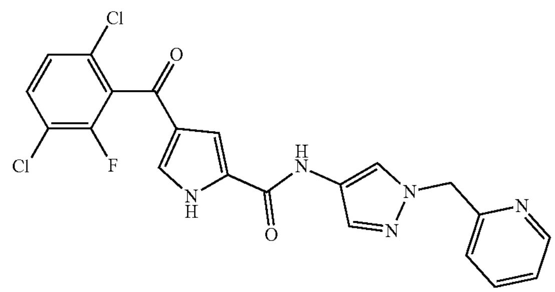 [SMILES: O=C(Nc1cnn(Cc2ccccn2)c1)c1cc(C(=O)c2c(Cl)ccc(Cl)c2F)c[nH]1] | 4-(3,6-Dichloro-2-fluorobenzoyl)-N-(1-(pyridin-2-ylmethyl)-1H-pyrazol-4-yl)-1H-pyrrole-2-carboxamide | 9 | 5.45 (2H, s, CH$_2$), 7.07 (1H, d, J = 7.9 Hz, H-pyridine), 7.32-7.39 (2H, m, H-pyrrole and H-4'), 7.56 (1H, dd, J = 0.9 and 8.7 Hz, H-5'), 7.60 (1H, s, H-pyrrole), 7.64 (1H, s, H-pyrazole), 7.78-7.85 (2H, m, 2 × H-pyridine), 8.15 (1H, s, H-pyrazole), 8.55-8.60 (1H, m, H-pyridine), 10.35 (CO—NH), 12.68 (NH-pyrrole) | 458.0 579. |
| 49. | 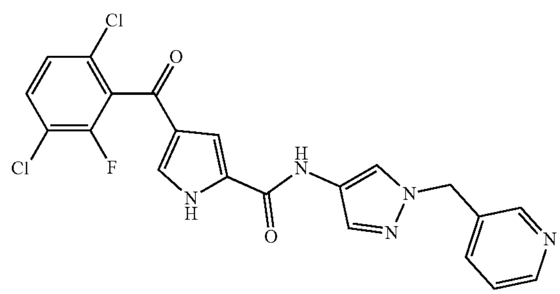 [SMILES: O=C(Nc1cnn(Cc2cccnc2)c1)c1cc(C(=O)c2c(Cl)ccc(Cl)c2F)c[nH]1] | 4-(3,6-Dichloro-2-fluorobenzoyl)-N-(1-(pyridin-3-ylmethyl)-1H-pyrazol-4-yl)-1H-pyrrole-2-carboxamide | 9 | 5.41 (2H, s, CH$_2$), 7.35 (1H, s, H-pyrrole), 7.41 (1H, ddd, J = 0.8, 4.9 and 7.9 Hz, H-5-pyridine), 7.55 (1H, dd, J = 1.3 and 8.6 Hz, H-5'), 7.60 (1H, s, H-pyrrole), 7.62 (1H, d, J = 0.6 Hz, H-pyrazole), 7.66-7.69 (1H, m, H-4-pyridine), 7.82 (1H, app t, J = 8.6 Hz, H-4'), 8.17 (1H, s, H-pyrazole), 8.52-8.56 (2H, m, H-2-pyridine and H-6-pyridine), 10.34 (1H, s, CO—NH), 12.66 (1H, br s, NH-pyrrole) | 458.0 579. |
| 50. | 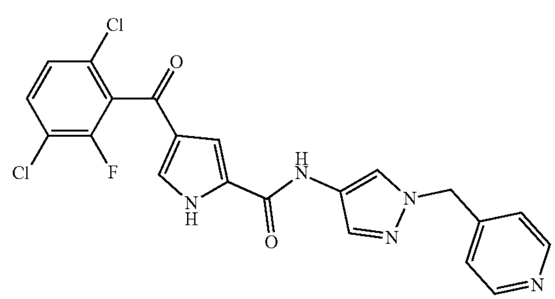 [SMILES: O=C(Nc1cnn(Cc2ccncc2)c1)c1cc(C(=O)c2c(Cl)ccc(Cl)c2F)c[nH]1] | 4-(3,6-Dichloro-2-fluorobenzoyl)-N-(1-(pyridin-4-ylmethyl)-1H-pyrazol-4-yl)-1H-pyrrole-2-carboxamide | 9 | 5.44 (2H, s, CH$_2$), 7.14-7.17 (2H, m, H-pyridine), 7.37 (1H, br s, H-pyrrole), 7.56 (1H, dd, J = 1.4 and 8.6 Hz, H-5'), 7.60 (1H, br s, H-pyrrole), 7.66 (1H, d, J = 0.5 Hz, H-pyrazole), 7.82 (1H, app t, J = 8.6 Hz, H-4'), 8.19 (1H, d, J = 0.5 Hz, H-pyrazole), 8.54-8.58 (2H, m, H-pyridine), 10.37 (1H, s, CO—NH), 12.69 (1H, br s, NH-pyrrole) | |
| 51. | 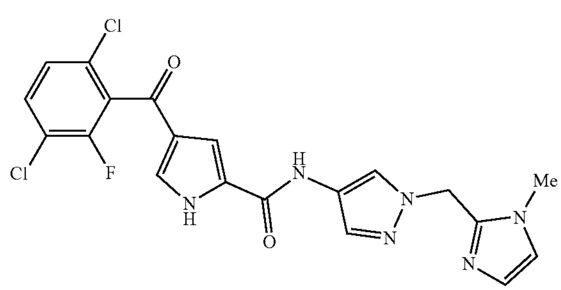 [SMILES: Cn1ccnc1Cn1cc(NC(=O)c2cc(C(=O)c3c(Cl)ccc(Cl)c3F)c[nH]2)cn1] | 4-(3,6-Dichloro-2-fluorobenzoyl)-N-(1-((1-methyl-1H-imidazol-2-yl)methyl)-1H-pyrazol-4-yl)-1H-pyrrole-2-carboxamide | 9 | 3.67 (3H, s, CH$_3$), 5.42 (2H, s, CH$_2$), 6.87 (1H, s, H-imidazole), 7.16 (1H, s, H-imidazole), 7.34 (1H, s, H-pyrrole), 7.55 (1H, d, J = 8.5 Hz, H-4'), 7.57-7.64 (2H, m, H-pyrazole and H-pyrrole), 7.81 (1H, app t, J = 8.5 Hz, H-4'), 8.00 (1H, s, H-pyrazole), 10.32 (1H, s, CO—NH), 12.68 (1H, br s, NH-pyrrole) | |

TABLE 6-continued

| Ex. | Structure | Name | General prep | 1H NMR Data | MS |
|---|---|---|---|---|---|
| 52. | 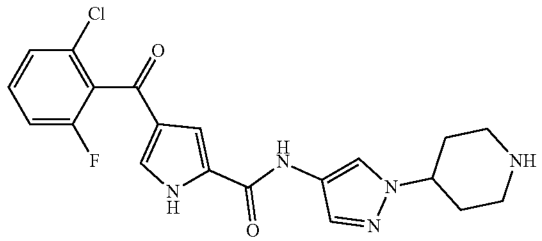 [SMILES: O=C(Nc1cnn(C2CCNCC2)c1)c1cc(C(=O)c2c(F)cccc2Cl)c[nH]1] | 4-(2-Chloro-6-fluorobenzoyl)-N-(1-(piperidin-4-yl)-1H-pyrazol-4-yl)-1H-pyrrole-2-carboxamide | 4 | 1.77 (2H, app qd, J = 4.1 and 12.1 Hz, 2 × H-piperidine), 1.90-1.97 (2H, m, 2 × H-piperidine), 2.55-2.64 (2H, m, 2 × H-piperidine), 3.02-3.10 (2H, m, 2 × H-piperidine), 4.19 (1H, tt, J = 4.1 and 11.5 Hz, $CH_2$—CH—$CH_2$-piperidine), 7.31 (1H, s, H-pyrrole), 7.39-7.47 (2H, m, H-pyrrole and H-5'), 7.50 (1H, d, J = 8.0 Hz, H-3'), 7.57 (1H, s, H-pyrazole), 7.61 (td, J = 6.3 and 8.0 Hz, H-4'), 7.98 (1H, s, H-pyrazole), 10.27 (1H, s, CO—NH) | 416.1 273. |
| 53. | 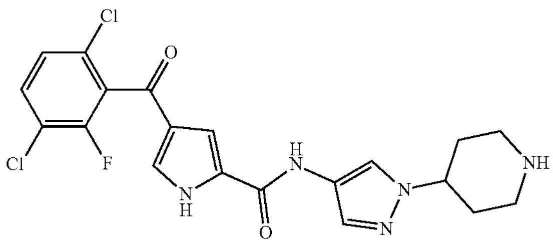 [SMILES: O=C(Nc1cnn(C2CCNCC2)c1)c1cc(C(=O)c2c(Cl)ccc(Cl)c2F)c[nH]1] | 4-(3,6-Dichloro-2-fluorobenzoyl)-N-(1-(piperidin-4-yl)-1H-pyrazol-4-yl)-1H-pyrrole-2-carboxamide | 4 | 1.78 (2H, app qd, J = 3.9 and 11.8 Hz, 2 × H-piperidine), 1.91-1.98 (2H, m, 2 × H-piperidine), 2.57-2.66 (2H, m, 2 × H-piperidine), 3.01-3.11 (2H, m, 2 × H-piperidine), 4.21 (1H, tt, J = 4.1 and 11.7 Hz, N—CH-piperidine), 7.35 (1H, s, H-pyrrole), 7.56 (1H, d, J = 8.6 Hz, H-5'), 7.57-7.61 (2H, m, H-pyrrole and H-pyrazole), 7.82 (1H, app t, J = 8.6 Hz, H-4'), 7.98 (1H, s, H-pyrazole), 10.27 (1H, s, CO—NH); | 450.0 888. |
| 54. | 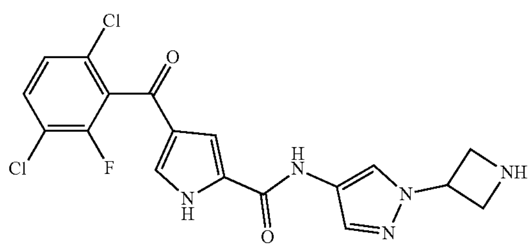 [SMILES: O=C(Nc1cnn(C2CNC2)c1)c1cc(C(=O)c2c(Cl)ccc(Cl)c2F)c[nH]1] | N-(1-(Azetidin-3-yl)-1H-pyrazol-4-yl)-4-(3,6-dichloro-2-fluorobenzoyl)-1H-pyrrole-2-carboxamide | 4 | 3.76 (2H, app t, J = 7.7 Hz, 2 × H-azetidine), 3.89-3.95 (2H, m, 2 × H-azetidine), 5.21 (1H, quin, J = 7.7 Hz, CH—N-azetidine), 7.36 (1H, s, H-pyrrole), 7.56 (1H, dd, J = 1.0 and 8.5 Hz, H-5'), 7.60 (1H, s, H-pyrrole), 7.64 (1H, s, H-pyrazole), 7.83 (1H, app t, J = 8.5 Hz, H-4'), 8.13 (1H, s, H-pyrazole), 10.32 (1H, s, CO—NH) | 422.0 578. |
| 55. | 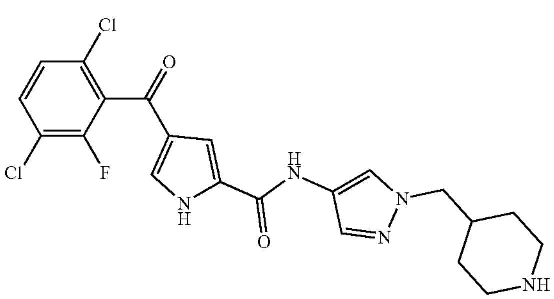 [SMILES: O=C(Nc1cnn(CC2CCNCC2)c1)c1cc(C(=O)c2c(Cl)ccc(Cl)c2F)c[nH]1] | 4-(3,6-Dichloro-2-fluorobenzoyl)-N-(1-(piperidin-4-ylmethyl)-1H-pyrazol-4-yl)-1H-pyrrole-2-carboxamide | 4 | 1.09 (2H, qd, J = 3.6 and 12.0 Hz, 2 × H-piperidine), 1.39-1.47 (2H, m, 2 × H-piperidine), 1.82-1.94 (1H, m, H-piperidine), 2.43 (td, J = 2.2 and 12.0 Hz, 2 × CH—N-piperidine), 2.90-2.97 (2H, m, 2 × CH—N-piperidine), 3.97 (2H, d, J = 7.1 Hz, pyrazole-$CH_2$-piperidine), 7.33 (1H, s, H-pyrrole), 7.55 (1H, dd, J = 1.3 and 8.7 Hz, H-4'), 7.57 (1H, s, H-pyrazole), 7.58 (1H, s, H-pyrrole), 7.82 (1H, app t, J = 8.7 Hz, H-3'), 7.97 (1H, s, H-pyrazole), 10.26 (1H, s, CO—NH) | 464.1 038 |

TABLE 6-continued

| Ex. | Structure | General Name | prep | 1H NMR Data | MS |
|---|---|---|---|---|---|
| 56. | 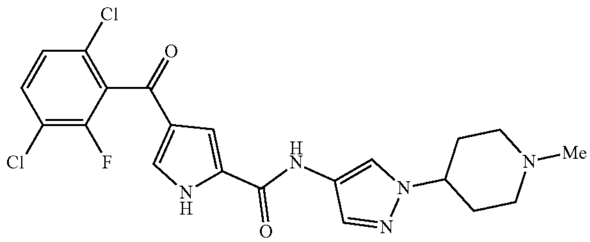 [SMILES: CN1CCC(n2cc(NC(=O)c3cc(C(=O)c4c(Cl)ccc(Cl)c4F)c[nH]3)cn2)CC1] | 4-(3,6-Dichloro-2-fluorobenzoyl)-N-(1-(1-methylpiperidin-4-yl)-1H-pyrazol-4-yl)-1H-pyrrole-2-carboxamide | 8 | 1.93-2.03 (4H, m, 4 × H-piperidine), 2.09-2.21 (2H, m, 2 × H-piperidine), 2.28 (3H, s, NCH₃), 2.88-2.98 (2H, m, 2 × H-piperidine), 4.10-4.211 (1H, m, N—CH-piperidine), 7.36 (1H, s, H-pyrrole), 7.56 (1H, dd, J = 1.3 and 8.6 Hz, H-5'), 7.58-7.61 (2H, m, H-pyrrole and H-pyrazole), 7.82 (1H, app t, J = 8.6 Hz, H-4'), 8.01 (1H, s, H-pyrazole), 10.29 (1H, s, CO—NH), 12.67 (1H, s, NH-pyrazole) | |
| 57. | 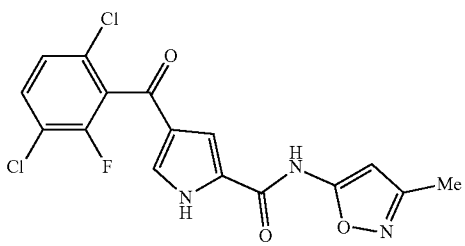 [SMILES: Cc1cc(NC(=O)c2cc(C(=O)c3c(Cl)ccc(Cl)c3F)c[nH]2)on1] | 4-(3,6-Dichloro-2-fluorobenzoyl)-N-(3-methylisoxazol-5-yl)-1H-pyrrole-2-carboxamide | 3 | 2.25 (3H, s, CH₃), 6.29 (1H, s, H-isoxazole), 7.57 (1H, dd, J = 1.3 and 8.4 Hz, H-3'), 7.62 (1H, br s, H-pyrrole), 7.74 (1H, s, H-pyrrole), 7.83 (1H, app t, J = 8.6 Hz, H-4'), 11.80 (1H, s, CO—NH), 12.94 (1H, s, NH-pyrrole) | |
| 58. | 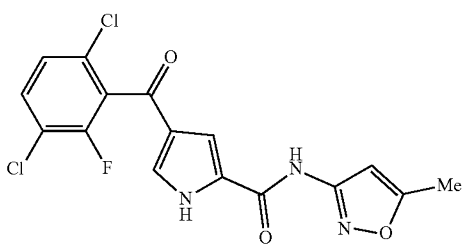 [SMILES: Cc1cc(NC(=O)c2cc(C(=O)c3c(Cl)ccc(Cl)c3F)c[nH]2)no1] | 4-(3,6-Dichloro-2-fluorobenzoyl)-N-(5-methylisoxazol-3-yl)-1H-pyrrole-2-carboxamide | 3 | 2.44 (3H, d, J = 0.7 Hz, CH₃), 6.76 (1H, d, J = 0.7 Hz, H-isoxazole), 7.56 (1H, dd, J = 1.4 and 8.4 Hz, H-3'), 7.64 (1H, br s, H-pyrrole), 7.69 (1H, s, H-pyrrole), 7.82 (1H, app t, J = 8.6 Hz, H-4'), 11.20 (1H, s, CO—NH), 12.83 (1H, s, NH-pyrrole) | |
| 59. | 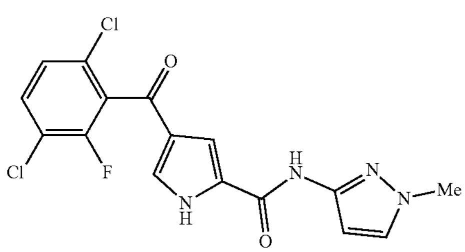 [SMILES: Cn1ccc(NC(=O)c2cc(C(=O)c3c(Cl)ccc(Cl)c3F)c[nH]2)n1] | 4-(3,6-Dichloro-2-fluorobenzoyl)-N-(1-methyl-1H-pyrazol-3-yl)-1H-pyrrole-2-carboxamide | 3 | 3.81 (3H, s, CH₃), 6.57 (1H, d, J = 2.2 Hz, H-pyrazole), 7.55 (1H, dd, J = 1.4 and 8.6 Hz, H-5'), 7.56 (1H, br s, H-pyrrole), 7.60 (1H, br s, H-pyrrole), 7.62 (1H, d, J = 2.2 Hz, H-pyrazole), 7.81 (1H, app t, J = 8.6 Hz, H-4'), 10.75 (1H, s, CO—NH), 12.64 (1H, br s, NH-pyrrole) | |
| 60. | 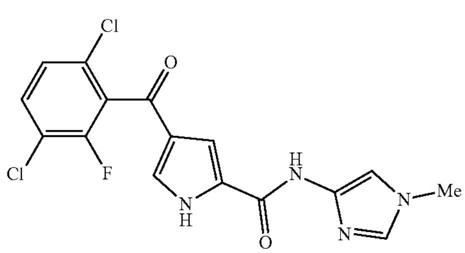 [SMILES: Cn1cnc(NC(=O)c2cc(C(=O)c3c(Cl)ccc(Cl)c3F)c[nH]2)c1] | 4-(3,6-Dichloro-2-fluorobenzoyl)-N-(1-methyl-1H-imidazol-4-yl)-1H-pyrrole-2-carboxamide | 3 | 3.68 (3H, CH₃), 7.33 (1H, s, H-imidazole), 7.47 (1H, s, H-imidazole), 7.52-7.60 (3H, m, H-5' and 2 × H-pyrrole), 7.81 (1H, app t, J = 8.3 Hz, H-4'), 10.67 (1H, s, CO—NH), 12.61 (1H, s, NH-pyrrole) | |

TABLE 6-continued

| Ex. | Structure | Name | General prep | 1H NMR Data | MS |
|---|---|---|---|---|---|
| 61. | 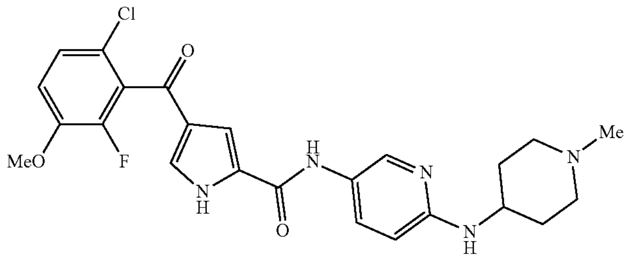 [SMILES: COc1ccc(Cl)c(C(=O)c2c[nH]c(C(=O)Nc3ccc(NC4CCN(C)CC4)nc3)c2)c1F] | 4-(6-Chloro-2-fluoro-3-methoxy-benzoyl)-N-(6-((1-methylpiperidin-4-yl)amino)pyridin-3-yl)-1H-pyrrole-2-carboxamide | 2 | 1.38-1.50 (2H, m, 2 × CH-piperidine), 1.84-1.94 (2H, m, 2 × CH-piperidine), 1.96-2.05 (2H, m, 2 × CH-piperidine), 2.19 (3H, s, NCH$_3$), 2.71-2.80 (2H, m, 2 × CH-piperidine), 3.58-3.69 (1H, m, CH—NH-piperidine), 3.94 (OCH$_3$), 6.32 (1H, d, J = 7.7 Hz, NH-piperidine), 6.49 (1H, d, J = 9.0 Hz, H-3-pyridine), 7.32-7.47 (4H, m, 2 × H-pyrazole, H-4' and H-5'), 7.64 (1H, dd, J = 2.1 & 8.9 Hz, H-4-pyridine), 8.23 (1H, d, J = 2.1 Hz, H-6-pyridine), 9.84 (1H, s, CO—NH), 12.60 (1H, br s, NH-pyrrole) | 486.1 689 |
| 62. | 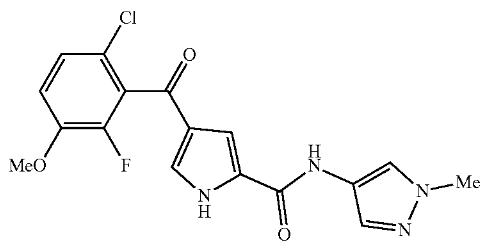 [SMILES: COc1ccc(Cl)c(C(=O)c2c[nH]c(C(=O)Nc3cnn(C)c3)c2)c1F] | 4-(6-Chloro-2-fluoro-3-methoxy-benzoyl)-N-(1-methyl-1H-pyrazol-4-yl)-1H-pyrrole-2-carboxamide | 9 | 3.85 (3H, s, N—CH$_3$), 3.94 (3H, s, O—CH$_3$), 7.31 (1H, s, H-pyrrole), 7.36 (1H, app t, J = 9.0 Hz, H-4'), 7.42 (1H, dd, J = 1.0 and 9.0 Hz, H-5'), 7.45 (1H, s, H-pyrrole), 7.53 (1H, s, H-pyrazole), 7.98 (1H, s, H-pyrazole), 10.27 (1H, s, CO—NH), 12.60 (1H, s, NH-pyrrole) | |
| 63. | 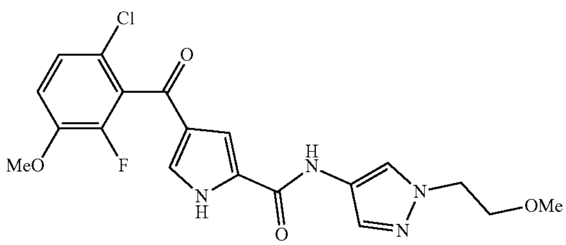 [SMILES: COCCn1cc(NC(=O)c2cc(C(=O)c3c(Cl)ccc(OC)c3F)c[nH]2)cn1] | 4-(6-Chloro-2-fluoro-3-methoxy-benzoyl)-N-(1-(2-methoxyethyl)-1H-pyrazol-4-yl)-1H-pyrrole-2-carboxamide | 9 | 3.27 (3H, s, CH$_2$—O—CH$_3$), 3.70 (2H, t, J = 5.3 Hz, CH$_2$—N), 3.94 (1H, s, Ar—O—CH$_3$), 4.27 (2H, t, J = 5.3 Hz, CH$_2$—O), 7.32 (1H, s, H-pyrrole), 7.36 (1H, app t, J = 8.9 Hz, H-4'), 7.42 (1H, dd, J = 1.0 Hz and 8.9 Hz, H-5'), 7.46 (1H, s, H-pyrrole), 7.57 (1H, s, H-pyrazole), 8.00 (1H, s, H-pyrazole), 10.28 (1H, s, CO—NH), 12.60 (1H, s, NH-pyrrole) | |

Example 64: 4-(6-Chloro-2-fluoro-3-methoxybenzoyl)-N-(1-(1-(2,2,2-trifluoroethyl) piperidin-4-yl)-1H-pyrazol-4-yl)-1H-pyrrole-2-carboxamide

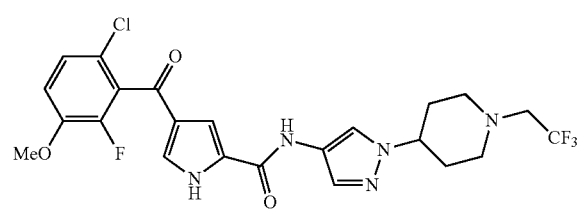 [SMILES: COc1ccc(Cl)c(C(=O)c2c[nH]c(C(=O)Nc3cnn(C4CCN(CC(F)(F)F)CC4)c3)c2)c1F]

Palladium on carbon (10%, 40 mg) was added to 90 (370 mg, 1.3 mmol) in MeOH (30 mL), and the mixture was stirred at r.t. under an atmosphere of hydrogen for 18 h. The reaction was filtered through celite, and the solvent removed in vacuo to give 1-(1-(2,2,2-trifluoroethyl)piperidin-4-yl)-1H-pyrazol-4-amine as a deep red solid (321 mg, 97%); $^1$H NMR (500 MHz; DMSO-d$_6$) $\delta_H$ 1.82-1.96 (4H, m, H-piperidine), 2.46-2.58 (2H, m, H-piperidine), 2.95-3.04 (2H, m, H-piperidine), 3.24 (2H, q, J$_{HF}$=10.3 Hz, CH$_2$CF$_3$), 3.79 (2H, s, NH$_2$), 3.93-4.01 (1H, m, H-piperidine), 6.93 (1H, d, J=0.8 Hz, H-pyrazole), 7.10 (1H, d, J=0.8 Hz, H-pyrazole).

Methyl 4-(6-chloro-2-fluoro-3-methoxybenzoyl)-1H-pyrrole-2-carboxylate was prepared by using an analogous procedure to that used to prepare 4-(2-Chloro-6-fluorobenzoyl)-1H-pyrrole-2-carboxylic acid.

Prepared according to general procedure 9 using Methyl 4-(6-chloro-2-fluoro-3-methoxybenzoyl)-1H-pyrrole-2-carboxylate (80 mg, 0.27 mmol, 1 eq.), Et$_3$N (93 µL, 0.67 mmol, 2.5 eq.), and 2-chloromethylpyridinium iodide (76 mg, 0.30 mmol, 1.1 eq.) in DCM (4 mL) followed by the addition of 1-(1-(2,2,2-trifluoroethyl)piperidin-4-yl)-1H-pyrazol-4-amine (83 mg, 0.34 mmol, 1.25 eq.) with stirring at r.t. for 18 h. The residue was purified by MPLC on SiO$_2$ with gradient elution from 40% to 80% EtOAc/petrol to give a white solid (70 mg, 49%); $^1$H NMR (500 MHz; DMSO-d$_6$) $\delta_H$ 1.93-2.01 (4H, m, H-piperidine), 2.53-2.60 (2H, m, H-piperidine), 3.00-3.07 (2H, m, H-piperidine), 3.27 (2H, q, $J_{HF}$=10.3 Hz, CH$_2$CF$_3$), 3.94 (3H, s, OCH$_3$), 4.14-4.23 (1H, m, H-piperidine), 7.32 (1H, s, H-pyrrole), 7.36 (1H, app t, J=9.0 Hz, H-4'), 7.42 (1H, dd, J=1.3 and 9.0 Hz, H-5'), 7.46 (1H, s, H-pyrrole), 7.59 (1H, s, H-pyrazole), 8.01 (1H, s, H-pyrazole), 10.28 (1H, s, CO—NH), 12.59 (1H, br s, NH-pyrrole)

By following methods similar and/or analogous to those described herein, the compounds set out in the Table 7 below were prepared from the corresponding starting materials.

TABLE 7

| Ex. | Structure | Name | General prep | 1H NMR Data | MS |
|---|---|---|---|---|---|
| 65. | 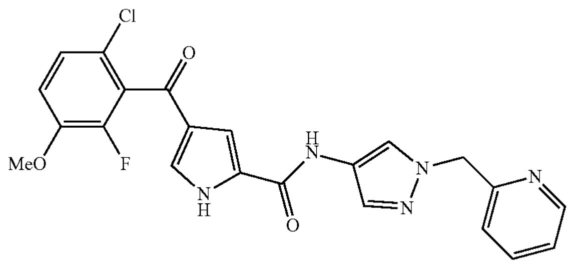 [SMILES: COc1ccc(Cl)c(C(=O)c2c[nH]c(C(=O)Nc3cnn(Cc4ccccn4)c3)c2)c1F] | 4-(6-Chloro-2-fluoro-3-methoxybenzyl)-N-1-(pyridin-2-ylmethyl)-1H-pyrazol-4-yl)-1H-pyrrole-2-carboxamide | 9 | 3.94 (CH3), 5.45 (2H, s, CH$_2$), 7.07 (1H, d J = 7.9 Hz, H-pyridine), 7-30-7.40 (3H, m, H-pyrrole, H-4' and H-pyridine), 7.42 (1H, dd, J = 1.1 and 9.0 Hz, H-5'), 7.46 (1H, s, H-pyrrole), 7.63 (1H, s, H-pyrazole), 7.80 (1H, td, J = 7.7 and 1.9 Hz, H-pyridine), 8.15 (1H, s, H-pyrazole), 8.55-8.60 (1H, m, H-pyridine), 10.34 (1H, s, CO—NH), 12.61 (1H, s, NH-pyrrole) | 454.1 072 |
| 66. | 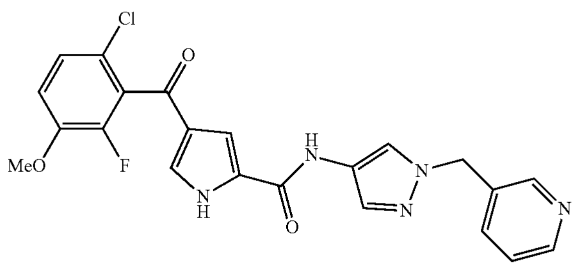 [SMILES: COc1ccc(Cl)c(C(=O)c2c[nH]c(C(=O)Nc3cnn(Cc4cccnc4)c3)c2)c1F] | 4-(6-Chloro-2-fluoro-3-methoxybenzoyl)-N-(1-(pyridin-3-ylmethyl)-1H-pyrazol-4-yl)-1H-pyrrole-2-carboxamide | 9 | 3.94 (3H, s, CH$_3$), 5.40 (2H, s, CH$_2$), 7.31 (1H, s, H-pyrrole), 7.36 (1H, app t, J = 9.1 Hz, H-4'), 7.39-7.44 (2H, m, H-5-pyridine and H-5'), 7.46 (1H, s, H-pyrrole), 7.61 (1H, s, H-pyrazole), 7.65-7.69 (1H, m, H-4-pyridine), 8.17 (1H, s, H-pyrazole), 8.52-8.56 (2H, m, H-2-pyridine and H-6-pyridine), 10.33 (1H, s, CO—NH), 12.60 (1H, brs, NH-pyrrole) | 454.1 072 |
| 67. | 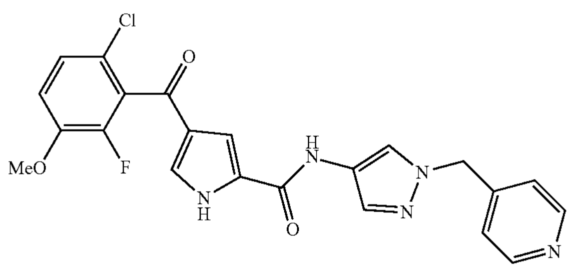 [SMILES: COc1ccc(Cl)c(C(=O)c2c[nH]c(C(=O)Nc3cnn(Cc4ccncc4)c3)c2)c1F] | 4-(6-Chloro-2-fluoro-3-methoxybenzoyl)-N-ylmethyl)-1H-pyrazol-4-yl)-1H-pyrrole-2-carboxamide | 9 | 3.94 (3H, s, CH$_3$), 5.43 (2H, s, CH$_2$), 7.13-7.18 (2H, m, H-pyridine), 7.33 (1H, br s, H-pyrrole), 7.36 (1H, app t, J = 9.0 Hz, H-4'), 7.42 (1H, dd, J = 1.3 and 9.0 Hz, H-5'), 7.47 (1H, br s, H-pyrrole), 7.65 (1H, d, J = 0.5 Hz, H-pyrazole), 8.18 (1H, d, J = 0.5 Hz, H-pyrazole), 8.53-8.58 (2H, m, H-pyridine), 10.36 (1H, s, CO—NH), 12.61 (1H, br s, NH-pyrrole) | |
| 68. | 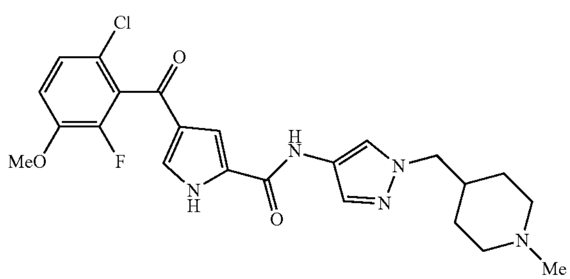 [SMILES: COc1ccc(Cl)c(C(=O)c2c[nH]c(C(=O)Nc3cnn(CC4CCN(C)CC4)c3)c2)c1F] | 4-(6-Chloro-2-fluoro-3-methoxybenzoyl)-N-(1-((1-methylpiperidin-4-yl)methyl)-1H-pyrazol-4-yl)-1H-pyrrole-2-carboxamide | 2 | 1.23 (2H, qd, J = 12.0 and 3.1 Hz, 2 × CH-piperidine), 1.41-1.51 (2H, m, 2 × CH-piperidine), 1.69-1.86 (3H, m, 3 × CH-piperidine), 2.15 (3H, s, NCH$_3$), 2.72-2.79 (2H, m, 2 × CH-piperidine), 3.94 (3H, s, OCH$_3$), 3.99 (2H, d, J = 7.1 Hz, N-CH$_2$—CH), 7.32 (1H, s, H-pyrrole), 7.37 (1H, app t, J = 9.0 Hz, H-4'), 7.42 (1H, dd, J = 0.8 and 9.0 Hz, H-5'), 7.46 (H-pyrrole), 7.56 (H-pyrazole), 7.97 (H-pyrazole), 10.28 (CO—NH), 12.58 (1H, brs, NH-pyrrole) | 474.1 691 |

TABLE 7-continued

| Ex. | Structure | Name | General prep | 1H NMR Data | MS |
|---|---|---|---|---|---|
| 69. | 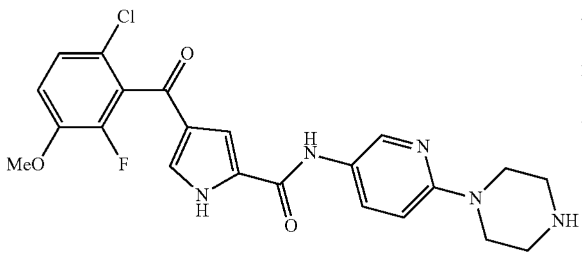 [SMILES: COc1ccc(Cl)c(C(=O)c2c[nH]c(C(=O)Nc3ccc(N4CCNCC4)nc3)c2)c1F] | 4-(6-Chloro-2-fluoro-3-methoxybenzoyl)-N-(6-(piperazin-1-yl)pyridin-3-yl)-1H-pyrrole-2-carboxamide | 4 | 2.73-2.84 (4H, m, 4 × CH-piperazine), 3.34-3.41 (4H, m, 4 × CH-piperazine), 3.94 (3H, s OCH$_3$), 6.84 (1H, d, J = 9.1 Hz, H-3-pyridine), 7.36 (1H, app t, J = 8.9 Hz, H-4'), 7.39-7.44 (2H, m, H-pyrrole and H-3'), 7.47 (H-pyrrole), 7.85 (1H, dd, J = 2.6 and 9.1 Hz, H-4-pyridine'), 8.42 (1H, d, J = 2.6 Hz, H-6-pyridine), 9.98 (1H, s, CO—NH) | 458.1 382 |
| 70. | 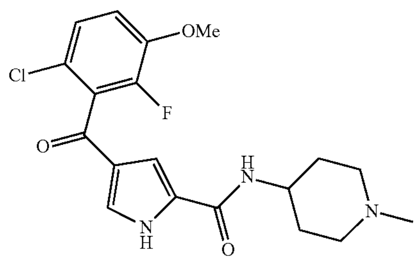 [SMILES: COc1ccc(Cl)c(C(=O)c2c[nH]c(C(=O)NC3CCN(C)CC3)c2)c1F] | 4-(6-chloro-2-fluoro-3-methoxybenzoyl)-N-(1-methylpiperidin-4-yl)-1H-pyrrole-2-carboxamide, | 12 | 1.52 (2H, tt, J = 12.9, 6.5 Hz, H-3''), 1.72 (2H, d, J = 10.7 Hz, H-3''), 1.91 (2H, t, J = 11.6 Hz, H-2''), 2.14 (3H, s, NCH3), 2.74 (2H, d, J = 11.0 Hz, H-2''), 3.75-3.54 (1H, m, H-4''), 3.89 (3H, s, ArOCH3), 7.19 (1H, s, H-3), 7.40-7.26 (3H, m, H-5, H-4', H-5'), 8.09 (1H, d, J = 8.2 Hz, NH amide), 12.39 (1H, s, NH pyrrole); | 394.4 |
| 71. | 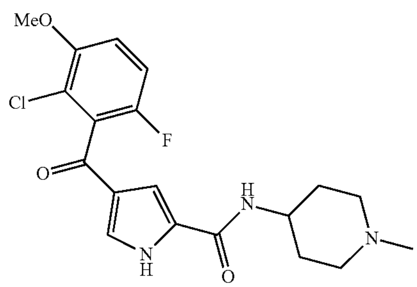 [SMILES: COc1ccc(F)c(C(=O)c2c[nH]c(C(=O)NC3CCN(C)CC3)c2)c1Cl] | 4-(2-chloro-6-fluoro-3-methoxybenzoyl)-N-(1-methylpiperidin-4-yl)-1H-pyrrole-2-carboxamide, (14 | 12 | 1.52 (1H, dd, J = 11.2, 4.3 Hz, H-3''), 1.73 (2H, d, J = 10.9 Hz, H-3''), 1.98 (2H, dd, J = 14.6, 9.0 Hz, H-2''), 2.18 (3H, S, NCH3), 2.64-2.93 (2H, m, H-2''), 3.57-3.76 (1H, m, H4''), 3.89 (3H, s, ArOCH3), 7.18 (1H, s, H-3), 7.41-7.21 (3H, m, H-5, H-4', H-5'), 8.10 (1H, d, J = 8.0 Hz, NH amide), 12.37 (1H, s, NH pyrrole) | 394.3, 396.3 |
| 72. | 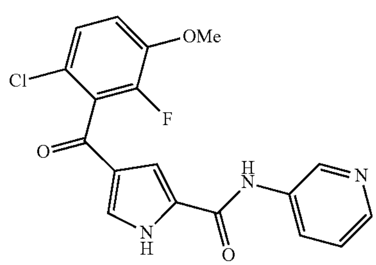 [SMILES: COc1ccc(Cl)c(C(=O)c2c[nH]c(C(=O)Nc3cccnc3)c2)c1F] | 4-(6-chloro-2-fluoro-3-methoxybenzoyl)-N-(pyridin-3-yl)-1H-pyrrole-2-carboxamide, | 13 | 3.90 (3H, s, ArOCH3), 7.33 (1H, dd, J = 9.1, 9.1 Hz, H-4'), 7.43-7.36 (2H, m, H-5', H-5''), 7.49 (2H, s, H-3, H-5), 8.13 (1H, d, J = 8.2 Hz, H-4''), 8.29 (1H, d, J = 4.8 Hz, H-6''), 8.89 (1H, s, H-2''), 10.24 (1H, s, NH Amide), 12.71 (1H, s, NH pyrrole); | 374.3, 376.3 |
| 73. | 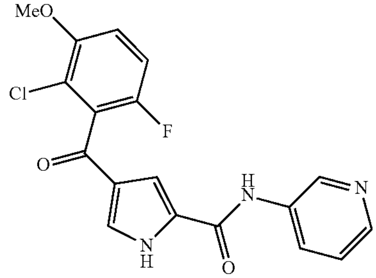 [SMILES: COc1ccc(F)c(C(=O)c2c[nH]c(C(=O)Nc3cccnc3)c2)c1Cl] | 4-(2-chloro-6-fluoro-3-methoxybenzoyl)-N-(pyridin-3-yl)-1H-pyrrole-2-carboxamide, | 13 | 3.90 (3H, s, ArOCH3), 7.42-7.16 (3H, m, H-5'', H-4', H-5'), 7.48 (2H, s, H-5, H-3), 8.13 (1H, d, J = 8.4 Hz, H-4''), 8.29 (1H, d, J = 5.0 Hz, H-6''), 8.89 (1H, s, H-2''), 10.23 (1H, s, Amide NH), 12.69 (1H, s, pyrrole NH); | 374.3, 376.3 |

TABLE 7-continued

| Ex. | Structure | Name | General prep | 1H NMR Data | MS |
|---|---|---|---|---|---|
| 74. | 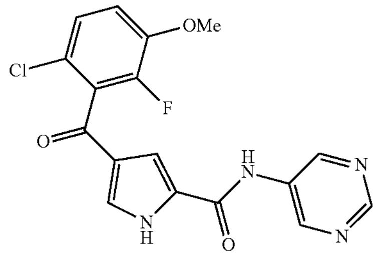 [SMILES: COc1ccc(Cl)c(C(=O)c2c[nH]c(C(=O)Nc3cncnc3)c2)c1F] | 4-(6-chloro-2-fluoro-3-methoxybenzoyl)-N-(pyrimidin-5-yl)-1H-pyrrole-2-carboxamide, | 13 | 3.90 (3H, s, ArOCH3), 7.34 (1H, d, J = 8.7 Hz, H-4'), 7.38 (1H, s, H-5'), 7.51 (2H, d, J = 37.0 Hz, H-3, H-5), 8.91 (1H, s, H-2"), 9.12 (2H, S, H-6", H-4"), 10.43 (1H, s, Amide NH), 12.80 (1H, s, pyrrole NH) | 375.3, 377.3 |
| 75. | 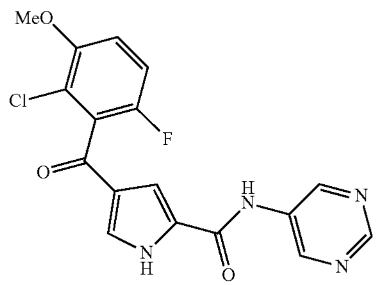 [SMILES: COc1ccc(F)c(C(=O)c2c[nH]c(C(=O)Nc3cncnc3)c2)c1Cl] | 4-(2-chloro-6-fluoro-3-methoxybenzoyl)-N-(pyrimidin-5-yl)-1H-pyrrole-2-carboxamide, | 13 | 3.90 (3H, s, ArOCH3), 7.30 (1H, dd, J = 9.0, 4.8 Hz, H-4'), 7.37 (1H, t, J = 9.0 Hz, H-5'), 7.44-7.50 (1H, m, H-3), 7.51-7.57 (1H, m, H-5), 8.91 (1H, s, H-2"), 9.12 (2H, s, H-6", H-4"), 10.42 (1H, s, Amide NH), 12.79 (1H, s, Pyrrole NH); | 375.3, 377.3 |
| 76. | 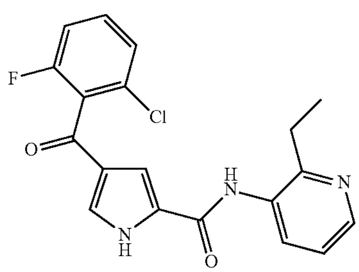 [SMILES: CCc1ncccc1NC(=O)c1cc(C(=O)c2c(F)cccc2Cl)c[nH]1] | 4-(2-Chloro-6-fluorobenzoyl)-N-(2-ethylpyridin-3-yl)-1H-pyrrole-2-carboxamide, | 13 | 1.18 (t, J = 7.5 Hz, 3H, ArCH2CH3), 2.77 (q, J = 7.5 Hz, 2H, ArCH2CH3), 7.27 (dd, J = 7.8, 4.6 Hz, 1H, H-5"), 7.51-7.34 (m, 4H, H-3 and H-5 and H-3' and H-5'), 7.57 (ddd, J = 8.3, 8.3, 6.3 Hz, 1H, H-4'), 7.68 (d, J = 7.9 Hz, 1H, H-4"), 8.40 (d, J = 4.9 Hz, 1H, H-6"), 9.90 (s, 1H, CONHAr), 12.65 (s, 1H, NH-pyrrole); | 369.7, 370.3 |

Example 80: 4-(2-Chloro-6-fluorobenzoyl)-N-(2-(pyrrolidin-1-yl)pyridin-3-yl)-1H-pyrrole-2-carboxamide

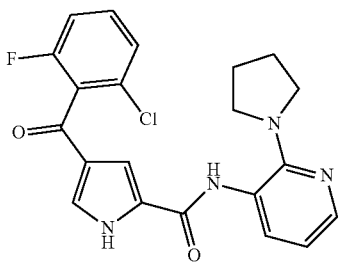 [SMILES: O=C(Nc1cccnc1N1CCCC1)c1cc(C(=O)c2c(F)cccc2Cl)c[nH]1]

To a solution of 4-(2-chloro-6-fluorobenzoyl)-1H-pyrrole-2-carboxylic acid (100 mg, 0.37 mmol) in DCM (3.7 mL) was added triethylamine (131 μL, 95 mg, 0.94 mmol), 2-chloro-1-methylpyridinium iodide (105 mg, 0.41 mmol) and 2-(pyrrolidin-1-yl)pyridin-3-amine (76 mg, 0.56 mmol). The resulting solution was stirred at 42° C. overnight. Upon completion, the solvent removed in vacuo. The crude residue was dissolved in EtOAc (30 mL), washed with sat. aq. NaHCO₃ (20 mL) and extracted with EtOAc (2×20 mL). The pooled organic extracts were washed with brine (30 mL), dried over MgSO₄ and concentrated in vacuo. The crude yellow solid was purified by column chromatography (silica gel, petrol:EtOAc—1:0→3:7) to yield the title compound as a yellow solid (48 mg, 31%); ¹H NMR (500 MHz, DMSO-d₆) δ 1.81 (t, J=6.4 Hz, 4H, NCH₂CH₂), 3.44 (t, J=6.3 Hz, 4H, NCH₂CH₂), 6.66 (dd, J=7.4, 4.7 Hz, 2H, H-5"), 7.41-7.30 (m, 3H, H-5 and H-5' and H-4"), 7.42 (s, 1H, H-3), 7.45 (d, J=8.2 Hz, 2H, H-3'), 7.57 (ddd, J=8.3, 8.3, 6.0 Hz, 2H, H-4'), 8.01 (dd, J=4.8, 1.8 Hz, 2H, H-6"), 9.84 (s, 1H, CONHAr), 12.56 (s, 1H, NH-pyrrole); LRMS (ES⁻) m/z 411.3 [M−H]⁻; HRMS (NSI) calcd for C₂₁H₁₇ClFN₄O₂ [M−H]⁻: 411.1030; found 411.1024.

By following methods similar and/or analogous to those described herein, the compounds set out in the Table 8 below were prepared from the corresponding starting materials.

TABLE 8

| Ex. | Structure | Name | General prep | 1H NMR Data | MS |
|---|---|---|---|---|---|
| 81. | 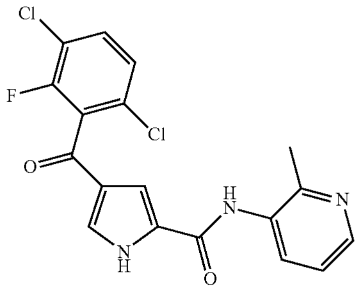 [SMILES: Cc1ncccc1NC(=O)c1cc(C(=O)c2c(Cl)ccc(Cl)c2F)c[nH]1] | 4-(3,6-Dichloro-2-fluorobenzoyl)-N-(2-methylpyridin-3-yl)-1H-pyrrole-2-carboxamide, | 13 | 2.44 (s, 3H, ArCH3), 7.27 (dd, J = 7.9, 4.7 Hz, 1H, H-5"), 7.50 (s, 1H, H-3), 7.51 (d, J = 9.1 Hz. 2H, H-5'), 7.59 (s, 1H, H-5), 7.72 (dd, J = 7.7, 1 8 Hz, 1H, H-4"), 7.77 (dd, J = 8.3, 8.3 Hz, 1H, H-4'), 8.34 (dd, J = 4.9, 1.8 Hz, 1H, H-6"), 9.90 (s, 1H, CONHAr), 12.74 (s, 1H, NH-pyrrole) | 389.6, 390.3 |
| 82. | 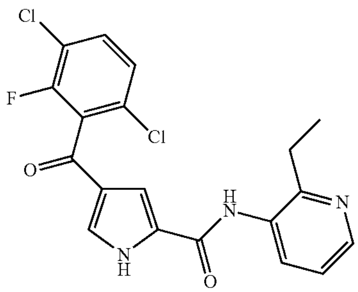 [SMILES: CCc1ncccc1NC(=O)c1cc(C(=O)c2c(Cl)ccc(Cl)c2F)c[nH]1] | 4-(3,6-Dichloro-2-fluorobenzoyl)-N-(2-ethylpyridin-3-yl)-1H-pyrrole-2-carboxamide, | 13 | 1.18 (t, J = 7.4 Hz, 3H, ArCH2CH3), 2.77 (q, J = 7.6 Hz, 2H, ArCH2CH3), 7.28 (dd, J = 7.4, 4.4 Hz, 1H, H-5"), 7.55-7.48 (m, 2H, H-3 and H-5'), 7.59 (s, 1H, H-5), 7.69 (d, J = 7.9 Hz, 1H, H-4"), 7.77 (dd, J = 8.3, 8.3 Hz, 1H, H-4'), 8.41 (d, J = 5.1 Hz, 1H, H-6"), 9.91 (s, 1H, CONHAr), 12.72 (s, 1H, NH-pyrrole); | 404.2, 404.3 |
| 83. | 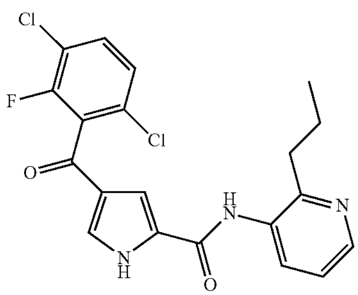 [SMILES: CCCc1ncccc1NC(=O)c1cc(C(=O)c2c(Cl)ccc(Cl)c2F)c[nH]1] | 4-(3,6-Dichloro-2-fluorobenzoyl)-N-(2-propylpyridin-3-yl)-1H-pyrrole-2-carboxamide, | 13 | 0.87 (t, J = 7.4 Hz, 3H, ArCH2CH2CH3), 1.67 (tq, J = 7.5 Hz, 2H, ArCH2CH2CH3), 2.74 (t, J = 7.6 Hz, 2H, ArCH2CH2CH3), 7.27 (dd, J = 7.9, 4.7 Hz, 1H, H-5"), 7.49 (s, 1H, H-3), 7.51 (d, J = 9.0 Hz, 1H, H-5'), 7.58 (s, 1H, H-5), 7.69 (dd, J = 7.8, 1.7 Hz, 1H, H-4"), 7.77 (dd, J = 8.3, 8.3 Hz, 1H, H-4'), 8.40 (dd, J = 4.8, 1.7 Hz, 1H, H-6"), 9.90 (s, 1H, CONHAr), 12.72 (s 1H, NH-pyrrole) | 418.2, 420.2 |
| 84. | 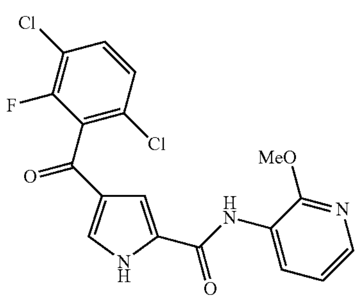 [SMILES: COc1ncccc1NC(=O)c1cc(C(=O)c2c(Cl)ccc(Cl)c2F)c[nH]1] | 4-(3,6-Dichloro-2-fluorobenzoyl)-N-(2-methoxypyridin-3-yl)-1H-pyrrole-2-carboxamide, | 14 | 3.92 (s, 3H, ArOCH3), 7.03 (dd, J = 7.6, 4 9 Hz. 1H, C-5"), 7.55-7.47 (m, 2H, H-3 and H-5'), 7.60 (s, 1H, H-5), 7.78 (dd, J = 8.4 Hz, 1H, H-4'), 7.98 (dd, J = 7.7, 1.6 Hz, 1H, H-4"), 8.00 (dd, J = 5.0, 1.9 Hz, 1H, H-6"), 9.61 (s, 1H, CONHAr), 12.72 (s, 1H, NH-pyrrole) | 406.4, 407.8 |
| 85. | 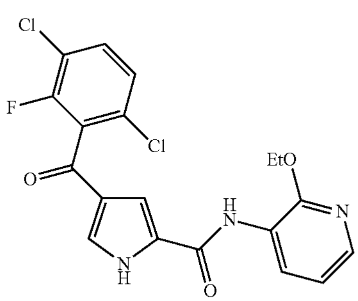 [SMILES: CCOc1ncccc1NC(=O)c1cc(C(=O)c2c(Cl)ccc(Cl)c2F)c[nH]1] | 4-(3,6-Dichloro-2-fluorobenzoyl)-N-(2-ethoxypyridin-3-yl)-1H-pyrrole-2-carboxamide, | 14 | 1.34 (t, J = 7.0 Hz, 3H, ArOCH2CH3), 4.39 (q, J = 7.0 Hz, 2H, ArOCH2CH3), 7.00 (dd, J = 7.5, 5.0 Hz, 1H, H-5"), 7.49 (s, 1H, H-3), 7.51 (dd, J = 8.5, 1.3 Hz, 1H, H-5'), 7.59 (s, 1H, H-5), 7.77 (dd, J = 8.4, 8.4 Hz, 1H, H-4'), 8.04-7.89 (m, 2H, H-4" and H-6"), 9.52 (s, 1H, CONHAr), 12.73 (s, 1H, NH-pyrrole) | 420.2 |

Example 86: 4-(3,6-Dichloro-2-fluorobenzoyl)-N-(2-(pyrrolidin-1-yl)pyridin-3-yl)-1H-pyrrole-2-carboxamide

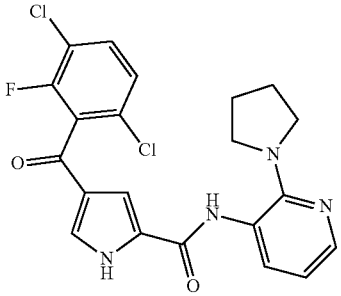 [SMILES: O=C(Nc1cccnc1N1CCCC1)c1cc(C(=O)c2c(Cl)ccc(Cl)c2F)c[nH]1]

To a solution of 4-(3,6-dichloro-2-fluorobenzoyl)-1H-pyrrole-2-carboxylic acid (100 mg, 0.33 mmol) in DCM (3.3 mL) was added triethylamine (115 μL, 84 mg, 0.83 mmol), 2-chloro-1-methylpyridinium iodide (93 mg, 0.36 mmol) and 2-(pyrrolidin-1-yl)pyridin-3-amine (67 mg, 0.41 mmol). The resulting solution was stirred at 42° C. overnight. Upon completion, the solvent removed in vacuo. The crude residue was dissolved in EtOAc (30 mL), washed with sat. aq. NaHCO$_3$ (20 mL) and extracted with EtOAc (2×20 mL). The pooled organic extracts were washed with brine (30 mL), dried over MgSO$_4$ and concentrated in vacuo. The crude yellow solid was purified by column chromatography (silica gel, petrol:EtOAc—1:0→4:6) to yield the title compound as a pale yellow solid (45 mg, 30%); $^1$H NMR (500 MHz, DMSO-d$_6$) δ 1.81 (t, J=6.5 Hz, 4H, NCH$_2$CH$_2$), 3.44 (t, J=6.4 Hz, 4H, NCH$_2$CH$_2$), 6.67 (dd, J=7.5, 4.7 Hz, 1H, H-5"), 7.38 (dd, J=7.3, 1.9 Hz, 1H, H-4"), 7.44 (s, 1H, H-3), 7.51 (d, J=9.2 Hz, 1H, H-5'), 7.53 (s, 1H, H-5), 7.77 (dd, J=8.3, 8.3 Hz, 1H, H-4'), 8.02 (dd, J=4.8, 1.9 Hz, 1H, H-6"), 9.84 (s, 1H, CONHAr), 12.64 (s, 1H, NH-pyrrole); LRMS (ES$^+$) m/z 447.3, 448.3, 449.3, 450.3 [M+H]$^+$; HRMS (NSI) calcd for C$_{21}$H$_{16}$Cl$_2$FN$_4$O$_2$ [M−H]$^−$: 445.0640; found 445.0636.

By following methods similar and/or analogous to those described herein, the compounds set out in the Table 9 below were prepared from the corresponding starting materials.

TABLE 9

| Ex. | Structure | Name | General prep | 1H NMR Data | MS |
|---|---|---|---|---|---|
| 87. | 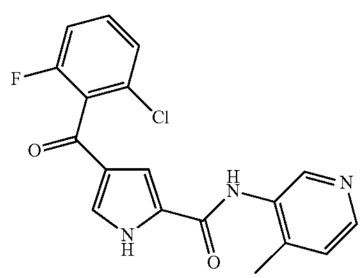 [SMILES: Cc1ccncc1NC(=O)c1cc(C(=O)c2c(F)cccc2Cl)c[nH]1] | 4-(2-Chloro-6-fluorobenzoyl)-N-(4-methylpyridin-3-yl)-1H-pyrrole-2-carboxamide, | 13 | 2.24 (s, 3H, ArCH3), 7.31 (d, J = 4.9 Hz, 1H, H-5"), 7.39 (ddd, J = 8.6, 8.6, 0.9 Hz, 1H, H-5'), 7.49-7.42 (m, 3H, H-3 and H-5 and H-3'), 7.57 (ddd, J = 8.3, 8.3, 6.2 Hz, 1H, H-4'), 8.31 (d, J = 4.9 Hz, 1H, H-6"), 8.45 (s, 1H, H-2"), 9.95 (s, 1H, CONHAr), 12.67 (s, 1H, NH-pyrrole) | 356.0, 358.2 |
| 88. | 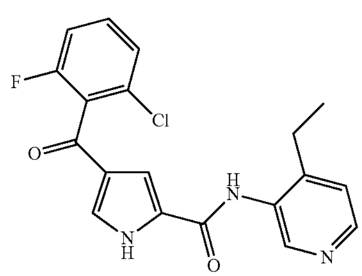 [SMILES: CCc1ccncc1NC(=O)c1cc(C(=O)c2c(F)cccc2Cl)c[nH]1] | 4-(2-Chloro-6-fluorobenzoyl)-N-(4-ethylpyridin-3-yl)-1H-pyrrole-2-carboxamide. | 13 | 1.14 (t, J = 7.5 Hz, 3H, ArCH2CH3), 2.62 (q, J = 7.5 Hz, 2H, ArCH2CH3), 7.34 (d, J = 5.0 Hz, 1H, H-5"), 7.30 (dd, J = 9.0, 9.0 Hz, 1H, H-5'), 7.42 (s, 1H, H-5), 7.46 (d, J = 7.7 Hz, 2H, H-3 and H-3'), 7.57 (ddd, J = 8.3, 8.3, 6.2 Hz, 1H, H-4'), 8.38 (d, J = 5.0 Hz, 1H, H-6"), 8.42 (s, 1H, H-2"), 9.93 (s, 1H, CONHAr), 12.66 (s, 1H, NH-pyrrole) | 370.2, 372.2 |
| 89. | 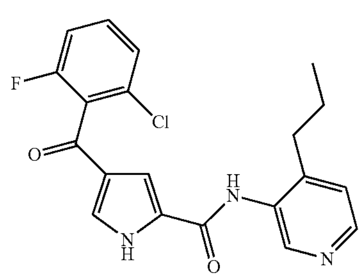 [SMILES: CCCc1ccncc1NC(=O)c1cc(C(=O)c2c(F)cccc2Cl)c[nH]1] | 4-(2-Chloro-6-fluorobenzoyl)-N-(4-propylpyridin-3-yl)-1H-pyrrole-2-carboxamide. | 13 | 0.86 (t, J = 7.3 Hz, 3H, ArCH2CH2CH3), 1.57 (tq, J = 7.4, 7.4 Hz, 2H, ArCH2CH2CH3), 2 58 (t, J = 7.7 Hz, 2H, ArCH2CH2CH3), 7.32 (d, J = 5.0 Hz, 1H, H-5"), 7.39 (dd, J = 9.0, 8.6 Hz, 1H, H-5'), 7.42 (s, 1H, H-5), 7.49-7.44 (m, 2H, H-3 and H-3'), 7.57 (ddd, J = 8.3, 8.3, 6.1 Hz, 1H, H-4'), 8.36 (d, J = 5.0 Hz, 1H, H-6"), 8.43 (s, 1H, H-2"), 9.93 (s, 1H, CONHAr), 12.66 (s, 1H, NH-pyrrole) | 384.2, 386.2 |

TABLE 9-continued

| Ex. | Structure | Name | General prep | 1H NMR Data | MS |
|---|---|---|---|---|---|
| 90. | 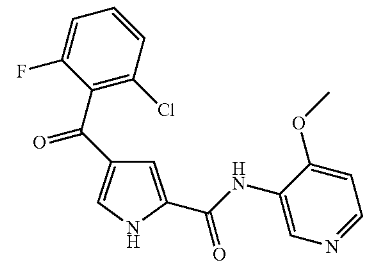 [SMILES: COc1ccncc1NC(=O)c1cc(C(=O)c2c(F)cccc2Cl)c[nH]1] | 4-(2-Chloro-6-fluorobenzoyl)-N-(4-methoxypyridin-3-yl)-1H-pyrrole-2-carboxamide, | 18 | 3.88 (s, 3H, ArOCH3), 7.15 (d, J = 5.7 Hz, 1H, H-5"), 7.39 (dd, J = 8.6, 8.6 Hz, 1H, H-5'), 7.44 (d, J = 2.8 Hz, 2H, H-3 and H-5), 7.46 (d, J = 8.3 Hz, 1H, H-3'), 7.58 (ddd, J = 8 2, 8.2, 6.2 Hz, 1H, H-4'), 8.33 (d, J = 5.7 Hz, 1H, H-6"), 8.52 (s, 1H, H-2"), 9.68 (s, 1H, CONHAr), 12.63 (s, 1H, NH-pyrrole) | 372.2, 374.2 |

Example 91: 4-(2-Chloro-6-fluorobenzoyl)-N-(4-ethoxypyridin-3-yl)-1H-pyrrole-2-carboxamide

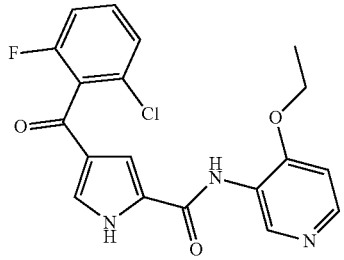 [SMILES: CCOc1ccncc1NC(=O)c1cc(C(=O)c2c(F)cccc2Cl)c[nH]1]

To a solution of 4-(2-chloro-6-fluorobenzoyl)-1H-pyrrole-2-carboxylic acid (100 mg, 0.37 mmol) in DCM (3.7 mL) was added 4-ethoxypyridin-3-amine (65 mg, 0.47 mmol) followed by 2-chloro-1-methylpyridinium iodide (105 mg, 0.41 mmol). The resulting solution was stirred at 42° C. for 72 h. Upon completion, the solvent removed in vacuo. The crude residue was dissolved in EtOAc (30 mL), washed with sat. aq. NaHCO₃ (20 mL) and extracted with EtOAc (2×20 mL). The pooled organic extracts were washed with brine (30 mL), dried over MgSO₄ and concentrated in vacuo. The crude yellow solid was purified by column chromatography (amine silica gel, petrol:EtOAc—1:0→1:9) to yield the title compound as a white solid (30 mg, 21%); ¹H NMR (500 MHz, DMSO-d₆) δ 1.34 (t, J=6.9 Hz, 3H, ArOCH₂CH₃), 4.18 (q, J=7.0 Hz, 2H, ArOCH₂CH₃), 7.13 (d, J=5.7 Hz, 1H, H-5"), 7.39 (dd, J=9.0, 8.5 Hz, 1H, H-5'), 7.42 (s, 1H, H-5), 7.44 (s, 1H, H-3), 7.46 (d, J=8.2 Hz, 1H, H-3'), 7.57 (ddd, J=8.2, 8.2, 6.1 Hz, 1H, H-4'), 8.30 (d, J=5.6 Hz, 1H, H-6"), 8.52 (s, 1H, H-2"), 9.62 (s, 1H, CONHAr), 12.64 (s, 1H, NH-pyrrole); LRMS (ES⁻) m/z 386.2, 388.2 [M−H]⁻; HRMS (NSI) calcd for C₁₉H₁₄ClFN₃O₃ [M−H]⁻: 386.0713; found 386.0708.

Example 92: 4-(2-Chloro-6-fluorobenzoyl)-N-(4-(pyrrolidin-1-yl)pyridin-3-yl)-1H-pyrrole-2-carboxamide

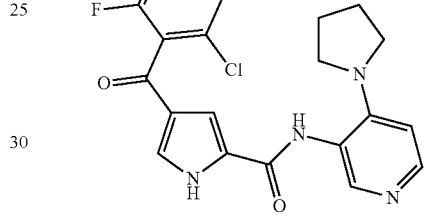

To a solution of 4-(2-chloro-6-fluorobenzoyl)-1H-pyrrole-2-carboxylic acid (100 mg, 0.37 mmol) in DCM (3.7 mL) was added 4-(pyrrolidin-1-yl)pyridin-3-amine (76 mg, 0.56 mmol) followed by 2-chloro-1-methylpyridinium iodide (105 mg, 0.41 mmol). The resulting solution was stirred at 42° C. for 72 h. Upon completion, the solvent removed in vacuo. The crude residue was dissolved in EtOAc (30 mL), washed with sat. aq. NaHCO₃ (20 mL) and extracted with EtOAc (2×20 mL). The pooled organic extracts were washed with brine (30 mL), dried over MgSO₄ and concentrated in vacuo. The crude yellow solid was purified by column chromatography (amine silica gel, EtOAc:MeOH—1:0→95:5) to yield the title compound as an off-white solid (35 mg, 23%); ¹H NMR (500 MHz, DMSO-d₆) δ 1.84 (t, J=6.6 Hz, 4H, NCH₂CH₂), 3.37 (t, J=6.2 Hz, 4H, NCH₂CH₂), 6.59 (d, J=5.8 Hz, 1H, H-5"), 7.35 (s, 1H, H-5), 7.43-7.36 (m, 2H, H-3 and H-5'), 7.46 (d, J=8.1 Hz, 1H, H-3'), 7.57 (ddd, J=8.3, 8.3, 6.2 Hz, 1H, H-4'), 7.92 (s, 1H, H-2"), 8.03 (d, J=5.8 Hz, 1H, H-6"), 9.82 (s, 1H, CONHAr), 12.57 (s, 1H, NH-pyrrole); LRMS (ES⁺) m/z 413.4, 415.4 [M+H]⁺; HRMS (NSI) calcd for C₂₁H₁₉ClFN₄O₂ [M+H]⁺: 413.1175; found 413.1170.

By following methods similar and/or analogous to those described herein, the compounds set out in the Table 10 below were prepared from the corresponding starting materials.

TABLE 10

| Ex. | Structure | Name | General prep | 1H NMR Data | MS |
|---|---|---|---|---|---|
| 93. | 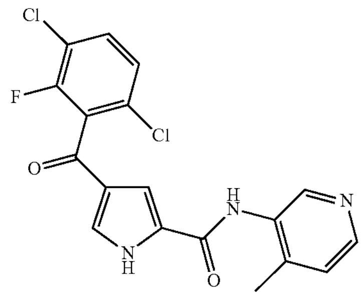 [SMILES: Cc1ccncc1NC(=O)c1cc(C(=O)c2c(Cl)ccc(Cl)c2F)c[nH]1] | 4-(3,6-Dichloro-2-fluorobenzoyl)-N-(4-methylpyridin-3-yl)-1H-pyrrole-2-carboxamide, | 13 | 2.25 (s, 3H, ArCH3), 7.32 (d, J = 4.9 Hz, 1H, H-5''), 7.49 (s, 1H, H-3), 7.52 (dd, J = 8.8, 1.3 Hz, 1H, H-5'), 7.60 (s, 1H, H-5), 7.78 (dd, J = 8.4, 8.4 Hz, 1H, H-4'), 8.32 (d, J = 4.9 Hz, 1H, H-6''), 8.46 (s, 1H, H-2''), 9.95 (s, 1H, CONHAr), 12.74 (s, 1H, NH-pyrrole) | 392.1, 392.4, 394.1 |
| 94. | 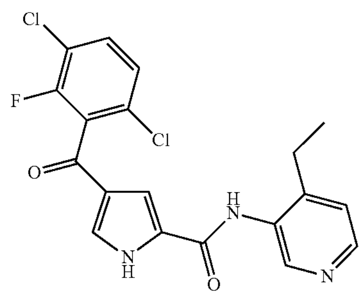 [SMILES: CCc1ccncc1NC(=O)c1cc(C(=O)c2c(Cl)ccc(Cl)c2F)c[nH]1] | 4-(3,6-Dichloro-2-fluorobenzoyl)-N-(4-ethylpyridin-3-yl)-1H-pyrrole-2-carboxamide, | 13 | 1.14 (t, J = 7.5 Hz, 3H, ArCH2CH3), 2.62 (q, J = 7.5 Hz, 2H, ArCH2CH3), 7.35 (d, J = 5.0 Hz, 1H, H-5''), 7.49 (s, 1H, H-3), 7.52 (dd, J = 8.9, 1.3 Hz, 1H, H-5'), 7.59 (s, 1H, H-5), 7.78 (dd, J = 8.4, 8.4 Hz, 1H, H-4'), 8.38 (d, J = 5.0 Hz, 1H, H-6''), 8.43 (s, 1H, H-2''), 9.94 (s, 1H, CONHAr), 12.73 (s, 1H, NH-pyrrole) | 404.2, 406.2 |
| 95. | 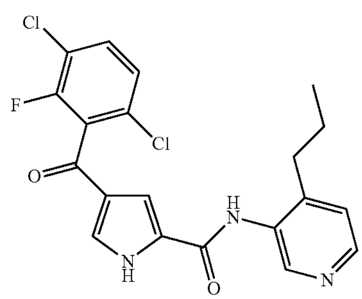 [SMILES: CCCc1ccncc1NC(=O)c1cc(C(=O)c2c(Cl)ccc(Cl)c2F)c[nH]1] | 4-(3,6-Dichloro-2-fluorobenzoyl)-N-(4-propylpyridin-3-yl)-1H-pyrrole-2-carboxamide, | 13 | 0.86 (t, J = 7.3 Hz, 3H, ArCH2CH2CH3), 1.57 (tq, J = 7 4, 7.4 Hz, 2H, ArCH2CH2CH3), 2.59 (t, J = 7.7 Hz, 2H, ArCH2CH2CH3), 7.32 (d, J = 5.0 Hz, 1H, H-5''), 7.49 (s, 1H, H-3), 7.52 (dd, J = 8.8, 1.4 Hz, 1H, H-5'), 7.59 (dd, J = 3.4, 1.7 Hz, 1H), 7.78 (dd, J = 8.4, 8.4 Hz, 1H, H-4'), 8.37 (d, J = 5.0 Hz, 1H, H-6''), 8.44 (s, 1H, H-2''), 9.93 (s, 1H, CONHAr), 12.73 (s, 1H, NH-pyrrole) | 418.3, 420.3 |
| 96. | 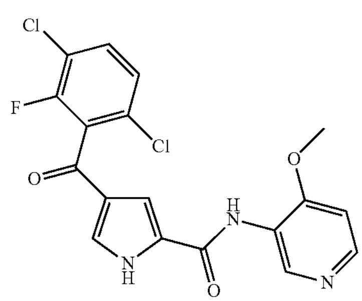 [SMILES: COc1ccncc1NC(=O)c1cc(C(=O)c2c(Cl)ccc(Cl)c2F)c[nH]1] | 4-(3,6-Dichloro-2-fluorobenzoyl)-N-(4-methoxypyridin-3-yl)-1H-pyrrole-2-carboxamide, | 17 | 3.89 (s, 3H, ArOCH3), 7.16 (d, J = 5.6 Hz, 1H, H-5''), 7.48 (s, 1H, H-3), 7.52 (d, J = 8.7 Hz, 1H, H-5'), 7.59 (s, 1H, H-5), 7.78 (dd, J = 8.3, 8.3 Hz, 1H, H-4'), 8.33 (d, J = 5.6 Hz, 1H, H-6''), 8.53 (s, 1H, H-2''), 9.68 (s, 1H, CONHAr), 12.71 (s, 1H, NH-pyrrole) | 406.2, 408.2 |

Example 97: 4-(3,6-Dichloro-2-fluorobenzoyl)-N-(4-ethoxypyridin-3-yl)-1H-pyrrole-2-carboxamide Example 98: 4-(3,6-Dichloro-2-fluorobenzoyl)-N-(4-(pyrrolidin-1-yl)pyridin-3-yl)-1H-pyrrole-2-carboxamide

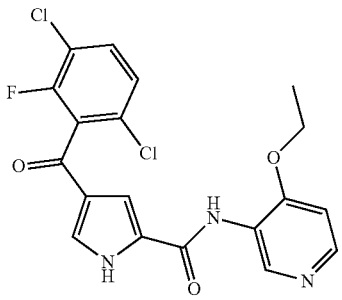 [SMILES: CCOc1ccncc1NC(=O)c1cc(C(=O)c2c(Cl)ccc(Cl)c2F)c[nH]1]

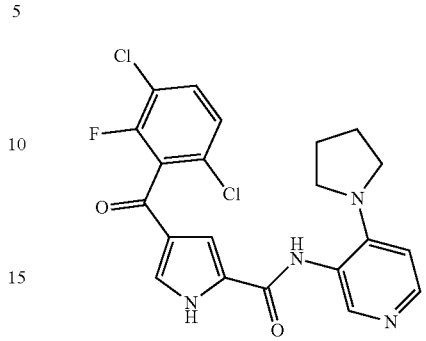

To a solution of 4-(3,6-dichloro-2-fluorobenzoyl)-1H-pyrrole-2-carboxylic acid (100 mg, 0.33 mmol) in DCM (3.3 mL) was added 4-ethoxypyridin-3-amine (57 mg, 0.41 mmol) followed by 2-chloro-1-methylpyridinium iodide (93 mg, 0.36 mmol). The resulting solution was stirred at 42° C. for 72 h. Upon completion, the solvent removed in vacuo. The crude residue was dissolved in EtOAc (30 mL), washed with sat. aq. NaHCO$_3$ (20 mL) and extracted with EtOAc (2×20 mL). The pooled organic extracts were washed with brine (30 mL), dried over MgSO$_4$ and concentrated in vacuo. The crude yellow solid was purified by column chromatography (amine silica gel, petrol:EtOAc—1:0→85:15) to yield the title compound as an off-white solid (18 mg, 13%); $^1$H NMR (500 MHz, DMSO-d$_6$) δ 1.34 (t, J=6.9 Hz, 3H, ArOCH$_2$CH$_3$), 4.18 (q, J=7.0 Hz, 2H, ArOCH$_2$CH$_3$), 7.14 (d, J=5.7 Hz, 1H, H-5"), 7.47 (s, 1H, H-3), 7.51 (dd, J=8.7, 1.3 Hz, 1H, H-5'), 7.58 (s, 1H, H-5), 7.78 (dd, J=8.4 Hz, 1H, H-4'), 8.30 (d, J=5.6 Hz, 1H, H-6"), 8.53 (s, 1H, H-2"), 9.61 (s, 1H, CONHAr), 12.71 (s, 1H, NH-pyrrole); LRMS (ES$^-$) m/z 420.2, 422.2 [M−H]$^-$ To a solution of 4-(3,6-dichloro-2-fluorobenzoyl)-1H-pyrrole-2-carboxylic acid (100 mg, 0.33 mmol) in DCM (3.3 mL) was added 4-(pyrrolidin-1-yl)pyridin-3-amine (67 mg, 0.41 mmol) followed by 2-chloro-1-methylpyridinium iodide (93 mg, 0.36 mmol). The resulting solution was stirred at 42° C. overnight. Upon completion, the solvent removed in vacuo. The crude residue was dissolved in EtOAc (30 mL), washed with sat. aq. NaHCO$_3$ (20 mL) and extracted with EtOAc (2×20 mL). The pooled organic extracts were washed with brine (30 mL), dried over MgSO$_4$ and concentrated in vacuo. The crude yellow solid was purified by column chromatography (amine silica gel, EtOAc:MeOH—1:0→95:5) to yield the title compound as an off-white solid (50 mg, 34%); $^1$H NMR (500 MHz, DMSO-d$_6$) δ 1.84 (t, J=6.6 Hz, 4H, NCH$_2$CH$_2$), 3.37 (t, J=6.3 Hz, 4H, NCH$_2$CH$_2$), 6.59 (d, J=5.9 Hz, 1H, H-5"), 7.43 (s, 1H, H-3), 7.51 (dd, J=8.7, 1.3 Hz, 1H, H-5'), 7.53 (s, 1H, H-5), 7.77 (dd, J=8.3, 8.3 Hz, 1H, H-4'), 7.93 (s, 1H, H-2"), 8.03 (d, J=5.8 Hz, 1H, H-6"), 9.83 (s, 1H, CONHAr), 12.66 (s, 1H, NH-pyrrole); LRMS (ES$^-$) m/z 445.2, 447.2 [M−H]$^-$; HRMS (NSI) calcd for C$_{21}$H$_{16}$Cl$_2$FN$_4$O$_2$ [M−H]$^-$: 445.0640; found 445.0633.

By following methods similar and/or analogous to those described herein, the compounds set out in the Table 11 below were prepared from the corresponding starting materials.

TABLE 11

| Ex. | Structure | Name | General prep | 1H NMR Data | MS |
| --- | --- | --- | --- | --- | --- |
| 99. | (structure shown) | 4-(3,6-Dichloro-2-fluorobenzoyl)-N-(2-((2-(dimethylamino)ethyl)amino)pyrimidin-5-yl)-1H-pyrrole-2-carboxamide, | 17 | 2.16 (6H, s, CH2N(CH3)2), 2.39 (2H, t, J = 6.8 Hz, CH2CH2NMe2), 3.30-3.39 (2H, m, NHCH2CH2), 6.86 (1H, t, J = 5.8 Hz, ArNHCH2), 7.39 (1H, s, H-3), 7.51 (1H, dd, J = 8.7, 1.2 Hz, H-5'), 7.59 (1H, d, J = 0.9 Hz, H-5), 7.77 (1H, dd, J = 8.4, 8.4 Hz, H-4'), 8.49 (2H, s, H-4", 6"), 9.95 (1H, s, CONHAr), 12.71 (1H, s, NH-pyrrole) | 465.4, 467.4 |

TABLE 11-continued

| Ex. | Structure | Name | General prep | 1H NMR Data | MS |
|---|---|---|---|---|---|
| 100 | 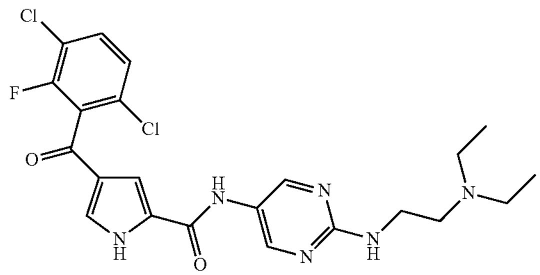 [SMILES: CCN(CC)CCNc1ncc(NC(=O)c2cc(C(=O)c3c(Cl)ccc(Cl)c3F)c[nH]2)cn1] | 4-(3,6-Dichloro-2-fluorobenzoyl)-N-(2-((2-(diethylamino)ethyl)amino)pyrimidin-5-yl)-1H-pyrrole-2-carboxamide, | 17 | 0.95 (6H, t, J = 7.1 Hz, N(CH2CH3)2), 2.52-2.47 (4H, m, N(CH2CH3)2), 2.54 (2H, t, J = 7.1 Hz, CH2NEt2), 3.38-3.26 (2H, m, ArNHCH2CH2), 6.81 (1H, t, J = 5.8 Hz, ArNHCH2), 7.38 (1H, s, H-3), 7.51 (1H, dd, J = 8.8, 1.3 Hz, H-5'), 7.59 (1H, s, H-5), 7.78 (1H, dd, J = 8.4, 8.4 Hz, H-4'), 8.48 (2H, s, H-4", 6"), 9.94 (1H, s, CONHAr), 12.69 (1H, s, NH-pyrrole) | 491.3, 493.3 |
| 101 | 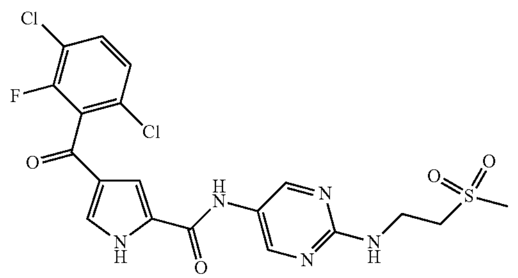 [SMILES: CS(=O)(=O)CCNc1ncc(NC(=O)c2cc(C(=O)c3c(Cl)ccc(Cl)c3F)c[nH]2)cn1] | 4-(3,6-Dichloro-2-fluorobenzoyl)-N-(2-((2-(methylsulfonyl)amino)ethyl)amino)pyrimidin-5-yl)-1H-pyrrole-2-carboxamide, | 17 | 3.02 (3H, s, SO2CH3), 3.37 (2H, t, J = 6.9 Hz, CH2SO2CH3), 3.69 (2H, td, J = 6.9, 5.9 Hz, ArNHCH2CH2), 7.27 (1H, t, J = 5.9 Hz, ArNHCH2), 7.40 (1H, s, H-3), 7.52 (1H, dd, J = 8.7, 1.2 Hz, H-5'), 7.60 (1H, S, H-5), 7.78 (1H, dd, J = 8.4, 8 4 Hz, H-4'), 8.56 (2H, s, H-4", 6"), 10.01 (1H, s, CONHAr), 12.73 (1H, s, NH-pyrrole); | 500.3, 502.3 |
| 102 | 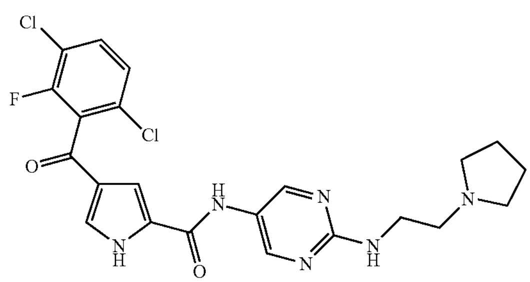 [SMILES: O=C(Nc1cnc(NCCN2CCCC2)nc1)c1cc(C(=O)c2c(Cl)ccc(Cl)c2F)c[nH]1] | 4-(3,6-Dichloro-2-fluorobenzoyl)-N-(2-((2-(pyrrolidin-1-yl)ethyl)amino)pyrimidin-5-yl)-1H-pyrrole-2-carboxamide, | 17 | 1.61-1.72 (4H, m, NCH2CH2 pyrrolidine), 2.42-2.49 (4H, m, NCH2CH2 pyrrolidine), 2.56 (2H, t, J = 6.9 Hz, ArNHCH2CH2N), 3.37 (2H, td, J = 6.9, 5.8 Hz, ArNHCH2CH2), 6.93 (1H, t, J = 5.8 Hz, ArNHCH2), 7.38 (1H, S, H-3), 7.51 (1H, dd, J = 8.8, 1.4 Hz, H-5'), 7.59 (1H, s, H-5), 7.78 (1H, dd, J = 8.4 Hz, H-4'), 8.48 (2H, s, H-4", 6"). 9.94 (1H, s, CONHAr), 12.70 (1H, s, NH-pyrrole) | 491.4, 493.4 |
| 103 | 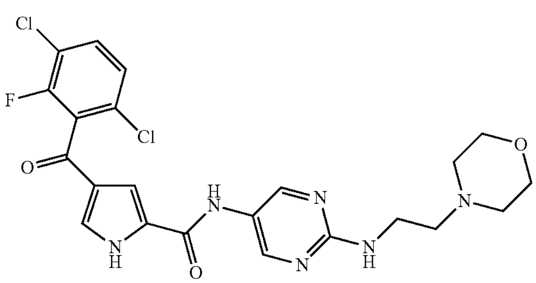 [SMILES: O=C(Nc1cnc(NCCN2CCOCC2)nc1)c1cc(C(=O)c2c(Cl)ccc(Cl)c2F)c[nH]1] | 4-(3,6-Dichloro-2-fluorobenzoyl)-N-(2-((2-morpholinoethyl)amino)pyrimidin-5-yl)-1H-pyrrole-2-carboxamide, | 17 | 2.40 (4H, brs, NCH2 morpholine), 2.46 (2H, t, J = 6.8 Hz, ArNHCH2CH2N), 3.38 (2H, td, J = 6.8, 5.8 Hz, ArNHCH2CH2), 3.56 (4H, t, J = 4.6 Hz, OCH2 morpholine), 6.90 (1H, t, J = 5.8 Hz, ArNHCH2), 7.39 (1H, s, H-3), 7.51 (1H, dd, J = 8.8, 1.4 Hz, H-5'), 7.59 (1H, s, H-5), 7.77 (1H, dd, J = 8 4 Hz, H-4'), 8.49 (2H, s, H-4", 6"), 9.95 (1H, s, CONHAr), 12.71 (1H, s, NH-pyrrole) | 507.4, 509.4 |

TABLE 11-continued

| Ex. | Structure | Name | General prep | 1H NMR Data | MS |
|---|---|---|---|---|---|
| 104 | 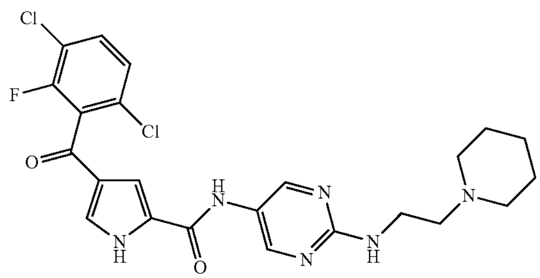 [SMILES: O=C(Nc1cnc(NCCN2CCCCC2)nc1)c1cc(C(=O)c2c(Cl)ccc(Cl)c2F)c[nH]1] | 4-(3,6-Dichloro-2-fluorobenzoyl)-N-(2-((2-(piperidin-1-yl)ethyl)amino)pyrimidin-5-yl)-1H-pyrrole-2-carboxamide, | 17 | 1.32-1.40 (2H, m, NCH2CH2CH2 piperidine), 1.48 (4H, p, J = 5.6 Hz, NCH2CH2CH2 piperidine), 2.36 (4H, brs, NCH2CH2CH2 piperidine), 2.42 (2H, t, J = 6.9 Hz, ArNHCH2CH2N), 3.36 (2H, td, J = 6.9, 5.7 Hz, ArNHCH2CH2), 6.83 (1H, t, J = 5.7 Hz, ArNHCH2), 7.39 (1H, s, H-3), 7.51 (1H, dd, J = 8.8, 14 Hz, H-5'), 7.59 (1H, s, H-5), 7.78 (1H, dd, J = 8.4, 8.4 Hz, H-4 ), 8.48 (2H, s, H-4", 6"), 9.95 (1H, s, CONHAr), 12.71 (1H, s, NH-pyrrole) | 505.4, 507.4 |
| 105 | 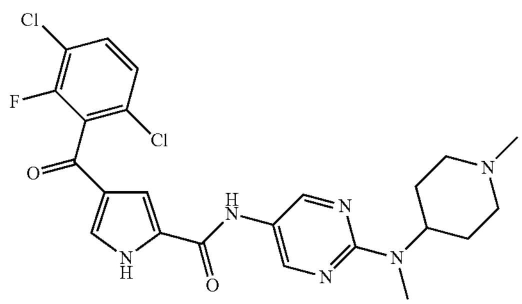 [SMILES: CN1CCC(N(C)c2ncc(NC(=O)c3cc(C(=O)c4c(Cl)ccc(Cl)c4F)c[nH]3)cn2)CC1] | 4-(3,6-Dichloro-2-fluorobenzoyl)-N-(2-(methyl(1-methylpiperidin-4-yl)amino)pyrimidin-5-yl)-1H-pyrrole-2-carboxamide, | 17 | 1.40-1.63 (2H, m, CH2CH2NMe), 1.80 (2H, dddd, J = 12.2, 12.2, 12.2, 3.7 Hz, CH2CH2NMe), 1.93-2.11 (2H, m, CH2CH2NMe), 2.21 (3H, s, NCH3), 2.88 (2H, d, J = 11.1 Hz, CH2CH2NMe), 2.96 (3H, s, NCH3), 4.52 (1H, tt, J = 12.0, 3.9 Hz, ArN(CH3)CH), 7.40 (1H, s, H-3), 7.52 (2H, dd, J = 8.8, 1.0 Hz, H-5'), 7.60 (1H, s, H-5), 7.78 (1H, dd, J = 8.4, 8.4 Hz, H-4'), 8.57 (2H, s, H-4", 6"), 10.01 (1H, s, CONHAr), 12.74 (1H, s, NH-pyrrole) | 503.3, 505.3 |
| 106 | 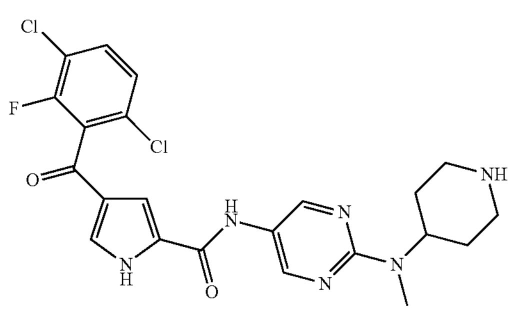 [SMILES: CN(c1ncc(NC(=O)c2cc(C(=O)c3c(Cl)ccc(Cl)c3F)c[nH]2)cn1)C1CCNCC1] | 4-(3,6-Dichloro-2-fluorobenzoyl)-N-(2-(methyl(piperidin-4-yl)amino)pyrimidin-5-yl)-1H-pyrrole-2-carboxamide, | 17 | 1.42-1.56 (2H, m, CH2CH2NH), 1.62 (2H, dddd, J = 12.1, 12.1, 12.1, 4.2 Hz, CH2CH2NH), 2.56 (2H, ddd, J = 12.1, 12.1, 2.6 Hz, CH2CH2NH), 2.95 (3H, s, NCH3), 2.98-3.09 (2H, m, CH2CH2NH), 4.61 (1H, tt, J = 11.9, 3.9 Hz, ArN(CH3)CH), 7.37 (1H, s, H-3), 7.51 (1H, dd, J = 8.8, 1.4 Hz, H-5'), 7.58 (1H, s, H-5), 7.77 (1H, dd, J = 8.4 Hz, H-4'), 8.57 (2H, S, H-4", 6"), 9.98 (1H, S, CONHAr) | 489.3, 491.3 |

TABLE 11-continued

| Ex. | Structure | Name | General prep | 1H NMR Data | MS |
|---|---|---|---|---|---|
| 107 | 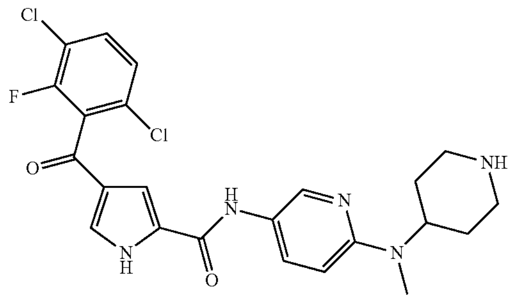 [SMILES: CN(c1ccc(NC(=O)c2cc(C(=O)c3c(Cl)ccc(Cl)c3F)c[nH]2)cn1)C1CCNCC1] | 4-(3,6-Dichloro-2-fluorobenzoyl)-N-(6-(methyl(piperidin-4-yl)amino)pyridin-3-yl)-1H-pyrrole-2-carboxamide, | 17 | 1.49 (d, J = 9.7 Hz, 2H, CH2CH2NH), 1.59 (dddd, J = 12.0, 12.0, 12.0, 4.1 Hz, 2H, CH2CH2NH), 2.57 (ddd, J = 12.1, 12.1, 2.7 Hz, 2H, CH2CH2NH), 2.81 (s, 3H, NCH3), 3.01 (d, J = 12.0 Hz, 2H, CH2CH2NH), 4.43 (tt, J = 11.8, 4.0 Hz, 1H, ArN(CH3)CH), 6.64 (d, J = 9.1 Hz, 1H, H-5"), 7.39 (s, 1H, H-3), 7.51 (dd, J = 8.8, 1.3 Hz, 1H, H-5'), 7.55 (s, 1H, H-5), 7.71-7.82 (m, 2H, H-4' and H-4"), 8.35 (d, J = 2.7 Hz, 1H, H-2"), 9.89 (s, 1H, CONHAr) | 488.3, 490.3 |
| 108 | 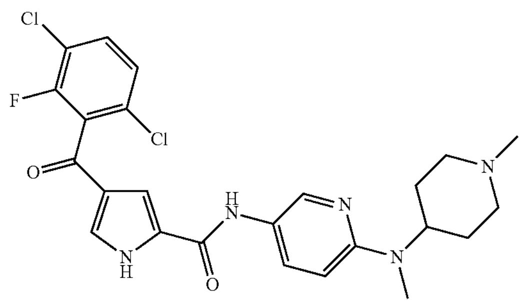 | 4-(3,6-Dichloro-2-fluorobenzoyl)-N-(6-(methyl(1-methylpiperidin-4-yl)amino)pyridin-3-yl)-1H-pyrrole-2-carboxamide, | 20 | 1.42-1.57 (m, 2H, CH2CH2NMe), 1.75 (dddd, J = 12.2, 12 2, 12.2, 3.8 Hz, 2H, CH2CH2NMe), 1.99 (ddd, J = 11.7, 11.7, 2.5 Hz, 2H, CH2CH2NMe), 2.17 (s, 3H, NCH3), 2.81 (s, 3H, NCH3), 2.82-2.85 (m, 2H, CH2CH2NMe), 4.34 (tt, J = 12.1, 4.0 Hz, 1H, ArN(CH3)CH), 6.64 (d, J = 9.1 Hz, 1H, H-5"), 7.41 (s, 1H, H-3), 7.51 (dd, J = 8.8, 1.4 Hz, 1H, H-5'), 7.56 (s, 1H, H-5), 7.75 (dd, J = 9.1, 2.6 Hz, 1H, H-4"), 7.77 (dd, J = 8.5, 8.5 Hz, 1H, H-4'), 8.35 (d, J = 2.7 Hz, 1H, H-2"), 9.89 (s, 1H, CONHAr), 12.66 (s, 1H, NH-pyrrole) | 502.3, 504.3 |
| 109 | 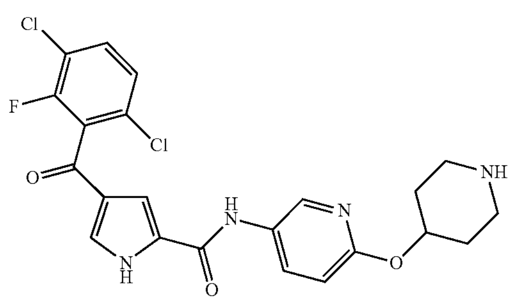 | 4-(3,6-Dichloro-2-fluorobenzoyl)-N-(6-(piperidin-4-yloxy)pyridin-3-yl)-1H-pyrrole-2-carboxamide, | 17 | 1.47 (dddd, J = 13.8, 10.3, 10.2, 4.0 Hz, 2H, CH2CH2NH), 1.84-2.00 (m, 2H, CH2CH2NH), 2.57 (ddd, J = 12.9, 10.5, 2.9 Hz, 2H, CH2CH2NH), 2.95 (ddd, J = 12.7, 4.1, 4.1 Hz, 2H, CH2CH2NH), 4.99 (tt, J = 9.2, 4.2 Hz, 1H, ArOCH), 6.78 (d, J = 8.8 Hz, 1H, H-5"), 7.42 (s, 1H, H-3), 7.51 (dd, J = 8.8, 1.3 Hz, 1H, H-5'), 7.58 (s, 1H, H-5), 7.77 (dd, J = 8.4, 8.4 Hz, 1H, H-4'), 7.96 (dd, J = 8.9, 2.8 Hz, 1H, H-4"), 8.42 (d, J = 2.7 Hz, 1H, H-2"), 10.07 (s, 1H, CONHAr) | 473.3, 475.3 |

| Ex. | Structure | Name | General prep | 1H NMR Data | MS |
|---|---|---|---|---|---|
| 110 | 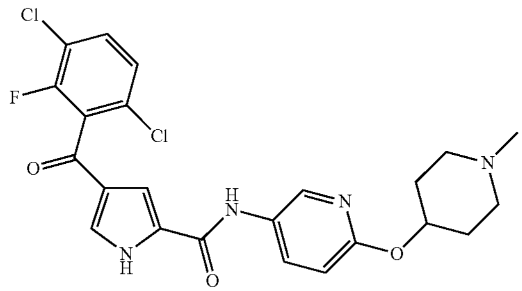 [SMILES: CN1CCC(Oc2ccc(NC(=O)c3cc(C(=O)c4c(Cl)ccc(Cl)c4F)c[nH]3)cn2)CC1] | 4-(3,6-Dichloro-2-fluorobenzoyl)-N-(6-((1-methylpiperidin-4-yl)oxy)pyridin-3-yl)-1H-pyrrole-2-carboxamide | 20 | 1.64 (dddd, J = 12.9, 9.3, 9.3, 3.6 Hz, 2H, CH2CH2NMe), 1.89-2.00 (m, 2H, CH2CH2NMe), 2.14 (dd, J = 11.6, 11.6 Hz, 2H, CH2CH2NMe), 2.17 (s, 3H, NCH3), 2.63 (ddd, J = 13.4, 4.5, 4.5 Hz, 2H, CH2CH2NMe), 4.92 (tt, J = 8.6, 3.9 Hz, 1H, ArOCH), 6.79 (d, J = 8 9 Hz, 1H, H-5"), 7.45 (d, J = 1.9 Hz, 1H, H-3), 7.52 (dd, J = 8.8, 1.4 Hz, 1H, H-5'), 7.59 (d, J = 1.6 Hz, 1H, H-5), 7.78 (dd, J = 8.4 Hz, 1H, H-4'), 7.96 (dd, J = 8.9, 2.7 Hz, 1H, H-4"), 8.43 (d, J = 2.7 Hz, 1H, H-2"), 10.09 (s, 1H, CONHAr), 12.72 (s, 1H, NH-pyrrole) | 489.3, 491. |
| 111 | 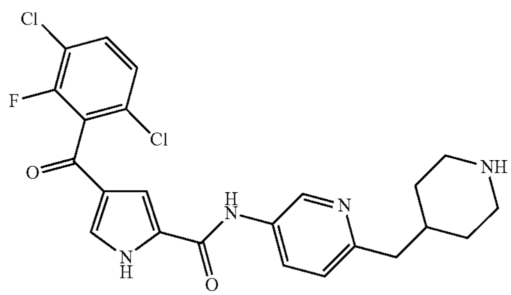 | 4-(3,6-Dichloro-2-fluorobenzoyl)-N-(6-(piperidin-4-ylmethyl)pyridin-3-yl)-1H-pyrrole-2-carboxamide | 18 | 1.00-1.17 (m, 2H, CH2CH2NH), 1 39-1.54 (m, 2H, CH2CH2NH), 1.68-1.88 (m, 1H, ArCH2CH), 2.43 (dd, J = 11.5, 11.5 Hz, 2H, CH2CH2NH), 2.58 (d, J = 7.0 Hz, 2H, ArCH2CH), 2.91 (ddd, J = 11.4, 3.4, 3.4 Hz, 2H, CH2CH2NH), 7.19 (d, J = 8.3 Hz, 1H, H-5"), 7.42 (s, 1H, H-3), 7.51 (d, J = 8.7 Hz, 1H, H-5'), 7.57 (s, 1H, H-5), 7.77 (dd, J = 8.3, 8.3 Hz, 1H, H-4'), 8.02 (dd, J = 8 4, 2.8 Hz, 1H, H-4"), 8.78 (d, J = 2.7 Hz, 1H, H-2"), 10.14 (s, 1H, CONHAr) | 473.3, 475.3 |
| 112 | 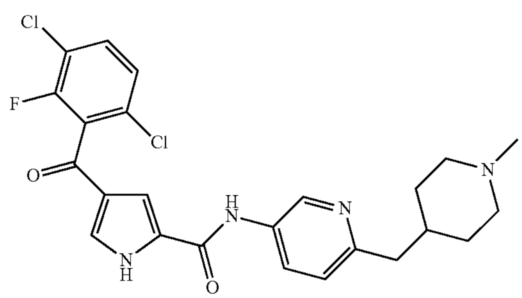 [SMILES: CN1CCC(Cc2ccc(NC(=O)c3cc(C(=O)c4c(Cl)ccc(Cl)c4F)c[nH]3)cn2)CC1] | 4-(3,6-Dichloro-2-fluorobenzoyl)-N-(6-((1-methylpiperidin-4-yl)methyl)pyridin-3-yl)-1H-pyrrole-2-carboxamide | 20 | 1.11-1.31 (m, 2H, CH2CH2NMe), 1.50 (d, J = 12.0 Hz, 2H, CH2CH2NMe), 1.57-1.70 (m, 1H, ArCH2CH), 1.77 (dd, J = 11.6, 11.6 Hz, 2H, CH2CH2NMe), 2.11 (s, 3H, NCH3), 2.59 (d, J = 7.0 Hz, 2H, ArCH2CH), 2.70 (d, J = 10.9 Hz, 2H, CH2CH2NMe), 7.20 (d, J = 8.4 Hz, 1H, H-5"), 7.49 (s, 1H, H-3), 7.52 (d, J = 8.8 Hz, 1H, H-5'), 7.61 (s, 1H, H-5), 7.78 (dd, J = 8.3, 8.3 Hz, 1H, H-4'), 8.02 (d, J = 8.2 Hz, 1H, H-4"), 8.78 (s, 1H, H-2"), 10.17 (s, 1H, CONHAr), 12.72 (s, 1H, NH-pyrrole) | 487.3, 489.3 |

TABLE 11-continued

| Ex. | Structure | Name | General prep | 1H NMR Data | MS |
|---|---|---|---|---|---|
| 113 | 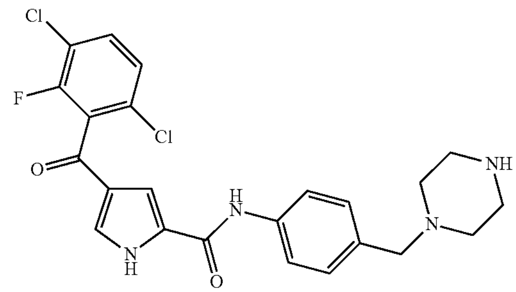 [SMILES: O=C(Nc1ccc(CN2CCNCC2)cc1)c1cc(C(=O)c2c(Cl)ccc(Cl)c2F)c[nH]1] | 4-(3,6-Dichloro-2-fluorobenzoyl)-N-(6-(piperazin-1-ylmethyl)pyridin-3-yl)-1H-pyrrole-2-carboxamide | 18 | 2.33 (4H, brs, NCH2 piperazine), 2.70 (4H, t, J = 4.8 Hz, NCH2 piperazine), 3.51 (2H, s, ArCH2N), 7.40 (1H, d, J = 8.5 Hz, H-5″), 7.49 (1H, s, H-3), 7.52 (1H, dd, J = 8.8, 0.6 Hz, H-5′), 7.60 (1H, s, H-5), 7.78 (1H, dd, J = 8.3, 8.3 Hz, H-4′), 8.09 (1H, dd, J = 8.5, 2.6 Hz, H-4″), 8.79 (1H, d, J = 2.5 Hz, H-2″), 10.20 (1H, s, CONHAr) | 476.5, 478.5 |
| 114 | 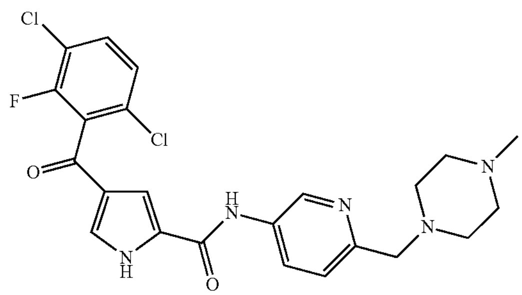 | 4-(3,6-Dichloro-2-fluorobenzoyl)-N-(6-((4-methylpiperazin-1-yl)methyl)pyridin-3-yl)-1H-pyrrole-2-carboxamide | 20 | 2.16 (3H, s, NCH3), 2.22-2.49 (8H, m, NCH2 piperazine), 3.53 (2H, s, ArCH2N), 7.39 (1H, d, J = 8.5 Hz, H-5″), 7.47-7.55 (2H, m, H-3 and H-5′), 7.61 (1H, s, H-5), 7.73 (1H, t, J = 8.4 Hz, H-4′), 8.10 (1H, dd, J = 8.4, 2.3 Hz, H-4″), 8.79 (1H, d, J = 2.5 Hz, H-2″), 10.22 (1H, s, CONHAr), 12.76 (1H, s, NH-pyrrole) | 490.4, 492.5 |
| 115 | 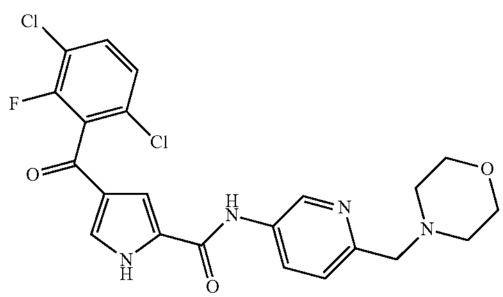 [SMILES: O=C(Nc1ccc(CN2CCOCC2)nc1)c1cc(C(=O)c2c(Cl)ccc(Cl)c2F)c[nH]1] | 4-(3,6-Dichloro-2-fluorobenzoyl)-N-(6-(morpholinomethyl)pyridin-3-yl)-1H-pyrrole-2-carboxamide | 18 | 2.40 (4H, t, J = 4.7 Hz, NCH2 morpholine), 3.55 (2H, s, ArCH2N), 3.58 (4H, t, J = 4.5 Hz, CH2O morpholine), 7.42 (1H, d, J = 8.5 Hz, H-5″), 7.49-7.54 (2H, m, H-3 and H-5′), 7.62 (1H, s, H-5), 7.78 (1H, dd, J = 8.4, 8.4 Hz, H-4′), 8.11 (1H, dd, J = 8.5, 2.4 Hz, H-4″), 8.80 (1H, d, J = 2.3 Hz, H-2″), 10.22 (1H, s, CONHAr), 12.75 (1H, s, NH-pyrrole) | 477.4, 479.4 |
| 116 | 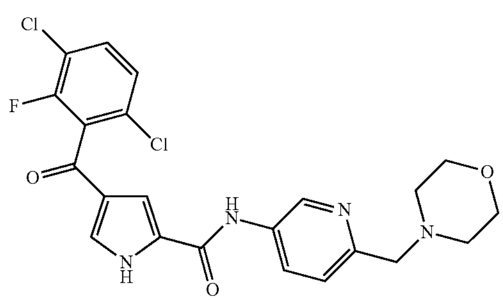 [SMILES: O=C(Nc1ccc(CN2CCOCC2)nc1)c1cc(C(=O)c2c(Cl)ccc(Cl)c2F)c[nH]1] | 4-(6-Chloro-2-fluoro-3-methoxybenzoyl)-N-(6-(morpholinomethyl)pyridin-3-yl)-1H-pyrrole-2-carboxamide | 18 | 2.40 (4H, t, J = 4.5 Hz, NCH2 morpholine), 3.54 (2H, s, ArCH2N), 3.58 (4H, t, J = 4.6 Hz, CH2O morpholine), 3.90 (3H, s, ArOCH3), 7.33 (1H, dd, J = 8.9, 8.9 Hz, H-4′), 7.39 (1H, dd, J = 9.0, 0.9 Hz, H-5′), 7.42 (1H, d, J = 8.5 Hz, H-5″), 7.47 (1H, s, H-3 or H-5), 7.48 (1H, s, H-3 or H-5), 8.10 (1H, dd, J = 8.5, 2.5 Hz, H-4″), 8.80 (1H, d, J = 2.4 Hz, H-2″), 10.22 (1H, s, CONHAr), 12.68 (1H, s, NH-pyrrole) | 473.5, 475.4 |

TABLE 11-continued

| Ex. | Structure | Name | General prep | 1H NMR Data | MS |
|---|---|---|---|---|---|
| 117 | 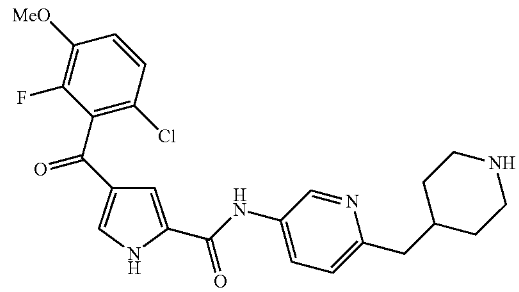 [SMILES: COc1ccc(Cl)c(C(=O)c2c[nH]c(C(=O)Nc3ccc(CC4CCNCC4)nc3)c2)c1F] | 4-(6-Chloro-2-fluoro-3-methoxy-benzoyl)-N-(6-(piperidin-4-ylmethyl)pyridin-3-yl)-1H-pyrrole-2-carboxamide | 18 | 1.02 -1.15 (2H, m, CH2CH2NH), 1.44-1.52 (2H, m, CH2CH2NH), 1.71-1.85 (1H, m, ArCH2CH), 2.42 (2H, ddd, J = 12.1, 12.1, 2.6 Hz, CH2CH2NH), 2.58 (2H, d, J = 7.1 Hz, ArCH2CH), 2.90 (2H, ddd, J = 12.6, 3.4, 3.4 Hz, CH2CH2NH), 3.90 (3H, s, ArOCH3), 7.19 (1H, d, J = 8.4 Hz, H-5″), 7.31 (1H, dd, J = 8.9, 8.9 Hz, H-4′), 7.38 (1H, dd, J = 9.0, 1.4 Hz, H-5′), 7.41 (1H, s, H-3 or H-5), 7.45 (1H, s, H-3 or H-5), 8.02 (1H, dd, J = 8.4, 2.5 Hz, H-4″), 8.77 (1H, d, J = 2.4 Hz, H-2″), 10.15 (1H,s, CONHAr) | 471.5, 473.5 |

Example 118: 5-(4-(2-Chloro-6-fluorobenzoyl)-1H-pyrrole-2-carboxamido)-2-methylpyridine 1-oxide

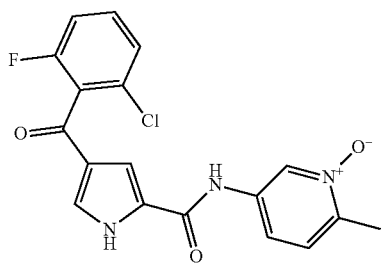 [SMILES: Cc1ccc(NC(=O)c2cc(C(=O)c3c(F)cccc3Cl)c[nH]2)c[n+]1[O-]]

Under nitrogen flow, 4-(2-chloro-6-fluorobenzoyl)-1H-pyrrole-2-carboxylic acid (53 mg, 0.198 mmol) was dissolved in anhydrous acetonitrile (1.5 mL) and 5-amino-2-methylpyridine (53 mg, 0.495 mmol) added at room temperature, followed by phosphorus trichloride (20 μL, 0.198 mmol). The mixture was heated using microwave irradiation at 150° C. for 5 min. The reaction was quenched with a few drops of water and the solvent removed in vacuo. The residue was taken up in ethyl acetate (20 mL) and washed with saturated aqueous sodium bicarbonate (10 mL), before the organics were combined, dried over anhydrous $Na_2SO_4$, filtered and the filtrate concentrated in vacuo. FCC [petrol-ethyl acetate (70:30)→(0:100)] of the crude residue afforded the title compound (38 mg, 53%) as a beige solid; $R_f$ 0.1 (50% EtOAc-petrol); $^1$H NMR (500 MHz, MeOD) δ 2.52 (3H, s, $CH_3$), 7.24-7.31 (2H, m, ArH), 7.39-7.46 (3H, m, ArH), 7.52 (1H, q, J=6.0 Hz, ArH), 8.09 (1H, dd, J=2.5 and 8.5 Hz, ArH) and 8.75 (1H, d, J=2.5 Hz, ArH); LRMS (ESI+) m/z 358.3 [M+H]$^+$ Under a nitrogen flow, 4-(2-chloro-6-fluorobenzoyl)-N-(6-methylpyridin-3-yl)-1H-pyrrole-2-carboxamide (70 mg, 0.196 mmol) was dissolved in anhydrous acetonitrile (3 mL) and mCPBA (66 mg, 0.293 mmol) was added in one portion at room temperature. The reaction mixture was stirred for 64 h, before being quenched with 3 drops of water and the solvent removed in vacuo. FCC [dichloromethane-methanol (100:0)→(80:20)] of the crude residue afforded the title compound (66 mg, 90%) as an off-white solid; $^1$H NMR (500 MHz, DMSO) δ 2.32 (3H, s, $CH_3$), 7.37-7.64 (7H, m, ArH), 8.86 (1H, s, HC=N$^+$—O$^-$), 10.3 (1H, s, NH) and 12.8 (1H, s, NH); LRMS(ESI+) m/z 374.3 [M+H]$^+$; HRMS calcd for $C_{18}H_{14}ClFN_3O_3$ [M+H]$^+$ 374.0708, found 374.0708.

Example 119: 4-(2-chloro-6-fluorobenzoyl)-N-(6-(hydroxymethyl)pyridin-3-yl)-1H-pyrrole-2-carboxamide

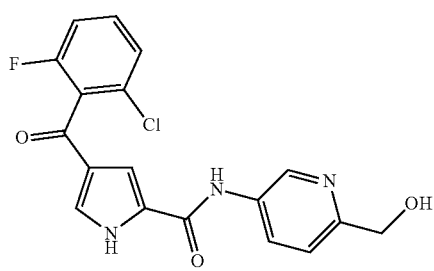 [SMILES: O=C(Nc1ccc(CO)nc1)c1cc(C(=O)c2c(F)cccc2Cl)c[nH]1]

To a solution of 5-aminopicolinic acid (194 mg, 1.40 mmol) in ethanol (5 mL), was added thionyl chloride (0.20 mL, 2.80 mmol) at 0° C. The mixture was then stirred under reflux for 19 h, after which time it was cooled to room temperature and the reaction mixture concentrated under reduced pressure. Saturated aqueous sodium carbonate solution was added to the resulting solid to adjust the pH to 9, followed by saturated aqueous sodium hydrogen carbonate.

Ethyl acetate (10 mL) and water (10 mL) were added and the organic phase was washed with brine (10 mL), dried (Na$_2$SO$_4$), filtered and the filtrate concentrated in vacuo. Ethyl 5-aminopicolinate (184 mg, 79%) was obtained as an off-white solid, with no need for further purification; $^1$H NMR (500 MHz, MeOD) δ 1.37 (3H, t, J=7.1 Hz, CH$_3$), 4.35 (2H, q, J=7.2 Hz), 7.02 (1H, dd, J=2.7 and 8.6 Hz, Ar), 7.85 (1H, d, J=8.6 Hz) and 7.98 (1H, d, J=2.7 Hz). LRMS (ESI+) m/z 167.2 [M+H]$^+$.

Under a nitrogen atmosphere, lithium aluminium hydride, 2 M in THF (2.3 mL, 4.59 mmol) was added slowly to a solution of ethyl 5-aminopicolinate (255 mg, 1.53 mmol) in anhydrous THF (14 mL) with ice-cooling. The mixture was then allowed to warm to room temperature and stirred for 4.25 h. Ethyl acetate (13 mL) was then added dropwise, whilst maintaining the temperature of the mixture below 0° C. Saturated aqueous Rochelle's salt (13 mL) was added and the mixture stirred for 16 h at room temperature. The resulting salts were filtered off and the filtrate dried (Na$_2$SO$_4$) and concentrated to provide (5-Aminopyridin-2-yl)methanol (151 mg, 79%) as a dark orange thick gum which was used without purification; R$_f$=0.51 (50% CH$_3$OH—CH$_2$Cl$_2$); $^1$H NMR (500 MHz, MeOD) δ 4.54 (2H, s, CH$_2$), 7.12 (1H, dd, J=2.8 and 8.4 Hz, ArH), 7.24 (1H, d, J=8.4 ArH) and 7.90 (1H, d, J=2.8 Hz, ArH).

Under a nitrogen atmosphere, a mixture of (5-aminopyridin-2-yl)methanol (330 mg, 2.66 mmol), TBDMSCl (481 mg, 3.19 mmol) and imidazole (434 mg, 6.38 mmol) in anhydrous DMF (7 mL) were stirred at room temperature overnight. The solvent was removed using the V10 apparatus, then the residue dissolved in methanol and absorbed onto silica. FCC [dichloromethane-methanol (100:0)→(90:10)] of the crude residue afforded (5-aminopyridin-2-yl)methanol (322 mg, 51%) as a pale yellow solid; $^1$H NMR (500 MHz, MeOD) δ 0.09 (6H, s, (CH$_3$)$_2$), 0.93 (9H, s, (CH$_3$)$_3$), 4.65 (2H, s, CH$_2$), 7.12 (1H, dd, J=2.7 and 8.4 Hz, ArH), 7.23 (1H, dd, J=0.5 and 8.4 Hz, ArH) and 7.88 (1H, dd, J=0.5 and 2.7 Hz, ArH); LRMS (ESI+) m/z 239.4 [M+H]$^+$.

4-(2-Chloro-6-fluorobenzoyl)-1H-pyrrole-2-carboxylic acid (27 mg, 0.100 mmol) was dissolved in anhydrous THF (3 mL) before carbonyldiimidazole (32 mg, 0.200 mmol) was added and the reaction mixture was heated to reflux at 70° C. for 3 h. After this time, the reaction was cooled to 50° C. before 6-(((tert-butyldimethylsilyl)oxy)methyl)pyridin-3-amine (59 mg, 0.247 mmol) was added and the mixture heated at 50° C. for a further 3 h. Cooled to room temperature and stirred for 90 h. The reaction mixture was diluted with EtOAc (5 mL) and washed with water (10 mL), then brine (10 mL). The combined organics were dried over anhydrous Na$_2$SO$_4$, filtered and the solvent removed in vacuo. FCC [petrol-ethyl acetate (100:0)→(60:40)→(0:100)] of the crude residue afforded N-(6-(((tert-Butyldimethylsilyl)oxy)methyl)pyridin-3-yl)-4-(2-chloro-6-fluorobenzoyl)-1H-pyrrole-2-carboxamide (28 mg, 58%) as a white solid; R$_f$=0.67 (50% petrol-EtOAc)), as well recovered amine (~30 mg); $^1$H NMR (500 MHz, THF) δ 0.00 (6H, s, (CH$_3$)$_2$), 0.96 (9H, s, (CH$_3$)$_3$), 4.75 (2H, s, CH$_2$), 7.19 (1H, t, J=8.5 Hz, ArH), 7.23 (1H, t, J=1.5 Hz, ArH), 7.32 (1H, d, J=8.1 Hz, ArH), 7.39-7.47 (3H, m, 3×ArH), 8.19 (1H, dd, J=2.5 and 8.5 Hz, ArH), 8.71 (1H, br. s, ArH), 9.43 (1H, br. s, NH) and 12.00 (1H, br. s, NH); LRMS (ESI+) m/z 488.5 [M]$^+$.

N-(6-(((tert-Butyldimethylsilyl)oxy)methyl)pyridin-3-yl)-4-(2-chloro-6-fluorobenzoyl)-1H-pyrrole-2-carboxamide (48.3 mg, 0.100 mmol) was taken up in anhydrous THF (3 mL) and cooled to 0° C. for the addition of TBAF, 1 M in THF (0.2 mL, 0.200 mmol). Cooling was removed after 5 minutes and the reaction mixture allowed to warm to room temperature. After 2 h, the mixture was diluted with EtOAc (2 mL) and washed with H$_2$O (2×5 mL). The combined organics were dried over anhydrous Na$_2$SO$_4$ and the solvent removed in vacuo. FCC [dichloromethane-methanol (95:0)→(90:10)] of the crude residue afforded the title compound (19 mg, 51%) as an off-white solid, $^1$H NMR (500 MHz, MeOD) δ 4.67 (2H, s, CH$_2$), 7.25 (1H, t, J=8.7 Hz, ArH), 7.38 (1H, d, J=8.1 Hz, ArH), 7.44 (2H, dd, J=1.3 and 10.5 Hz, ArH), 7.49-7.55 (2H, m, ArH), 8.20 (1H, dd, J=2.5 and 8.5 Hz, ArH) and 8.81 (1H, d, J=2.4 Hz, ArH); LRMS (ESI+) m/z 374.4 [M+H]$^+$; HRMS calcd for C$_{18}$H$_{13}$ClFN$_3$O$_3$ [M+H]$^+$ 374.0708, found 374.0700.

Example 120: 4-(3,6-dichloro-2-fluorobenzoyl)-N-(6-(hydroxymethyl)pyridin-3-yl)-1H-pyrrole-2-carboxamide

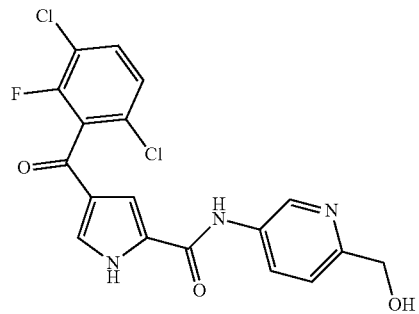 [SMILES: O=C(Nc1ccc(CO)nc1)c1cc(C(=O)c2c(Cl)ccc(Cl)c2F)c[nH]1]

To a solution of 4-(3,6-dichloro-2-fluorobenzoyl)-1H-pyrrole-2-carboxylic acid (117 mg, 0.387 mmol) in anhydrous CH$_2$Cl$_2$ (3 mL) was added anhydrous Et$_3$N (0.13 mL, 0.967 mmol) and 2-chloro-1-methylpyridinium iodide (109 mg, 0.425 mmol) at room temperature, followed by 6-(((tert-butyldimethylsilyl)oxy)methyl)pyridin-3-amine (115 mg, 0.483 mmol) after 15 min. The resulting yellow solution was stirred at room temperature for 18 h and then absorbed directly onto silica. FCC [petrol-ethyl acetate (100:0)→(50:50))→(0:100)] of the crude residue afforded the title compound (64 mg, 32%) as a pale orange solid; $^1$H NMR (500 MHz, THF) δ 0.12 (6H, s, (CH$_3$)$_2$), 0.96 (9H, s, (CH$_3$)$_3$), 4.75 (2H, s, CH$_2$), 7.23 (1H, s, ArH), 7.36 (1H, dd, J=1.5 and 8.7 Hz, ArH), 7.41 (1H, d, J=8.5 Hz, ArH), 7.47-7.49 (1H, m, ArH), 7.59 (1H, t, J=8.0 Hz, ArH), 8.17 (1H, dd, J=2.6 and 8.5 Hz, ArH), 8.70 (1H, d, J=2.5 Hz, ArH) and 9.38 (1H, br. s, NH) and 12.1 (1H, br. s, NH); LRMS (ESI+) m/z 522.4 [M]$^+$; HRMS calcd for C$_{24}$H$_{26}$Cl$_2$FN$_3$O$_3$Si [M+H]$^+$ 522.1183, found 522.1165.

A solution of N-(6-(((tert-butyldimethylsilyl)oxy)methyl)pyridin-3-yl)-4-(3,6-dichloro-2-fluorobenzoyl)-1H-pyrrole-2-carboxamide (60 mg, 0.115 mmol) and ammonium fluoride (60 mg, 1.61 mmol) in reagent grade MeOH (3 mL) and THF (10 drops) to aid solubility, was stirred at 60° C. for 2.2 h. After cooling to room temperature the solvent was removed in vacuo. FCC [dichloromethane-methanol (100:0)→(90:10)] of the crude residue afforded the title compound (31 mg, 66%) as an off-white solid; $^1$H NMR (500 MHz, THF) δ 4.29 (1H, t, J=5.6 Hz, OH), 4.57 (2H, d, J=5.6 Hz, CH$_2$), 7.22 (1H, s, ArH), 7.35 (1H, dd, J=1.5 and 8.7 Hz, ArH), 7.38 (1H, d, J=8.6 Hz, ArH), 7.47 (1H, dd, J=1.3 and 3.1 Hz, ArH), 7.58 (1H, t, J=8.5 Hz, ArH), 8.16 (1H, dd, J=2.5 and 8.5 Hz, ArH), 8.68 (1H, d, J=2.3 Hz, ArH), 9.36 (1H, br. s, NH) and 12.0 (1H, br. S, NH); LRMS (ESI+) m/z 408.3 [M]$^+$; HRMS calcd for $C_{18}H_{12}Cl_2FN_3O_3$[M+H]$^+$ 408.0318, found 408.0306.

By following methods similar and/or analogous to those described herein, the compounds set out in the Table 12 below were prepared from the corresponding starting materials.

TABLE 12

| Ex. | Structure | Name | General prep | $^1$H NMR Data | MS |
|---|---|---|---|---|---|
| 121. | 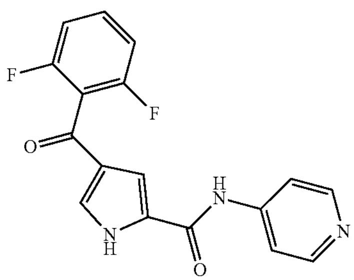 [SMILES: O=C(Nc1ccncc1)c1cc(C(=O)c2c(F)cccc2F)c[nH]1] | 4-(2,6-Difluorobenzoyl)-N-(pyridin-4-yl)-1H-pyrrole-2-carboxamide | 24 | 7.26-7.30 (2H, m, H-3' and H-5'); 7.57 (1H, s, H-3); 7.58 (1H, s, H-5), 7.64 (1H, dddd, J = 6.7, 6.7, 8.5 and 8.5 Hz, H-4'), 7.75 (2H, d, J = 6.4 Hz, CH-pyridine), 8.47 (2H, d, J= 6.4 Hz, CH—N-pyridine), 10.36 (1H, s, CONH), 12.78 (1H, br s, NH) | 328.0890 |
| 122. | 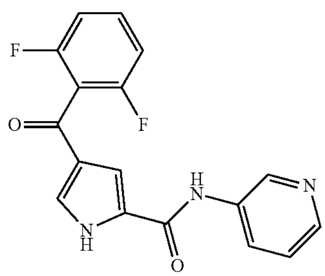 [SMILES: O=C(Nc1cccnc1)c1cc(C(=O)c2c(F)cccc2F)c[nH]1] | 4-(2,6-Difluorobenzoyl)-N-(pyridin-3-yl)-1H-pyrrole-2-carboxamide | 24 | 7.04-7.07 (2H, m, H-3' and H-5'), 7.15-7.17 (1H, m, H-3), 7.30-7.32 (2H, m, CH-pyridine), 7.41 (1H, dddd, J = 6.8, 6.8, 8.5 and 8.5 Hz, H-4'), 7.90-7.93 (1H, m, H-5), 8.08 (1H, dd, J = 1.5 and 4.7 Hz, CH-pyridine), 8.67 (1H, d, J = 2.5 Hz CH—N-pyridine), 10.02 (1H, t, CONH), 12.50 (1H, brs, NH) | 328.0895. |
| 123. | 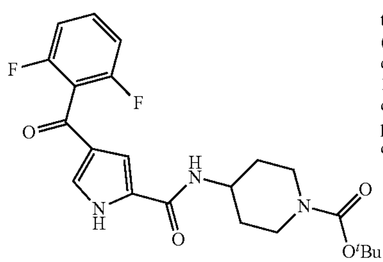 [SMILES: CC(C)(C)OC(=O)N1CCC(NC(=O)c2cc(C(=O)c3c(F)cccc3F)c[nH]2)CC1] | tert-Butyl 4-(4-(2,6-difluorobenzoyl)-1H-pyrrole-2-carboxamido)piperidine-1-carboxylate | 24 | $^1$H NMR (500 MHz, MeOD) δ 1.48 (9H, s, 3 × CH$_3$), 1.85-1.92 (4H, m, 2 × CH$_2$), 3 64-3.69 (1H, m, CH), 3.96-4.03 (4H, m, 2 × CH$_2$N), 7.10-7.14 (2H, m, H-3' and H-5'); 7.24 (1H, d, J = 1.50 Hz, H-3), 7.43 (1H, d, J = 1.50 Hz, H-5), 7.56 (1H, dddd, J = 6.5, 6.5, 8.6 and 8.6 15.5 Hz, H-4'); | 434.1888. |
| 124. | 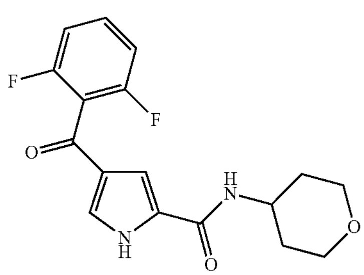 [SMILES: O=C(NC1CCOCC1)c1cc(C(=O)c2c(F)cccc2F)c[nH]1] | 4-(2,6-Difluorobenzoyl)-N-(tetrahydro-2H-pyran-4-yl)-1H-pyrrole-2-carboxamide | 24 | $^1$H NMR 470 MHz, DMSO-d$_6$) δ 1.47-1.55 (2H, m, CH$_2$-THP), 1.71-1.74 (2H, m, CH$_2$-THP), 3.34-3.39 (2H, m, CH$_2$-O-THP), 3.85-3.87 (2H, m, CH2-O-THP), 3.90-3.98 (1H, m, CH), 7.24-7.27 (3H, m, H-3', H-5' and H-3), 7.28 (1H, br s, H-5), 7.61 (1H, dddd, J = 6.9, 6.9, 8.5 and 8.5 Hz, H-4'), 8.20 (1H, d, J = 7.9 Hz, CONH), 12.47 (1H, br s, NH) | 335.1203. |
| 125. | 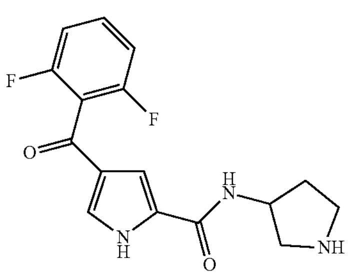 [SMILES: O=C(NC1CCNC1)c1cc(C(=O)c2c(F)cccc2F)c[nH]1] | 4-(2,6-Difluorobenzoyl)-N-(pyrrolidin-3-yl)-1H-pyrrole-2-carboxamide | 24 | 1.60-2.04 (2H, m, CH$_2$), 3.39-3.75 (4H, m, 2 × CH$_2$), 3.82-3 84 (1H, m CH), 6.95 (1H, d, J = 1.1 Hz, H-3), 7.23-7.27 (2H, m, H-3' and H-5'), 7.33 (1H, d, J = 1.1 Hz, H-5), 7.61 (1H, dddd, J = 6.7, 6.7, 8.5 and 8.5 Hz, H-4' | 320.30 |

Example 126: 4-(2,6-Difluorobenzoyl)-N-(piperidin-4-yl)-1H-pyrrole-2-carboxamide

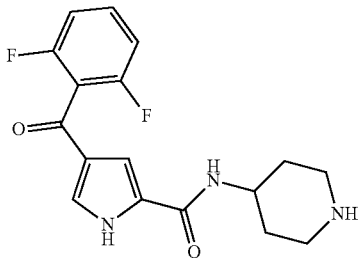 [SMILES: O=C(NC1CCNCC1)c1cc(C(=O)c2c(F)cccc2F)c[nH]1]

Example 123 (30 mg, 0.07 mmol) was dissolved in TFA (3 mL) and stirred at RT for 30 min. The solvent was removed in vacuo and the residue was dissolved in EtOAc before being washed with a saturated aqueous solution of NaHCO$_3$ (20 mL). The organic extract was dried over Na$_2$SO$_4$ and the solvent removed in vacuo to afford the crude compound as a white solid, which was purified by recrystallisation from MeOH (20 mg, 0.06 mmol, 87%); Rf=0.50 (10% MeOH in EtOAc); M.p.: 150-151 OC; $\lambda_{max}$ (EtOH)/nm: 286, 237; $v_{max}$/cm$^{-1}$: 3313, 2974, 2873, 1773; $^1$H NMR (500 MHz, CDCl$_3$) δ 0.88-0.92 (4H, m, 2×CH$_2$-piperidine) 1.19-1.35 (5H, m, 2×CH$_2$—N-piperidine and CH-piperidine), 7.49-7.53 (2H, m, H-3' and H-5'), 7.60-7.63 (1H, m, H-4'), 7.82 (1H, br s, H-3), 7.84 (1H, br s, H-5); $^{13}$C NMR (125 MHz, CDCl$_3$) δ 38.1 (2×CH$_2$), 39.0 (2×CH$_2$), 48.2 (NHCH), 91.0 (C—Ar), 96.7 (C—Ar), 114.1 (C—Ar), 121.7 (C-3), 125.9 (C-2 and C-5), 129.9 (C-4), 156.1 (d, $J_{CF}$=256.4 Hz, CF), 164.2 (CONH), 186.9 (CO); $^{19}$F NMR (470 MHz, MeOD) δ −112.3; LRMS (ES$^+$) m/z 334.30 [M+H]$^+$; HRMS m/z calcd for C$_{17}$H$_{18}$F$_2$N$_3$O$_2$ [M+H]$^+$ 334.1364, found 334.1365.

Example 127: 4-(4-(2,6-Difluorobenzoyl)-1H-pyrrole-2-carboxamido)pyridine 1-oxide

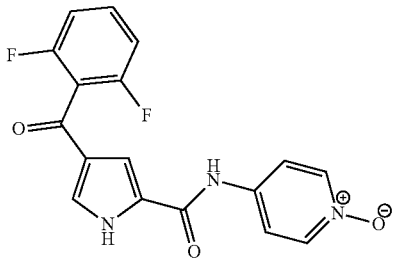 [SMILES: O=C(Nc1cc[n+]([O-])cc1)c1cc(C(=O)c2c(F)cccc2F)c[nH]1]

Example 121 was dissolved in DCM (2 mL) before m-CPBA (65%, 38 mg, 0.22 mmol) was added and the reaction was stirred at RT for 18 h. The reaction mixture was diluted with DCM and washed with an aqueous saturated solution of NaHSO$_3$. The organic extract was dried over Na$_2$SO$_4$, and the solvent removed in vacuo to give the crude product. Purification was achieved using MPLC (silica, 0-20% MeOH in EtOAc) to give the title compound as a white solid (30 mg, 65%); $^1$H NMR (500 MHz, DMSO-d$_6$) δ 7.26-7.30 (2H, m, H-3' and H-5'), 7.54 (1H, br s, H-3), 7.56 (1H, br s, H-5), 7.65 (1H, dddd, J=6.8, 6.8, 8.6 and 8.6 Hz, H-4'), 7.78 (2H, d, J=6.2 Hz, CH-pyridine), 8.15 (2H, d, J=6.2 Hz, CH—N-pyridine), 10.50 (1H, s, CONH), 12.79 (1H, br s, NH); LRMS (ES$^+$) m/z 344.20 [M+H]$^+$; HRMS m/z calcd for C$_{17}$H$_{12}$F$_2$N$_3$O$_3$ [M+H]$^+$ 344.0831, found: 344.0832.

Example 128: 3-(4-(2,6-Difluorobenzoyl)-1H-pyrrole-2-carboxamido)pyridine 1-oxide

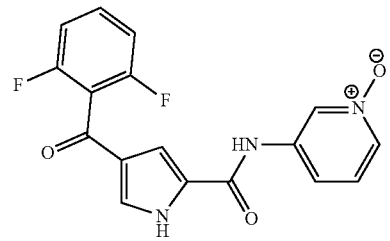 [SMILES: O=C(Nc1ccc[n+]([O-])c1)c1cc(C(=O)c2c(F)cccc2F)c[nH]1]

Example 122 (30 mg, 0.09 mmol) was dissolved in DCM (2 mL) before m-CPBA (65%, 38 mg, 0.22 mmol) was added and the reaction was stirred at RT for 18 h. The reaction mixture was diluted with DCM and washed with an aqueous saturated solution of NaHSO$_3$. The organic extracts were dried over Na$_2$SO$_4$, and the solvent was removed in vacuo to give the crude product. Purification was achieved using MPLC (silica, 0-20% MeOH in EtOAc) to give the title compound as a white solid (23 mg, 77%); $^1$H NMR (500 MHz, DMSO-d$_6$) δ 7.25-7.28 (2H, m, H-3' and H-4'), 7.40 (1H, dd, J=6.4 and 8.7 Hz, CH-pyridine), 7.53 (1H, br s, H-3), 7.56 (1H, br-s, H-5), 7.59 (1H, d, J=6.4 Hz, CH-pyridine), 7.64 (1H, dddd, J=6.5, 6.5, 8.1 and 8.1 Hz, H—Ar), 7.98 (1H, d, J=6.4 Hz, CH—N-pyridine), 8.81 (1H, s, CH—N-pyridine), 10.35 (1H, s, CONH), 12.79 (1H, br s, NH); LRMS (ES$^+$) m/z 344.3 [M+H]$^+$; HRMS m/z calcd for C$_{17}$H$_{12}$F$_2$N$_3$O$_3$ [M−H]$^−$ 342.0688, found 342.0689.

By following methods similar and/or analogous to those described herein, the compounds set out in the Table 13 below were prepared from the corresponding starting materials.

TABLE 13

| Ex. | Structure | Name | General prep | 1H NMR Data | MS |
|---|---|---|---|---|---|
| 129. | 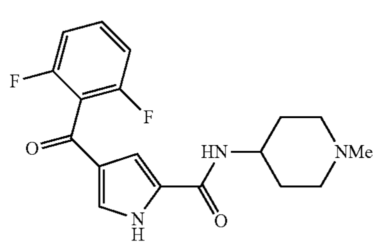 [SMILES: CN1CCC(NC(=O)c2cc(C(=O)c3c(F)cccc3F)c[nH]2)CC1] | 4-(2,6-Difluorobenzoyl)-N-(1-methylpiperidin-4-yl)-1H-pyrrole-2-carboxamide | 25 | 1.48-1.56 (2H, m, CH$_2$), 1.73 (2H, d, J = 11.5 Hz, CH$_2$), 1.93 (2H, t, J = 11.5 Hz, CH$_2$N), 2.16 (3H, s, NCH$_3$), 2.74 (2H, d, J = 11.5 Hz, CH$_2$N), 3.64-3.71 (1H, m, CH), 7.18 (1H, br s, H-3), 7.23-7.26 (2H, m, H-3' and H-5'), 7.34 (1H, br s, H-5), 7.59 (1H, dddd, J = 6.3, 6.3, 8.4 and 8.4 Hz, H-4'), 8.01 (1 H, br s, CONH) 12.39 (1 H, br s, NH) | 348.3 |

TABLE 13-continued

| Ex. | Structure | Name | General prep | 1H NMR Data | MS |
|---|---|---|---|---|---|
| 130. | 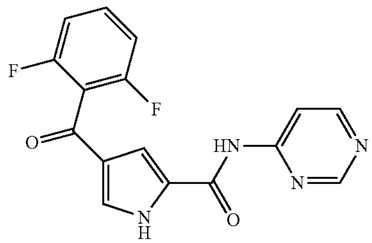 [SMILES: O=C(Nc1ccncn1)c1cc(C(=O)c2c(F)cccc2F)c[nH]1] | 4-(2,6-Difluorobenzoyl)-N-(pyrimidin-4-yl)-1H-pyrrole-2-carboxamide | 25 | 7.26-7.29 (2H, m. H-3' and H-5'), 7.60-7.67 (2H, m, H-4' and CH-pyrimidine), 7.79 (1H, br s, H-3), 8.29 (1H, dd, J = 1.5 and 6.0 Hz, CH-pyrimidine), 7.69 (1H, d, J = 6.0 Hz, CH-pyrimidine), 8.92 (1H, br s, H-5), 11.16 (1H, br s, CONH), 12.79 (1H, br s, NH) | 329.3 |
| 131. | 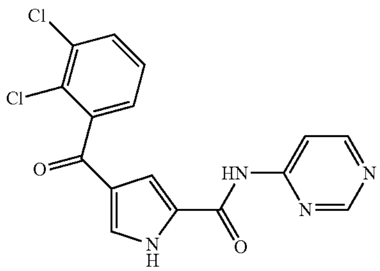 [SMILES: O=C(Nc1ccncn1)c1cc(C(=O)c2cccc(Cl)c2Cl)c[nH]1] | 4-(2,3-Dichlorobenzoyl)-N-(pyrimidin-4-yl)-1H-pyrrole-2-carboxamide | 25 | 7.47-7.53 (3H, m, H-Ar), 7.74 (1H, br s, H-3), 7.81 (1H, dd, J = 1.8 and 6.0 Hz, CH-pyrimidine), 8.18 (1H, dd, J = 1.8 and 6.0 Hz, CH-pyrimidine), 8.69 (1H, d, J = 6.0 Hz, CH-pyrimidine) 8.92 (1H, br s, H-5), 11.14 (1H, br s, CONH), 12.76 (1H, br s, NH) | 361.3 |
| 132. | 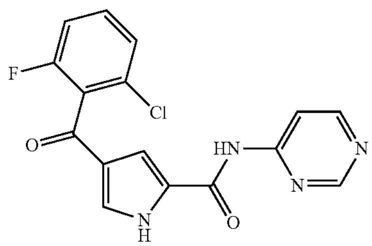 [SMILES: O=C(Nc1ccncn1)c1cc(C(=O)c2c(F)cccc2Cl)c[nH]1] | 4-(2-Chloro-6-fluorobenzoyl)-N-(pyrimidin-4-yl)-1H-pyrrole-2-carboxamide | 25 | 7.39-7.43 (1H, m, H-3'), 7.47-7.79 (1H, m, H-5'), 7.57-7.62 (2H, m, H-4' and CH-pyrimidine), 7.74 (1H, s, H-3), 8.18 (1H, dd, J = 1.2 and 5.8 Hz, CH-pyrimidine), 8.69 (1H, d, J = 5.8 Hz, CH-pyrimidine), 8.92 (1H, d, J = 1.0 Hz, H-5), 11.14 (1H, s, CONH), 12.82 (1H, s, NH) | 345.0554 |
| 133. | 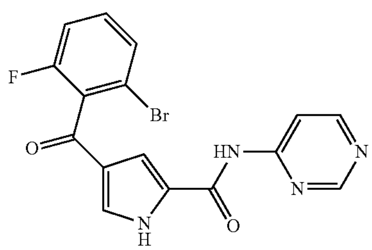 [SMILES: O=C(Nc1ccncn1)c1cc(C(=O)c2c(F)cccc2Br)c[nH]1] | 4-(2-Bromo-6-fluorobenzoyl)-N-(pyrimidin-4-yl)-1H-pyrrole-2-carboxamide | 25 | 7.42-7.45 (1H, m, H-5'), 7.51 (1H, ddd, J = 6.0, 8.4 and 8.4 Hz, H-4'), 7.56 (1H, s, CH-pyrimidine), 7.60-7.62 (1H, m, H-Ar), 7.74 (1H, s, H-3), 8.18 (1H, dd, J = 1.4 and 5.8 Hz, CH-pyrimidine), 8.69 (1H, d, J = 5.8 Hz, CH-pyrimidine), 8 92 (1H, s, H-5), 11.35 (1H, s, CONH), 12.89 (1H, s, NH) | 389.0048 |
| 134. | 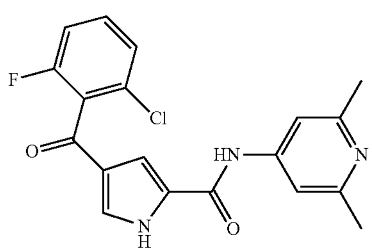 [SMILES: Cc1cc(NC(=O)c2cc(C(=O)c3c(F)cccc3Cl)c[nH]2)cc(C)n1] | 4-(2-Chloro-6-fluorobenzoyl)-N-(2,6-dimethylpyridin-4-yl)-1H-pyrrole-2-carboxamide | 25 | 2.39 (6H, s, 2 × CH₃), 7.40-7.43 (3H, m, H-3' and 2 × CH-pyridine), 7.48-7.52 (3H, m, H-3, H-5 and H-5'), 7.60 (1H, ddd, J = 6.3, 8.4 and 8.4 Hz, H-4'), 10.16 (1H, s, CONH), 12.69 (1H, s, NH) | 372.0913. |
| 135. | 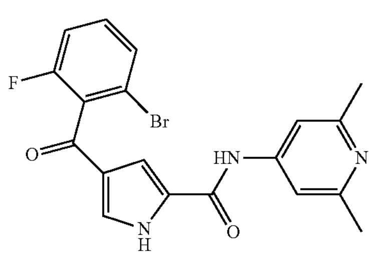 [SMILES: Cc1cc(NC(=O)c2cc(C(=O)c3c(F)cccc3Br)c[nH]2)cc(C)n1] | 4-(2-Bromo-6-fluorobenzoyl)-N-(2,6-dimethylpyridin-4-yl)-1H-pyrrole-2-carboxamide | 25 | 2.39 (6H, s, 2 × CH₃), 7.41 (2H, s, 2 × pyridine CH), 7.44-7.46 (1H, m, H-5'), 7.48 (1H, s, H-3), 7.51-7.54 (2H, m, H-3 and H-4'), 7.62 (1H, d, J = 8.0 Hz, H-3'), 10.16 (1H, s, CONH), 12.68 (1H, s, NH); 416.0404 | |

TABLE 13-continued

| Ex. | Structure | Name | General prep | 1H NMR Data | MS |
|---|---|---|---|---|---|
| 136. | 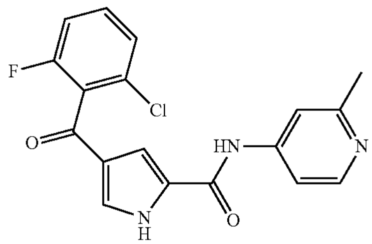 [SMILES: Cc1cc(NC(=O)c2cc(C(=O)c3c(F)cccc3Cl)c[nH]2)ccn1] | 4-(2-Chloro-6-fluorobenzoyl)-N-(2-methylpyridin-4-yl)-1H-pyrrole-2-carboxamide | 25 | 2.44 (3H, s, CH₃), 7.39-7.43 (1H, m, H-5'), 7.48 (1H, d, J = 8.1 Hz, H-3'), 7.51 (1H, s, H-3), 7.53 (1H, s, H-5), 7.56-7.62 (3H, m, H-4' and 2 × CH-pyridine), 8.33 (1H, d, J = 5.5 Hz, CH—N-pyridine) 10.25 (1H, s, CONH), 12.73 (1H, s, NH) | 358.0756 |
| 137. | 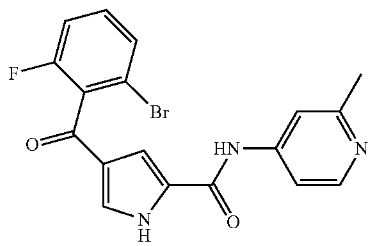 [SMILES: Cc1cc(NC(=O)c2cc(C(=O)c3c(F)cccc3Br)c[nH]2)ccn1] | 4-(2-Bromo-6-fluorobenzoyl)-N-(2-methylpyridin-4-yl)-1H-pyrrole-2-carboxamide | 25 | 2.48 (3H, s, CH₃), 7.42-7.46 (1H, m, H-5'), 7.50-7.56 (3H, m, CH-pyridine and H-4' and H-3), 7.61 (1H, d, J = 8.2 Hz, H-3'), 7.67-7.69 (2H, m, H-5 and CH-pyridine), 8.38 (1H, d, J = 5.7 Hz, CH-N-pyridine) 10.44 (1H, s, CONH), 12.77 (1H, s, NH) | 402.0250 |
| 138. | 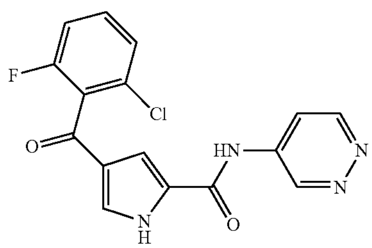 [SMILES: O=C(Nc1ccnnc1)c1cc(C(=O)c2c(F)cccc2Cl)c[nH]1] | 4-(2-Chloro-6-fluorobenzoyl)-N-(pyridazin-4-yl)-1H-pyrrole-2-carboxamide | 25 | 7.39-7.42 (1H, m, H-5'), 7.48 (1H, d, J= 8.3 Hz, H-3'), 7.54 (1H, s, H-3), 7.57 (1H, s, H-5), 7.60 (1H, ddd, J = 6.3, 8.3 and 8.3 Hz, H-4'), 8.05 (1H, dd, J = 2.7 and 5.9 Hz, CH-pyridazine), 9.06 (1H, dd, J = 1.0 and 5.9 Hz, CH—N-pyridazine) 9.47 (1H, dd, J = 1.0 and 2.7 Hz, CH—N-pyridazine), 10.58 (1H, s, CONH), 12.87 (1H, s, NH) | 345.0554 |
| 139. | 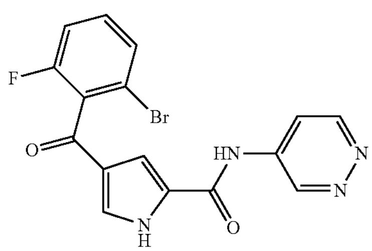 [SMILES: O=C(Nc1ccnnc1)c1cc(C(=O)c2c(F)cccc2Br)c[nH]1] | 4-(2-Bromo-6-fluorobenzoyl)-N-(pyridazin-4-yl)-1H-pyrrole-2-carboxamide | 25 | 7.43-7.46 (1H, m, H-5'), 7.50-7.55 (3H, m, H-3, H-5 and H-4'), 7.62 (1H, d, J = 7.8 Hz, H-3'), 8.05 (1H, dd, J = 2.7 and 6.0 Hz, CH-pyridazine), 9.06 (1H, d, J = 6.0 Hz, CH—N-pyridazine) 9.48 (1H, dd, J = 1.0 and 2.7 Hz, CH—N-pyridazine), 10.58 (1H, s, CONH), 12.86 (1H, s, NH) | 389.0034 |
| 140. | 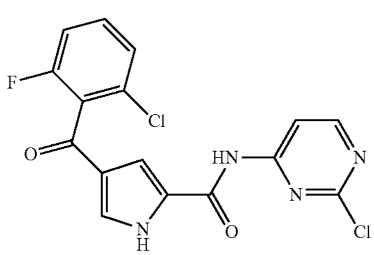 | 4-(2-Chloro-6-fluorobenzoyl)-N-(2-chloropyrimidin-4-yl)-1H-pyrrole-2-carboxamide | 25 | 7.39-7.43 (1H, m, H-5'), 7.48 (1H, d, J = 7.8 Hz, H-3'), 7.57-7.62 (2H, m, H-3 and H-4') 7.77 (1H, s, H-5), 8.18 (1H, d, J = 5.8 Hz, CH-pyrimidine), 8.63 (1H, d, J = 5.8 Hz, CH—N-pyrimidine), 11.49 (1H, s, CONH), 12.85 (1H,s, NH) | 379.0152 |
| 141. | 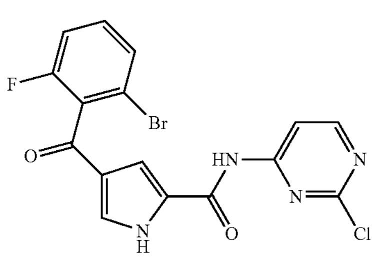 [SMILES: O=C(Nc1ccnc(Cl)n1)c1cc(C(=O)c2c(F)cccc2Cl)c[nH]1] | 4-(2-Bromo-6-fluorobenzoyl)-N-(2-chloropyrimidin-4-yl)-1H-pyrrole-2-carboxamide | 25 | 7.44 (1H, dd, J = 1.0 and 9.0 Hz, H-5'), 7.52 (1H, ddd, J = 6.2, 8.2 and 8.2 Hz, H-4'), 7.60-7.63 (2H, m, H-3 and H-3') 7.76 (1H, s, H-5), 8.18 (1H, d, J = 5.8 Hz, CH-pyrimidine), 8.62 (1H, d, J = 5.8 Hz, CH—N-pyrimidine), 11.50 (1H, s, CONH), 12.84 (1H, s, NH); 422.9647 | |

TABLE 13-continued

| Ex. | Structure | Name | General prep | 1H NMR Data | MS |
|---|---|---|---|---|---|
| 142. | 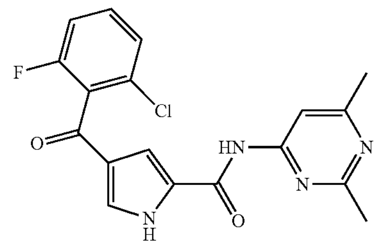 [SMILES: Cc1cc(NC(=O)c2cc(C(=O)c3c(F)cccc3Cl)c[nH]2)nc(C)n1] | 4-(2-Chloro-6-fluorobenzoyl)-N-(2,6-dimethylpyrimidin-4-yl)-1H-pyrrole-2-carboxamide | 25 | 2.45 (3H, s, CH$_3$), 2.54 (3H, s, NCH$_3$N), 7.41 (1H, dd, J = 1.0 and 9.0 Hz, H-5'), 7.48 (1H, d, J = 8.1 Hz, H-3'), 7.57-7.61 (2H, m, H-4' and H-3), 7.75 (1H, s, H-5), 7.96 (CH-pyrimidine), 11.20 (CONH), 12.78 (1H, s, NH) | 373.0861 |
| 143. | 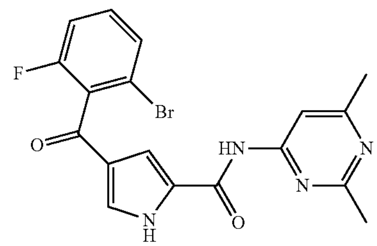 [SMILES: Cc1cc(NC(=O)c2cc(C(=O)c3c(F)cccc3Br)c[nH]2)nc(C)n1] | 4-(2-Bromo-6-fluorobenzoyl)-N-(2,6-dimethylpyrimidin-4-yl)-1H-pyrrole-2-carboxamide | 25 | 2.42 (3H, s, CH$_3$), 2.50 (3H, s, NCH$_3$N), 7.41 (1H, dd, J = 1.0 and 9.0 Hz, H-5'), 7.51 (1H, ddd, J = 6.3, 8.1 and 8.1 Hz, H-4'), 7.55 (1H, s, H-3), 7.61 (1H, d, J = 8 1 Hz, H-3'), 7.73 (1H, s, H-5), 7.90 (CH-pyrimidine), 11.04 (CONH), 12.73 (1H, s, NH) | 417.0359 |
| 144. | 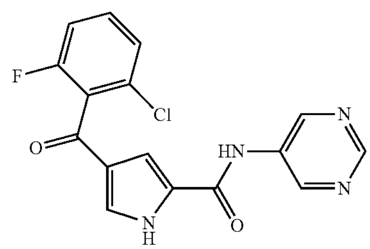 [SMILES: O=C(Nc1cncnc1)c1cc(C(=O)c2c(F)cccc2Cl)c[nH]1] | 4-(2-Chloro-6-fluorobenzoyl)-N-(pyrimidin-5-yl)-1H-pyrrole-2-carboxamide | 25 | 7.42 (1H, dd, J = 1.0 and 9.0 Hz, H-5'), 7.48-7.50 (2H, m, H-3' and H-3), 7.55 (1H, s, H-5), 7.60 (1H, ddd, J = 6.3, 8.3 and 8.3 Hz, H-4'), 8.92 (1H, s, N—CH—N-pyrimidine), 9.13 (2H, s, 2 × CH—N-pyrimidine), 10 44 (1H, s, CONH), 12.93 (1H, s, NH) | 345.055 |
| 145. | 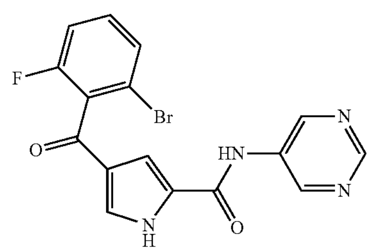 [SMILES: O=C(Nc1cncnc1)c1cc(C(=O)c2c(F)cccc2Br)c[nH]1] | 4-(2-Bromo-6-fluorobenzoyl)-N-(pyrimidin-5-yl)-1H-pyrrole-2-carboxamide | 25 | 7.43-7.46 (2H, H-5' and H-3), 7.50-7.54 (2H, m, H-4' and H-5), 7.60 (1H, d, J = 7.9 Hz, H-3'), 8.92 (1H, s, N—CH—N-pyrimidine), 9.13 (2H, s, 2 × CH—N-pyrimidine), 10.45 (1H, s, CONH), 12.83 (1H, s, NH) | 389.0044. |
| 146. | 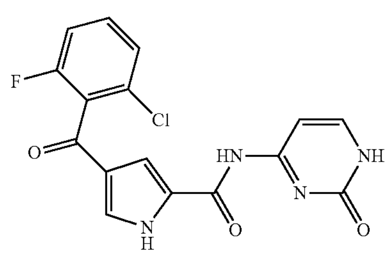 [SMILES: O=C(Nc1cc[nH]c(=O)n1)c1cc(C(=O)c2c(F)cccc2Cl)c[nH]1] | 4-(2-Chloro-6-fluorobenzoyl)-N-(2-oxo-1,2-dihydropyrimidin-4-yl)-1H-pyrrole-2-carboxamide | 25 | 7.22 (1H, br s, H-3), 7.38-7.42 (1H, m, H-5'), 7.47 (1H, d, J = 8.1 Hz, H-3'), 7.56-7.61 (2H, m, pyrimidone CH and H-4'), 7.70 (1H, br s, H-5), 7.85 (1H, d, J = 6.0 Hz, pyrimidone CH), 11.04 (1H, br s, CONH), 11.60 (1H, brs, pyrimidone NH), 12.77 (1H, br s, NH) | 361.0500. |
| 147. | 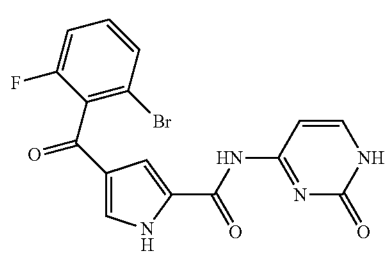 [SMILES: O=C(Nc1cc[nH]c(=O)n1)c1cc(C(=O)c2c(F)cccc2Br)c[nH]1] | 4-(2-Bromo-6-fluorobenzoyl)-N-(2-oxo-1,2-dihydropyrimidin-4-yl)-1H-pyrrole-2-carboxamide | 25 | 7.23 (1H, br s, H-3), 7.41-7.44 (1H, m, H-5'), 7.50 (1H, ddd, J = 6.3, 8.2 and 8.2 Hz, H-4'), 7.55 (1H, br s, pyrimidone CH), 7.60 (1H, d, J = 6 3 Hz, H-3'), 7.72 (1H, br s, H-5), 7.86 (1H, d, J = 6.3 Hz, pyrimidone CH), 11.02 (1H, br s, CONH), 11.60 (1H, br s, pyrimidone NH), 12.79 (1H, br s, NH) | 404.9996. |

TABLE 13-continued

| Ex. | Structure | Name | General prep | 1H NMR Data | MS |
|---|---|---|---|---|---|
| 148. | 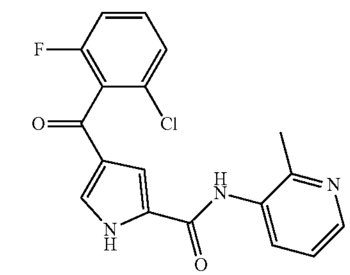 [SMILES: Cc1ncccc1NC(=O)c1cc(C(=O)c2c(F)cccc2Cl)c[nH]1] | 4-(2-Chloro-6-fluorobenzoyl)-N-(2-methylpyridin-3-yl)-1H-pyrrole-2-carboxamide | 25 | 2.44 (3H, s, CH$_3$), 7.28 (1H, dd, J = 4.4 and 7.9 Hz, CH-pyridine), 7.38-7.48 (4H, m, H-3, CH-pyridine, H-3' and H-5'), 7.58 (1H, ddd, J = 6.3, 8.1 and 8.1 Hz, H-4'), 7.73 (1H, s, H-5), 8.93 (1H, d, J = 4.4 Hz, CH—N-pyridine), 9.90 (1H, s, CONH), 12.66 (1H, s, NH) | 358.0758 |
| 149. | 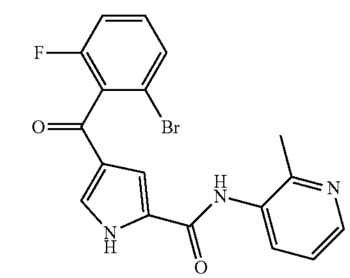 | 4-(2-Bromo-6-fluorobenzoyl)-N-(2-methylpyridin-3-yl)-1H-pyrrole-2-carboxamide | 25 | 2.44 (3H, s, CH$_3$), 7.28 (1H, dd, J = 4.7 and 7.9 Hz, CH-pyridine), 7.40-7.45 (3H, m, H-3, H-5 and H-5'), 7.51 (1H, ddd, J = 6.4, 8.7 and 8.7 Hz, H-4'), 7.61 (1H, d, J = 7.8 Hz, H-3'), 7.72 (1H, d, J = 7.9 Hz, CH-pyridine), 8.34 (1H, dd, J = 1.4 and 4.7 Hz, CH—N-pyridine), 9.91 (1H, s, CONH), 12.66 (1H, s, NH) | 402.0246 |
| 150. | 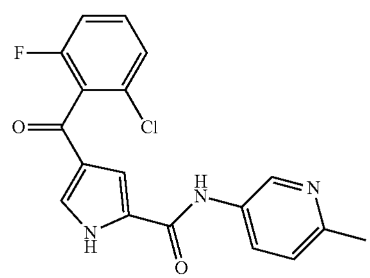 [SMILES: Cc1ccc(NC(=O)c2cc(C(=O)c3c(F)cccc3Cl)c[nH]2)cn1] | 4-(2-Chloro-6-fluorobenzoyl)-N-(6-methylpyridin-3-yl)-1H-pyrrole-2-carboxamide | 25 | 2.25 (3H, s, CH$_3$), 7.33 (1H, d, J = 4.9 Hz, CH-pyridine), 7.39-7.48 (4H, m, H-3, H-5, H-3' and H-5'), 7.58 (1H, ddd, J = 6.2, 8.3 and 8.3 Hz, H-4'), 8.32 (1H, d, J = 4.9 Hz, CH—N-pyridine), 8.46 (1H, s, CH—N-pyridine), 9.95 (1H, s, CONH), 12.67 (1H, s, NH) | 358.0758. |
| 151. | 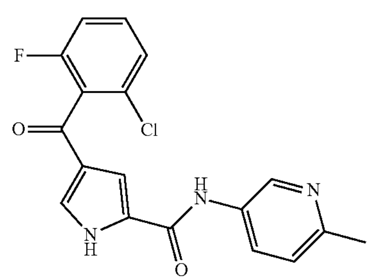 [SMILES: Cc1ccc(NC(=O)c2cc(C(=O)c3c(F)cccc3Cl)c[nH]2)cn1] | 4-(2-Bromo-6-fluorobenzoyl)-N-(6-methylpyridin-3-yl)-1H-pyrrole-2-carboxamide | 25 | 2.25 (3H, s, CH$_3$), 7.33 (1H, d, J = 5.1 Hz, CH-pyridine), 7.42 (1H, s, H-3), 7.43-7.45 (2H, m, H-5 and H-5'), 7.51 (1H, ddd, J = 6.2, 8.3 and 8.3 Hz, H-4'), 7.61 (1H, d, J = 7.9 Hz, H-3'), 8.32 (1H, d, J = 5.1 Hz, CH-pyridine), 8.46 (1H, s, CH—N-pyridine), 9.96 (1H, s, CONH), 12.66 (1H, s, NH) | 402.0250. |
| 152. | 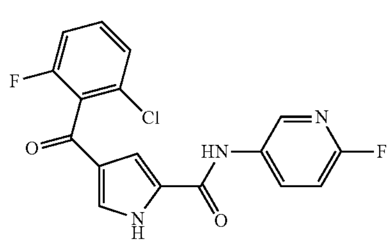 [SMILES: O=C(Nc1ccc(F)nc1)c1cc(C(=O)c2c(F)cccc2Cl)c[nH]1] | 4-(2-Chloro-6-fluorobenzoyl)-N-(6-fluoropyridin-3-yl)-1H-pyrrole-2-carboxamide | 25 | 7.21 (1H, dd, J = 3.3 and 9.0 Hz, CH-pyridine), 7.39-7.43 (1H, m, H-3'), 7.46-7.49 (3H, m, H-5', H-3 and H-5), 7.59 (1H, ddd, J = 6.1, 8.4 and 8.4 Hz, H-4'), 8.26-8.29 (1H, m, CH-pyridine), 8.54 (1H, s, CH—N-pyridine), 10.30 (1H, s, CONH), 12.74 (1H, s, NH) | 362.0508 |

TABLE 13-continued

| Ex. | Structure | Name | General prep | 1H NMR Data | MS |
|---|---|---|---|---|---|
| 153. | 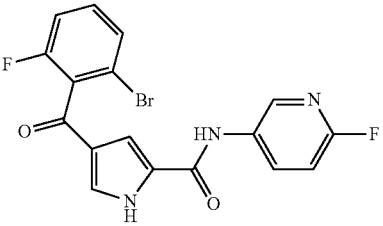 | 4-(2-Bromo-6-fluorobenzoyl)-N-(6-fluoropyridin-3-yl)-1H-pyrrole-2-carboxamide | 25 | 7.21 (1H, dd, J = 3.2 and 8.9 Hz, CH-pyridine), 7.42-7.46 (3H, m, H-5', H-3 and H-5), 7.52 (1H, ddd, J = 6.0, 8.3 and 8.3 Hz, H-4'), 7.62 (1H, d, J = 8.3 Hz, H-3'), 8.26-8.30 (1H, m, CH-pyridine), 8.54 (1H, s, CH—N-pyridine), 10.33 (1H, s, CONH), 12.72 (1H, s, NH) | 405.9999 |
| 154. | 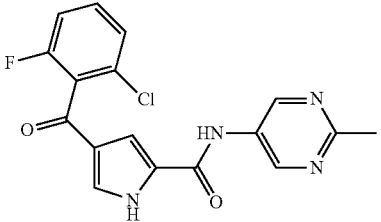 [SMILES: Cc1ncc(NC(=O)c2cc(C(=O)c3c(F)cccc3Cl)c[nH]2)cn1] | 4-(2-Chloro-6-fluorobenzoyl)-N-(2-methylpyrimidin-5-yl)-1H-pyrrole-2-carboxamide | 25 | $^1$H NMR (500 MHz, MeOD) δ 2.68 (3H, s, CH$_3$), 7.25-7.28 (1H, m, H-5'), 7.40 (1H, d, J = 8.5 Hz, H-3'), 7.44 (1H, d, J = 1.5 Hz, H-3), 7.49 (1H, d, J = 1.5 Hz, H-5), 7.53 (1H, ddd, J = 6.1, 8.5 and 8.5 Hz, H-4'), 9.07 (2H, s, CH-pyrimidine) | 359.0710 |
| 155. | 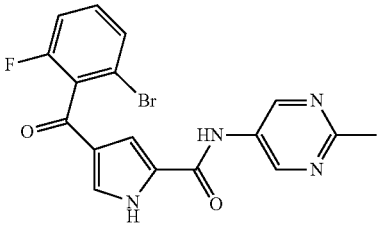 | 4-(2-Bromo-6-fluorobenzoyl)-N-(2-methylpyrimidin-5-yl)-1H-pyrrole-2-carboxamide | 25 | $^1$H NMR (500 MHz, MeOD) δ 2.68 (3H, s, CH$_3$), 7.28-7.32 (1H, m, H-5'), 7.43-7.49 (3H, m, H-3', H-3 and H-5), 7.54-7.58 (1H, m, H-4'), 9.06 (2H, s, CH-pyrimidine) | 403.0202 |
| 156. | 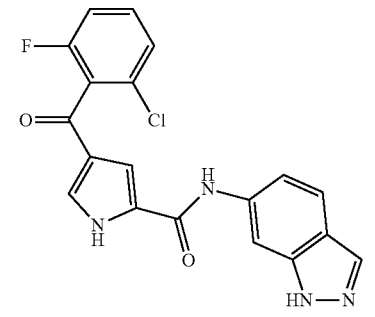 [SMILES: O=C(Nc1ccc2cn[nH]c2c1)c1cc(C(=O)c2c(F)cccc2Br)c[nH]1] | 4-(2-Chloro-6-fluorobenzoyl)-N-(1H-indazol-6-yl)-1H-pyrrole-2-carboxamide | 24 | 7.34 (1H, d, J = 8.0 Hz, H-3'), 7.39-7.44 (2H, m, H-3 and H-5'), 7.48 (1H, d, J = 9.0 Hz, Indazole-H-Ar), 7.59 (1H, ddd, J = 5.8, 8.3 and 8.3 Hz, H-4'), 7.70 (1H, d, J = 9.0 Hz, Indazole-H-Ar), 7.99 (1H, s, Indazole-H—Ar), 8.20 (1H, s, Indazole-H—Ar), 10.14 (1H, s, CONH), 12.65 (1H, s, NH), 12.94 (1H, s, Indazole-NH) | 383.0709 |
| 157. | 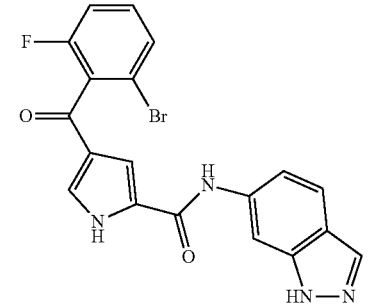 | 4-(2-Bromo-6-fluorobenzoyl)-N-(1H-indazol-6-yl)-1H-pyrrole-2-carboxamide | 24 | 7.35 (1H, d, J = 8.0 Hz, H-3'), 7.42-7.46 (2H, m, H-3 and H-5'), 7.49-7.54 (2H, m, H-5 and H-4'), 7.62 (1H, d, J = 8.9 Hz, Indazole-H—Ar), 7.69 (1H, d, J = 8.9 Hz, Indazole-H—Ar), 7.99 (1H, s, Indazole-H—Ar), 8.19 (1H, s, Indazole-H-Ar), 10.16 (1H, s, CONH), 12.64 (1H, s, NH), 12.94 (1H, s, Indazole-NH) | 427.0202 |

TABLE 13-continued

| Ex. | Structure | Name | General prep | 1H NMR Data | MS |
|---|---|---|---|---|---|
| 158. | 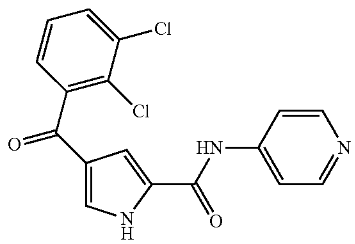 [SMILES: O=C(Nc1ccncc1)c1cc(C(=O)c2cccc(Cl)c2Cl)c[nH]1] | 4-(2,3-Dichlorobenzoyl)-N-(pyridin-4-yl)-1H-pyrrole-2-carboxamide | 24 | 7.45-7.56 (4 H, m, 2 × H—Ar, H-3 and H-5), 7.74 (2H, d, J = 5.9 Hz, CH-pyridine), 7 80 (2 H, dd, J = 2.4 and 7.8 Hz, H—Ar), 8.46 (2 H, d, J = 5.9 Hz, CH—N-pyridine), 10.33 (1H, s, CONH) 12.71 (1 H, br s, NH) | 359.0214 |
| 159. | 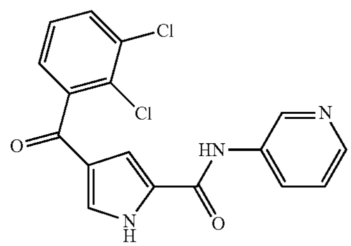 [SMILES: O=C(Nc1cccnc1)c1cc(C(=O)c2cccc(Cl)c2Cl)c[nH]1] | 4-(2,3-Dichlorobenzoyl)-N-(pyridin-3-yl)-1H-pyrrole-2-carboxamide | 24 | 7.37 (1 H, dd, J = 4.9 and 8.2 Hz, H—Ar), 7.42 (1H, s, H-3), 7.47-7.53 (3 H, m, 2 × H—Ar and H-5), 7.79 (1 H, dd, J = 1.4 and 7.5 Hz, CH-pyridine), 8.13-8.16 (1H, m, CH-pyridine), 8.29 (1 H, dd, J = 1.4 and 4.7 Hz, CH—N-pyridine), 8.90 (1 H, d, J = 2.4 Hz, CH—N-pyridine), 10.22 (1 H, s, CONH), 12.67 (1 H, br s, NH) | 358.0161 |
| 160. | 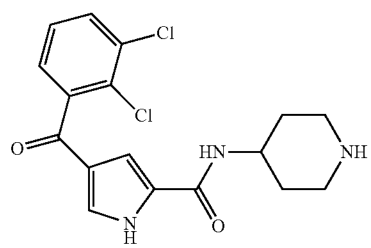 [SMILES: O=C(NC1CCNCC1)c1cc(C(=O)c2cccc(Cl)c2Cl)c[nH]1] | 4-(2,3-Dichlorobenzoyl)-N-(piperidin-4-yl)-1H-pyrrole-2-carboxamide | 26 | 1.28-1.38 (2H, m, CH$_2$), 1.69 (2H, d, J = 12.3 Hz, CH$_2$), 2.45-2.48 (2H, m, CH$_2$N), 2.95 (2H, d, J = 12.3 Hz, CH$_2$N), 3.71-3.81 (1H, m, CH), 7.18 (1H, br s, H-3), 7.25 (1H, br s, H-5), 7.42 (1H, d, J = 7.3 Hz, H-Ar), 7.47-7.50 (2H, m, H-Ar), 7.77 (1H, d, J = 7.3 Hz, H—Ar), 8.06 (1H, b r s, CONH) | 366.0775 |
| 161. | 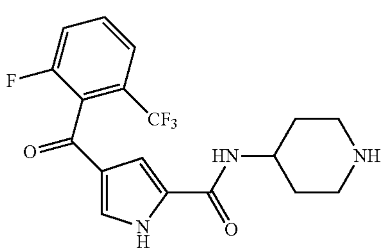 [SMILES: O=C(NC1CCNCC1)c1cc(C(=O)c2c(F)cccc2C(F)(F)F)c[nH]1] | 4-(2-Fluoro-6-(trifluoromethyl)benzoyl)-N-(piperidin-4-yl)-1H-pyrrole-2-carboxamide | 26 | $^1$H NMR (500 MHz, MeOD) δ 1.34-1.42 (2H, m, CH$_2$), 1.79 (2H, d, J = 11.9 Hz, CH$_2$), 2.52-2.57 (2H, m, CH$_2$N), 2.95 (2H, d, J = 11.9 Hz, CH$_2$N), 3.77-3.83 (1H, m, CH), 7.05 (1 H, s, H-3), 7.21 (1 H, s, H-5), 7.39-7.42 (1H, m, H-4'), 7.52-7.61 (2H, m, H-3' and H-4') | 392.1019 |
| 162. | 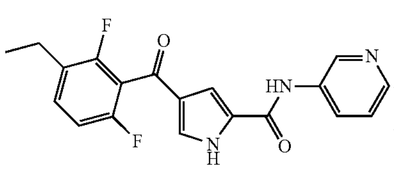 [SMILES: CCc1ccc(F)c(C(=O)c2c[nH]c(C(=O)Nc3cccnc3)c2)c1F] | (3-Ethyl-2,6-difluorophenyl)(5-((pyridin-3-ylamino)methyl)-1H-pyrrol-3-yl)methanone | 25 | $^1$H NMR (500 MHz, MeOD) δ 1.15 (3H, t, J = 7.6 Hz, CH$_2$CH$_3$), 2.62 (2H, q, J = 7.6 Hz, CH$_2$CH$_3$), 6.92-6.96 (1H, m, H—Ar), 7.31-7.35 (2H, m, H—Ar and CH-pyridine), 7.37 (1H, s, H-3), 7.39 (1H, s, H-5), 8.13 (1H, d, J = 6.6 Hz, CH-pyridine), 8.18 (1H, br s, CH—N-pyridine), 8.80 (1H, br s, CH—N-pyridine); | 356.1056 |
| 163. | 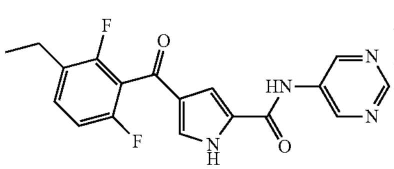 [SMILES: CCc1ccc(F)c(C(=O)c2c[nH]c(C(=O)Nc3cncnc3)c2)c1F] | 4-(3-Ethyl-2,6-difluorobenzoyl)-N-(pyrimidin-5-yl)-1H-pyrrole-2-carboxamide | 25 | 1.29 (3H, t, J = 7.7 Hz, CH$_2$CH$_3$), 2.75 (2H, q, J = 7.7 Hz, CH$_2$CH$_3$), 7.27-7.30 (1H, m, H—Ar), 7.57-7.64 (3H, m, H-3, H-5 and H—Ar), 9.00 (1H, s, CH-pyrimidine), 9.22 (2H, s, 2 × CH-pyrimidine), 10.52 (1H, br s, CONH), 12.89 (1H, br s, NH) | 357.1158 |

TABLE 13-continued

| Ex. | Structure | Name | General prep | 1H NMR Data | MS |
|-----|-----------|------|--------------|-------------|-----|
| 164. | 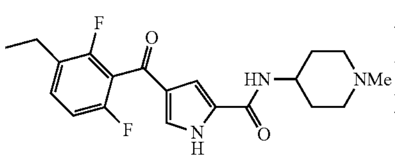 [SMILES: CCc1ccc(F)c(C(=O)c2c[nH]c(C(=O)NC3CCN(C)CC3)c2)c1F] | 4-(3-Ethyl-2,6-difluorobenzoyl)-N-(1-methylpiperidin-4-yl)-1H-pyrrole-2-carboxamide | 25 | $^1$H NMR (500 MHz, CDCl$_3$) δ 1.15 (3H, t, J = 7.5 Hz, CH$_2$CH$_3$), 2.03 (4H, br s, 2 × CH$_2$), 2.58 (2H, q, J = 7.5 Hz, CH$_2$CH$_3$), 2.60-2.64 (5H, m, NCH$_3$ + CH$_2$N), 3.32 (2H, br s, CH$_2$), 6.80-6.84 (1H, m, H—Ar), 7.14-7.20 (1H, m, H—Ar), 7.26 (1H, s, H-3), 7.61 (1H, s, H-5), 8.44 (1H, br s, CONH), 10.63 (1H, br s, NH) | 376.1023 |
| 165. | 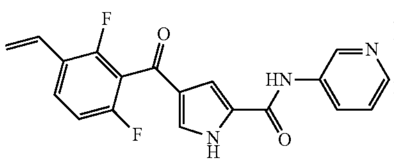 [SMILES: C=Cc1ccc(F)c(C(=O)c2c[nH]c(C(=O)Nc3cccnc3)c2)c1F] | 4-(2,6-Difluoro-3-vinylbenzoyl)-N-(pyridin-3-yl)-1H-pyrrole-2-carboxamide | 24 | $^1$H NMR (500 MHz, CDCl$_3$) δ 5.35 (1H, d, J = 11.3 Hz, vinyl CH), 5.73 (1H, d, J = 17.6 Hz, vinyl CH), 6.73 (1H, dd, J = 11.3 and 17.6 Hz, vinyl CH), 6.90-6.93 (1H, m, H-5'), 7.38 (d, J = 2.4 Hz, pyridine-CH), 7.39 (1H, s, H-3), 7.52 (1H, ddd, J = 6.4, 8.6 and 8.6 Hz, H-4), 8.04-8.06 (1H, m, pyridine-CH), 8.17 (1H, s, H-5), 8.29 (1H, dd, J = 1.4 and 5.0 Hz, pyridine-CH), 8.69 (1H, d, J = 2.4 Hz, pyridine-CH), 9.90 (1H, br s, CONH) | 354.1051 |

Example 166: 4-(2,6-Difluoro-3-vinylbenzoyl)-N-(pyrimidin-5-yl)-1H-pyrrole-2-carboxamide

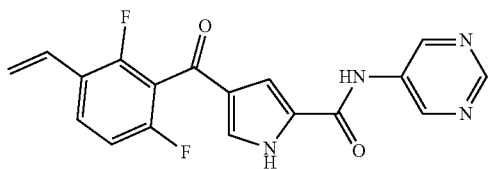 [SMILES: C=Cc1ccc(F)c(C(=O)c2c[nH]c(C(=O)Nc3cncnc3)c2)c1F]

4-(2,6-Difluoro-3-vinylbenzoyl)-1H-pyrrole-2-carboxylic acid was synthesised according to general procedure 24 using, Methyl 4-(2,6-difluoro-3-vinylbenzoyl)-1H-pyrrole-2-carboxylate (165 mg, 0.57 mmol), THF (5 mL), LiOH (271 mg, 11.33 mmol) in H$_2$O (7 mL). The pure product was obtained as a white solid (156 mg, 99%); M.p. 190-191° C.; λ$_{max}$ (EtOH)/nm 236, 280; ν$_{max}$/cm$^{-1}$: 2965, 1720, 1658, 1610; $^1$H NMR (500 MHz, DMSO-d$_6$) δ 5.41 (1H, d, J=11.1 Hz, vinyl CH), 5.76 (1H, d, J=17.5 Hz, vinyl CH), 6.87 (1H, dd, J=11.1 and 17.5 Hz, vinyl CH), 6.95-67.01 (1H, m, H-5'), 7.35 (1H, s, H-3), 7.48 (1H, s, H-5), 7.60 (1H, dddd, J=6.7, 6.7, 8.6 and 8.6 Hz, H-4'), 12.75 (1H, br s, NH) 12.94 (1H, br s, CO$_2$H); $^{13}$C NMR (125 MHz, DMSO-d$_6$) δ 112.2 (CH$_2$ vinyl) 112.3 (C—Ar), 112.4 (C—Ar), 112.8 (CH vinyl), 119.0 (C—Ar), 120.9 (C-3), 125.4 (C-2 and C-5), 129.5 (C-4), 132.2 (C—Ar), 132.9 (C—Ar), 153.0 (d, J$_{CF}$=235.6 Hz, CF), 165.2 (CO$_2$H), 169.1 (d, J$_{CF}$=225.4 Hz, C—Ar), 183.9 (CO); $^{19}$F NMR (470 MHz, DMSO-d$_6$) δ −113.6, −117.5; LRMS (ES$^+$) m/z 276.2 [M−H]

4-(2,6-Difluoro-3-vinylbenzoyl)-1H-pyrrole-2-carboxylic acid (60 mg, 0.21 mmol) was dissolved in acetonitrile (1 mL) before cyanuric fluoride (7 μL, 0.08 mmol) and pyridine (17 μL, 0.21 mmol) were added. The mixture was stirred at RT for 30 min before 5-aminopyrimidine (50 mg, 0.53 mmol) was added and the reaction was left to stir for 18 h. Brine was added and the product was extracted using ethyl acetate. The combined organic layers were dried over Na$_2$SO$_4$ and the solvent was removed in vacuo. The crude mixture was purified by semi-prep. HPLC (C-18 silica; 5-100% Acetonitrile in H$_2$O (0.1% Formic acid)) to give the title compound as a white solid (15 mg, 20%); Rf=0.39 (5% DCM in MeOH); M.p. 250-251° C.; λ$_{max}$ (EtOH)/nm 243, 293; ν$_{max}$/cm$^{-1}$: 3333, 3252, 3118, 1626, 1586; $^1$H NMR (500 MHz, DMSO-d$_6$) δ 5.49 (1H, d, J=11.4 Hz, vinyl CH), 5.97 (1H, d, J=17.7 Hz, vinyl CH), 6.84 (1H, dd, J=11.4 and 17.7 Hz, vinyl CH), 7.26-7.31 (1H, m, H-5'), 7.50 (1H, s, H-3), 7.61 (1H, s, H-5), 7.85-7.90 (1H, m, H-4'), 8.46 (1H, br s, CONH), 8.91 (1H, s, CH-pyrimidine), 9.15 (2H, s, 2×CH-pyrimidine), 10.60 (1H, br s, NH); $^{13}$C NMR (125 MHz, DMSO-d$_6$) δ 112.5 (C—Ar), 112.6 (CH$_2$ vinyl), 118.2 (C—Ar), 121.7 (C-3), 125.9 (C-2 and C-5), 127.5 (C-4), 129.2 (CH vinyl), 130.1 (C—Ar), 134.4, 141.8 (C-pyrimidine), 153.5 (d, J$_{CF}$=258.7 Hz, CF), 158.9 (CON), 181.7 (CO); $^{19}$F NMR (470 MHz, CDCl$_3$) δ −119.5, −114.7; LRMS (ES$^+$) m/z 355.3 [M+H]$^+$; HRMS m/z calcd for C$_{18}$H$_{13}$F$_2$N$_4$O$_2$ [M+H]$^+$ 355.1001, found 355.1003.

By following methods similar and/or analogous to those described herein, the compounds set out below was prepared from the corresponding starting materials.

| Ex. | Structure | Name | General prep | 1H NMR Data | MS |
|---|---|---|---|---|---|
| 167. | 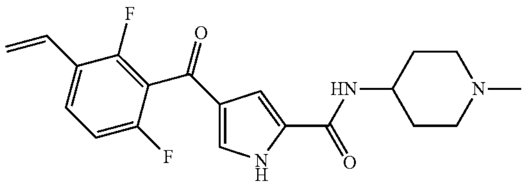 [SMILES: C=Cc1ccc(F)c(C(=O)c2c[nH]c(C(=O)NC3CCN(C)CC3)c2)c1F] | 4-(2,6-Difluoro-3-vinylbenzoyl)-N-(1-methyl-piperidin-4-yl)-1H-pyrrole-2-carboxamide | 24 | $^1$H NMR (500 MHz, CDCl$_3$) δ 2.03 (2H, br s, CH$_2$), 2.70 (4H, br s, CH$_2$ and CH$_2$N), 3.4 Hz (5H, s CH$_2$N and CH$_3$), 4.09 (2H, br s, CH), 5.32 (1H, d, J = 11.1 Hz, vinyl CH), 5.70 (1H, d, J = 17.6 Hz, vinyl CH), 6.72 (1H, dd, J = 11.1 and 17.6 Hz, vinyl CH), 6.86-6.89 (1H, m, H-5'), 7.24 (1H, s, H-3), 7.29 (1H, s, H-5), 7.45-7.49 (1H, m, H-4'), 8.38 (1H, br s, CONH), 10.79 (1H, br s, NH) | 374.1677 |

Example 168: 4-(2,6-Difluoro-3-(prop-1-en-2-yl)benzoyl)-N-(pyridin-3-yl)-1H-pyrrole-2-carboxamide

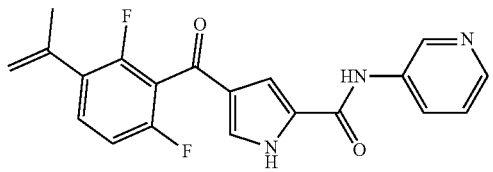 [SMILES: C=C(C)c1ccc(F)c(C(=O)c2c[nH]c(C(=O)Nc3cccnc3)c2)c1F]

4-(2,6-Difluoro-3-(prop-1-en-2-yl)benzoyl)-1H-pyrrole-2-carboxylic acid was synthesised according to general procedure 24 using, methyl 4-(2,6-difluoro-3-(prop-1-en-2-yl)benzoyl)-1H-pyrrole-2-carboxylate (170 mg, 0.56 mmol), THF (5 mL), LiOH (267 mg, 11.1 mmol) in H$_2$O (7 mL). The pure product was obtained as a colourless oil (160 mg, 98%); $^1$H NMR (500 MHz, CDCl$_3$) δ 2.14 (3H, s, CH$_3$), 5.21 (1H, s, alkene-CH), 5.30 (1H, s, alkene-CH), 6.96-6.99 (1H, m, H-5'), 7.36 (1H, s, H-3), 7.57 (1H, s, H-5), 7.64 (1H, dddd, J=6.6, 6.6, 8.4 and 8.4 Hz, H-4'), 9.75 (1H, br s, NH); LRMS (ES$^+$) m/z 290.2 [M+H]$^+$ 4-(2,6-Difluoro-3-(prop-1-en-2-yl)benzoyl)-1H-pyrrole-2-carboxylic acid (167 mg, 0.57 mmol) was dissolved in acetonitrile (4 mL) before cyanuric fluoride (20 μL, 0.23 mmol) and pyridine (46 μL, 0.57 mmol) were added. The mixture was stirred at RT for 30 min before 3-aminopyridine (135 mg, 1.43 mmol) was added and the reaction was left to stir for 18 h. Brine was added and the product was extracted using ethyl acetate. The combined organic layers were dried over Na$_2$SO$_4$ and the solvent was removed in vacuo. The crude mixture was purified by MPLC (0-8% MeOH in DCM) to give the title compound as a white solid (84 mg, 0.23 mmol, 40%); $^1$H NMR (500 MHz, CDCl$_3$) δ 2.13 (3H, s, CH$_3$), 5.23 (1H, s, alkene-CH), 5.29 (1H, s, alkene-CH), 6.96-6.70 (1H, m, H-5'), 7.42 (1H, ddd, J=6.5, 8.6 and 8.6 Hz, H-4'), 7.46 (1H, s, H-3), 7.71 (1H, s, H-5), 8.17-8.20 (1H, m, pyridine-CH), 8.37 (1H, br s, pyridine-CH), 8.91 (2H, br s, pyridine-CH), 10.47 (1H, br s, CONH); LRMS (ES$^+$) m/z 368.3 [M+H]$^+$.

By following methods similar and/or analogous to those described herein, the compounds set out in the Table below were prepared from the corresponding starting materials.

| Ex. | Structure | Name | General prep | 1H NMR Data | MS |
|---|---|---|---|---|---|
| 169. | 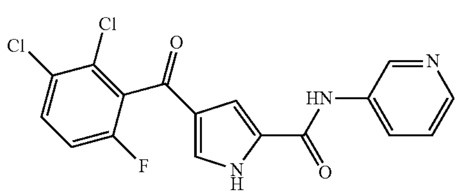 [SMILES: O=C(Nc1cccnc1)c1cc(C(=O)c2c(F)ccc(Cl)c2Cl)c[nH]1] | 4-(2,3-Dichloro-6-fluorobenzoyl)-N-(pyridin-3-yl)-1H-pyrrole-2-carboxamide | 25 | 7.39 (1H, dd, J = 4.7 and 8.2 Hz, CH-pyridine), 7.48-7.51 (2H, m, H-5' and H-3), 7.62 (1H, s, H-5), 7.86 (1H, dd, J = 4.7 and 8.2 Hz, CH-pyridine), 8.14 (1H, d, J = 7.3 Hz, H-4'), 8.30 (1H, d, J = 4.7 Hz, CH-pyridine), 8.89 (1H, s, CH—N-pyridine), 10.24 (1H, s, CONH), 12.70 (1H, br s, NH); | 378.0210 |
| 170. | 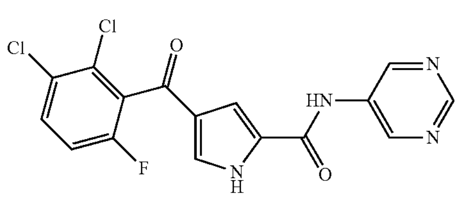 [SMILES: O=C(Nc1cncnc1)c1cc(C(=O)c2c(F)ccc(Cl)c2Cl)c[nH]1] | 4-(2,3-Dichloro-6-fluorobenzoyl)-N-(pyrimidin-5-yl)-1H-pyrrole-2-carboxamide | 25 | 7.46-7.52 (2H, m, H-3 and H-5'), 7.68 (1H, br s, H-5), 7.87 (1H, dd, J = 5.5 and 9.1 Hz, H-4'), 8.93 (1H, s, CH-pyrimidine), 9.13 (2H, s, CH-pyrimidine), 10.45 (1H, br s, CONH), 12.89 (1H, br s, NH); | 379.1061 |

| | | | | |
|---|---|---|---|---|
| 171. | | 4-(2,3-Dichloro-6-fluorobenzoyl)-N-(1-methyl-piperidin-4-yl)-1H-pyrrole-2-carboxamide | 25 | $^1$H NMR (500 MHz, CDCl$_3$) δ 1.65-1.67 (2H, m, CH$_2$), 2.01-2.03 (2H, m, CH$_2$), 2.07-2.19 (2H, m, CH$_2$N), 2.36 (3H, s, NCH$_3$), 2.87-2.90 (2H, m, CH$_2$N), 3.51-3.53 (1H, m, CH), 6.04 (1H, br s, CONH), 7.00 (1H, s, H-5), 7.10 (1H, dd, J = 7.6 and 8.9 Hz, H-5'), 7.33 (1H, s, H-5), 7.54 (1H, dd, J = 5.2 and 8.9 Hz, H-4') | 398.0835 |
| 172. | | 4-(3,6-Dichloro-2-fluorobenzoyl)-N-(pyridin-3-yl)-1H-pyrrole-2-carboxamide | 25 | 7.39 (1H, dd, J = 4.5 and 7.6 Hz, CH-pyridine), 7.52 (1H, br s, H-5'), 7.54 (1H, br s, H-3), 7.64 (1H, s, H-5), 7.78-7.81 (1H, m, H-4'), 8.14 (1H, d, J = 7.6 Hz, CH-pyridine), 8.30 (1H, d, J = 4.5 Hz, CH-pyridine), 8.90 (1H, s, CH—N-pyridine), 10.25 (1H, br s, CONH), 12.77 (1H, br s, NH); | 378.0210 |
| 173. | | 4-(3,6-Dichloro-2-fluorobenzoyl)-N-(pyrimidin-5-yl)-1H-pyrrole-2-carboxamide | 25 | 7.53-7.55 (2H, m, H-3 and H-5'), 7.69 (1H, br s, H-5), 7.79-7.82 (1H, m, H-4'), 8.93 (1H, s, CH-pyrimidine), 9.13 (2H, s, CH-pyrimidine), 10.45 (1H, br s, CONH), 12.90 (1H, br s, NH) | 379.1060 |
| 174. | | 4-(3,6-dichloro-2-fluorobenzoyl)-N-(1-methyl-piperidin-4-yl)-1H-pyrrole-2-carboxamide | 25 | 1.80 (2H, br s, CH$_2$), 1.91 (2H, br s, CH$_2$), 2.36 (5H, br s, CH$_2$N and CH$_3$), 2.97 (2H, br s, CH$_2$N), 2.98 (1H, br s, CH), 7.25 (1H, s, H-3), 7.48 (1H, s, H-5), 7.50 (1H, d, J = 8.4 Hz, H-5'), 7.76-7.79 (1H, m, H-4'), 8.21 (1H, d, J = 7.02 Hz, CONH), 12.51 (1H, br s, NH) | 398.0834. |
| 175. | | 4-(2-Chloro-6-fluoro-3-methyl-benzoyl)-N-(pyridin-3-yl)-1H-pyrrole-2-carboxamide | 25 | 2.37 (3H, s, CH$_3$), 7.29-7.33 (1H, m, H-5'), 7.39 (1H, dd, J = 4.8 and 8.6 Hz, CH-pyridine), 7.46 (1H, br s, H-3), 7.48 (1H, br s, H-5), 7.54 (1H, dd, J = 6.5 and 8.5 Hz, H-4'), 8.13-8.15 (1H, m, CH-pyridine), 8.30 (1H, dd, J = 1.5 and 4.8 Hz, CH-pyridine), 8.90 (1H, d, J = 2.5 Hz, CH-pyridine), 10.20 (1H, s, CONH), 12.71 (1H, br s, NH) | 358.0755 |
| 176. | | 4-(2-Chloro-6-fluoro-3-methyl-benzoyl)-N-(pyrimidin-5-yl)-1H-pyrrole-2-carboxamide | 25 | $^1$H NMR (500 MHz, MeOD) δ 2.30 (3H, s, CH$_3$), 7.03-7.06 (1H, m, H-5'), 7.33 (1H, s, H-3), 7.34-7.36 (1H, m, H-4'), 7.37 (1H, s, H-5), 8.77 (1H, s, CH-pyrimidine), 9.07 (2H, s, CH-pyrimidine) | 359.0711 |
| 177. | | 4-(2-Chloro-6-fluoro-3-methyl-benzoyl)-N-(1-methylpiperidin-4-yl)-1H-pyrrole-2-carboxamide | 25 | $^1$H NMR (500 MHz, CDCl$_3$) δ 1.69-1.78 (4H, m, 2 × CH$_2$), 2.07 (2H, br t, J = 11.1 Hz, CH$_2$N), 2.39 (3H, s, NCH$_3$), 2.41 (3H, s, CH$_3$), 2.97 (2H, br d, J = 11.1 Hz, CH$_2$N), 3.97-4.04 (1H, m, CH), 6.23 (1H, br d, J = 8.06 Hz, CONH), 7.00-7.04 (2H, m, H-4' and H-5'), 7.31 (1H, d, J = 2.4 Hz, H-3), | 359.0712 |

| # | Structure | Name | | NMR | Mass |
|---|---|---|---|---|---|
| | | | | 7.32 (1H, br s, H-5), 10.14 (1H, br s, NH) | |
| 178. | 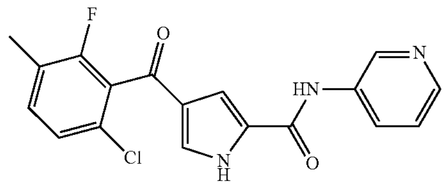 [SMILES: Cc1ccc(Cl)c(C(=O)c2c[nH]c(C(=O)Nc3cccnc3)c2)c1F] | 4-(6-Chloro-2-fluoro-3-methyl-benzoyl)-N-(pyridin-3-yl)-1H-pyrrole-2-carboxamide | 25 | 2.29 (3H, s, CH₃), 7.36 (1H, d, J = 8.0 Hz, H-5'), 7.39 (1H, dd, J = 4.7 and 8.4 Hz, CH-pyridine), 7.45-7.49 (3H, m, H-3, H-5 and H-4'), 8.13-8.15 (1H, m, CH-pyridine), 8.30 (1H, dd, J = 1.4 and 4.7 Hz, CH-pyridine), 8.90 (1H, d, J = 2.5 Hz, CH-pyridine), 10.24 10.24 (1H, s, CONH), 12.70 (1H, br s, NH) | 358.0754 |
| 179. | 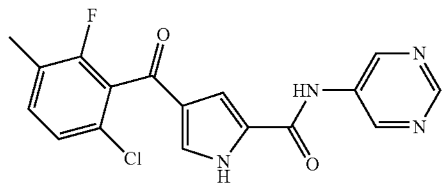 [SMILES: Cc1ccc(Cl)c(C(=O)c2c[nH]c(C(=O)Nc3cncnc3)c2)c1F] | 4-(6-Chloro-2-fluoro-3-methyl-benzoyl)-N-(pyrimidin-5-yl)-1H-pyrrole-2-carboxamide | 25 | ¹H NMR (500 MHz, MeOD) δ 2.20 (3H, s, CH₃), 7.10 (1H, d, J = 8.5 Hz, H-5'), 7.18-7.21 (1H, m, H-4'), 7.28 (1H, d, J = 3.4 Hz, , H-3), 8.04 (1H, s, H-5), 8.85 (1H, s, CH-pyrimidine), 8.98 (2H, s, CH-pyrimidine), 9.21 (1H, br s, CONH), 10.08 (1H, br s, NH); | 359.0711 |
| 180. | 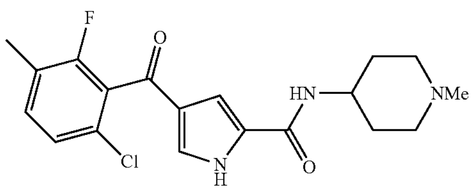 [SMILES: Cc1ccc(Cl)c(C(=O)c2c[nH]c(C(=O)NC3CCN(C)CC3)c2)c1F] | 4-(6-Chloro-2-fluoro-3-methyl-benzoyl)-N-(1-methylpiperidin-4-yl)-1H-pyrrole-2-carboxamide | 25 | ¹H NMR (500 MHz, CDCl₃) δ 1.59-1.67 (2H, m, CH₂), 1.90 (2H, br d, J = 11.1 Hz, CH₂), 2.14-2.19 (2H, m, CH₂N), 2.19 (3H, s, NCH₃), 2.27 (3H, s, CH₃), 2.83(2H, br d, J = 11.1 Hz, CH₂N), 3.86-3.98 (1H, m, CH), 6.57 (1H, br d, J = 7.9 Hz, CONH), 7.05 (1H, d, J = 8.4 Hz, H-5'), 7.07 (1H, br s, H-3), 7.10-7.13 (1H, m, H-4'), 7.20 (1H, br s, H-5), 10.97 (1H, br s, NH) | |
| 181. | 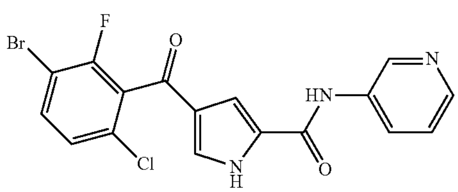 | 4-(3-Bromo-6-chloro-2-fluoro-benzoyl)-N-(pyridin-3-yl)-1H-pyrrole-2-carboxamide | 25 | ¹H NMR (500 MHz, MeOD) δ 7.24 (1H, dd, J = 1.3 and 8.7 Hz, H-5'), 7.31-7.34 (2H, m, H-3 and CH-pyridine), 7.42 (1H, d, J = 1.4 Hz, H-5), 7.66 (1H, dd, J = 7.5 and 8.9 Hz, H-4'), 8.11-8.14 (1H, m, CH-pyridine), 8.17 (d, J = 4.3 Hz, CH-pyridine), 8.78 (1H, d, J = 2.3 Hz, CH—N-pyridine) | 421.9702 |
| 182. | 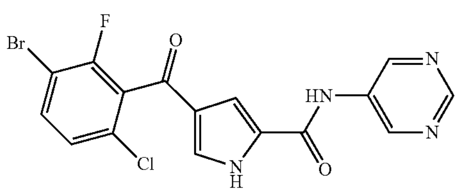 | 4-(3-Bromo-6-chloro-2-fluoro-benzoyl)-N-(pyrimidin-5-yl)-1H-pyrrole-2-carboxamide | 25 | ¹H NMR (500 MHz, CDCl₃) δ 7.21 (1H, dd, J = 1.4 and 8.7 Hz, H-5'), 7.41 (1H, d, J = 2.6 Hz, H-3), 7.64 (1H, dd, J = 7.3 and 8.7 Hz, H-4'), 7.82 (1H, s, H-5), 8.78 (1H, br s, CONH), 8.99 (1H, s, pyrimidine-CH), 9.09 (2H, s, pyrimidine-CH), 10.15 (1H, br s, NH) | 421.9810 |
| 183. | 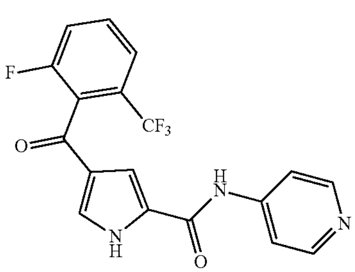 [SMILES: O=C(Nc1ccncc1)c1cc(C(=O)c2c(F)cccc2C(F)(F)F)c[nH]1] | 4-(2-Fluoro-6-(trifluoromethyl)-benzoyl)-N-(pyridin-4-yl)-1H-pyrrole-2-carboxamide | 25 | 7.50-7.54 (2H, m, CH-pyridine), 7.72-7.83 (5H, m, H-3', H-4', H-5', H-3 and H-5), 8.46 (2H, d, J = 6.4 Hz, N—CH-pyridine), 10.34 (1H, s, CO—NH), 12.75 (1H, s, NH-pyrrole) | 378.0859 |

-continued

| Ex. | Structure | Name | General prep | ¹H NMR Data | MS |
|---|---|---|---|---|---|
| 184. | | 4-(2-Fluoro-6-(trifluoromethyl)benzoyl)-N-(pyridin-3-yl)-1H-pyrrole-2-carboxamide | 25 | 7.39 (1H, dd, J = 4.6 and 8.3 Hz, CH-pyridine), 7.46-7.50 (2H, m, H-3 and H-5), 7.72-7.82 (3H, m, H-3', H-4', and H-5'), 8.13 (1H, ddd, J = 1.5, 2.5 and 8.3 Hz, CH-pyridine), 8.30 (1H, dd, J = 1.5 and 3.3 Hz, N—CH-pyridine), 8.90 (1H, d, J = 2.4 Hz, N—CH-pyridine), 10.22 (1H, br s, CO—NH), 12.70 (1H, s, NH-pyrrole) | 378.0860. |
| 185. | 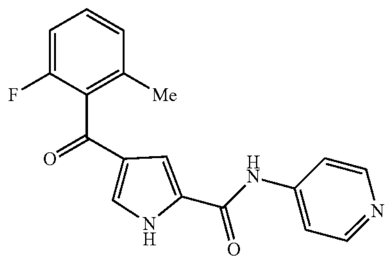 [SMILES: Cc1cccc(F)c1C(=O)c1c[nH]c(C(=O)Nc2ccncc2)c1] | 4-(2-Fluoro-6-methylbenzoyl)-N-(pyridin-4-yl)-1H-pyrrole-2-carboxamide | 32 | 2.19 (3H, s, CH₃), 7.15-7.20 (2H, m, H-3' and H-5'), 7.39 (1H, br s, H-3), 7.43 (1H, ddd, J = 6.2, 8.3 and 8.4 Hz, H-4'), 7.51 (1H, br s, H-5), 7.73 (2H, d, J = 6.4 Hz, CH-pyridine), 8.46 (2H, d, J = 6.4 Hz, N—CH-pyridine), 10.34 (1H, s, CO—NH), 12.66 (NH-pyrrole) | 324.1146 |
| 186. | 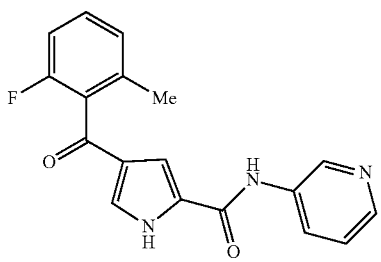 [SMILES: Cc1cccc(F)c1C(=O)c1c[nH]c(C(=O)Nc2cccnc2)c1] | 4-(2-Fluoro-6-methylbenzoyl)-N-(pyridin-3-yl)-1H-pyrrole-2-carboxamide | 32 | 2.20 (3H, s, CH₃), 7.15-7.20 (2H, m, H-3' and H-5'), 7.37-7.40 (2H, m, H-3 and CH-pyridine), 7.43 (1H, ddd, J = 6.2, 8.3 and 8.4 Hz, H-4'), 7.47 (1H, br s, H-5), 8.14 (1H, ddd, J = 1.5, 2.5 and 8.3 Hz, CH-pyridine), 8.30 (1H, dd, J = 1.5 and 4.7 Hz, N—CH-pyridine), 8.89 (1H, d, J = 2.5 Hz, N—CH-pyridine), 10.23 (1H, s, CO—NH), 12.60 (1H, s, NH-pyrrole) | 324.1147 |
| 187. | 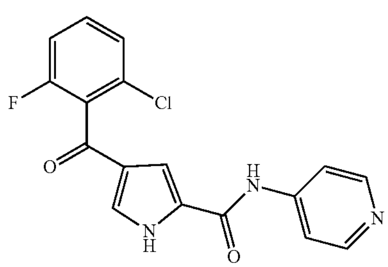 [SMILES: O=C(Nc1ccncc1)c1cc(C(=O)c2c(F)cccc2Cl)c[nH]1] | 4-(2-Chloro-6-fluorobenzoyl)-N-(pyridin-4-yl)-1H-pyrrole-2-carboxamide | 32 | 7.40-7.43 (1H, m, H-5'), 7.47-7.48 (1H, m, H-3'), 7.51 (1H, br s, H-3), 7.55 (1H, br s, H-5), 7.59 (1H, ddd, J = 6.2, 8.3 and 8.4 Hz, H-4'), 7.74 (2H, d, J = 6.3 Hz, CH-pyridine), 8.47 (2H, d, J = 6.3 Hz, N—CH-pyridine), 10.36 (1H, s, CO—NH), 12.76 (1H, s, NH-pyrrole) | 344.0592 |
| 188. | 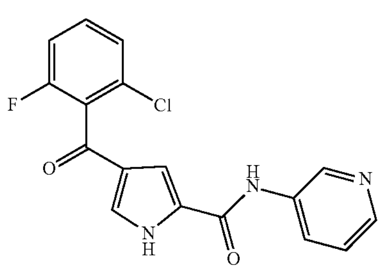 [SMILES: O=C(Nc1cccnc1)c1cc(C(=O)c2c(F)cccc2Cl)c[nH]1] | 4-(2-Chloro-6-fluorobenzoyl)-N-(pyridin-3-yl)-1H-pyrrole-2-carboxamide | 32 | 7.38-7.43 (2H, m, H-3 and H-5'), 7.47-7.50 (3H, m, H-5, H-3' and CH-pyridine), 7.59 (1H, ddd, J = 6.2, 8.3 and 8.4 Hz, H-4'), 8.14 (1H, ddd, J = 1.5, 2.5 and 8.3 Hz, CH-pyridine), 8.30 (1H, dd, J = 1.5 and 4.7 Hz, N—CH-pyridine), 8.89 (1H, d, J = 2.5 Hz, N—CH-pyridine), 10.24 (1H, s, CO—NH), 12.71 (1H, s, NH-pyrrole) | 344.0592 |

| # | Structure | Name | | NMR | MS |
|---|---|---|---|---|---|
| 189. | 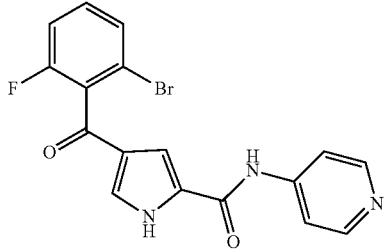 [SMILES: O=C(Nc1ccncc1)c1cc(C(=O)c2c(F)cccc2Br)c[nH]1] | 4-(2-Bromo-6-fluorobenzoyl)-N-(pyridin-4-yl)-1H-pyrrole-2-carboxamide | 32 | 7.42-7.46 (1H, m, H-5'), 7.49-7.54 (3H, m, H-3, H-4' and H-5), 7.61-7.62 (1H, m, H-3'), 7.73 (2H, d, J = 6.4 Hz, CH-pyridine), 8.46 (2H, d, J = 6.4 Hz, N—CH-pyridine), 10.35 (1H, s, CO—NH), 12.74 (1H, s, NH-pyrrole) | 388.0088 |
| 190. | 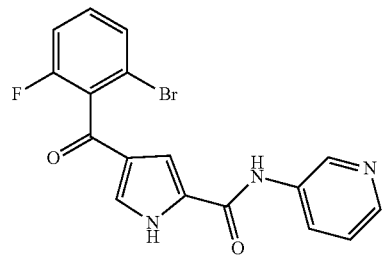 [SMILES: O=C(Nc1cccnc1)c1cc(C(=O)c2c(F)cccc2Br)c[nH]1] | 4-(2-Bromo-6-fluorobenzoyl)-N-(pyridin-3-yl)-1H-pyrrole-2-carboxamide | 32 | 7.39 (1H, dd, J = 4.7 and 8.4 Hz, CH-pyridine), 7.42-7.48 (3H, m, H-3, H-5' and H-5), 7.52 (1H, ddd, J = 6.2, 8.3 and 8.4 Hz, H-4'), 7.61-7.63 (1H, m, H-3'), 8.14 (1H, ddd, J = 1.5, 2.5 and 8.4 Hz, CH-pyridine), 8.30 (1H, dd, J = 1.5 and 4.7 Hz, N—CH-pyridine), 8.89 (1H, d, J = 2.5 Hz, N—CH-pyridine), 10.24 (1H, s, CO—NH), 12.70 (1H, s, NH-pyrrole) | 388.0090 |
| 191. | 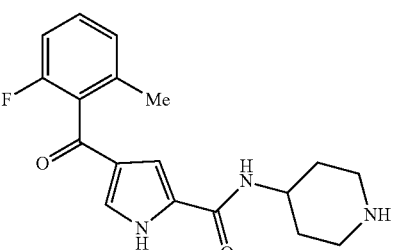 | 4-(2-Fluoro-6-methylbenzoyl)-N-(piperidin-4-yl)-1H-pyrrole-2-carboxamide | 31 | 1.35 (2H, m, CH-piperidine), 1.68-171 (2H, m, CH-piperidine), 2.17 (3H, s, CH₃), 2.46-2.51 (2H, m, N—CH-piperidine), 2.92-2.96 (2H, m, N CH-piperidine), 3.72-3.80 (1H, m, N CH-piperidine), 7.12-7.20 (4H, m, H-3, H-3', H-5', and H-5), 7.41 (1H, ddd, J = 6.2, 8.3 and 8.4 Hz, H-4'), 8.08 (1H, d, J = 8.0 Hz, CO—NH), 12.33 (1H, br s, NH-pyrrole) | 330.1615 |
| 192. | 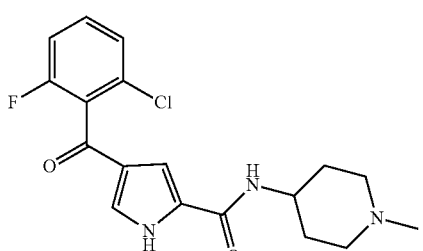 | 4-(2-Chloro-6-fluorobenzoyl)-N-(1-methyl-piperidin-4-yl)-1H-pyrrole-2-carboxamide | 27 | 1.48-1.56 (2H, m, CH-piperidine), 1.71-1.74 (2H, m, CH-piperidine), 1.88-1.95 (2H, m, N—CH-piperidine), 2.16 (3H, s, CH₃), 2.74-2.77 (2H, m, N—CH-piperidine), 3.64-3.70 (1H, m, N—CH-piperidine), 7.20 (1H, br s, H-3), 7.32 (1H, br s, H-5), 7.37-7.40 (1H, m, H-5'), 7.45-7.46 (1H, m, H-3'), 7.57 (1H, ddd, J = 6.4, 8.2 and 8.3 Hz, H-4'), 8.10 (1H, d, J = 8.0 Hz, CO—NH), 12.40(1H, s, NH-pyrrole) | 364.1226. |
| 193. | 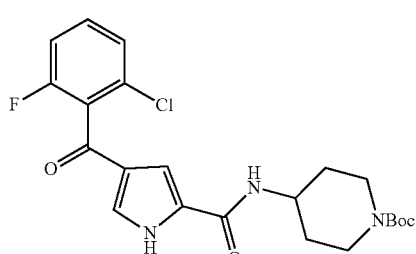 | tert-Butyl 4-(4-(2-chloro-6-fluorobenzoyl)-1H-pyrrole-2-carboxamido)-piperidine-1-carboxylate | 32 | 1.31-1.39 (2H, m, CH-piperidine), 1.41 (9H, s, C—CH₃), 1.75-1.78 (2H, m, CH-piperidine), 2.84 (2H, br s, N—CH-piperidine), 3.89-3.96 (3H, m, N—CH-piperidine), 7.18 (1H, br s, H-3), 7.33 (1H, br s, H-5), 7.37-7.39 (1H, m, H-5'), 7.45-7.46 (1H, m, H-3'), 7.57 (1H, ddd, J = 6.2, 8.3 and 8.4 Hz, H-4'), 8.11 (1H, d, J = 7.8 Hz, CO—NH), 12.42 (1H, s, NH-pyrrole) | 467.1855. |

| # | Structure | Name | | | Mass |
|---|---|---|---|---|---|
| 194. | 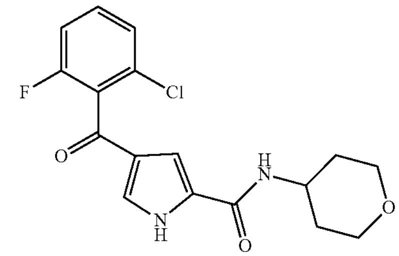 [SMILES: O=C(NC1CCOCC1)c1cc(C(=O)c2c(F)cccc2Cl)c[nH]1] | 4-(2-Chloro-6-fluorobenzoyl)-N-(tetrahydro-2H-pyran-4-yl)-1H-pyrrole-2-carboxamide | 27 | 1.48-1.57 (2H, m, CH-THP), 1.72-1.75 (2H, m, CH-THP), 3.34-3.40 (2H, m, O—CH-THP), 3.35-3.88 (2H, m, O—CH-THP), 3.91-3.99 (1H, m, N—CH-THP), 7.21 (1H, br s, H-3), 7.33 (1H, br s, H-5), 7.37-7.41 (1H, m, H-5'), 7.45-7.47 (1H, m, H-3'), 7.57 (1H, ddd, J = 6.3, 8.3 and 8.4 Hz, H-4'), 8.17 (1H, d, J = 8.0 Hz, CO—NH), 12.43 (1H, s, NH-pyrrole) | 351.0910 |
| 195. | 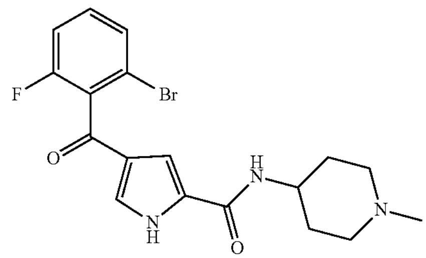 [SMILES: CN1CCC(NC(=O)c2cc(C(=O)c3c(F)cccc3Br)c[nH]2)CC1] | 4-(2-Bromo-6-fluorobenzoyl)-N-(1-methyl-piperidin-4-yl)-1H-pyrrole-2-carboxamide | 27 | 1.48-1.56 (2H, m, CH-piperidine), 1.72-1.74 (2H, m, CH-piperidine), 1.90-1.94 (2H, N—CH-piperidine), 2.15 (3H, s, CH₃), 2.74-2.77 (2H, m, N—CH-piperidine), 3.64-3.70 (1H, m, N—CH-piperidine), 7.19 (1H, br s, H-3), 7.30 (1H, br s, H-5), 7.40-7.43 (1H, m, H-5'), 7.49 (1H, ddd, J = 6.3, 8.3 and 8.4 Hz, H-4'), 7.58-7.60 (1H, m, H-3'), 8.10 (1H, d, J = 7.8 Hz, CO—NH), 12.39 (1H, s, NH-pyrrole) | 408.0719. |
| 196. | 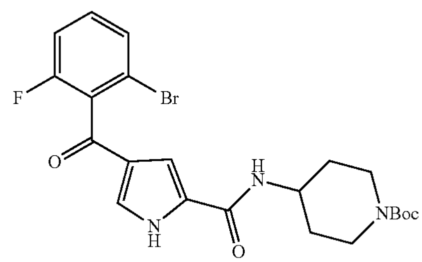 [SMILES: CC(C)(C)OC(=O)N1CCC(NC(=O)c2cc(C(=O)c3c(F)cccc3Br)c[nH]2)CC1] | tert-Butyl 4-(4-(2-bromo-6-fluorobenzoyl)-1H-pyrrole-2-carboxamido)-piperidine-1-carboxylate | 27 | 1.31-1.40 (2H, m, CH-piperidine), 1.41 (9H, s, C—CH$_3$), 1.75-1.78 (2H, m, CH-piperidine), 2.84 (2H, br s, N—CH-piperidine), 3.89-3.97 (3H, m, N—CH-piperidine), 7.18 (1H, br s, H-3), 7.30 (1H, br s, H-5), 7.39-7.43 (1H, m, H-5'), 7.49 (1H, ddd, J = 6.2. 8.3 and 8.4 Hz, H-4'), 7.58-7.60 (1H, m, H-3'), 8.12 (1H, d, J = 8.0 Hz, CO—NH), 12.40 (1H, s, NH-pyrrole) | 494.1082 |
| 197. | 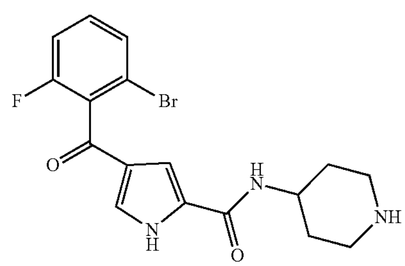 [SMILES: O=C(NC1CCNCC1)c1cc(C(=O)c2c(F)cccc2Br)c[nH]1] | 4-(2-Bromo-6-fluorobenzoyl)-N-(piperidin-4-yl)-1H-pyrrole-2-carboxamide | 31 | 1.33-1.41 (2H, m, CH-piperidine), 1.69-1.73 (2H, m, CH-piperidine), 2.48-2.54 2H, m, N—CH-piperidine), 2.94-2.98 (2H, m, N—CH-piperidine), 3.74-3.81 (1H, m, N—CH-piperidine), 7.21 (1H, br s, H-3), 7.29 (1H, br s, H-5), 7.39-7.43 (1H, m, H-5'), 7.49 (1H, ddd, J = 6.2, 8.2 and 8.3 Hz, H-4'), 7.58-7.60 (1H, m, H-3'), 8.10 (1H, d, J = 8.0 Hz, CO—NH), NH-pyrrole not observed | 394.0564 |
| 198. | 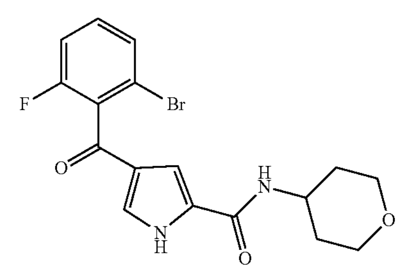 [SMILES: O=C(NC1CCOCC1)c1cc(C(=O)c2c(F)cccc2Br)c[nH]1] | 4-(2-Bromo-6-fluorobenzoyl)-N-(tetrahydro-2H-pyran-4-yl)-1H-pyrrole-2-carboxamide | 27 | 1.48-1.56 (2H, m, CH-THP), 1.72-1.75 (2H, m, CH-THP), 3.35-3.40 (2H, m, O—CH-THP), 3.85-3.88 (2H, m, O—CH-THP), 3.91-3.99 (1H, m, N—CH-THP), 7.20 (1H, br s, H-3), 7.31 (1H, br s, H-5), 7.40-7.44 (1H, m, H-5'), 7.49 (1H, ddd, J = 6.3, 8.2 and 8.3 Hz, H-4'), 7 59-7 60 (1H, m, H-3), 8.17 (1H, d, J = 8.0 Hz, CO—NH), 12.42 (1H, s, NH-pyrrole) | 395.0403 |

| | | | | | |
|---|---|---|---|---|---|
| 199. | 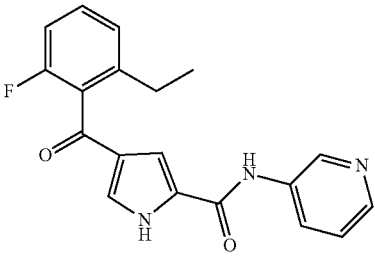 [SMILES: CCc1cccc(F)c1C(=O)c1c[nH]c(C(=O)Nc2cccnc2)c1] | 4-(2-Ethyl-6-fluorobenzoyl)-N-(pyridin-3-yl)-1H-pyrrole-2-carboxamide | 32 | 1.10 (3H, t, J = 7.5 Hz, CH$_3$), 2.49 (2H, t, J = 7.5 Hz, CH$_2$), 7.16-7.19 (1H, m, H-5'), 7.22-7.24 (1H, m, H-3'), 7.37 (1H, br s, H-3), 7.39 (1H, dd, J = 4.7 and 8.4 Hz, CH-pyridine), 7.45-7.50 (2H, m, H-5 and H-4'), 3.14 (1H, ddd, J = 1.5, 2.5, and 8.4 Hz, CH-pyridine), 8.30 (1H, dd, J = 1.5 and 4.7 Hz, N—CH-pyridine), 8.89 (1H, d, J = 2.5 Hz, N—CH-pyridine), 10.24 (1H, s, CO—NH), 12.62 (1H, s, NH-pyrrole) | 338.1304 |
| 200. | 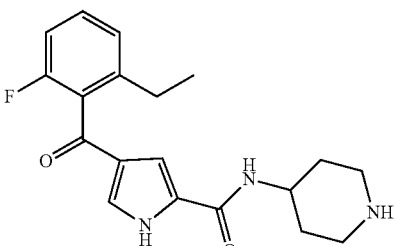 | 4-(2-Ethyl-6-fluorobenzoyl)-N-(piperidin-4-yl)-1H-pyrrole-2-carboxamide | 32 | 1.03 (3H, t, J = 7.5 Hz, CH$_3$), 1.58-1.67 (2H, m, CH-piperidine), 1.89-1.93 (2H, m, CH-piperidine), 2.45 (2H, q, J = 7.5 Hz, CH$_2$), 2.95-3.01 (2H, m, N—CH-piperidine), 3.26-3.29 (2H, m, N—CH-piperidine), 3.95-4.02 (1H, m, N—CH-piperidine), 7.09-7.12 (1H, m, H-5'), 7.15-7.16 (1H, m, H-3'), 7.41 (1H, ddd, J = 6.3, 8.3 and 8.4 Hz, H-4'), 8.24 (1H, d, J = 8.0 Hz, CO—NH), 8.33 (1H, br s, H-3), 8.56 (1H, br s, H-5), 12.30 (1H, s, NH) | 344.1771 |
| 201. | 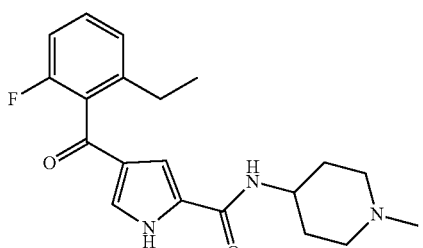 | 4-(2-Ethyl-6-fluorobenzoyl)-N-(1-methyl-piperidin-4-yl)-1H-pyrrole-2-carboxamide | 27 | 1.07 (3H, t, J = 7.5 Hz, CH$_3$), 1.48-1.56 (2H, m, CH-piperidine), 1.71-1.75 (2H, m, CH-piperidine), 1.89-1.95 (2H, m, N—CH-piperidine), 2.16 (3H, s, N—CH$_3$), 2.49 (2H, q, J = 7.5 Hz, CH$_2$), 2.74-2.76 (2H, m, N—CH-piperidine), 3.63-3.71 (1H, m, N—CH-piperidine), 6.92 (1H, br s, H-3), 7.12-7.21 (3H, m, H-5, H-3', H-5'), 7.45 (1H, ddd, J = 6.3, 8.3 and 8.4 Hz, H-4'), 8.09 (1H, d, J = 8.0 Hz, CO—NH), 12.01 (1H, s, NH-pyrrole) | 358.1929 |
| 202. | 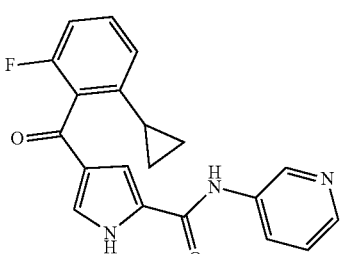 | 4-(2-Cyclopropyl-6-fluorobenzoyl)-N-(pyridin-3-yl)-1H-pyrrole-2-carboxamide | 32 | $^1$H NMR (500 MHz, MeOD) δ ppm 0.59-0.62 (2H, m, CH-cyclopropane), 0.75-0.79 (2H, m, CH-cyclopropane), 1.69-1.75 (1H, m, CH-cyclopropane), 6.75-6.77 (1H, m, H-3'), 6.90-6.93 (1H, m, H-5'), 7.26-7.34 (4H, m, H-4', H-3, H-5 and CH-pyridine), 8.11 (1H, ddd, J = 1.5, 2.5 and 8.3 Hz, CH-pyridine), 8.16 (1H, dd, J = 1.5 and 4.7 Hz, N—CH-pyridine), 8.77 (1H, d, J = 2.5 Hz, N—CH-pyridine), CO—NH and NH-pyrrole not visualised | |

| | | | | | |
|---|---|---|---|---|---|
| 203. | 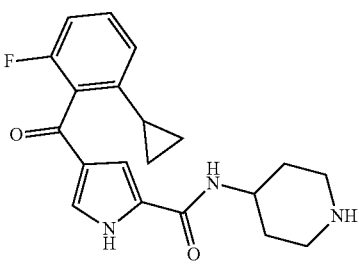 [SMILES: O=C(NC1CCNCC1)c1cc(C(=O)c2c(F)cccc2C2CC2)c[nH]1] | 4-(2-Cyclopropyl-6-fluorobenzoyl)-N-(piperidin-4-yl)-1H-pyrrole-2-carboxamide | 31 | 0.67-0.68 (2H, m, CH-cyclopropane), 0.83-0.86 (2H, m, CH-cyclopropane), 1.31-1.39 (2H, m, CH-piperidine), 1.67-1.72 (3H, m, CH-cyclopropane and CH-piperidine), 2.46-2.50 (2H, m, N—CH-piperidine), 2.92-2.96 (2H, m, N—CH-piperidine), 3.72-3.80 (1H, m, N—CH-piperidine), 6.83-6.84 (1H, m, H-3'), 7.08-7.11 (1H, m, H-5'), 7.20 (1H, br s, H-3), 7.22 (1H, br s, H-5), 7.39 (1H, ddd, J = 6.3, 8.3 and 8.4 Hz, H-4'), 8.10 (1H, d, J = 8.0 Hz, CO—NH), 12.26 (1H, br s, NH-pyrrole) | 356.1774 |
| 204. | 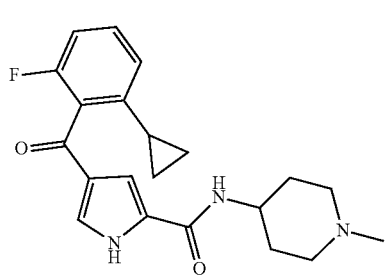 [SMILES: CN1CCC(NC(=O)c2cc(C(=O)c3c(F)cccc3C3CC3)c[nH]2)CC1] | 4-(2-Cyclopropyl-6-fluorobenzoyl)-N-(1-methyl-piperidin-4-yl)-1H-pyrrole-2-carboxamide | 27 | $^1$H NMR (500 MHz, MeOD) δ ppm 0.57-0.60 (2H, m, CH-cyclopropane), 0.74-0.76 (2H, m, CH-cyclopropane), 1.51-1.59 (2H, m, CH-piperidine), 1.66-1.72 (1H, m, CH-cyclopropane), 1.79-1.84 (2H, m, CH-piperidine), 2.06-2.11 (2H, m, N—CH-piperidine), 2.21 (3H, s, N—CH$_3$), 2.80-2.84 (2H, m, N—CH-piperidine), 3.70-3.76 (1H, m, N—CH-piperidine), 6.73-6.75 (1H, m, H-3'), 6.87-6.91 (1H, m, H-5'), 7.02 (1H, d, J = 1.3 Hz, H-3), 7.23-7.28 (2H, m, H-5 and H-4'), NH peaks not observed | |
| 205. | 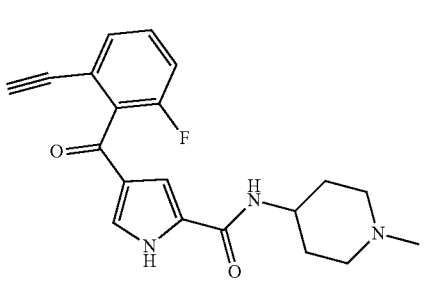 [SMILES: C#Cc1cccc(F)c1C(=O)c1c[nH]c(C(=O)NC2CCN(C)CC2)c1] | 4-(2-Ethynyl-6-fluorobenzoyl)-N-(1-methyl-piperidin-4-yl)-1H-pyrrole-2-carboxamide | 27 | 1.53-1.60 (2H, m, CH-piperidine), 1.75-1.77 (2H, m, CH-piperidine), 2.07-2.12 (2H, m, N—CH-piperidine), 2.24 (1H, s, C—CH-alkyne), 2.84-2.86 (2H, m, N—CH-piperidine), 3.68-3.76 (1H, m, N—CH-piperidine), 7.20 (1H, br s, H-3), 7.25 (1H, br s, H-5), 7.40-7.45 (2H, m, H-3' and H-5'), 7.51-7.56 (1H, m, H-4'), 8.14 (1H, d, J = 7.7 Hz, CO—NH), 12.34 (1H, s, NH-pyrrole) | 354.1610 |
| 206. | 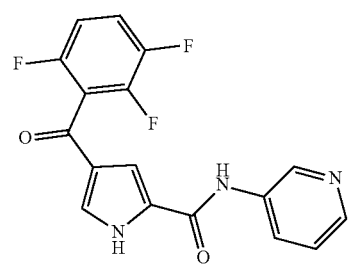 [SMILES: O=C(Nc1cccnc1)c1cc(C(=O)c2c(F)ccc(F)c2F)c[nH]1] | N-(Pyridin-3-yl)-4-(2,3,6-trifluorobenzoyl)-1H-pyrrole-2-carboxamide | 32 | 7.31-7.35 (1H, m, H-5'), 7.40 (1H, dd, J = 4.7 and 8.3 Hz, CH-pyridine), 7.58 (1H, d, J = 1.4 Hz, H-3), 7.67-7.74 (2H, m, H-5 and H-4'), 8.15 (1H, ddd, J = 1.5, 2.5 and 8.3 Hz, CH-pyridine), 8.31 (1H, dd, J = 1.5 and 4.7 Hz, N—CH-pyridine), 8.90 (1H, d, J = 2.5 Hz, N—CH-pyridine), 10.26 (1H, s, CO—NH), 12.00 (1H, br s, NH-pyrrole) | 346.0800 |

| # | Structure | Name | | NMR | MS |
|---|---|---|---|---|---|
| 207. | 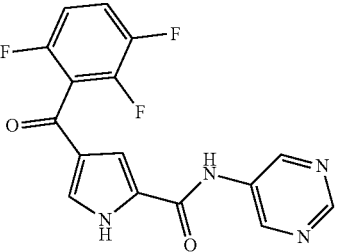 [SMILES: O=C(Nc1cncnc1)c1cc(C(=O)c2c(F)ccc(F)c2F)c[nH]1] | N-(Pyrimidin-5-yl)-4-(2,3,6-trifluorobenzoyl)-1H-pyrrole-2-carboxamide | 32 | 7.32-7.35 (1H, m, H-5'), 7.58 (1H, br s, H-3), 7.68-7.73 (2H, m, H-4' and H-5), 8.93 (1H, s, N—CH-pyrimidine), 9.14 (2H, s, N—CH-pyrimidine), 10.46 (1H, s, CO—NH), 12.89 (1H, s, NH-pyrrole) | 347.0755 |
| 208. | 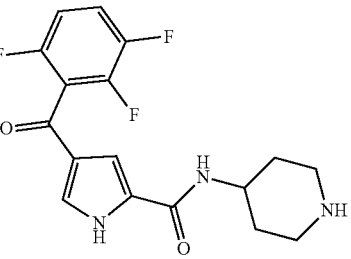 | N-(Piperidin-4-yl)-4-(2,3,6-trifluorobenzoyl)-1H-pyrrole-2-carboxamide | 31 | 1.41-1.49 (2H, m, CH-piperidine), 1.77-1.80 (2H, m, CH-piperidine), 2.62-2.68 (2H, m, N—CH-piperidine), 3.04-3.07 (2H, m, N—CH-piperidine), 3.81-3.89 (1H, m, N—CH-piperidine), 7.28-7.33 (2H, m, H-3 and H-5'), 7.51 (1H, d, J = 1.5 Hz, H-5), 7.65-7.72 (1H, m, H-4'), 8.17 (1H, d, J = 7.8 Hz, CO—NH) | 352.1268 |
| 209. | 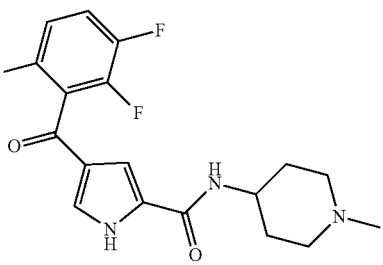 | N-(1-Methyl-pipendin-4-yl)-4-(2,3,6-trifluoro-benzoyl)-1H-pyrrole-2-carboxamide | 27 | 1.49-1.57 (2H, m, CH-piperidine), 1.72-1.75 (2H, m, CH-piperidine), 1.90-1.95 (2H, m, N—CH-piperidine), 2.16 (3H, s, N—CH$_3$), 2.74-2.77 (2H, m, N—CH-piperidine), 3.64-3.72 (1H, m, N—CH-piperidine), 7.28-7.33 (2H, m, H-3 and H-5'), 7.51 (1H, br s, H-5), 7.65-7.71 (1H, m, H-4'), 8.10 (1H, d, J = 7.8 Hz, CO—NH), 12.47 (1H, s, NH-pyrrole) | 366.1430 |
| 210. | 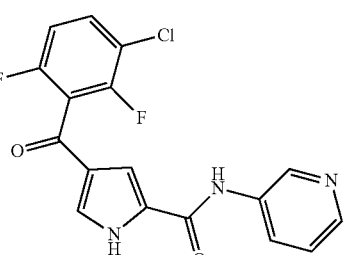 | 4-(3-Chloro-2,6-difluorobenzoyl)-N-(pyridin-3-yl)-1H-pyrrole-2-carboxamide | 32 | 7.35-7.41 (2H, m, H-5' and CH-pyridine), 7.57 (1H, br s, H-3), 7.68 (1H, br s, H-5), 7.82-7.86 (1H, m, H-4'), 8.15 (1H, ddd, J =1.5, 2.5 and 8.3 Hz, CH-pyridine), 8.31 (1H, dd, J = 1.5 and 4.6 Hz, N—CH-pyridine), 8.90 (1H, d, J = 2.5 Hz, N—CH-pyridine), 10.26 (1H, s, CO—NH), 12.80 (1H, s, NH-pyrrole) | 362.0503 |
| 211. | 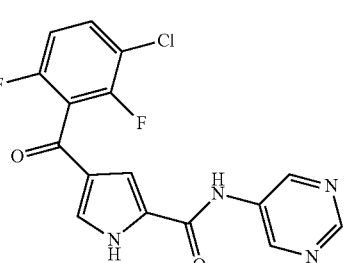 | 4-(3-Chloro-2,6-difluorobenzoyl)-N-(pyrimidin-5-yl)-1H-pyrrole-2-carboxamide | 32 | 7.37 (1H, dd, J = 7.6 and 9.0 Hz, H-5'), 7.57 (1H, br s, H-3), 7.73 (1H, br s, H-5), 7.83-7.87 (1H, m, H-4'), 8.93 (1H, s, CH-pyrimidine), 9.14 (2H, s, CH-pyrimidine), 10.45 (1H, s, CO—NH), 12.89 (1H, s, NH-pyrrole) | 363.0460 |
| 212. | 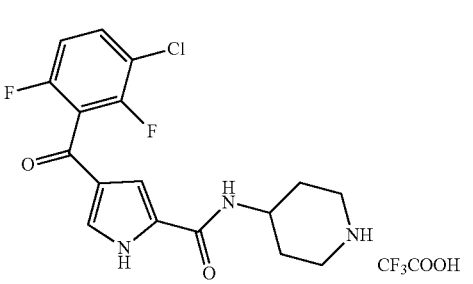 | 4-(3-Chloro-2,6-difluorobenzoyl)-N-(piperidin-4-yl)-1H-pyrrole-2-carboxamide | 31 | 1.65-1.73 (2H, m, CH-piperidine), 1.95-1.98 (2H, m, CH-piperidine), 2.30-2.37 (2H, m, N—CH-piperidine), 3.32-3.34 (2H, m, N—CH-piperidine), 4.00-4.07 (1H, m, N—CH-piperidine), 7.33-7.36 (2H, m, H-3 and H-5'), 7.54 (1H, br s, H-5), 7.78-7.84 (1H, m, H-4'), 8.32 (1H, d, J = 7.4 Hz, CO—NH), 8.61 (1H, br s, NH-piperidine), 8.78 | 368.0971 |

| | | | | |
|---|---|---|---|---|
| | | | | (1H, br s, NH-piperidine), 12.52 (1H, s, NH-pyrrole) |
| 213. | 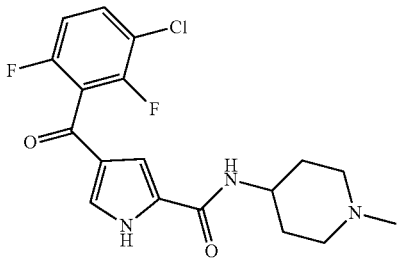 [SMILES: CN1CCC(NC(=O)c2cc(C(=O)c3c(F)ccc(F)c3F)c[nH]2)CC1] | 4-(3-Chloro-2,6-difluorobenzoyl)-N-(1-methyl-piperidin-4-yl)-1H-pyrrole-2-carboxamide | 27 | $^1$H NMR (500 MHz, DMSO-$d_6$) δ ppm 1.49-1.56 (2H, m, CH-piperidine), 1.73-1.75 (2H, m, CH-piperidine), 1.90-1.95 (2H, m, N—CH-piperidine), 2.16 (3H, m, N—CH$_3$), 2.74-2.78 (2H, m, N—CH-piperidine), 3.64-3.72 (1H, m, N—CH-piperidine), 7.27 (1H, br s, H-3), 7.35 (1H, dd, J = 7.9 and 9.2 Hz, H-5'), 7.51 (1H, br s, H-5), 7.79-7.84 (1H, m, H-4'), 8.10 (1H, d, J = 7.9 Hz, CO—NH), 12.47 (1H, s, NH-pyrrole) | 468.1495 |
| 214. | 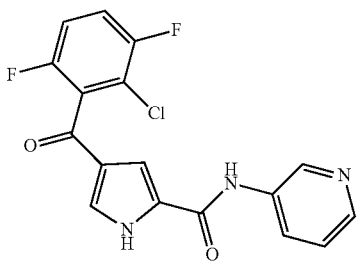 [SMILES: O=C(Nc1cccnc1)c1cc(C(=O)c2c(F)ccc(F)c2Cl)c[nH]1] | 4-(2-Chloro-3,6-difluorobenzoyl)-N-(pyridin-3-yl)-1H-pyrrole-2-carboxamide | 32 | 7.39 (1H, dd, J = 4.7 and 8.4 Hz, CH-pyridine), 7.47-7.51 (1H, m, H-5'), 7.54 (1H, br s, H-3), 7.61 (1H, br s, H-5), 7.63-7.68 (1H, m, H-4'), 8.14 (1H, ddd, J = 1.5, 2.5 and 8.4 Hz, CH-pyridine), 8.31 (1H, dd, J = 1.5 and 4.7 Hz, N—CH-pyridine), 8.99 (1H, d, J = 2.5 Hz, N—CH-pyridine), 10.25 (1H, s, CO—NH), 12.79 (1H, s, NH-pyrrole) | 362.0508 |
| 215. | 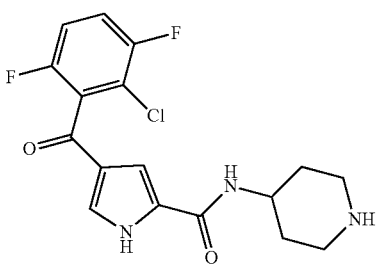 [SMILES: O=C(NC1CCNCC1)c1cc(C(=O)c2c(F)ccc(F)c2Cl)c[nH]1] | 4-(2-Chloro-3,6-difluorobenzoyl)-N-(piperidin-4-yl)-1H-pyrrole-2-carboxamide | 31 | 1.48-1.56 (2H, m, CH-piperidine), 1.82-1.86 (2H, m, CH-piperidine), 2.74-2.80 (2H, m, N—CH-piperidine), 3.12-3.16 (2H, m, N—CH-piperidine), 3.87-3.95 (1H, m, N—CH-piperidine), 7.27 (1H, br s, H-3), 7.45-7.49 (2H, m, H-3 and H-5), 7.61-7.66 (1H, m, H-4'), 8.20 (1H, d, J = 7.8 Hz, CO—NH), NH-pyrrole not observed | 368.0977 |
| 216. | 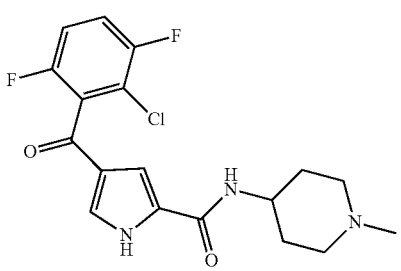 [SMILES: CN1CCC(NC(=O)c2cc(C(=O)c3c(F)ccc(F)c3Cl)c[nH]2)CC1] | 4-(2-Chloro-3,6-difluorobenzoyl)-N-(1-methyl-piperidin-4-yl)-1H-pyrrole-2-carboxamide | 27 | 1.49-1.56 (2H, m, CH-piperidine), 172-1.75 (2H, m, CH-piperidine), 1.90-1.95 (2H, m, N—CH-piperidine), 2.16 (3H, s, N—CH$_3$), 2.74-2.77 (2H, m, N—CH-piperidine), 3.64-372 (1H, m, N—CH-piperidine), 7.24 (1H, br s, H-3), 7.44-7.48 (2H, m, H-5 and H-5'), 7.61-7.65 (1H, m, H-4'), 8.09 (1H, d, J = 7.8 Hz, CO—NH), 12.46 (1H, s, NH-pyrrole) | 382.1134 |
| 217. | 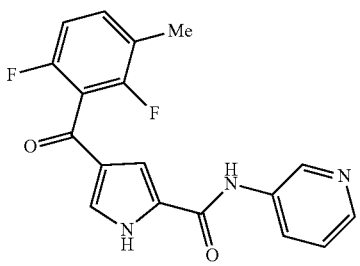 | 4-(2,6-Difluoro-3-methyl-benzoyl)-N-(pyridin-3-yl)-1H-pyrrole-2-carboxamide | 32 | 2.27 (3H, s, CH$_3$), 7.17 (1H, dd, J = 8.6 and 8.7 Hz, H-5'), 7.39 (1H, dd, J = 4.7 and 8.2 Hz, CH-pyridine), 4.47-4.53 (3H, m, H-3, H-5 and H-4'), 8.14-8.16 (1H, m, CH-pyridine), 8.30 (1H, dd, J = 1.5 and 4.7 Hz, N—CH-pyridine), 8.90 (1H, d, J = 2.5 Hz, N—CH-pyridine), 10.25 (1H, s, CO—NH), 12.71 (1H, s, NH-pyrrole) | 342.1049 |

| # | Structure | Name | | NMR | Mass |
|---|---|---|---|---|---|
| 218. | 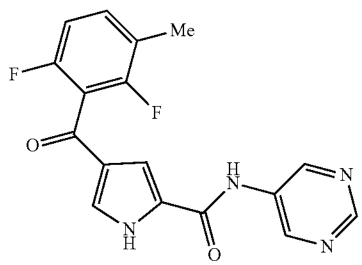 [SMILES: Cc1ccc(F)c(C(=O)c2c[nH]c(C(=O)Nc3cncnc3)c2)c1F] | 4-(2,6-Difluoro-3-methylbenzoyl)-N-(pyrimidin-5-yl)-1H-pyrrole-2-carboxamide | 32 | 2.27 (3H, s, CH₃), 7.17 (1H, dd, J = 8.6 and 8.7 Hz, H-5'), 7.57-7.53 (2H, m, H-3 and H-4'), 7.58 (1H, br s, H-5), 8.92 (1H, s, CH-pyrimidine), 9.13 (2H, s, CH-pyrimidine), 10.44 (1H, s, CO—NH), 12.81 (1H, s, NH-pyrrole) | 343.1003 |
| 219. | 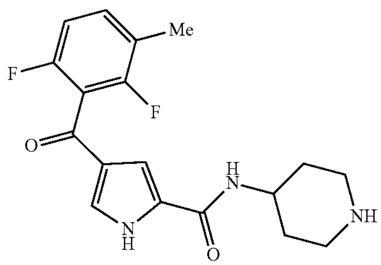 [SMILES: Cc1ccc(F)c(C(=O)c2c[nH]c(C(=O)NC3CCNCC3)c2)c1F] | 4-(2,6-Difluoro-3-methylbenzoyl)-N-(piperidin-4-yl)-1H-pyrrole-2-carboxamide | 31 | 1.46-1.53 (2H, m, CH-piperidine), 1.79-182 (2H, m, CH-piperidine), 2.25 (3H, s, CH₃), 2.69-2.74 (2H, m, N—CH-piperidine), 3.09-3.12 (2H, m, N—CH-piperidine), 3.85-3.91 (1H, m, N—CH-piperidine), 7.12-7.16 (1H, dd, J = 7.6 and 8.6 Hz, H-5'), 7.26 (1H, br s, H-3), 7.37 (1H, br s, H-5), 7.43-7.49 (1H, m, H-4'), 8.20 (1H, d, J = 7.9 Hz, CO—NH) | 348.1520 |
| 220. | 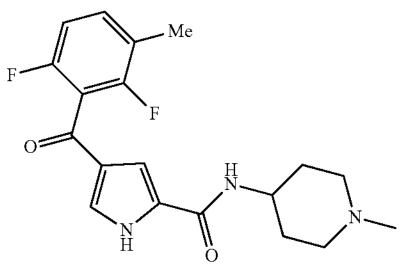 [SMILES: Cc1ccc(F)c(C(=O)c2c[nH]c(C(=O)NC3CCN(C)CC3)c2)c1F] | 4-(2,6-Difluoro-3-methylbenzoyl)-N-(1-methyl-piperidin-4-yl)-1H-pyrrole-2-carboxamide | 27 | 1.48-1.56 (2H, m, CH-piperidine), 1.72-1.75 (2H, m, CH-piperidine), 1.90-1.95 (2H, m, N—CH-piperidine), 2.16 (3H, s, N—CH₃), 2.26 (3H, s, CH₃), 2.74-2.77 (2H, m, N—CH-piperidine), 3.64-3.72 (1H, m, N—CH-piperidine), 7.14 (1H, dd, J = 8.6 and 9.1 Hz, H-5'), 7.24 (1H, br s, H-3), 7.36 (1H, br s, H-5), 7.44-7.49 (1H, m, H-4'), 8.09 (1H, d, J = 7.9 Hz., CO—NH), 12.37 (1H, s, NH-pyrrole) | 362.1674 |
| 221. | 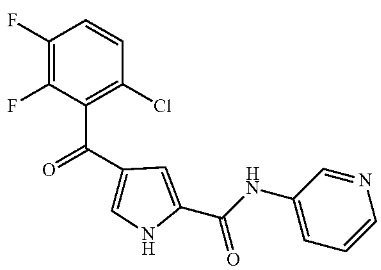 [SMILES: O=C(Nc1cccnc1)c1cc(C(=O)c2c(Cl)ccc(F)c2F)c[nH]1] | 4-(6-Chloro-2,3-difluorobenzoyl)-N-(pyridin-3-yl)-1H-pyrrole-2-carboxamide | 32 | 7.40 (1H, dd, J = 4.7 and 8.4 Hz, CH-pyridine), 7.52 (1H, ddd, J = 1.8, 4.1 and 9.1 Hz, H-5'), 7.55 (1H, br s, H-3), 7.64-7.70 (2H, m, H-5 and H-4'), 8.14 (1H, ddd, J = 1.5, 2.5 and 8.3 Hz, CH-pyridine), 8.31 (1H, dd, J = 1.5 and 4.7 Hz, N—CH-pyridine), 8.90 (1H, d, J = 2.5 Hz, N—CH-pyridine), 10.25 (1H, s, CO—NH), 12.79 (1H, s, NH-pyrrole) | 362.0503 |
| 222. | 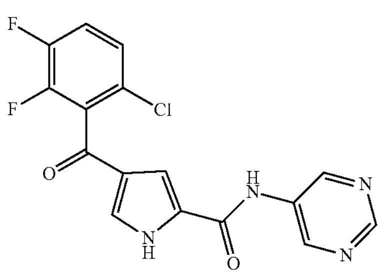 [SMILES: O=C(Nc1cncnc1)c1cc(C(=O)c2c(Cl)ccc(F)c2F)c[nH]1] | 4-(6-Chloro-2,3-difluorobenzoyl)-N-(pyrimidin-5-yl)-1H-pyrrole-2-carboxamide | 32 | 7.51-7.54 (2H, m, H-5' and H-3), 7.65-7.70 (2H, m, H-4' and H-5), 8.93 (1H, s, N—CH-pyrimidine), 9.13 (2H, s, N—CH-pyrimidine), 10.45 (1H, s, CO—NH), 12.88 (1H, s, NH-pyrrole) | 363.0472 |

| | | | | |
|---|---|---|---|---|
| 223. | | 4-(6-Chloro-2,3-difluorobenzoyl)-N-(1-methyl-piperidin-4-yl)-1H-pyrrole-2-carboxamide | 27 | 1.49-1.57 (2H, m, CH-piperidine), 1.72-1.75 (2H, m, CH-piperidine), 1.90-1.95 (2H, m, N—CH-piperidine), 2.16 (3H, s, N—CH$_3$), 2.74-2.78 (2H, m, N—CH-piperidine), 3.64-3.72 (1H, m, N—CH-piperidine), 7.25 (1H, br s, H-3), 7.47-7.51 (2H, m, H-5 and H-5'), 7.62-7.67 (1H, m, H-4'), 8.10 (1H, d, J = 7.9 Hz, CO—NH), 12.47 (1H, s, NH-pyrrole) | 382.1130 |
| 224. | | 4-(6-Chloro-2,3-difluorobenzoyl)-N-(piperidin-4-yl)-1H-pyrrole-2-carboxamide | 31 | 1.32-1.39 (2H, m, CH-piperidine), 1.69-1.72 (2H, m, CH-piperidine), 2.46-2.51 (2H, m, N—CH-piperidine), 2.93-2.96 (2H, m, N—CH-piperidine), 373-3.81 (1H, m, N—CH-piperidine), 7.25 (1H, br s, H-3), 7.46 (1H, br s, H-5), 7.49 (1H, ddd, J = 1.7, 4.0 and 9.1 Hz, H-5'), 7.62-7.67 (1H, m, H-4'), 8.10 (1H, d, J = 77 Hz, CO—NH), NH-piperidine and NH-pyrrole not visualised | 368.0976 |
| 225. | | 4-(2,5-Difluoro-benzoyl)-N-(pyridin-3-yl)-1H-pyrrole-2-carboxamide | 32 | 7.40 (1H, dd, J = 4.7 and 8.3 Hz, CH-pyridine), 7.42-7.50 (3H, m, H-3', H-4' and H-6'), 7.54 (1H, br s, H-3), 7.58 (1H, br s, H-5), 8.15 (1H, ddd, J = 1.5, 2.5 and 8.3 Hz, CH-pyridine), 8.30 (1H, dd, J = 1.5 and 4.7 Hz, N—CH-pyridine), 8.91 (1H, d, J = 2.5 Hz, N—CH-pyridine), 10.25 (1H, s, CO—NH), 12.68 (1H, s, NH-pyrrole); | 328.0897 |
| 226. | | 4-(2,5-Difluoro-benzoyl)-N-(piperidin-4-yl)-1H-pyrrole-2-carboxamide | 31 | 1.46-1.54 (2H, m, CH-piperidine), 1.80-1.84 (2H, m, CH-piperidine), 2.70-2.75 (2H, m, N—CH-piperidine), 3.09-3.13 (2H, m, N—CH-piperidine), 3.86-3.92 (1H, m, N—CH-piperidine), 7.30 (1H, d, J = 1.5 Hz, H-3), 7.38 (1H, br s, H-5), 7.39-7.49 (3H, m, H-2', H-4' and H-5'), 8.19 (1H, d, J = 7.8 Hz, CO—NH), 12.35 (1H, br s, NH-pyrrole) | 334.1364 |
| 227. | | 4-(2,5-Difluoro-benzoyl)-N-(1-methylpiperidin-4-yl)-1H-pyrrole-2-carboxamide | 27 | $^1$H NMR (500 MHz, DMSO-d$_6$) δ ppm 1.49-1.57 (2H, m, CH-piperidine), 1.72-1.75 (2H, m, CH-piperidine), 1.90-1.95 (2H, m, N—CH-piperidine), 2.16 (3H, s, N—CH$_3$), 2.75-2.77 (2H, m, N—CH-piperidine), 3.64-3.72 (1H, m, N—CH-piperidine), 7.27 (1H, d, J = 1.5 Hz, H-3), 7.37 (1H, br s, H-5), 7.39-7.47 (3H, m, H-2' H-4' and H-5'), 8.10 (1H, d, J = 7.9 Hz, CO—NH), 12.34 (1H, s, NH-pyrrole) | 485.1754 |

-continued

| | | | | | |
|---|---|---|---|---|---|
| 228. | 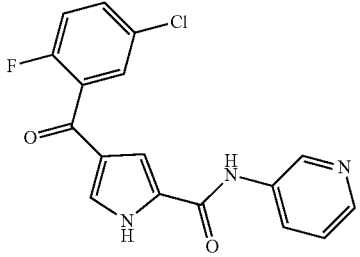 | 4-(5-Chloro-2-fluorobenzoyl)-N-(pyridin-3-yl)-1H-pyrrole-2-carboxamide | 32 | 7.39-7.47 (2H, m, H-6' and H-3'), 7.54 (1H, br s, H-3), 7.58 (1H, br s, H-5), 7.64-7.69 (2H, m, H-4' and CH-pyridine), 8.16 (1H, ddd, J = 1.5, 2.5 and 8.3 Hz, CH-pyridine), 8.31 (1H, br s, N—CH-pyridine), 8.92 (1H, br s, N—CH-pyridine), 10.26 (1H, s, CO—NH), 12.69 (1H, s, NH-pyrrole) | 344.0599 |
| 229. | 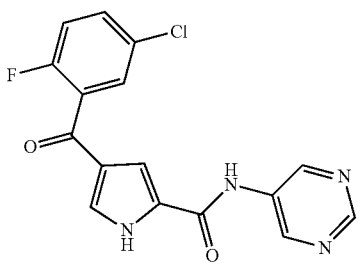 [SMILES: O=C(Nc1cncnc1)c1cc(C(=O)c2cc(Cl)ccc2F)c[nH]1] | 4-(5-Chloro-2-fluorobenzoyl)-N-(pyrimidin-5-yl)-1H-pyrrole-2-carboxamide | 32 | 7.45 (1H, dd, J = 8.9 and 9.1 Hz, H-3'), 7.57 (1H, br s, H-3), 7.59 (1H, br s, H-5), 7.64-7.70 (2H, m, H-5' and H-4'), 8.92 (1H, s, CH-pyrimidine), 9.15 (2H, s, CH-pyrimidine), 10.51 (1H, s, CO—NH), 12.67 (1H, s, NH-pyrrole) | 345.0555 |
| 230. | 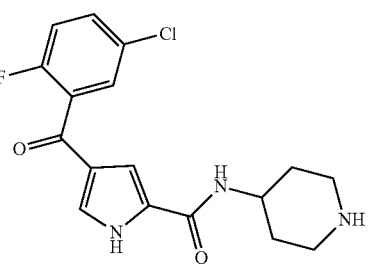 | 4-(5-Chloro-2-fluorobenzoyl)-N-(piperidin-4-yl)-1H-pyrrole-2-carboxamide | 31 | 1.39-1.44 (2H, m, CH-piperidine), 1.73-1.76 (2H, m, CH-piperidine), 2.55-2.60 (2H, m, N—CH-piperidine), 2.99-3.01 (2H, m, N—CH-piperidine), 3.78-3.85 (1H, m, N—CH-piperidine), 7.29 (1H, br s, H-3), 7.38 (1H, br s, H-5), 7.41-7.45 (1H, m, H-6'), 7.58-7.60 (1H, m, H-3'), 7.65-7.68 (1H, m, H-4'), 8.14 (1H, d, J = 7.9 Hz, CO—NH) | 350.1073 |
| 231. | 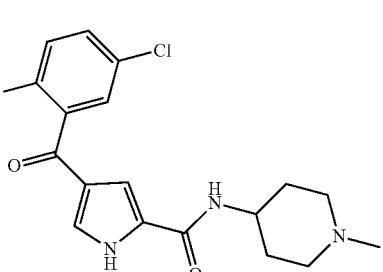 | 4-(5-Chloro-2-fluorobenzoyl)-N-(1-methyl-piperidin-4-yl)-1H-pyrrole-2-carboxamide | 27 | 1.49-1.57 (2H, m, CH-piperidine), 1.72-1.75 (2H, m, CH-piperidine), 1.90-1.95 (2H, m, N—CH-piperidine), 2.16 (3H, s, N—CH$_3$), 2.74-2.77 (2H, m, N—CH-piperidine), 3.64-3.72 (1H, m, N—CH-piperidine), 7.27 (1H, br s, H-3), 7.37 (1H, br s, H-5), 7.42 (1H, dd, J = 9.0 and 9.1 Hz, H-3'), 7.58 (1H, dd, J = 2.7 and 5.8 Hz, H-6'), 7.64-7.67 (1H, m, H-4'), 8.09 (1H, d, J = 7.9 Hz, CO—NH), 12.35 (1H, s, NH-pyrrole) | 364.1225 |
| 232. | 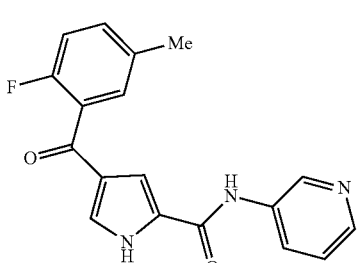 | 4-(2-Fluoro-5-methylbenzoyl)-N-(pyridin-3-yl)-1H-pyrrole-2-carboxamide | 32 | 2.36 (3H, s, CH$_3$), 7.25 (1H, dd, J = 8.2 and 8.3 Hz, H-3'), 7.36-7.41 (3H, m, H-6', H'4' and CH-pyridine), 7.46 (1H, br s, H-3), 7.57 (1H, br s, H-5), 8.15-8.17 (1H, m, CH-pyridine), 8.30 (1H, br s, N—CH-pyridine), 8.92 (1H, br s, N—CH-pyridine), 10.24 (1H, s, CO—NH), 12.61 (1H, s, NH-pyrrole) | 324.1145 |

| | | | | | |
|---|---|---|---|---|---|
| 233. | | 4-(2-Fluoro-5-methylbenzoyl)-N-(pyrimidin-5-yl)-1H-pyrrole-2-carboxamide | 32 | 2.36 (3H, s, CH$_3$), 7.25 (1H, dd, J = 8.6 and 8.7 Hz, H-3'), 7.37-7.41 (2H, m, H-4' and H-6'), 7.50 (1H, br s, H-3), 7.56 (1H, br s, H-5), 8.92 (1H, s, CH-pyrimidine), 9.15 (2H, s, CH-pyrimidine), 10.44 (1H, s, CO—NH), 12.70 (1H, s, NH-pyrrole) | 325.1098 |
| 234. | | 4-(2-Fluoro-5-methylbenzoyl)-N-(1-methyl-piperidin-4-yl)-1H-pyrrole-2-carboxamide | 27 | $^1$H NMR (500 MHz, CDCl$_3$) δ ppm 1.49-1.57 (2H, m, CH-piperidine), 1.72-1.75 (2H, m, CH-piperidine), 1.90-1.95 (2H, m, N—CH-piperidine), 2.16 (3H, s, N—CH$_3$), 2.34 (3H, s, CH$_3$), 2.74-2.78 (2H, m, N—CH-piperidine), 3.64-3.72 (1H, m, N—CH-piperidine), 7.22 (1H, dd, J = 9.0 and 9.1 Hz, H-3'), 7.26 (1H, br s, H-3), 7.29-7.32 (2H, m, H-5 and H-6'), 7.36-7.39 (1H, m, H-4'), 8.09 (1H, d, J = 7.9 Hz, CO—NH), 12.27 (1H, s, NH-pyrrole) | 344.1771 |

Example 235: 4-(3,6-Dichloro-2-fluorobenzo)-N-(1-(2-hydroxyethyl)-1H-pyrazol-4-yl)-1H-pyrrole-2-carboxamide

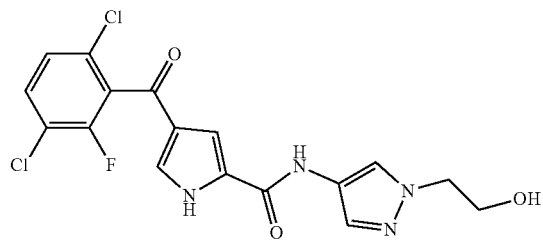 [SMILES: O=C(Nc1cnn(CCO)c1)c1cc(C(=O)c2c(Cl)ccc(Cl)c2F)c[nH]1]

A solution of 4-nitropyrazole (300 mg, 0.27 mmol, 1 eq.), 2-bromoethanol (206 μL, 0.29 mmol, 1.1 eq.) and K$_2$CO$_3$ (549 mg, 0.40 mmol, 1.5 eq.) in CH$_3$CN (5 mL) was heated to 80° C. for 18 h. The mixture was allowed to cool and partitioned between EtOAc (3×30 mL) and water (20 mL). The organic layers were dried over MgSO4, evaporated, and the residue purified by MPLC on SiO$_2$ with gradient elution from 30-60% EtOAc/petrol to give 2-(4-Nitro-1H-pyrazol-1-yl)ethanol as a white solid (256 mg, 61%).

2-(4-Amino-1H-pyrazol-1-yl)ethanol was prepared according to general procedure D, using 2-(4-Nitro-1H-pyrazol-1-yl)ethanol (230 mg) and MeOH (20 mL) to give a red oil (180 mg, 99%).

4-(3,6-Dichloro-2-fluorobenzoyl)-N-(1-(2-hydroxy-ethyl)-1H-pyrazol-4-yl)-1H-pyrrole-2-carboxamide was prepared according to general procedure 38, using 4-(3,6-dichloro-2-fluorobenzoyl)-1H-pyrrole-2-carboxylic acid (100 mg, 0.33 mmol, 1 eq.), 2-(4-Amino-1H-pyrazol-1-yl) ethanol (52 mg, 0.41 mmol, 1.25 eq.), 1-methyl-2-chloro-pyridinium iodide (93 mg, 0.36 mmol, 1.1 eq.), Et$_3$N (116 μL, 0.83 mmol, 2.5 eq.) and DCM (1.5 mL). The residue was purified by MPLC on SiO$_2$ with gradient elution from 0-6% MeOH/EtOAc to give an off-white solid (52 mg, 38%).

R$_f$ 0.1 (7% MeOH/EtOAc); m.p. 184-185° C.; λ$_{max}$ (EtOH)/nm 229, 280; IR λ$_{max}$/cm$^{-1}$ 3363, 3214, 3128, 1629; $^1$H NMR (500 MHz; DMSO-d$_6$) δ$_H$ 3.75 (2H, t, J=5.2 Hz, CH$_2$), 4.15 (2H, t, J=5.2 Hz, CH$_2$), 4.92 (1H, br s, OH), 7.36 (1H, s, H-pyrrole), 7.53-7.64 (3H, m, H-pyrrole, H-pyrazole and H-5'), 7.82 (1H, app t, J=8.4 Hz, H-4'), 8.01 (1H, s, H-pyrazole), 10.29 (1H, s, CO—NH), 12.68 (1H, s, NH-pyrrole); $^{19}$F NMR (470 MHz; DMSO-d$_6$) δ$_F$ −116.6; δC NMR (125 MHz; DMSO-d$_6$) δ$_C$ 54.2 (CH$_2$), 60.2 (CH$_2$), 110.1 (CH-pyrrole), 119.3 (d, J$_{CF}$=18.1 Hz, C-3'), 120.9 (C-pyrazole), 121.2 (CH-pyrazole), 124.7 (C-pyrrole), 126.9 (d, J$_{CF}$=3.6 Hz, C-5'), 128.7 (C-pyrrole), 129.2 (d, J$_{CF}$=22.7 Hz, C-1'), (d, J$_{CF}$=5.2 Hz, C-6'), 129.5 (C-pyrrole), 130.0 (CH-pyrazole), 131.8 (C-4'), 153.8 (d, J$_{CF}$=248.9 Hz, C-2'), 156.7 (CO—NH), 182.6, (CO); MS (ES+) m/z 411.2 [M($^{35,35}$Cl)+H]$^+$, 413.3 [M($^{35,37}$Cl)+H]$^+$; HRMS calc for C$_{17}$H$_{14}$O$_3$N$_4$Cl$_2$F$_1$ 411.0422, found 411.0413.

| | | | | |
|---|---|---|---|---|
| 236. | ![structure] 4-(6-Chloro-2-fluoro-3-methoxybenzoyl)-N-(6-((1-methylpiperidin-4-yl)methyl)pyridin-3-yl)-1H-pyrrole-2-carboxamide | 36 | ¹H NMR (500 MHz, DMSO-d₆) δ 1.20 (2H, dddd, J = 12.1, 12.1, 12.1 and 4.1 Hz, CH₂CH₂NMe), 1.50 (2H, d, J = 12.1 Hz, CH₂CH₂NMe), 1.58-1.68 (1H, m, ArCH₂CH), 1.77 (2H, dd, J = 10.8, 10.8 Hz, CH₂CH₂NMe), 2.11 (3H, s, NCH₃), 2.59 (2H, d, J = 7.1 Hz, ArCH₂CH), 2.70 (2H, d, J = 11.3 Hz, CH₂CH₂NMe), 3.90 (3H, s, ArOCH₃), 7.20 (1H, d, J = 8.4 Hz, H-5″), 7.32 (1H, dd, J = 9.6, 8.9 Hz, H-4′), 7.38 (1H, d, J = 9.6 Hz, H-5′), 7.45 (1H, s, H-3 or H-5), 7.47 (1H, s, H-3 or H-5), 8.01 (1H, dd, J = 8.4, 2.5 Hz, H-4″), 8.77 (1H, d, J = 2.5 Hz, H-2″), 10.16 (1H, s, CONHAr), 12.66 (1H, s, NH-pyrrole) | 485.1736 |
| 237. | 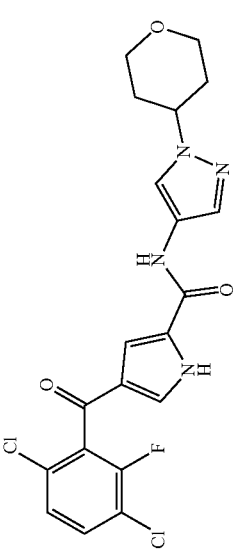 4-(3,6-Dichloro-2-fluorobenzoyl)-N-(1-(tetrahydro-2H-pyran-4-yl)-1H-pyrazol-4-yl)-1H-pyrrole-2-carboxamide | 35 | ¹H NMR (500 MHz; DMSO-d₆) δ_H 1.91-2.02 (4H, m, 2 × CH₂), 3.45-3.54 (2H, m, 2 × CH—O tetrahydropyran), 3.95-4.03 (2H, m, 2 × CH—O tetrahydropyran), 4.38-4.47 (CH-tetrahydropyran), 7.36 (1H, s, H-pyrrole), 7.56 (1H, dd, J = 0.8 and 8.6 Hz, H-5′), 7.60 (1H, s, H-pyrrole), 7.61 (1H, s, H-pyrazole), 7.82 (1H, app t, J = 8.6 Hz, H-4′), 8.03 (1H, s, H-pyrazole), 10.30 (1H, s, CO—NH), 12.67 (1H, s, NH-pyrrole) | 451.0723 |
| 238. | 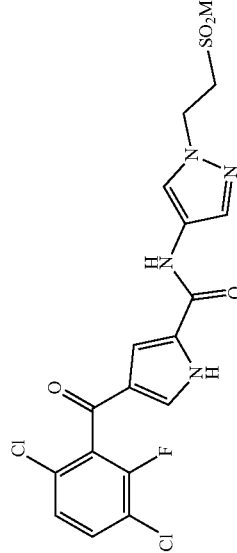 4-(3,6-Dichloro-2-fluorobenzoyl)-N-(1-(2-(methylsulfonyl)ethyl)-1H-pyrazol-4-yl)-1H-pyrrole-2-carboxamide | 35 | ¹H NMR (500 MHz; DMSO-d₆) δ_H 2.92 (3H, s, CH₃), 4.57 (2H, t, J = 6.9 Hz, CH₂), 3.72 (2H, t, J = 6.9 Hz, CH₂), 7.36 (1H, s, H-pyrrole), 7.56 (1H, dd, J = 1.1 and 8.6 Hz, H-5′), 7.60 (1H, s, H-pyrrole), 7.64 (1H, s, H-pyrazole), 7.82 (1H, app t, J = 8.6 Hz, H-4′), 8.12 (1H, s, H-pyrazole), 10.34 (1H, s, CO—NH), 12.70 (1H, s, NH-pyrrole); | 473.0235 |

| # | Structure | Name | | NMR | MS |
|---|---|---|---|---|---|
| 239. | (structure with oxetane-pyrazole, pyrrole carboxamide, 3,6-dichloro-2-fluorobenzoyl) | 4-(3,6-Dichloro-2-fluorobenzoyl)-N-(1-(oxetan-3-yl)-1H-pyrazol-4-yl)-1H-pyrrole-2-carboxamide | 35 | $^1$H NMR (500 MHz; DMSO-d$_6$) $\delta_H$ 4.89-4.96 (4H, m, 2 × CH$_2$), 5.63 (1H, q, J = 7.0 Hz, CH-oxetane), 7.37 (1H, s, H-pyrrole), 7.56 (1H, dd, J = 0.9 and 8.6 Hz, H-5'), 7.61 (1H, s, H-pyrrole), 7.72 (1H, s, H-pyrazole), 7.82 (1H, app t, J = 8.6 Hz, H-4'), 8.14 (1H, s, H-pyrazole), 10.36 (1H, s, CO—NH), 12.70 (1H, s, NH-pyrrole) | 423.0412 |
| 240. | (structure with tetrahydrofuran-pyrazole, pyrrole carboxamide, 3,6-dichloro-2-fluorobenzoyl) | 4-(3,6-Dichloro-2-fluorobenzoyl)-N-(1-(tetrahydrofuran-3-yl)-1H-pyrazol-4-yl)-1H-pyrrole-2-carboxamide | 35 | $^1$H NMR (500 MHz; DMSO-d$_6$) $\delta_H$ 2.22-2.30 (1H, m, CH—THF), 2.35-2.45 (1H, m, CH—THF), 3.81-3.93 (2H, m, 2 × CH—THF), 3.96-4.04 (2H, m, 2 × CH—THF), 5.03-5.09 (1H, m, CH—THF), 7.36 (1H, s, H-pyrrole), 7.56 (1H, dd, J = 0.8 and 8.6 Hz, H-5'), 7.58-7.63 (2H, m, H-pyrrole and H-pyrazole), 7.82 (1H, app t, J = 8.6 Hz, H-4'), 8.04 (1H, s, H-pyrazole), 10.31 (1H, s, CO—NH), 12.67 (1H, s, NH-pyrrole) | 437.0573 |

241. (S)-4-(3,6-Dichloro-2-fluorobenzoyl)-N-(pyrrolidin-3-yl)-1H-pyrrole-2-carboxamide

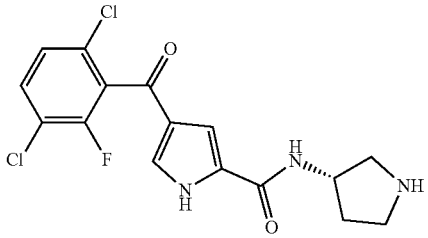 [SMILES: O=C(N[C@H]1CCNC1)c1cc(C(=O)c2c(Cl)ccc(Cl)c2F)c[nH]1]

(S)-tert-Butyl 3-(4-(3,6-dichloro-2-fluorobenzoyl)-1H-pyrrole-2-carboxamido) pyrrolidine-1-carboxylate was prepared according to general procedure 45, using 4-(3,6-dichloro-2-fluorobenzoyl)-1H-pyrrole-2-carboxylic acid (300 mg, 0.99 mmol, 1 eq.), (S)-Boc-3-aminopyrrolidine (461 mg, 2.48 mmol, 2.5 eq.), CDI (321 mg, 1.98 mmol, 2 eq.), and THF (5 mL). The residue was purified by MPLC on $SiO_2$ with gradient elution from 25-60% EtOAc/petrol to give a white solid (425 mg, 91%).

TFA (2 mL) was added to a mixture of (S)-tert-butyl 3-(4-(3,6-dichloro-2-fluorobenzoyl)-1H-pyrrole-2-carboxamido) pyrrolidine-1-carboxylate (310 mg, 0.66 mmol), $Et_3SiH$ (263 μL, 1.65 mmol, 2.5 eq.) and DCM (2 mL), and the mixture stirred at r.t. for 3 h. The solvent was removed in vacuo, and the residue partitioned between EtOAc (3×20 mL) and $K_2CO_3$ (10% aq.). The organic layers were combined, dried over $MgSO_4$, and the solvent removed in vacuo. The crude product was run through an SCX ion exchange cartridge eluting with 50% EtOAc/MeOH followed by 50/50/10 EtOAc/MeOH/$NH_4OH$, to give a white solid (179 mg, 73%).

$R_f$ 0.1 (20% MeOH/EtOAc; $NH_2SiO_2$); m.p. 206° C. dec.; $\lambda_{max}$(EtOH)/nm 236, 286; IR $\lambda_{max}$/cm$^{-1}$ 3262 br, 1622, 1561; $^1$H NMR (500 MHz; DMSO-$d_6$) $\delta_H$ 1.60-1.69 (1H, m, CH-pyrrolidine), 1.93-2.03 (1H, m, CH-pyrrolidine), 2.62-2.69 (1H, m, CH-pyrrolidine), 2.74-2.81 (1H, m, CH-pyrrolidine), 2.89-2.99 (2H, m, 2×CH-pyrrolidine), 4.25-4.33 (1H, m, H3-pyrrolidine), 7.26 (H-pyrrole), 7.50 (H-pyrrole), 7.54 (1H, dd, J=1.0 and 8.6 Hz, H-5'), 7.80 (1H, app t, J=8.6 Hz, H-4'), 8.20 (1H, d, J=6.3 Hz, NH); $^{19}$F NMR (470 MHz; DMSO-$d_6$) $\delta_F$ –116.75; $^{13}$C NMR (125 MHz; DMSO-$d_6$) $\delta_C$ 32.5 ($CH_2$), 45.3 ($CH_2$), 50.2 ($CH_2$), 52.8 ($CH_2$), 109.9 (CH-pyrrole), 119.3 (d, $J_{CF}$=18.3 Hz, C-3'), 124.5 (C-pyrrole), 126.8 (d, $J_{CF}$=3.6 Hz, C-5'), 129.0 (C-pyrrole), 129.2 (d, $J_{CF}$=23.8 Hz, C-1'), 129.2 (C-6'), 129.4 (C-pyrrole), 131.7 (C-4'), 153.8 (d, $J_{CF}$=248.1 Hz, C-2'), 159.4 (CO—NH), 182.5 (CO); MS (ES+) m/z 370.3 [M($^{35,35}$Cl)+H]$^+$, 372.3 [M($^{35,37}$Cl)+H]$^+$. HRMS calc for $C_{16}H_{15}O_2N_3Cl_2F_1$ 370.0520, found 370.0519.

| # | Structure | Name | Yield (%) | ¹H NMR | MS |
|---|---|---|---|---|---|
| 242. | Cl, F, Cl substituted benzoyl-pyrrole-carboxamide with pyridine-morpholinomethyl | 4-(3,6-Dichloro-2-fluorobenzoyl)-N-(2-(morpholinomethyl)pyrimidin-5-yl)-1H-pyrrole-2-carboxamide | 35 | ¹H NMR (500 MHz, DMSO-d₆) δ 2.43-2.49 (4H, m, NCH₂ $_{morpholine}$), 3.52-3.59 (4H, m, CH₂O $_{morpholine}$), 3.66 (2H, s, ArCH₂N), 7.50 (1H, s, H-3), 7.51-7.55 (1H, m, H-5'), 7.68 (1H, s, H-5), 7.79 (1H, dd, J = 8.7, 8.4 Hz, H-4'), 9.08 (2H, s, H-4'', 6''), 10.43 (1H, s, CONHAr), 12.87 (1H, s, NH-pyrrole) | 478.0838 |
| 243. | MeO, F, Cl substituted benzoyl-pyrrole-carboxamide with pyrimidine-morpholinomethyl | 4-(6-Chloro-2-fluoro-3-methoxybenzoyl)-N-(2-(morpholinomethyl)pyrimidin-5-yl)-1H-pyrrole-2-carboxamide | 35 | ¹H NMR (500 MHz, DMSO-d₆) δ 2.47 (4H, t, J = 4.7 Hz, NCH₂ $_{morpholine}$), 3.56 (4H, t, J = 4.7 Hz, CH₂O $_{morpholine}$), 3.66 (2H, s, ArCH₂N), 3.90 (3H, s, ArOCH₃), 7.33 (1H, dd, J = 9.0, 9.0 Hz, H-4), 7.39 (1H, dd, J = 9.0, 1.4 Hz, H-5), 7.46 (1H, s, H-3), 7.55 (1H, s, H-5), 9.08 (2H, s, H-4'', 6''), 10.42 (1H, s, CONHAr), 12.81 (1H, s, NH-pyrrole) | 474.1331 |
| 244. | Cl, F, Cl substituted benzoyl-pyrrole-carboxamide with pyrimidine-methylpiperazinylmethyl | 4-(3,6-Dichloro-2-fluorobenzoyl)-N-(2-((4-methylpiperazin-1-yl)methyl)pyrimidin-5-yl)-1H-pyrrole-2-carboxamide | 36 | ¹H NMR (500 MHz, DMSO-d₆) δ 2.13 (3H, s, NCH₃), 2.29 (4H, brs, NCH₂ $_{piperazine}$), 2.47 (4H, brs, NCH₂ $_{piperazine}$), 3.64 (2H, s, ArCH₂N), 7.50 (1H, s, H-3), 7.52 (1H, dd, J = 8.8, 1.4 Hz, H-5'), 7.67 (1H, s, H-5), 7.79 (1H, dd, J = 8.8, 8.4 Hz, H-4'), 10.41 (1H, s, CONHAr), 12.85 (1H, s, NH-pyrrole) | 491.1154 |

| # | Structure | | NMR | Mass |
|---|---|---|---|---|
| 245. | [Structure: MeO/F/Cl-benzoyl-pyrrole-carboxamide with pyrimidine-CH2-(4-methylpiperazine)] 4-(6-Chloro-2-fluoro-3-methoxybenzoyl)-N-(2-((4-methylpiperazin-1-yl)methyl)pyrimidin-5-yl)-1H-pyrrole-2-carboxamide | 36 | $^1$H NMR (500 MHz, DMSO-d$_6$) δ 2.13 (3H, s, NCH$_3$), 2.29 (4H, brs, NCH$_2$ $_{piperazine}$), 2.47 (4H, brs, NCH$_2$ $_{piperazine}$), 3.64 (2H, s, ArCH$_2$N), 3.90 (3H, s, ArOCH$_3$), 7.33 (1H, dd, J = 9.0, 9.0 Hz, H-4'), 7.39 (1H, dd, J = 9.0, 1.4 Hz, H-5'), 7.46 (1H, s, H-3), 7.54 (1H, s, H-5), 9.07 (2H, s, H-4", 6"), 10.41 (1H, s, CONHAr), 12.79 (1H, s, NH-pyrrole) | 487.1655 |
| 246. | [Structure: with pyridine-CH2-(4-methylpiperazine)] 4-(6-Chloro-2-fluoro-3-methoxybenzoyl)-N-(6-((4-methylpiperazin-1-yl)methyl)pyridin-3-yl)-1H-pyrrole-2-carboxamide | 36 | $^1$H NMR (500 MHz, DMSO-d$_6$) δ 2.14 (3H, s, NCH$_3$), 2.32 (4H, brs, NCH$_2$ $_{piperazine}$), 2.40 (4H, brs, NCH$_2$ $_{piperazine}$), 3.53 (2H, s, ArCH$_2$N), 3.90 (3H, s, ArOCH$_3$), 7.33 (1H, dd, J = 8.9, 8.9 Hz, H-4'), 7.39 (2H, d, J = 8.9 Hz, H-5' and H-5'"), 7.47 (1H, s, H-3), 7.48 (1H, s, H-5), 8.10 (1H, dd, J = 8.9, 2.6 Hz, H-4'"), 8.78 (1H, d, J = 2.6 Hz, H-2'"), 10.22 (1H, s, CONHAr), 12.69 (1H, s, NH-pyrrole) | 486.1695 |
| 247. | [Structure: with pyrimidine-CH2-(1-methylpiperidine)] 4-(6-Chloro-2-fluoro-3-methoxybenzoyl)-N-(2-((1-methylpiperidin-4-yl)methyl)pyrimidin-5-yl)-1H-pyrrole-2-carboxamide | 36 | $^1$H NMR (500 MHz, DMSO-d$_6$) δ 1.23 (2H, dddd, J = 12.4, 12.4, 12.4 and 3.6 Hz, CH$_2$CH$_2$NCH$_3$), 1.52 (2H, d, J = 12.4 Hz, CH$_2$CH$_2$NCH$_3$), 1.74-1.84 (3H, m, CH$_2$CH$_2$NCH$_3$ and ArCH$_2$CH), 2.11 (3H, s, NCH$_3$), 2.70 (2H, d, J = 12.4 Hz, CH$_2$CH$_2$NCH$_3$), 2.74 (2H, d, J = 7.1 Hz, ArCH$_2$CH), 3.90 (3H, s, ArOCH$_3$), 7.33 (1H, dd, J = 9.0, 8.9 Hz, H-4'), 7.39 (1H, dd, J = 9.0, 1.4 Hz, H-5'), 7.44 (1H, s, H-3), 7.52 (1H, s, H-5), 9.02 (2H, s, H-4", 6"), 10.35 (1H, s, CONHAr), 12.75 (1H, s, NH-pyrrole) | 463.1695 |

| # | Structure | Name | NMR | MS |
|---|---|---|---|---|
| 248. | | 4-(3,6-Dichloro-2-fluorobenzoyl)-N-(2-((1-methylpiperidin-4-yl)methyl)pyrimidin-5-yl)-1H-pyrrole-2-carboxamide | 36 ¹H NMR (500 MHz, DMSO-d₆) δ 1.24 (2H, dddd, J = 12.3, 12.3, 12.3 and 3.6 Hz, CH₂CH₂NCH₃), 1.52 (2H, d, J = 12.3 Hz, CH₂CH₂NCH₃), 1.80 (3H, dd, J = 12.3, 12.3 Hz, CH₂CH₂NCH₃ and ArCH₂CH), 2.11 (3H, s, NCH₃), 2.70 (2H, d, J = 12.3 Hz, CH₂CH₂NCH₃), 2.75 (2H, d, J = 7.1 Hz, ArCH₂CH), 7.48 (1H, s, H-3), 7.52 (1H, dd, J = 8.7, 1.3 Hz, H-5'), 7.65 (1H, s, H-5), 7.78 (1H, dd, J = 8.7, 8.4 Hz, H-4'), 9.02 (2H, s, H-4", 6"), 10.35 (1H, s, CONHAr), 12.79 (1H, s, NH-pyrrole) | 490.1201 |
| 249. | | 4-(3,6-Dichloro-2-fluorobenzoyl)-N-(2-(piperazin-1-ylmethyl)pyrimidin-5-yl)-1H-pyrrole-2-carboxamide | 37 ¹H NMR (500 MHz, DMSO-d₆) δ 2.41 (4H, brs, NCH₂ piperazine), 2.70 (4H, t, J = 4.9 Hz, NCH₂ piperazine), 3.63 (2H, s, ArCH₂N), 7.48 (1H, s, H-3), 7.52 (1H, dd, J = 8.7, 1.4 Hz, H-5'), 7.66 (1H, s, H-5), 7.78 (1H, dd, J = 8.7, 8.4 Hz, H-4'), 9.08 (2H, s, H-4", 6"), 10.41 (1H, s, CONHAr) | 477.0999 |
| 250. | | 4-(6-Chloro-2-fluoro-3-methoxybenzoyl)-N-(2-(piperazin-1-ylmethyl)pyrimidin-5-yl)-1H-pyrrole-2-carboxamide | 37 ¹H NMR (500 MHz, DMSO-d₆) δ 2.40 (4H, brs, NCH₂ piperazine), 2.68 (4H, t, J = 4.8 Hz, NCH₂ piperazine), 3.62 (2H, s, ArCH₂N), 3.90 (3H, s, ArOCH₃), 7.33 (1H, dd, J = 9.1, 9.0 Hz, H-4'), 7.39 (1H, d, J = 9.1 Hz, H-5'), 7.45 (1H, s, H-3), 7.53 (1H, s, H-5), 9.07 (2H, s, H-4", 6"), 10.41 (1H, s, CONHAr) | 473.1491 |

-continued

| # | Structure | | NMR |  |
|---|---|---|---|---|
| 251. | 4-(6-Chloro-2-fluoro-3-methoxybenzoyl)-N-(6-(piperazin-1-ylmethyl)pyridin-3-yl)-1H-pyrrole-2-carboxamide | 37 | ¹H NMR (500 MHz, DMSO-d₆) δ 2.33 (4H, brs, NCH₂ piperazine), 2.70 (4H, t, J = 4.8 Hz, NCH₂ piperazine), 3.50 (2H, s, ArCH₂N), 3.90 (3H, s, ArOCH₃), 7.32 (1H, dd, J = 8.9, 8.6 Hz, H-4'), 7.38 (1H, dd, J = 8.6, 0.8 Hz, H-5'), 7.39 (1H, d, J = 8.4 Hz, H-5"), 7.46 (1H, s, H-3), 7.47 (1H, s, H-5), 8.09 (1H, dd, J = 8.4, 2.6 Hz, H-4"), 8.79 (1H, d, J = 2.6 Hz, H-2"), 10.21 (1H, s, CONHAr) | 472.1538 |
| 252. | 4-(6-Chloro-2-fluoro-3-methoxybenzoyl)-N-(2-(piperidin-4-ylmethyl)pyrimidin-5-yl)-1H-pyrrole-2-carboxamide | 37 | ¹H NMR (500 MHz, DMSO-d₆) δ 1.13 (2H, dddd, J = 12.3, 12.3, 12.3 and 3.8 Hz, CH₂CH₂NH), 1.51 (2H, d, J = 12.3 Hz, CH₂CH₂NH), 1.96 (1H, ttt, J = 12.3, 7.2 and 3.9 Hz, ArCH₂CH), 2.40-2.48 (2H, m, CH₂CH₂NH), 2.73 (2H, d, J = 7.2 Hz, ArCH₂CH), 2.93 (2H, d, J = 12.3 Hz, CH₂CH₂NH), 3.90 (3H, s, ArOCH₃), 7.32 (1H, dd, J = 9.0, 9.0 Hz, H-4'), 7.35-7.42 (2H, m, H-3 and H-5'), 7.49 (1H, s, H-5), 9.02 (2H, s, H-4", 6"), 10.32 (1H, s, CONHAr) | 472.1538 |
| 253. | 4-(3,6-Dichloro-2-fluorobenzoyl)-N-(2-(piperidin-4-ylmethyl)pyrimidin-5-yl)-1H-pyrrole-2-carboxamide | 37 | ¹H NMR (500 MHz, DMSO-d₆) δ 1.14 (2H, dddd, J = 12.4, 12.4, 12.4 and 3.8 Hz, CH₂CH₂NH), 1.52 (2H, d, J = 11.1 Hz, CH₂CH₂NH), 1.96 (1H, ttt, J = 12.4, 7.4 and 3.8 Hz, ArCH₂CH), 2.40-2.49 (2H, m, CH₂CH₂NH), 2.74 (2H, d, J = 7.4 Hz, ArCH₂CH), 2.94 (2H, d, J = 12.4 Hz, CH₂CH₂NH), 7.39 (1H, s, H-3), 7.51 (1H, dd, J = 8.9, 1.4 Hz, H-5'), 7.60 (1H, s, H-5), 7.77 (1H, dd, J = 8.9, 8.4 Hz, H-4'), 9.03 (2H, s, H-4", 6"), 10.31 (1H, s, CONHAr) | 476.1045 |

| | | | | |
|---|---|---|---|---|
| 254. | (structure) | 4-(6-Chloro-2-fluoro-3-hydroxybenzoyl)-N-(pyridin-3-yl)-1H-pyrrole-2-carboxamide | 42 | ¹H NMR (500 MHz, DMSO-d₆) δ 7.05 (1H, dd, 9.1, 8.7 Hz, H-4), 7.16 (1H, d, J = 8.7 Hz, H-5), 7.38 (1H, dd, J = 8.3, 4.9 Hz, H-5′), 7.46 (2H, s, H-3 and H-5), 8.11-8.17 (1H, m, H-4′), 8.29 (1H, dd, J = 4.9, 2.5 Hz, H-6′), 8.90 (1H, d, J = 2.5 Hz, H-2′), 10.32 (1H, s, CONHAr), 12.17 (2H, s, NH-pyrrole and ArOH) | 360.0549 |
| 255. | (structure) | 4-(6-Chloro-3-fluoro-2-hydroxybenzoyl)-N-(1-methyl-1H-pyrazol-4-yl)-1H-pyrrole-2-carboxamide | 42 | ¹H NMR (500 MHz, DMSO-d₆) δ 3.81 (3H, s, NCH₃), 7.07 (1H, dd, J = 9.0, 8.9 Hz, H-4), 7.20 (1H, dd, J = 8.9, 1.4 Hz, H-5′), 7.27 (1H, s, H-3), 7.40 (1H, s, H-5), 7.49 (1H, s, H-5′), 7.94 (1H, s, H-3′), 10.24 (1H, s, CONHAr), 10.48 (1H, s, ArOH), 12.54 (1H, s, NH-pyrrole) | 363.0658 |
| 256. | (structure) | 4-(6-Chloro-3-ethoxy-2-fluorobenzoyl)-N-(pyridin-3-yl)-1H-pyrrole-2-carboxamide | 42 | ¹H NMR (500 MHz, DMSO-d₆) δ 1.36 (3H, t, J = 7.0 Hz, OCH₂CH₃), 4.16 (2H, q, J = 7.0 Hz, OCH₂CH₃), 7.31 (1H, dd, J = 9.0, 8.8 Hz, H-4), 7.33-7.41 (2H, m, H-5′ and H-5′′), 7.49 (2H, s, H-3 and H-5), 8.13 (1H, ddd, J = 8.5, 2.6 and 1.5 Hz, H-4′′), 8.30 (1H, dd, J = 4.7, 1.5 Hz, H-6′′), 8.89 (1H, d, J = 2.6 Hz, H-2′′), 10.24 (1H, s, CONHAR), 12.71 (1H, s, NH-pyrrole) | 388.0860 |

| | | | | |
|---|---|---|---|---|
| 257. | 4-(6-Chloro-2-ethoxy-3-fluorobenzoyl)-N-(1-methyl-1H-pyrazol-yl)-1H-pyrrole-2-carboxamide | 42 | ¹H NMR (500 MHz, DMSO-d₆) δ 1.36 (3H, t, J = 7.0 Hz, OCH₂CH₃), 3.81 (3H, s, NCH₃), 4.16 (2H, q, J = 7.0 Hz, OCH₂CH₃), 7.25-7.32 (2H, m, H-3 and H-4), 7.35 (1H, dd, J = 9.0, 1.3 Hz, H-5'), 7.42 (1H, s, H-5), 7.50 (1H, s, H-5''), 7.94 (1H, s, H-3''), 10.25 (1H, s, CONHAr), 12.57 (1H, s, NH-pyrrole) | 391.0968 |
| 258. | 4-(6-Chloro-2-fluoro-3-(2-methoxyethoxy)benzoyl)-N-(pyridin-3-yl)-1H-pyrrole-2-carboxamide | 42 | ¹H NMR (500 MHz, DMSO-d₆) δ 3.31 (3H, s, CH₃OCH₂), 3.69 (2H, t, J = 4.3 Hz, CH₃OCH₂), 4.24 (2H, t, J = 4.3 Hz, CH₂OAr), 7.34 (1H, dd, J = 9.0, 9.0 Hz, H-4'), 7.36 (1H, d, J = 9.0 Hz, H-5'), 7.38 (1H, dd, J = 8.8, 4.4 Hz, H-5''), 7.48 (1H, s, H-3), 7.50 (1H, s, H-5), 8.13 (1H, ddd, J = 8.8, 2.5 and 14 Hz, H-4''), 8.30 (1H, dd, J = 4.4, 14 Hz, H-6''), 8.89 (1H, d, J = 2.5, H-2''), 10.25 (1H, s, CONHAr), 12.72 (1H, s, NH-pyrrole) | 418.0953 |
| 259. | 4-(6-Chloro-2-fluoro-3-((tetrahydrofuran-3-yl)oxy)benzoyl)-N-(pyridin-3-yl)-1H-pyrrole-2-carboxamide | 42 | ¹H NMR (500 MHz, DMSO-d₆) δ 2.02 (1H, dt, J = 12.7, 5.9 Hz, ArOCHCH₂CH₂), 2.26 (1H, dtd, J = 14.2, 8.2, 6.0 Hz, ArOCHCH₂CH₂), 3.76 (1H, td, J = 8.4, 4.6 Hz, OCH₂), 3.82-3.92 (3H, m, OCH₂), 5.09-5.20 (1H, m, ArOCH), 7.31 (1H, dd, J = 9.7, 8.8 Hz, H-4''), 7.37 (1H, d, J = 9.7 Hz, H-5'), 7.40 (1H, dd, J = 8.4, 4.3 Hz, H-5'''), 7.46-7.54 (2H, m, H-3 and H-5), 8.14 (1H, d, J = 8.4 Hz, H-4'''), 8.30 (1H, d, J = 4.3 Hz, H-6'''), 8.90 (1H, s, H-2'''), 10.26 (1H, s, CONHAr), 12.72 (1H, s, NH-pyrrole) | 430.0957 |

| | | | |
|---|---|---|---|
| 260. | 4-(6-Chloro-2-fluoro-3-(2-methoxyethoxy)benzoyl)-N-(1-methyl-1H-pyrazol-4-yl)-1H-pyrrole-2-carboxamide 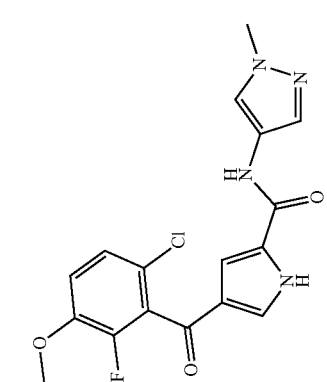 | 42 | ¹H NMR (500 MHz, DMSO-d₆) δ 3.31 (3H, s, CH₃OCH₂), 3.64-3.72 (2H, m, CH₃OCH₂), 3.81 (3H, s, NCH₃), 4.20-4.27 (2H, m, CH₂OAr), 7.28 (1H, s, H-3), 7.30-7.38 (2H, m, H-4', 5'), 7.43 (1H, s, H-5), 7.50 (1H, s, H-5''), 7.94 (1H, s, H-3''), 10.25 (1H, s, CONHAr), 12.57 (1H, s, NH-pyrrole) | 421.1064 |
| 261. | 4-(6-Chloro-2-fluoro-3-((tetrahydrofuran-3-yl)oxy)benzoyl)-N-(1-methyl-1H-pyrazol-4-yl)-1H-pyrrole-2-carboxamide 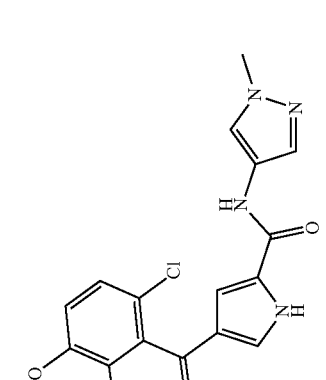 | 42 | ¹H NMR (500 MHz, DMSO-d₆) δ 2.02 (1H, dt, J = 12.7, 5.9 Hz, ArOCHCH₂CH₂), 2.26 (1H, dq, J = 12.7, 7.8 Hz, ArOCHCH₂CH₂), 3.76 (1H, td, J = 8.5, 4.7 Hz, OCH₂), 3.81 (3H, s, NCH₃), 3.83-3.93 (3H, m, OCH₃), 5.15 (1H, s, ArOCH), 7.25-7.33 (2H, m, H-3 and H-4'), 7.36 (1H, d, J = 9.0 Hz, H-5'), 7.44 (1H, s, H-5), 7.50 (1H, s, H-5''), 7.94 (1H, s, H-3''), 10.25 (1H, s, CONHAr), 12.58 (1H, s, NH-pyrrole) | 433.1062 |
| 262. | 4-(3,6-Dichloro-2-fluorobenzoyl)-N-(6-((2-(diethylamino)ethyl)amino)pyridin-3-yl)-1H-pyrrole-2-carboxamide 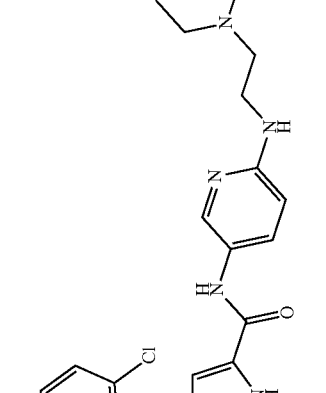 | 35 | ¹H NMR (500 MHz, DMSO-d₆) δ 0.95 (6H, t, J = 7.1 Hz, CH₂N(CH₂CH₃)₂), 2.46-2.51 (4H, q, J = 7.1 Hz, CH₂N(CH₂CH₃)₂), 2.53 (2H, t, J = 7.0 Hz, CH₂NEt₂), 3.25 (2H, td, J = 7.0, 5.6 Hz, ArNHCH₂), 6.17 (1H, t, J = 5.6 Hz, ArNHCH₂), 6.47 (1H, d, J = 8.9 Hz, H-5''), 7.38 (1H, s, H-3), 7.50 (1H, dd, J = 8.9, 1.2 Hz, H-5'), 7.54 (1H, s, H-5), 7.62 (1H, d, J = 8.9, 2.7 Hz, H-4'), 7.76 (1H, dd, J = 8.9, 8.3 Hz, H-4'), 8.21 (1H, d, J = 2.7 Hz, H-2''), 9.81 (1H, s, CONHAr), 12.61 (1H, s, NH-pyrrole) | 492.1343 |

-continued

| | | | | |
|---|---|---|---|---|
| 263. | 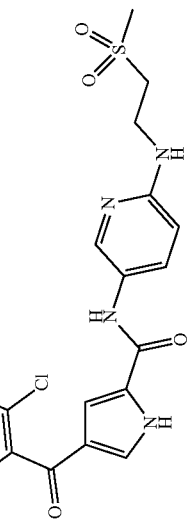4-(3,6-Dichloro-2-fluorobenzoyl)-N-(6-((2-(methylsulfonyl)ethyl)amino)pyridin-3-yl)-1H-pyrrole-2-carboxamide | 35 | ¹H NMR (500 MHz, DMSO-d₆) δ 3.01 (3H, s, SO₂CH₃), 3.36 (2H, t, J = 6.5 Hz, CH₂SO₂CH₃), 3.66 (2H, td, J = 6.5, 5.9 Hz, ArNHCH₂), 6.54 (1H, d, J = 8.9 Hz, H-5"), 6.69 (1H, t, J = 5.9 Hz, ArNHCH₂), 7.41 (1H, s, H-3), 7.51 (1H, dd, J = 8.6, 1.5 Hz, H-5'), 7.56 (1H, s, H-5), 7.68 (1H, dd, J = 8.9, 2.8 Hz, H-4"), 7.77 (1H, dd, J = 8.6, 8.3 Hz, H-4'), 8.30 (1H, d, J = 2.8 Hz, H-2"), 9.87 (1H, s, CONHAr), 12.65 (1H, s, NH-pyrrole) | 499.0389 |
| 264. | 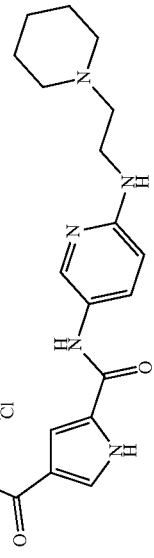4-(3,6-Dichloro-2-fluorobenzoyl)-N-(6-((2-(piperidin-1-yl)ethyl)amino)pyridin-3-yl)-1H-pyrrole-2-carboxamide | 35 | ¹H NMR (500 MHz, DMSO-d₆) δ 1.33-1.41 (2H, m, NCH₂CH₂CH₂ piperidine), 1.45-1.53 (4H, m, NCH₂CH₂CH₂ piperidine), 2.36 (4H, brs, NCH₂CH₂CH₂ piperidine), 2.42 (2H, t, J = 6.8 Hz, ArNHCH₂CH₂N), 3.30 (2H, td, J = 6.8, 5.6 Hz, ArNHCH₂N), 6.20 (1H, t, J = 5.6 Hz, ArNHCH₂), 6.49 (1H, d, J = 8.9 Hz, H-5"), 7.40 (1H, s, H-3), 7.51 (1H, dd, J = 8.8, 1.3 Hz, H-5'), 7.55 (1H, s, H-5), 7.63 (1H, dd, J = 8.9, 2.7 Hz, H-4"), 7.77 (1H, dd, J = 8.8, 8.4 Hz, H-4'), 8.22 (1H, d, J = 2.7 Hz, H-2"), 9.82 (1H, s, CONHAr), 12.64 (1H, s, NH-pyrrole) | 504.1347 |

Example 265: 4-(2,6-difluoro-3-formylbenzoyl)-N-(pyridin-3-yl)-1H-pyrrole-2-carboxamide

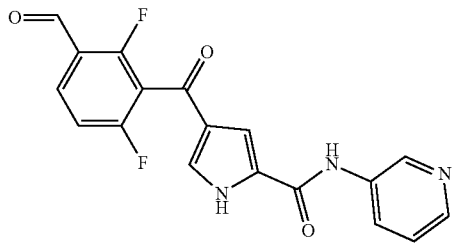 [SMILES: O=Cc1ccc(F)c(C(=O)c2c[nH]c(C(=O)Nc3cccnc3)c2)c1F]

OsO$_4$ (tBuOH 2.5% wt, 0.028 mL) was added to 4-(2,6-difluoro-3-vinylbenzoyl)-N-(pyridin-3-yl)-1H-pyrrole-2-carboxamide (100 mg, 0.284 mmol) dissolved in dioxane (0.84 mL) and H$_2$O (0.28 mL) and stirred for 5 min until mixture becomes a clear tan solution. Na$_2$H$_3$IO$_6$ (122 mg, 0.57 mmol) was added to the resulting mixture immediately forming a white precipitate and left to stir for 5 days. The reaction mixture was quenched with saturated aqueous sodium sulphite (10 mL), extracted with EtOAc (3×20 mL), dried over Na$_2$SO$_4$ and evaporated to dryness in vacuo. The crude product was purified by reverse phase MPLC on $^{18}$C (20-80% MeCN in H$_2$O) followed by semi-prep HPLC (0.1% Ammonia (aq)/MeCN) to afford a white solid product (40 mg, 40%).

Rf=0.33 (7:3 MeCN/H$_2$O); M.p. decomposes >150° C.; $\lambda_{max}$ (EtOH)/nm 249, 292; $v_{max}$/cm$^{-1}$: 3123, 1614 (CO), 1537 (CONH); $^1$H NMR (500 MHz, DMSO-d$_6$) δ 7.40 (1H, m, H-4"), 7.47 (1H, appt. t, J=8.4 Hz, H-5'), 7.60 (1H, s, H-3), 7.68 (1H, s, H-5), 8.07 (1H, dd, J=8.0 and 14.8 Hz, H-4'), 8.15 (1H, d, J=7.3 Hz H-6"), 8.31 (1H, m, H-5"), 8.91 (1H, s, H-2"), 10.19 (1H, s, CHO), 10.32 (1H, s, CONH), 12.86 (1H, br s, pyrrole NH); $^{13}$C NMR (125 MHz, DMSO-d$_6$) δ 112.0 (C-3), 113.8 (m, C-5'), 119.0 (m, C$_q$-1'), 121.8 (m, C$_q$-3'), 124.1 (C-4"), 126.0 (pyrrole C$_q$), 127.5 (C-6"), 128.9 (pyrrole C$_q$), 131.0 (C-5), 132.5 (d, J$_{CF}$=10.9 Hz, C-4'), 136.0 (C$_q$-3"), 142.1 (C-2"), 144.9 (C-5"), 159.2 (CONH), 160.7 (dd, J$_{CF}$=8.7 and 219.7 Hz, CF$_q$), 162.7 (dd, J$_{CF}$=8.7 and 217.6 Hz, CF$_q$), 181.1 (CO), 187.0 (CHO); LRMS (ES+) m/z 356.2 [M+H]$^+$

Example 266: 2,4-difluoro-3-(5-(pyridin-3-ylcarbamoyl)-1H-pyrrole-3-carbonyl) benzoic Acid

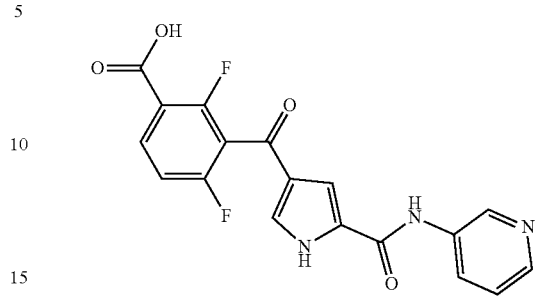

4-(2,6-difluoro-3-formylbenzoyl)-N-(pyridin-3-yl)-1H-pyrrole-2-carboxamide 145 (25.0 mg, 0.070 mmol) was added to NaClO$_2$ (16.3 mg, 0.18 mmol) dissolved in H$_2$O (1.30 mL). H$_3$NSO$_2$ (17.5 mg, 0.18 mmol) in H$_2$O (1.30 mL) was added to the resulting mixture and stirred for 5 min. 2-methyl-2-butene (29.6 mg, 0.42 mmol) in MeCN (1.2 mL) was added to the resulting mixture and stirred at RT for 3 h. The crude mixture was quenched with saturated aqueous NaCl, basified to pH 10 with NaHCO$_3$, washed with EtOAc (2×10 mL), re-acidified to pH 2 with 1.0M HCl, extracted with EtOAc (3×20 mL) and dried over Na$_2$SO$_4$. The crude product was purified by reverse phase MPLC on $^{18}$C (20-60% MeCN in H$_2$O). Product was a white powder (16 mg, 62%).

Rf=0.37 (3:1 MeCN/H$_2$O); M.p. decomposes >150° C.; $\lambda_{max}$(EtOH)/nm 251, 292; $v_{max}$/cm$^{-1}$: 3318, 1664 (CO), 1536 (CONH); $^1$H NMR (500 MHz, DMSO-d$_6$) δ 7.36 (1H, appt. d, J=8.96 Hz, H-5'), 7.39 (1H, m, H-4"), 7.55 (1H, s, H-3), 7.63 (1H, s, H-5), 8.06 (1H, dd, J=8.3 and 15.2 Hz, H-4'), 8.14 (1H, d, J=8.9 Hz, H-6"), 8.31 (1H, m, H-5"), 8.90 (1H, s, H-2"), 10.25 (1H, s, CONH), 12.77 (1H, br s, pyrrole NH); $^{13}$C NMR (125 MHz, DMSO-d$_6$) δ 112.0 (C-3), 112.9 (m, C-5'), 117.5 (m, C$_q$-1'), 119.3 (m, C$_q$-3'), 124.2 (C-4"), 126.1 (pyrrole C$_q$), 127.5 (C-6"), 128.7 (pyrrole C$_q$), 130.5 (C-5), 134.8 (m, C-4'), 136.0 (C$_q$-3"), 142.1 (C-2"), 144.9 (C-5"), 158.6 (dd, J$_{CF}$=8.5 and 258.0 Hz, CF$_q$), 159.2 (CONH), 161.2 (dd, J$_{CF}$=8.5 and 254.5 Hz, CF$_q$), 164.4 (CO$_2$H), 181.8 (CO); LRMS (ES+) m/z 372.1 [M+H]$^+$

| | | | | |
|---|---|---|---|---|
| 267. | ![structure] | 4-(6-Chloro-2-fluoro-3-((tetrahydro-2H-pyran-4-yl)oxy)benzoyl)-N-(pyridin-3-yl)-1H-pyrrole-2-carboxamide | 42 | ¹H NMR (500 MHz, DMSO-d₆) δ 1.63 (2H, dddd, J = 13.2, 8.9, 8.9 and 4.0 Hz, ArOCHCH₂), 1.93-2.07 (2H, m, ArOCHCH₂), 3.48 (2H, ddd, J = 13.2, 8.9 and 2.9 Hz, ArOCHCH₂CH₂O), 3.85 (2H, ddd, J = 13.2, 4.5 and 4.5 Hz, ArOCHCH₂CH₂O), 4.67 (1H, tt, J = 8.9, 4.0 Hz, ArOCH), 7.35 (1H, d, J = 9.0 Hz, H-5'), 7.38 (1H, dd, J = 8.2, 4.7 Hz, H-5''), 7.43 (1H, dd, J = 9.0, 8.9 Hz, H-4'), 7.50 (2H, s, H-3 and H-5), 8.13 (1H, d, J = 8.2 Hz, H-4''), 8.30 (1H, d, J = 4.7 Hz, H-6''), 8.89 (1H, s, H-2''), 10.25 (1H, s, CONHAr), 12.71 (1H, s, NH-pyrrole) | 444.1115 |
| 268. | ![structure] | 4-(6-Chloro-2-fluoro-3-((tetrahydro-2H-pyran-4-yl)oxy)benzoyl)-N-(1-methyl-1H-pyrazol-4-yl)-1H-pyrrole-2-carboxamide | 42 | ¹H NMR (500 MHz, DMSO-d₆) δ 1.63 (2H, dddd, J = 13.1, 9.0, 9.0 and 4.0 Hz, ArOCHCH₂), 1.94-2.03 (2H, m, ArOCHCH₂), 3.48 (2H, ddd, J = 13.1, 9.0 and 2.8 Hz, ArOCHCH₂CH₂O), 3.81 (3H, s, NCH₃), 3.85 (2H, ddd, J = 13.1, 4.2 and 4.2 Hz, ArOCHCH₂CH₂O), 4.66 (1H, tt, J = 9.0, 4.2 Hz, ArOCH), 7.29 (1H, s, H-3), 7.34 (1H, d, J = 9.3 Hz, H-5'), 7.42 (1H, dd, J = 9.3, 8.7 Hz, H-4'), 7.43 (1H, s, H-5), 7.50 (1H, s, H-5''), 7.94 (1H, s, H-3''), 10.25 (1H, s, CONHAr), 12.56 (1H, s, NH-pyrrole) | 447.1224 |
| 269. | ![structure] | 4-(2-Chloro-6-fluorobenzoyl)-N-(1-methyl-1H-pyrazol-4-yl)-1H-pyrrole-2-carboxamide | 42 | ¹H NMR (500 MHz, DMSO-d₆) δ 3.81 (3H, s, NCH₃), 7.29 (1H, s, H-3), 7.39 (1H, dd, J = 8.7, 8.7 Hz, H-5'), 7.42 (1H, s, H-5), 7.46 (1H, d, J = 8.1 Hz, H-3'), 7.50 (1H, s, H-5''), 7.57 (1H, ddd, J = 8.7, 8.1 and 6.4 Hz, H4'), 7.94 (1H, s, H-3''), 10.25 (1H, s, CONHAr), 12.57 (1H, s, NH-pyrrole) | 347.0707 |

| | | | | |
|---|---|---|---|---|
| 270. | 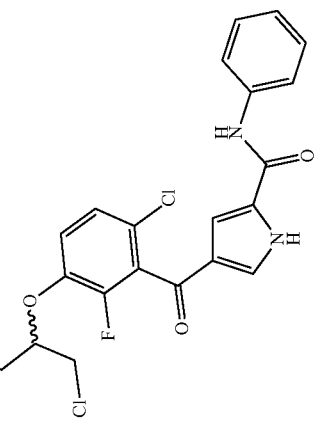 | 4-(6-Chloro-3-((1-chloro-3-hydroxypropan-2-yl)oxy)-2-fluorobenzoyl)-N-(pyridin-3-yl)-1H-pyrrole-2-carboxamide | 42 | ¹H NMR (500 MHz, DMSO-d₆) δ 3.68 (2H, dd, J = 5.4, 5.4 Hz, ArOCHCH₂OH), 3.86 (1H, dd, J = 11.9, 5.4 Hz, ArOCHCH₂Cl), 3.95 (1H, dd, J = 11.9, 4.0 Hz, ArOCHCH₂Cl), 4.65 (1H, p, J = 5.4 Hz, ArOCH), 5.14 (1H, t, J = 5.4 Hz, ArOCHCH₂OH), 7.35-7.41 (2H, m, H-5' and H-5"), 7.45 (1H, dd, J = 9.0, 9.0 Hz, H-4'), 7.49 (1H, s, H-3), 7.50 (1H, s, H-5), 8.13 (1H, dd, J = 8.5, 2.6 Hz, H-4"), 8.30 (1H, d, J = 4.0 Hz, H-6"), 8.89 (1H, d, J = 2.6 Hz, H-2"), 10.26 (1H, s, CONHAr), 12.72 (1H, s, NH-pyrrole) | 452.0570 |
| 271. | 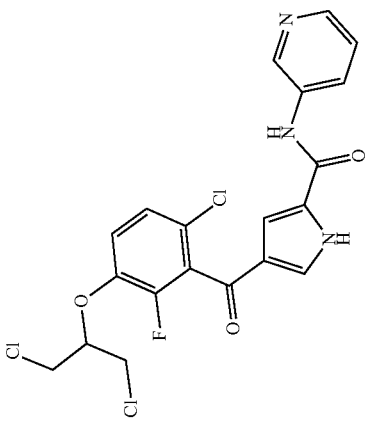 | 4-(6-Chloro-3-((1,3-dichloropropan-2-yl)oxy)-2-fluorobenzoyl)-N-(pyridin-3-yl)-1H-pyrrole-2-carboxamide | 42 | ¹H NMR (500 MHz, DMSO-d₆) δ 3.97 (4H, qd, J = 12.0, 4.9 Hz, ArOCH(CH₂Cl)₂), 4.99 (1H, p, J = 4.9 Hz, ArOCH), 7.36-7.44 (2H, m, H-5' and H-5"), 7.48-7.56 (3H, m, H-3, H-5 and H-4'), 8.13 (1H, dd, J = 8.4, 1.8 Hz, H-4"), 8.30 (1H, d, J = 3.9 Hz, H-6"), 8.89 (1H, s, H-2"), 10.26 (1H, s, CONHAr), 12.73 (1H, s, NH-pyrrole); | 470.0230 |

| 272. | 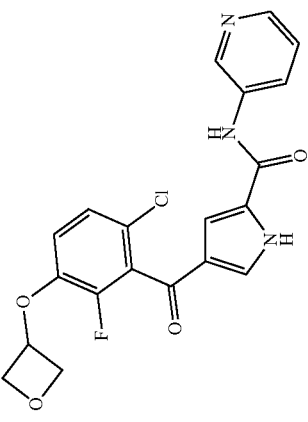 | 4-(6-Chloro-2-fluoro-3-(oxetan-3-yloxy)benzoyl)-N-(pyridin-3-yl)-1H-pyrrole-2-carboxamide | 35 | ¹H NMR (500 MHz, DMSO-d₆) δ 4.61 (2H, dd, J = 7.6, 4.8 Hz, ArOCHCH₂O), 4.95 (2H, t, J = 6.8 Hz, ArOCHCH₂O), 5.40 (1H, p, J = 5.5 Hz, ArOCHCH₂O), 7.00 (1H, dd, J = 9.0, 9.0 Hz, H-4'), 7.34 (1H, dd, J = 9.0, 1.6 Hz, H-5'), 7.39 (1H, dd, J = 8.3, 4.7 Hz, H-5''), 7.47–7.57 (2H, m, H-3 and H-5), 8.13 (1H, d, J = 8.3, H-4''), 8.30 (1H, d, 4.7 Hz, H-6''), 8.89 (1H, s, H-2''), 10.25 (1H, s, CONHAr), 12.74 (1H, s, NH-pyrrole) | 416.0803 |
| 273. | 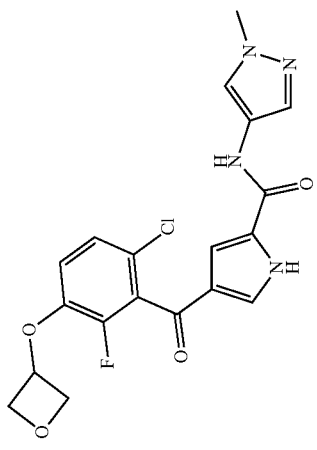 | 4-(6-Chloro-2-fluoro-3-(oxetan-3-yloxy)benzoyl)-N-(1-methyl-1H-pyrazol-4-yl)-1H-pyrrole-2-carboxamide | 35 | ¹H NMR (500 MHz, DMSO-d₆) δ 3.81 (3H, s, NCH₃), 4.61 (2H, dd, J = 7.4, 5.0 Hz, ArOCHCH₂O), 4.94 (2H, t, J = 6.9 Hz, ArOCHCH₂O), 5.40 (1H, p, J = 5.7 Hz, ArOCHCH₂O), 6.99 (1H, dd, J = 9.0, 8.9 Hz, H-4'), 7.31 (1H, s, H-3), 7.33 (1H, dd, J = 8.9, 1.3 Hz, H-5'), 7.45 (1H, s, H-5), 7.50 (1H, s, H-5''), 7.94 (1H, s, H-3''), 10.26 (1H, s, CONHAr), 12.60 (1H, s, NH-pyrrole) | 419.0912 |

Example 274: 4-(2,6-difluoro-3-((methylamino)methyl) benzoyl)-N-(pyridin-3-yl)-1H-pyrrole-2-carboxamide

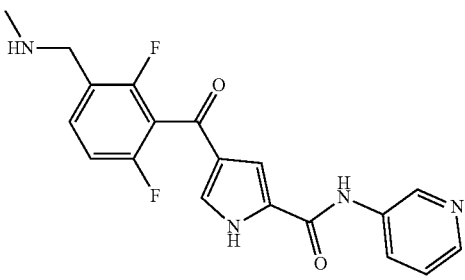 [SMILES: CNCc1ccc(F)c(C(=O)c2c[nH]c(C(=O)Nc3cccnc3)c2)c1F]

OsO$_4$ (tBuOH 2.5% wt, 0.028 mL) was added to 4-(2,6-difluoro-3-vinylbenzoyl)-N-(pyridin-3-yl)-1H-pyrrole-2-carboxamide (100 mg, 0.284 mmol) dissolved in dioxane (0.84 mL) and H$_2$O (0.28 mL) and stirred for 5 min until mixture becomes a clear tan solution. Na$_2$H$_3$IO$_6$ (122 mg, 0.57 mmol) was added to the resulting mixture immediately forming a white precipitate and left to stir for 5 days. The reaction mixture was quenched with saturated aqueous sodium sulphite (10 mL), extracted with EtOAc (3×20 mL), dried over Na$_2$SO$_4$ and evaporated to dryness in vacuo. The crude product was purified by reverse phase MPLC on $^{18}$C (20-80% MeCN in H$_2$O) followed by semi-prep HPLC (0.1% Ammonia (aq)/MeCN) to afford 4-(2,6-difluoro-3-formylbenzoyl)-N-(pyridin-3-yl)-1H-pyrrole-2-carboxamide (40 mg, 40%). 4-(2,6-difluoro-3-formylbenzoyl)-N-(pyridin-3-yl)-1H-pyrrole-2-carboxamide (25.0 mg, 0.070 mmol) was added to methylamine (2.0 M in THF, 0.035 mL, 0.070 mmol) dissolved in EtOH (0.035 mL) and MgSO$_4$ (40 mg) was added. The resulting mixture was stirred at 78° C. for 4 h before being allowed to cool to RT. NaBH$_4$ (2 mg, 0.077 mmol) was added portion wise and the mixture was stirred for 24 h. The mixture was quenched with NH$_4$Cl (10 mL), extracted with EtOAc (3×10 mL) and washed with water (2×10 mL) and brine (2×10 mL) respectively. The organic product was dried over Na$_2$SO$_4$ and evaporated to dryness in vacuo. The crude product was purified by reverse phase MPLC on $^{18}$C (20-70% MeCN in H$_2$O). Pure product was a white solid (20 mg, 77%).

Rf=(0.35 (3:1 MeCN/H$_2$O) M.p. 78-80° C.; $\lambda_{max}$ (EtOH)/nm 255, 293; $v_{max}$/cm$^{-1}$: 2921, 1639 (CO), 1535 (CONH); $^1$H NMR (500 MHz, DMSO-d$_6$) δ 2.37 (3H, s, CH$_3$), 3.82 (2H, s, CH$_2$), 7.28 (1H, appt. t, J=8.6 Hz, H-4'), 7.38 (1H, dd, J=3.5 and 7.9 Hz, H-4"), 7.51 (1H, s, H-5), 7.56 (1H, s, H-3), 7.66 (1H, dd, J=8.2 and 15.3 Hz, H-5'), 8.14 (1H, d, J=8.2 Hz, H-6"), 8.30 (1H, m, H-5"), 8.91 (1H, s, H-2"), 10.29 (1H, s, CONH), (pyrrole NH, not observed); $^{13}$C NMR (125 MHz, DMSO-d$_6$) δ 47.0 (CH$_2$), 112.2 (C-3), 112.4 (d, J$_{CF}$=29.0 Hz, C-4'), 124.1 (C-4"), 126.3 (pyrrole C$_q$), (C$_q$-3' not observed), (C$_q$-1' not observed), 127.5 (C-6"), 128.6 (pyrrole C$_q$), 130.0 (C-5), 133.1 (m, C-5'), 135.1 (C$_q$-3"), 142.1 (C-2"), 144.9 (C-5"), 159.2 (CONH), (CF$_q$ not observed), (CF$_q$ not observed), 182.4 (CO); LRMS (ES+) m/z 371.2 [M+H]$^+$

| # | Structure | Name | Yield | ¹H NMR | MS |
|---|---|---|---|---|---|
| 275. | (structure with pyrrolidine) | 4-(3,6-Dichloro-2-fluorobenzoyl)-N-(6-((2-(pyrrolidin-1-yl)ethyl)amino)pyridin-3-yl)-1H-pyrrole-2-carboxamide | 35 | ¹H NMR (500 MHz, DMSO-$d_6$) δ 1.68 (4H, p, J = 3.1 Hz, NCH$_2$CH$_{2\ pyrrolidine}$), 2.47 (4H, p, J = 3.1 Hz, NCH$_2$CH$_{2\ pyrrolidine}$), 2.57 (2H, t, J = 6.8 Hz, ArNHCH$_2$CH$_2$N), 3.25-3.38 (2H, m, ArNHCH$_2$CH$_2$N), 6.28 (1H, t, J = 5.7 Hz, ArNHCH$_2$), 6.49 (1H, d, J = 8.9 Hz, H-5"), 7.39 (1H, s, H-3), 7.51 (1H, dd, J = 8.8, 1.3 Hz, H-5), 7.54 (1H, s, H-5), 7.62 (1H, dd, J = 8.9, 2.7 Hz, H-4"), 7.77 (1H, dd, J = 8.8, 8.4 Hz, H-4), 8.21 (1H, d, J = 2.7 Hz, H-2"), 9.82 (1H, s, CONHAr), 12.63 (1H, s, NH-pyrrole) | 490.1193 |
| 276. | (structure with morpholine) | 4-(3,6-Dichloro-2-fluorobenzoyl)-N-(6-((2-morpholinoethyl)amino)pyridin-3-yl)-1H-pyrrole-2-carboxamide | 35 | ¹H NMR (500 MHz, DMSO-$d_6$) δ 2.40 (4H, t, J = 4.6 Hz, NCH$_{2\ morpholine}$), 2.46 (2H, t, J = 6.7 Hz, ArNHCH$_2$CH$_2$N), 3.34 (2H, m, ArNHCH$_2$CH$_2$N), 3.58 (4H, t, J = 4.6 Hz, OCH$_{2\ morpholine}$), 6.26 (1H, t, J = 5.6 Hz, ArNHCH$_2$), 6.50 (1H, d, J = 8.9 Hz, H-5"), 7.40 (1H, s, H-3), 7.51 (1H, dd, J = 8.8 Hz, H-5), 7.55 (1H, s, H-5), 7.63 (1H, dd, J = 8.9, 2.7 Hz, H-4"), 7.77 (1H, dd, J = 8.8, 8.4 Hz, H-4), 8.22 (1H, d, J = 2.7 Hz, H-2"), 9.82 (1H, s, CONHAr), 12.63 (1H, s, NH-pyrrole) | 506.1146 |
| 277. | (structure with dimethylaminomethyl) | 4-(3,6-Dichloro-2-fluorobenzoyl)-N-(6-((dimethylamino)methyl)pyridin-3-yl)-1H-pyrrole-2-carboxamide | 35 | ¹H NMR (500 MHz, DMSO-$d_6$) δ 2.18 (6H, s, CH$_2$N(CH$_3$)$_2$), 3.49 (2H, s, ArCH$_2$N), 7.40 (1H, d, J = 8.5 Hz, H-5"), 7.48-7.54 (2H, m, H-3 and H-5"), 7.62 (1H, s, H-5), 7.78 (1H, dd, J = 8.4, 8.4 Hz, H-4), 8.11 (1H, dd, J = 8.5, 2.5 Hz, H-4"), 8.79 (1H, d, J = 2.5 Hz, H-2"), 10.22 (1H, s, CONHAr), 12.76 (1H, s, NH-pyrrole) | 435.0785 |

| # | Structure/Name | | NMR | Mass |
|---|---|---|---|---|
| 278. | 4-(3,6-Dichloro-2-fluorobenzoyl)-N-(6-((2-methoxyethyl)(methyl)amino)methyl)pyridin-3-yl)-1H-pyrrole-2-carboxamide | 35 | ¹H NMR (500 MHz, DMSO-d₆) δ 2.20 (3H, s, NCH₃), 2.56 (2H, t, J = 5.9 Hz, NCH₂CH₂OMe), 3.23 (3H, s, CH₂OCH₃), 3.45 (2H, t, J = 5.9 Hz, NCH₂CH₂OMe), 3.59 (2H, s, ArCH₂N), 7.41 (1H, d, J = 8.5 Hz, H-5″), 7.48-7.54 (2H, m, H-3 and H-5), 7.62 (1H, s, H-5), 7.78 (1H, dd, J = 8.4, 8.4 Hz, H-4), 8.10 (1H, dd, J = 8.5, 2.6 Hz, H-4″), 8.79 (1H, d, J = 2.6 Hz, H-2″), 10.21 (1H, s, CONHAr), 12.76 (1H, s, NH-pyrrole) | 479.0135 |
| 279. | 4-(3,6-Dichloro-2-fluorobenzoyl)-N-(6-(oxetan-3-yloxy)pyridin-3-yl)-1H-pyrrole-2-carboxamide | 35 | ¹H NMR (500 MHz, DMSO-d₆) δ 4.55 (2H, dd, J = 7.4, 5.1 Hz, CHCH₂O), 4.89 (2H, t, J = 6.8 Hz, CHCH₂O), 5.53 (1H, p, J = 5.8 Hz, ArOCH), 6.92 (1H, d, J = 8.9 Hz, H-5″), 7.46 (1H, s, H-3), 7.49-7.54 (1H, m, H-5′), 7.60 (1H, s, H-5), 7.78 (1H, dd, J = 8.4, 8.4 Hz, H-4′), 8.02 (1H, dd, J = 8.9, 2.6 Hz, H-4″), 8.43 (1H, d, J = 2.6 Hz, H-2″), 10.12 (1H, s, CONHAr), 12.74 (1H, s, NH-pyrrole) | 450.0418 |
| 280. | 4-(3,6-Dichloro-2-fluorobenzoyl)-N-(6-(2-hydroxyethoxy)pyridin-3-yl)-1H-pyrrole-2-carboxamide | 35 | ¹H NMR (500 MHz, DMSO-d₆) δ 3.29 (3H, s, CH₂OCH₃), 3.60-3.68 (2H, m, CH₂CH₂OMe), 4.29-4.38 (2H, m, ArOCH₂CH₂), 6.85 (1H, d, J = 8.9 Hz, H-5″), 7.46 (1H, s, H-3), 7.49-7.56 (1H, m, H-5′), 7.60 (1H, s, H-5), 7.78 (1H, dd, J = 8.4, 8.4 Hz, H-4′), 7.99 (1H, dd, J = 8.9, 2.7 Hz, H-4″), 8.45 (1H, d, J = 2.7 Hz, H-2″), 10.10 (1H, s, CONHAr), 12.73 (1H, s, NH-pyrrole) | 438.0418 |

| | | | | |
|---|---|---|---|---|
| 281. | 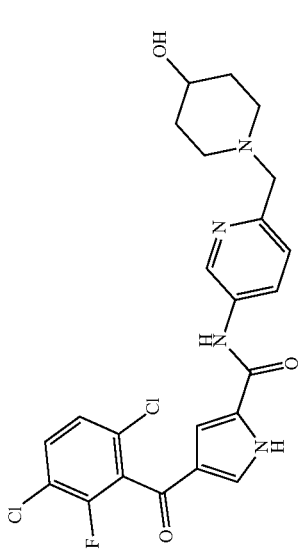4-(3,6-Dichloro-2-fluorobenzoyl)-N-(6-(2-hydroxyethoxy)pyridin-3-yl)-1H-pyrrole-2-carboxamide | 35 | ¹H NMR (500 MHz, DMSO-d₆) δ 3.70 (2H, dt, J = 5.4, 5.0 Hz, CH₂CH₂OH), 4.24 (2H, t, J = 5.0 Hz, ArOCH₂CH₂), 4.81 (1H, t, J = 5.4 Hz, CH₂OH), 6.83 (1H, d, J = 8.8 Hz, H-5'), 7.45 (1H, s, H-3), 7.52 (1H, d, J = 8.7 Hz, H-5"), 7.60 (1H, s, H-5), 7.78 (1H, dd, J = 8.7, 8.3 Hz, H-4), 7.99 (1H, dd, J = 8.8, 2.3 Hz, H-4"), 8.44 (1H, d, J = 2.3 Hz, H-2"'), 10.09 (1H, s, CONHAr), 12.73 (1H, s, NH-pyrrole) | 438.0418 |
| 282. | 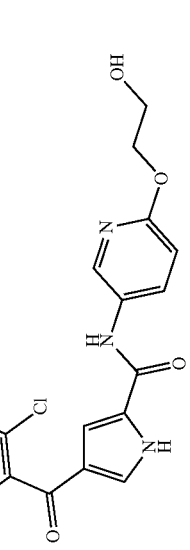4-(3,6-Dichloro-2-fluorobenzoyl)-N-(6-(4-hydroxypiperidin-1-yl)methyl)pyridin-3-yl)-1H-pyrrole-2-carboxamide | 35 | ¹H NMR (500 MHz, DMSO-d₆) δ 1.40 (2H, dddd, J = 13.1, 9.7, 9.7 and 3.7 Hz, CH₂CHOH), 1.71 (2H, ddd, J = 13.1, 3.6 and 3.6 Hz, CH₂CHOH), 2.02-2.17 (2H, m, NCH₂CH₂), 2.69 (2H, dd, J = 13.1, 5.6 Hz, NCH₂CH₂), 3.40-3.49 (1H, m, CH₂CHOH), 3.53 (2H, s, ArCH₂N), 4.47-4.62 (1H, m, CH₂CHOH), 7.40 (1H, d, J = 8.5 Hz, H-5"), 7.47-7.56 (2H, m, H-3 and H-5), 7.62 (1H, s, H-5), 7.78 (1H, dd, J = 8.4, 8.4 Hz, H-4), 8.10 (1H, dd, J = 8.5, 2.5 Hz, H-4"), 8.79 (1H, d, J = 2.5 Hz, H-2"'), 10.22 (1H, s, CONHAr), 12.76 (1H, s, NH-pyrrole) | 491.1038 |

| | | | | |
|---|---|---|---|---|
| 283. | N-(6-((bis(2-methoxyethyl)amino)methyl)pyridin-3-yl)-4-(3,6-dichloro-2-fluorobenzoyl)-1H-pyrrole-2-carboxamide | | 35 | $^1$H NMR (500 MHz, DMSO-d$_6$) δ 2.68 (4H, t, J = 6.0 Hz, N(CH$_2$CH$_2$OMe)$_2$), 3.21 (6H, s, N(CH$_2$CH$_2$OCH$_3$)$_2$), 3.40 (4H, t, J = 6.0 Hz, N(CH$_2$CH$_2$OMe)$_2$), 3.73 (2H, s, ArCH$_2$N), 7.44 (1H, d, J = 8.5 Hz, H-5"'), 7.48-7.56 (2H, m, H-3 and H-5'), 7.62 (1H, s, H-5), 7.78 (1H, dd, J = 8.4, 8.4 Hz, H-4'), 8.08 (1H, dd, J = 8.5, 2.6 Hz, H-4"'), 8.78 (1H, d, J = 2.6 Hz, H-2"'), 10.20 (1H, s, CONHAr), 12.75 (1H, s, NH-pyrrole) | 523.1294 |
| 284. | 4-(3,6-Dichloro-2-fluorobenzoyl)-N-(6-(piperidin-1-ylmethyl)pyridin-3-yl)-1H-pyrrole-2-carboxamide | | 35 | $^1$H NMR (500 MHz, DMSO-d$_6$) δ 1.33-1.44 (2H, m, NCH$_2$CH$_2$CH$_2$), 1.44-1.58 (4H, m, NCH$_2$CH$_2$CH$_2$), 2.37 (4H, brs, NCH$_2$CH$_2$CH$_2$), 3.51 (2H, s, ArCH$_2$N), 7.40 (1H, d, J = 8.5 Hz, H-5"'), 7.48-7.55 (2H, m, H-3 and H-5'), 7.62 (1H, s, H-5), 7.78 (1H, dd, J = 8.4, 8.4 Hz, H-4'), 8.09 (1H, dd, J = 8.5, 2.5 Hz, H-4"'), 8.79 (1H, d, J = 2.5 Hz, H-2"'), 10.22 (1H, s, CONHAr), 12.76 (1H, s, NH-pyrrole); | 475.1085 |

Example 285: 4-(2,6-Difluorobenzoyl)-N-(1-methyl-1H-pyrazol-4-yl)-1H-pyrrole-2-carboxamide

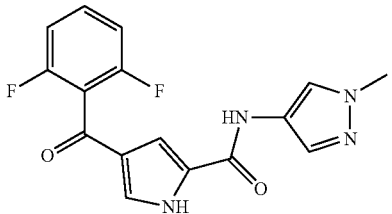 [SMILES: Cn1cc(NC(=O)c2cc(C(=O)c3c(F)cccc3F)c[nH]2)cn1]

To a suspension of aluminium trichloride (277 mg, 2.08 mmol) in DCM (2.1 mL), cooled at 0° C., was added 2,6-difluorobenzoyl chloride (209 µL, 1.66 mmol) followed by methyl 1H-pyrrole-2-carboxylate (104 mg, 0.83 mmol). The resulting solution was stirred at 0° C. for 30 min and allowed to warm to room temperature. After 20 h, the reaction mixture was cooled to 0° C. and quenched by cautious addition of 1 M aq. HCl (1 mL). The resulting solution was stirred at room temperature for 2 h. The reaction was then diluted with water (20 mL) and extracted with DCM (3×50 mL). The pooled organic extracts were washed with sat. aq. NaHCO3 and brine (50 mL, respectively), dried over $MgSO_4$ and concentrated in vacuo. The crude product was purified by MPLC on $SiO_2$ with gradient elution from 0-40% EtOAc in petroleum ether to give methyl 4-(2,6-difluorobenzoyl)-1H-pyrrole-2-carboxylate as an orange oil (201 mg, 91%); δH NMR (500 MHz; DMSO-$d_6$) $^1$H 3.80 (3H, s, $OCH_3$), 7.05 (1H, s, H-pyrrole), 7.26 (2H, app t, J=8.8 Hz, H—Ar), 7.58 (1H, m, H-pyrrole), 7.59-7.64 (1H, m, H—Ar), 12.90 (1H, br s, NH); MS (ES$^-$) m/z 264.3 [M−H]$^-$.

To a solution of methyl 4-(2,6-difluorobenzoyl)-1H-pyrrole-2-carboxylate (168 mg, 0.63 mmol) in THF (3.5 mL) was added a solution of lithium hydroxide (530 mg, 12.6 mmol) in $H_2O$ (2.8 mL). The resulting mixture was heated at 67° C. for 18 h. Upon completion, the mixture was acidified to pH 3 using a 4 M aq. solution of HCl. The reaction was then diluted with water (30 mL) and extracted with EtOAc (3×50 mL). The pooled organic extracts were washed with water and brine (50 mL, respectively), dried over $MgSO_4$ and concentrated in vacuo to give 4-(2,6-Difluorobenzoyl)-1H-pyrrole-2-carboxylic acid as a pink solid (148 mg, 94%); δH NMR (500 MHz; DMSO-$d_6$) $^1$H 6.99 (1H, s, H-pyrrole), 7.26 (2H, app t, J=7.7 Hz, H—Ar), 7.51 (1H, s, H-pyrrole), 7.58-7.64 (1H, m, H—Ar), 12.70 (1H, br s, NH), OH not visualised; MS (ES$^-$) m/z 250.2 [M−H]$^-$.

4-(2,6-Difluorobenzoyl)-N-(1-methyl-1H-pyrazol-4-yl)-1H-pyrrole-2-carboxamide was prepared using similar starting materials by procedures analogous to General Procedure 11: Acylation followed by General Procedure 12: Lithium hydroxide hydrolysis followed by General Procedure 9: Amide coupling using 2-chloro-1-methylpyridinium iodide.

4-(2,6-Difluorobenzoyl)-1H-pyrrole-2-carboxylic acid (25 mg, 0.10 mmol)), Et$_3$N (35 µL, 0.25 mmol), and 2-chloro-1-methylpyridinium iodide (28 mg, 0.11 mmol)) were combined in DCM (1.5 mL) and stirred at room temperature for 10 min, followed by the addition of 1-methyl-1H-pyrazol-4-amine (12 mg, 0.12 mmol) in DCM (0.3 mL). The resulting was stirred at room temperature for 18 h, the solvent evaporated, and the mixture partitioned between EtOAc (2×15 mL) and 10% aqueous $K_2CO_3$ (15 mL). The organic layers were combined, washed with brine, dried over MgSO4 and the solvent removed in vacuo. The crude product was purified by MPLC on $SiO_2$ with gradient elution from 0-90% EtOAc in petroleum ether to give a peach solid (7 mg, 21%); δH NMR (500 MHz; MeOD-$d_4$) $^1$H 3.89 (3H, s, $CH_3$), 7.13 (2H, dd, J=7.7 and 8.5 Hz, H-3' and H-5'), 7.33 (1H, s, H-pyrrole), 7.47 (1H, s, H-pyrrole), 7.54-7.61 (2H, m, H-4' and H-pyrazole), 7.97 (1H, s, H-pyrazole), 10.2 (1H, s, CONH), 12.1 (1H, s, NH-pyrrole); MS (ES$^+$) m/z 331.3 [M+H]$^+$.

Example 286: 4-(2-Fluoro-6-methylbenzoyl)-N-(1-methyl-1H-pyrazol-4-yl)-1H-pyrrole-2-carboxamide

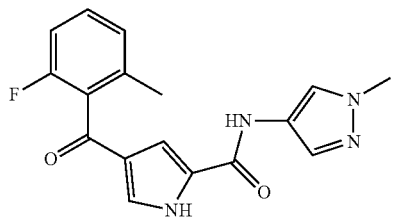 [SMILES: Cc1cccc(F)c1C(=O)c1c[nH]c(C(=O)Nc2cnn(C)c2)c1]

To a solution of 2-fluoro-6-methylbenzoic acid (123 mg, 0.80 mmol) in THF (1 mL), cooled at 0° C., was added thionyl chloride (87 µL, 1.20 mmol) and N,N-dimethylformamide (0.1 mL). The resulting solution was stirred at 0° C. for 4 h and allowed to warm to room temperature. Upon completion, the solvent was removed in vacuo. The crude material was used in the next step without further purification.

To a suspension of aluminium trichloride (133 mg, 1.00 mmol) in DCM (1 mL), cooled at 0° C., was added the above crude acyl chloride followed by methyl 1H-pyrrole-2-carboxylate (50 mg, 0.40 mmol). The resulting solution was stirred at 0° C. for 30 min and allowed to warm to room temperature. After 20 h, the reaction mixture was cooled to 0° C. and quenched by cautious addition of 1 M aq. HCl (0.5 mL). The resulting solution was stirred at room temperature for 2 h. The reaction was then diluted with water (20 mL) and extracted with DCM (3×50 mL). The pooled organic extracts were washed with sat. aq. NaHCO3 and brine (50 mL, respectively), dried over $MgSO_4$ and concentrated in vacuo. The crude product was purified by MPLC on $SiO_2$ with gradient elution from 0-40% EtOAc in petroleum ether to give methyl 4-(2-fluoro-6-methylbenzoyl)-1H-pyrrole-2-carboxylate an orange oil (40 mg, 38%); δH NMR (500 MHz; CDCl$_3$) $^1$H 2.28 (3H, s, Ar—$CH_3$), 3.89 (3H, s, $OCH_3$), 6.98 (1H, app t, J=8.9 Hz, H—Ar), 7.05 (1H, d, J=7.8 Hz, H—Ar), 7.22 (1H, s, H-pyrrole), 7.31 (1H, dt, J=5.9 and 7.8 Hz, H—Ar), 7.43-7.44 (1H, m, H-pyrrole), 9.80 (1H, br s, NH); MS (ES$^-$) m/z 261.1 [M−H]$^-$.

To a solution of methyl 4-(2-fluoro-6-methylbenzoyl)-1H-pyrrole-2-carboxylate (25 mg, 0.09 mmol) in THF (0.5 mL) was added a solution of lithium hydroxide (79 mg, 1.89 mmol) in $H_2O$ (0.4 mL). The resulting mixture was heated at 67° C. for 18 h. Upon completion, the mixture was acidified to pH 3 using a 4 M aq. solution of HCl. The reaction was then diluted with water (20 mL) and extracted with EtOAc (3×20 mL). The pooled organic extracts were washed with water and brine (20 mL, respectively), dried over $MgSO_4$ and concentrated in vacuo to give 4-(2-Fluoro-6-methylbenzoyl)-1H-pyrrole-2-carboxylic acid as an a yellow oil (15 mg, 66%); δH NMR (500 MHz; MeOD-$d_4$) $^1$H 2.13 (3H, s, CH₃), 6.93 (1H, app t, J=8.2 Hz, H—Ar), 7.01-7.03 (2H, m, H-pyrrole and H—Ar), 7.22 (1H, s, H-pyrrole), 7.24-7.29 (1H, m, H—Ar), 12.04 (1H, br s, NH), OH not visualised; MS (ES⁻) m/z 246.2 [M–H]⁻.

The compound was prepared using similar starting materials by procedures analogous to General Procedure 10: Thionyl chloride preparation of acid chloride followed by General Procedure 11: Acylation followed by General Procedure 12: Lithium hydroxide hydrolysis followed by General Procedure 9: Amide coupling using 2-chloro-1-methylpyridinium iodide. 4-(2-fluoro-6-methylbenzoyl)-1H-pyrrole-2-carboxylic acid (27 mg, 0.11 mmol)), Et₃N (38 μL, 0.27 mmol), and 2-chloro-1-methylpyridinium iodide (31 mg, 0.12 mmol)) were combined in DCM (1.6 mL) and stirred at room temperature for 10 min, followed by the addition of 1-methyl-1H-pyrazol-4-amine (13 mg, 0.14 mmol) in DCM (0.3 mL). The reaction was stirred at room temperature for 18 h, the solvent evaporated, and the mixture partitioned between EtOAc (2×15 mL) and 10% aqueous K₂CO₃ (15 mL). The organic layers were combined, washed with brine, dried over MgSO₄ and the solvent removed in vacuo. The crude product was purified by MPLC on SiO₂ with gradient elution from 30-90% EtOAc in petroleum ether to give an orange solid (7 mg, 21%); δH NMR (500 MHz; MeOD-d₄) ¹H 2.27 (1H, s, 6'-CH₃), 3.89 (1H, s, CH₃-pyrazole), 7.06 (1H, app t, J=8.7 Hz, H-3'), 7.15 (1H, d, J=7.9 Hz, H-5'), 7.27 (1H, s, H-pyrrole), 7.38-7.42 (2H, m, H-4' and H-pyrrole), 7.59 (1H, s, H-pyrazole), 7.96 (1H, s, H-pyrazole), two NH not visualised; MS (ES⁺) m/z 327.3 [M+H]⁺.

Example 287: 4-(2-Fluorobenzoyl)-N-(1-methyl-1H-pyrazol-4-yl)-1H-pyrrole-2-carboxamide

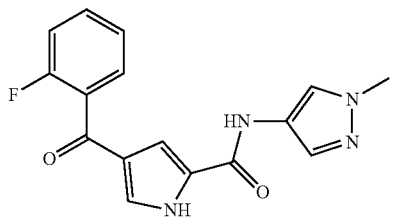 [SMILES: Cn1cc(NC(=O)c2cc(C(=O)c3ccccc3F)c[nH]2)cn1]

To a suspension of aluminium trichloride (274 mg, 2.06 mmol) in DCM (2.1 mL), cooled at 0° C., was added 2-fluorobenzoyl chloride (197 μL, 1.65 mmol) followed by methyl 1H-pyrrole-2-carboxylate (103 mg, 0.82 mmol). The resulting solution was stirred at 0° C. for 30 min and allowed to warm to room temperature. After 20 h, the reaction mixture was cooled to 0° C. and quenched by cautious addition of 1 M aq. HCl (1 mL). The resulting solution was stirred at room temperature for 2 h. The reaction was then diluted with water (20 mL) and extracted with DCM (3×50 mL). The pooled organic extracts were washed with sat. aq. NaHCO3 and brine (50 mL, respectively), dried over MgSO₄ and concentrated in vacuo. The crude product was purified by MPLC on SiO₂ with gradient elution from 0-40% EtOAc in petroleum ether to give methyl 4-(2-fluorobenzoyl)-1H-pyrrole-2-carboxylate as an orange oil (133 mg, 66%); δH NMR (500 MHz; DMSO-d₆) ¹H 3.80 (3H, s, OCH₃), 7.06 (1H, s, H-pyrrole), 7.32-7.38 (2H, m, H—Ar), 7.50 (1H, s, H-pyrrole), 7.55 (1H, dt, J=1.8 and 7.4 Hz, H—Ar), 7.60-7.64 (1H, m, H—Ar), 12.79 (1H, br s, NH); MS (ES⁻) m/z 246.9 [M–H]⁻.

To a solution of methyl 4-(2-fluorobenzoyl)-1H-pyrrole-2-carboxylate (116 mg, 0.47 mmol) in THF (2.6 mL) was added a solution of lithium hydroxide (393 mg, 9.37 mmol) in H₂O (2.1 mL). The resulting mixture was heated at 67° C. for 18 h. Upon completion, the mixture was acidified to pH 3 using a 4 M aq. solution of HCl. The reaction was then diluted with water (30 mL) and extracted with EtOAc (3×50 mL). The pooled organic extracts were washed with water and brine (50 mL, respectively), dried over MgSO₄ and concentrated in vacuo to give 4-(2-Fluorobenzoyl)-1H-pyrrole-2-carboxylic acid as a pink solid (109 mg, quant.); δH NMR (500 MHz; DMSO-d₆) ¹H 7.01 (1H, s, H-pyrrole), 7.32-7.37 (2H, m, H—Ar), 7.42 (1H, s, H-pyrrole), 7.55 (1H, dt, J=2.0 and 7.7 Hz, H—Ar), 7.58-7.63 (1H, m, H—Ar), 12.59 (1H, br s, NH), 12.87 (1H, br s, OH); MS (ES⁻) m/z 232.2 [M–H]⁻.

The compound was prepared using similar starting materials by procedures analogous to General Procedure 11: Acylation followed by General Procedure 12: Lithium hydroxide hydrolysis followed by General Procedure 9: Amide coupling using 2-chloro-1-methylpyridinium iodide. 4-(2-fluorobenzoyl)-1H-pyrrole-2-carboxylic acid (59 mg, 0.25 mmol)), Et₃N (88 μL, 0.63 mmol), and 2-chloro-1-methylpyridinium iodide (71 mg, 0.28 mmol)) were combined in DCM (3.8 mL) and stirred at room temperature for 10 min, followed by the addition of 1-methyl-1H-pyrazol-4-amine (31 mg, 0.79 mmol) in DCM (0.8 mL). The reaction was stirred at room temperature for 18 h, the solvent evaporated, and the mixture partitioned between EtOAc (2×30 mL) and 10% aqueous K₂CO₃ (30 mL). The organic layers were combined, washed with brine, dried over MgSO₄ and the solvent removed in vacuo. The crude product was purified by MPLC on SiO₂ with gradient elution from 30-90% EtOAc in petroleum ether to give a pale yellow solid (30 mg, 39%); δH NMR (500 MHz; MeOD-d₄) ¹H 3.89 (3H, s, CH₃), 7.28 (1H, app t, J=3.4 Hz, H-3'), 7.32-7.36 (2H, m, H—Ar), 7.47-7.48 (1H, m, H-4'), 7.59-7.61 (3H, m, H—Ar and H-pyrazole), 7.97 (1H, s, H-pyrazole), two NH not visualised; MS (ES⁺) m/z 313.3 [M+H]⁺.

Assays

ERK5 IMAP™ Assay

The assay buffer was prepared using 0.01% Tween®-20 5× stock, supplied as part of IMAP™ FP Progressive Binding System Kit (Molecular Devices R7436) and diluted to 1× using miliQ H₂O. 1 μL of a 1M DTT stock was added for every 1 mL of 1× assay buffer to give a final concentration of 1 mM DTT.

ERK5 was expressed and purified at CRT-DL by Leon Pang and Sue Young. Aliquots were stored at −80° C. The ERK5 working solution was used at a 1 in 1 in 350 final dilution in assay buffer. A 1:175 dilution of ERK5 stock was performed in 1× assay buffer. For 1 plate, 13 μL of ERK5 stock was added to 2262 μL of 1× assay buffer.

To prepare the ATP/substrate working solution for one plate, ATP disodium salt (90 μL, 20 mM) (Sigma A7699) and FAM-EGFR-derived peptide (15 μL, 100 μM) (LVE-PLTPSGEAPNQ(K-5FAM)-COOH) (Molecular Devices RP7129; reconstituted in miliQ H₂O to a stock concentration of 100 μL; Stored at −20° C.) was added to 2295 μL of 1× assay buffer.

To prepare the IMAP™ binding solution for one plate 20.5 μL of IMAP™ binding reagent stock, 1476 μL of 1× binding buffer A (60%), and 984 μL of binding buffer B (40%) (IMAP™ FP Progressive screening express kit (Molecular Devices R8127) was added to 9819.5 μL of milliQ H₂O.

1 µL of inhibitor (in 60:40 H$_2$O/DMSO) or 60:40 H$_2$O/DMSO (for controls and blanks) were dry-spotted into the relevant wells of a 384-well assay plate using the MATRIX PlateMate® Plus. 5 µL of ERK5 working solution was added to test and control wells, and 5 µL of 1× assay buffer added to blanks; 4 µL of ATP/substrate working solution was added to all wells using a Matrix multichannel pipette. The plate was sealed using DMSO resistant clear seal and incubated for 2 h at 37° C. 1 µL of the kinase reaction mixture from the first plate was dry spotted into a second 384-well assay plate using the MATRIX PlateMate® Plus. 9 µL of assay buffer was added, followed by 30 µL of IMAP™ binding solution using a multichannel pipette. The plate was incubated at RT in darkness for 2 h. The assay plate was then read on an Analyst HT plate reader (Molecular Devices) using the settings described below:

Measurement mode=Fluorescence polarisation; Method ID=ERK5; Integration time=100 ms; Excitation filter=Fluorescein 485-20; Emission filter=530-25; Dichroic mirror=505 nm; Plate definition file=Corning 384 black fb; Z-height=5.715 mm (middle); G-factor=1; Attenuator=out; Detector counting=Smartread+; Sensitivity=2.

Dual-Luciferase Reporter Assay

Agar plates for bacterial colony growth were prepared using 250 mL of lysogeny broth (LB) agar spiked with 250 µL of an antibacterial agent (kanomycin or ampicillin), and, using a sterile pipette, 25 mL of spiked LB agar was transferred into 12 petri dishes.

Transformed bacterial colonies were grown as follows: to a polypropylene tube was added 48 µL of *E. coli* in glycerol stock (prepared in-house at the Babraham Institute), and 2 µL of either the Gal4-Luciferase or MEK5D DNA plasmid. The resulting mixture was incubated at 0° C. for 15 min. Bacteria were subjected to stress by heating at 42° C. for 30 sec, then returning to 0° C. 200 µL of LB agar was added at 0° C., and the resulting mixture was incubated with shaking for 30 min to 1 h at 37° C.

At 37° C., 250 µL of the solution containing Gal4-Luciferase transformed bacteria was transferred onto one LB agar/kanomycin plate. 250 µL of the solution containing MEK5D transformed bacteria was transferred onto one LB agar/ampicillin plate. Agar plates were incubated for 24 h at 37° C. for bacterial colony growth.

To a conical flask was added 100 mL LB agar, 100 µL of the relevant antibiotic, and a sample of the bacterial colonies from the relevant petri dish. The flasks were incubated for a further 24 h at 37° C., with stirring (150-170 rpm).

For DNA purification, 2×50 mL portions of the incubated bacteria in agar obtained were transferred into 50 mL Falcon tubes and subjected to centrifugation at 6000 G for 15 min. DNA plasmids were isolated in aqueous media from the remaining bacterial pellet using a Qiagen Plasmid Plus Midi Kit, according to kit instructions.

In order to quantify the DNA, concentration of the purified aqueous DNA was determined using a NanoDrop 1000 spectrophotometer. DNA stock solutions were at 2419.4 ng/µL and 1965.6 ng/µL for Gal-4-Luciferase and MEK5D plasmid stocks respectively. All other DNA plasmid stocks used were prepared in house at the Babraham Institute by Dr Pamela Lochhead.

Cell Maintenance

HEK293 and HeLa cells were grown as adherent colonies on tissue culture dishes in Dulbecco's Modified Eagle Medium (DMEM) tissue culture medium (Gibco® 41966) containing L-glutamine (2 mM, Gibco® 1499), penicillin/streptomycin (100 µg/mL, PAA P11-010), foetal bovine serum (FBS) (10%, PAA A15-151) as additives (HEK293), or in RPMI-1640 (Sigma) containing 10% FBS (HeLa).

Penicillin and streptomycin are antibacterial agents, which minimise the risk of bacterial infection occurring in cell culture. FBS is a serum supplement, which contains growth factors that promote eukaryotic cell growth. L-glutamine is a nutrient which supports the growth of cells which have high energy demands, such as cells which synthesise large amounts of proteins and/or nucleic acids or those which use glucose inefficiently.

Trypsinizing of Adherent Cell Colonies

Cells were regularly passaged in order to maintain optimum colony sizes on plates. In order to do this, and to harvest cells for use in the dual-luciferase reporter assay, adherent cells were lifted from tissue culture dishes. Cell media was removed via aspiration, and the cell monolayer was washed with phosphate buffered saline (PBS) solution (10 mL), which was then aspirated. The cells were lifted from the plate through incubation at 37° C. for 5-10 min with 1 mL trypsin (0.5% trypsin-EDTA (1×), Gibco® 15400054).

PBS (10×): NaCl (4% w/v), KCl (0.1% w/v), Na$_2$HPO$_4$.7H$_2$O (0.6% w/v), KH$_2$PO$_4$ (0.1% w/v), NaN$_3$ (0.01% w/v).

Reverse Transfection of HEK293 Cells

Preparation of EGFP Control (C3) Working Solution (for 1×96 Well Plate)

To a 50 mL Falcon tube was added 250 µL Opti-MEM® growth media (reduced serum medium, Invitrogen 31985), and the following DNA plasmids; MEF2D-Gal4 (2.5 µL, 0.25 mg/mL stock), Gal4-Luc (2.5 µL, 1.25 mg/mL stock), *Renilla* Luciferase (2.5 µL, 0.1 mg/mL stock), EGFP construct, containing no MEK5D (0.25 µL, 0.5 mg/mL stock), and HA-ERK5 wt (2.5 µL, 0.5 mg/mL stock). To this mixture was then added 5 µL of Lipofectamine™ 2000 transfection reagent (Invitrogen 11668) and complexation allowed for 15-20 min.

Preparation of EGFP-MEK5D (5D) Working Solution (for 1×96 Well Plate)

To a 50 mL Falcon tube was added 1500 µL Opti-MEM® growth media (reduced serum medium, Invitrogen 31985), and the following DNA plasmids; MEF2D-Gal4 (15 µL, 0.25 mg/mL stock), Gal4-Luc (15 µL, 1.25 mg/mL stock), *Renilla* Luciferase (15 µL, 0.1 mg/mL stock), EGFP-MEK5D construct (1.5 µL, 0.5 mg/mL stock), HA-ERK5 wt (15 µL, 0.5 mg/mL stock). To this mixture was then added 30 µL of Lipofectamine™ 2000 transfection reagent (Invitrogen 11668) and complexation allowed for 15-20 min.

Preparation of HEK293 Cells for Reverse Transfection

Trypsinized HEK293 cells were re-suspended in 19 mL of fresh cell media and counted using haemocytometry. Cells were then diluted with fresh cell media to achieve a final cell concentration of 2×10$^5$ cells/mL. 1237.5 µL and 7425 µL of this cell media was added to the C3 and 5D working solutions respectively. 100 µL of the transfected cells were then aliquoted into the appropriate wells in a 96-well opaque sided tissue culture plate, and incubated at 37° C. for 6 h.

Addition of Compounds to HEK293 Cells

Each compound supplied was prepared as a 10 mM working solution in DMSO, from which the following stocks were prepared in DMSO; 3.33 mM, 1 mM, 0.11 mM and 10 µM. 4 compounds was assayed per 96-well plate. For each compound, 1 mL of growth media was added to eight 1.5 mL Eppendorf® tubes. 6 µL of DMSO was added to two tubes for C3 and blank 5D wells, and 6 µL of the relevant compound stock solution was added to the 6 remaining tubes. BIX02189 was added to each plate in varying concentrations as an indicator of assay reliability. Solutions of drug in media were thoroughly mixed, and 100 µL of the relevant compound was transferred (in triplicate) to the 96-well plate containing transfected HEK293 cells using an electronic multichannel pipette with variable tip spacing. Sealed plates were incubated at 37° C. for 24 h. Final compound concentrations were as follows; 30 µM, 10 µM, 3 µM, 1 µM and 0.3 µM.

Assay Plate Lysis 15 mL of 1× passive lysis buffer (PLB) was prepared using 5×PLB (Dual-Luciferase Reporter Assay System, Promega® E1960), diluting with H$_2$O. Assay plates prepared were removed from the incubator and the growth media removed by aspiration. 20 µL of 1×PLB was dispensed into each well and the plates shaken for 10 min. Assay plates were sealed and stored at −80° C. overnight.

Quantification of Cellular Inhibition of ERK5

Cellular inhibition of ERK5 was quantified using the Dual-Luciferase® Reporter Assay System (Promega® E1960). Luciferase assay buffer/Luciferase assay substrate and Stop and Glo® assay buffer/Stop and Glo® substrate were prepared according to kit instructions. 100 µL of the Luciferase system was added to each well using a multichannel pipette, before analysis using an EG&G Berthold Microlumat Plus luminometer. 100 µL of the Stop and Glo® system was subsequently added, and the plate was analysed once again by luminometer. Raw data was processed using Microsoft Excel, enabling generation of IC$_{50}$ values for each compound. IC$_{50}$ values obtained are based on the means of 3 experiments. Each data point is the mean of 3 values±standard deviation to produce one curve using Microsoft Excel. IC$_{50}$ values were calculated by eye.

Many compounds of the invention were found to have IC$_{50}$ values of less than 1 µM in ERK5 reporter and certain compounds have IC$_{50}$ values of less than 0.1 µM in ERK5 reporter.

EGF-Stimulated HeLa Cell Assay

The HeLa cell line is used commonly in the literature as a cell line in which the ERK5 pathway can be stimulated significantly by the addition of exogenous EGF. This provides a reproducible system to detect autophosphorylation of ERK5, and its inhibition (following compound treatment), in cells.

HeLa cells were serum starved overnight followed by treatment with ERK5 inhibitors for 1 hr. Cells were then stimulated with 100 ng/ml EGF for 10 or 15 min. The cells were harvested and lysed at 4° C. for 5-10 min in Laemmli buffer containing Halt protease and phosphate inhibitors (Pierce). The lysates were boiled for 10 min at 100° C. Twenty microliters sample was run on 6% or 7.5% Trisglycine gels and transferred to nitrocellulose. Western blotting was done with ERK5 antibody (Cell signalling #3372S). The IC$_{50}$ was calculated from densitometry of top bands.

Many compounds of the invention were found to have IC$_{50}$ values of less than 1 µM in Hela assay and certain compounds have IC$_{50}$ values of less than 0.1 µM in Hela assay.

p38α LANCE Assay

1× assay buffer was prepared consisting of the following reagents; 250 mM tris(hydroxymethyl)aminomethane (Tris) pH 7.5, 25 mM MgCl$_2$, 2.5 mM ethylene glycol tetraacetic acid (EGTA), 10 mM dithiothreitol (DTT) and 0.05% Tritonx100 in milliQ H$_2$O (NB: 1× buffer final assay concentrations were 5× lower than stated above).

The p38α/SAPK2 working solution was prepared using active N-terminal GST-tagged recombinant full length protein (Millipore 14-251) supplied as a 10 µg/4 µL stock. This was diluted to a 10 µg/40 µL (1 µM) concentration by addition of 156 µL of Tris/HCl (pH 7.5, 50 mM), NaCl (150 mM), EGTA (0.1 mM), Brij-35 surfactant (0.03%), glycerol (50%) and 0.1% 2-mercaptoethanol (0.1%). The final dilution was dependent on activity of the enzyme batches. The p38α concentration used in the assay was 1 nM. A 2× working stock solution (2 nM, 500 fold dilution of 1 µM stock) in 1× assay buffer was prepared. For one plate, 9.4 µL of p38α (1 µM) was added to 1870.6 µL of milliQ H$_2$O.

The ATP/substrate working solution for one plate used ATP disodium salt (17.5 µL, 200 mM stock), (Sigma A7699) and Ulight-MBP Peptide (50 µL, 5 µM stock) (Perkin Elmer TRF0109), which were added to 400 µL of 5× assay buffer and 1532.5 µL of milliQ H$_2$O.

The EDTA/antibody detection reagent for one plate consisted of; 84 µL of ethylenediaminetetraacetic acid (EDTA) (0.5 M) (Sigma E4378-100G) and 27 µL of Europium-antiphospho-MBP antibody (0.625 µM) (Perkin Elmer) added to 420 µL of LANCE detection buffer (1×) and 3669 of milliQ H$_2$O.

1 µL of compound (in 80:20 H$_2$O/DMSO) or 80:20 H$_2$O/DMSO was dry-spotted into the relevant wells of a 384-well assay plate using the MATRIX PlateMate® Plus. 5 µL of p38a working solution was added to test and control wells, and 5 µL of assay buffer added to blanks; 4 µL of ATP/substrate working solution was added to all wells using a Thermo Multidrop Combi or Matrix multichannel pipette. The plate was sealed using DMSO resistant clear seal and incubated for 1 h at 37° C. 10 µL of the EDTA/antibody working solution was added to all wells using a Thermo Multidrop Combi or Matrix multichannel pipette. The plate was incubated at RT in darkness for 2 h. The assay plate was then read on a PheraStar microplate reader using the settings described below and the IC$_{50}$ determined:

Pherastar: Measurement mode=TRF; Method ID=LANCE HTRF ERK5; Optic Module: 337, 665, 620 nm. Focal Height=6.0, Positioning delay, 0.1 sec, Number of flashes per well=100, Integration start=60 µs, Integration time=200 µs, Simultaneous dual emission, Ratio multiplicator=1000.

Certain compounds of the invention have 10-100 fold selectivity for ERK5 over p38.

Truncated Dual-Luciferase Reporter Assay

HEK293T and HeLa Forward Transfection

HEK293T or HeLa cells were seeded in 96-well luminescence (white) plates (1.68×10$^4$/well in 84 µl standard culture medium) and incubated overnight at 37° C. in a humidified atmosphere of 5% CO$_2$ in air. Next day, transfection mixtures were prepared as shown in Table 1. Plasmid DNA mastermix containing MEF2D-Gal4 (0.25 µg/µl), Gal4-Luc (1.25 µg/µl) and *Renilla* luciferase (0.1 µg/µl) was prepared in sterile distilled water. Constitutively-active, EGFP-tagged MEK5 (EGFP-MEK5D; 0.5 µg/µl), an EGFP-tagged construct containing no MEK5D (EGFP-C3; 0.5 µg/µl), and HA-tagged ERK5 with C-terminal truncation (HA-ERK5-ΔP493; 0.51 µg/µl) were diluted separately in sterile distilled water. Plasmid DNA and Lipofectamine 2000 (Invitrogen) were separately diluted in Opti-MEM growth media (reduced serum medium, Invitrogen), and incubated at room temperature for 5 min. Plasmid DNA (Tube A) and Lipofectamine 2000 (Tube B) were then combined and incubated for 20 min at room temperature to complex. Cells were then transfected by addition of 16 µl of the respective transfection mixture: 3 wells with EGFP-C3-containing (control) and 21 wells with MEK5D-containing transfection mixture (final volume, 100 µl). Cells were subsequently incubated for 4 h at 37° prior to addition of potential ERK5-inhibitory compounds.

Addition of Compounds to ERK5-Transfected HEK293T or HeLa Cells

Potential ERK5-inhibitory compounds were prepared as a 2× solution by addition of 2 μl compound (or DMSO as control) to 1 ml standard culture medium. Compounds were tested in triplicate at a concentration range of 0.003 μM, 0.01 μM, 0.03 μM, 0.1 μM, 0.3 μM and 1 μM (or 0.03 μM, 0.1 μM, 0.3 μM, 1 μM, 3 μM and 10 μM for BIX02189) by addition of 100 μl 2× solution to 100 μl transfected cells (final DMSO, 0.1% v/v). Cells were incubated for 24 h at 37° C.

Cell Lysis and Luciferase Quantification

After 24 h incubation in the absence (control) or presence of potential inhibitor, the culture medium was aspirated and cells lysed in 20 μl 1× passive lysis buffer (Dual-Luciferase Reporter Assay System, Promega) for a minimum of 15 min with agitation. Lysates were further processed immediately or stored at −80° C. Cellular inhibition of ERK5 was quantified using the Dual-Luciferase Reporter Assay System (Promega). Luciferase assay buffer/Luciferase assay substrate and Stop and Glo assay buffer/Stop and Glo substrate were prepared according to the manufacturer's instructions. Luciferase reagent (50 μl/well) was added immediately before luminescence detection using a FLUOstar Omega plate reader (BMG Labtech). Stop and Glo reagent (50 μl/well) was subsequently added, and the *Renilla* luciferase signal (transfection efficiency control) quantified.

Data Analysis

The ERK5-specific signalling activity was calculated by subtraction of the EGFP-C3 luciferase signal from the EGFP-MEK5D-induced luminescence. Luminescence in the absence of potential ERK5 inhibitor (DMSO control) was taken as 100% ERK5 activity. $IC_{50}$ values (the concentration of compound yielding 50% inhibition of ERK5 activity) were determined from point-to-point analyses using Graph-Pad Prism v.6. Unless stated otherwise, data are mean±standard deviation of three independent experiments.

TABLE 14

Transfection mixture volumes for the HEK293T and HeLa luciferase assay. Volumes are sufficient for the 3 control (EGFP-C3) and 21 test (MEK5D) wells required for each potential ERK5 inhibitory compound tested.

| Condition | Control | | MEK5D-activated ERK5 | |
| --- | --- | --- | --- | --- |
| Plasmid DNA | Tube A | Tube B | Tube A | Tube B |
| Mastermix | 1.6 μl | — | 11.0 μl | — |
| EGFP-C3 | 0.1 μl | — | — | — |
| EGFP-MEK5D | — | — | 0.4 μl | — |
| HA-ERK5-ΔP493 | 0.5 μl | — | 3.7 μl | — |
| Opti-MEM | 27 μl | 27 μl | 183 μl | 183 μl |
| Lipofectamine 2000 | — | 1.1 μl | — | 7.3 μl |

Proliferation Assay

The anti-proliferative activities of compounds of the invention can be determined by measuring the ability of the compounds to inhibition of cell growth in a number of cell lines. Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds for a further 72 hours. At the end of the incubation period 10% (v/v) Alamar Blue is added and incubated for a further 6 hours prior to determination of fluorescent product at 535 nM ex/590 nM em. In the case of the non-proliferating cell assay cells are maintained at confluence for 96 hour prior to the addition of inhibitor compounds for a further 72 hours. The number of viable cells is determined by Alamar Blue assay as before. In addition, any morphological changes are recorded. Cell lines can be obtained from the ECACC (European Collection of cell Cultures), DMSZ, or ATCC.

Data for the compounds of the invention in the above assays are provided in the table below.

| Ex | ERK5 $IC_{50}$ (uM) | HeLa $IC_{50}$ (uM) | ERK 5 Reporter Assay (uM) | Truncated ERK 5 Reporter Assay (uM) |
| --- | --- | --- | --- | --- |
| 1. | 0.657 | | | |
| 2. | 1.3539 | | | |
| 3. | 0.4866 | | 3.5 | |
| 4. | 0.0819 | | 2.3395 | |
| 5. | 0.4375 | | | |
| 6. | 0.4585 | | | |
| 7. | 0.0878 | | 0.968 | |
| 8. | 0.2977 | | | |
| 9. | 0.1438 | | 0.826 | |
| 10. | 0.2637 | | | |
| 11. | 0.5206 | | | |
| 12. | 1.7475 | | | |
| 13. | 3.4782 | | | |
| 14. | 4.1094 | | | |
| 15. | 0.0721 | 6.9 | 0.817 | |
| 16. | 0.037 | 0.32 | 0.56 | |
| 17. | 1.7467 | | | |
| 18. | ND | | | |
| 19. | 2.0814 | | | |
| 20. | 1.5028 | | | |
| 21. | 5.385 | | | |
| 22. | 9.6608 | | | |
| 23. | 0.093 | | | |
| 24. | 0.0141 | 0.080 | 1.1815 | |
| 25. | 0.0497 | 5.1 | | |
| 26. | 0.0888 | | | |
| 27. | 0.0132 | 0.1 | 0.242 | |
| 28. | 2.2322 | | | |
| 29. | 0.5368 | | | |
| 30. | 0.7896 | | | |
| 31. | 0.0915 | | 1.181 | |
| 32. | 0.0238 | | | |
| 33. | 0.0132 | 1.7 | 0.2832 | |
| 34. | 2.3223 | | | |
| 35. | 0.5231 | | | |
| 36. | 0.137 | | | |
| 37. | 0.036 | | | |
| 38. | 0.3428 | | | |
| 39. | ND | | | |
| 40. | 1.8273 | | | |
| 41. | 0.0166 | 2.7 | 0.1456 | |
| 42. | 3.5462 | | | |
| 43. | 0.2072 | | | |
| 44. | 0.0988 | 0.79 | | |
| 45. | 0.0267 | 0.22 | | 0.073 |
| 46. | 0.0665 | | | |
| 47. | 0.0752 | | | |
| 48. | 0.0807 | | | |
| 49. | 0.0202 | | | |
| 50. | 0.021 | | | |
| 51. | 0.0176 | | | |
| 52. | 0.1226 | | 8.8055 | |
| 53. | 0.0187 | 0.79 | | |
| 54. | 0.0317 | 0.14 | | |
| 55. | 0.0073 | 0.83 | 1.656 | |
| 56. | 0.0216 | | | |
| 57. | 0.725 | | | |
| 58. | 2.4822 | | | |
| 59. | 0.9518 | | | |

| # | Col2 | Col3 | Col4 | Col5 | Col6 |
|---|---|---|---|---|---|
| 60. | 0.5288 | | | | |
| 61. | 0.0269 | | | | |
| 62. | 0.0843 | | | | |
| 63. | 0.1044 | | | | |
| 64. | 2.9941 | | | | |
| 65. | 0.0538 | | | | |
| 66. | 0.0166 | | | | |
| 67. | 0.0163 | | | | |
| 68. | 0.0199 | | | | |
| 69. | 0.0157 | 0.7 | | | |
| 70. | 0.0579 | 1.7 | 0.477 | | |
| 71. | 0.1731 | | | | |
| 72. | 0.0908 | 1.9 | 2.9837 | | |
| 73. | 0.2547 | | | | |
| 74. | 0.2022 | | | | |
| 75. | 0.4365 | | | | |
| 76. | 1.5849 | | | | |
| 77. | 5.2847 | | | | |
| 78. | 2.82 | | | | |
| 79. | 5.8598 | | | | |
| 80. | 7.9814 | | | | |
| 81. | 0.3943 | | | | |
| 82. | 1.0475 | | | | |
| 83. | 3.5401 | | | | |
| 84. | 1.1841 | | | | |
| 85. | 6.0537 | | | | |
| 86. | 12.235 | | | | |
| 87. | 1.2602 | | | | |
| 88. | 2.1444 | | | | |
| 89. | 3.3366 | | | | |
| 90. | 2.1932 | | | | |
| 91. | 2.306 | | | | |
| 92. | 16.488 | | | | |
| 93. | 0.4831 | | | | |
| 94. | 1.6652 | | | | |
| 95. | 2.8226 | | | | |
| 96. | 1.0017 | | | | |
| 97. | 1.3793 | | | | |
| 98. | 8.7063 | | | | |
| 99. | 0.0153 | | | 0.122 | |
| 100. | 0.0193 | 0.49 | | 0.151 | |
| 101. | 0.1154 | | | | |
| 102. | 0.0166 | | | 0.085 | |
| 103. | 0.0368 | | | 0.135 | |
| 104. | 0.0104 | | | 0.090 | |
| 105. | 0.0207 | | | | |
| 106. | 0.02 | | | | |
| 107. | 0.0246 | 0.45 | | | |
| 108. | 0.022 | 0.48 | | | |
| 109. | 0.0108 | 0.05 | | 0.092 | |
| 110. | 0.0136 | 0.06 | | 0.026 | |
| 111. | 0.0051 | 0.29 | | | |
| 112. | 0.0061 | 0.30 | | 0.026 | |
| 113. | 0.0038 | | | | |
| 114. | 0.0040 | | | 0.022 | |
| 115. | 0.0265 | | | 0.031 | |
| 116. | 0.0218 | | | | |
| 117. | 0.0092 | | | | |
| 118. | 1.3101 | | | | |
| 119. | 0.5296 | | | | |
| 120. | 0.1995 | | | | |
| 121. | 0.9 | | | | |
| 122. | 1.1151 | | 26 | | |
| 123. | 2.8564 | | 25 | | |
| 124. | 2.2504 | | 23.3 | | |
| 125. | 31.04 | | | | |
| 126. | 1.2621 | | 18.3 | | |
| 127. | 11.516 | | | | |
| 128. | 13.764 | | | | |
| 129. | 1.1279 | | 6 | | |
| 130. | 2.14 | | | | |
| 131. | 2.6599 | | | | |
| 132. | 1.1461 | | | | |
| 133. | 1.7978 | | | | |
| 134. | 0.3676 | | | | |
| 135. | 0.6533 | | | | |
| 136. | 0.4009 | | | | |
| 137. | 1.0801 | | | | |
| 138. | 0.4394 | | | | |
| 139. | 0.8175 | | | | |
| 140. | 4.3466 | | | | |
| 141. | 7.7597 | | | | |
| 142. | 4.1273 | | | | |
| 143. | 4.9505 | | | | |
| 144. | 0.4037 | | | | |
| 145. | 0.6536 | | | | |
| 146. | 2.9376 | | | | |
| 147. | 34.203 | | | | |
| 148. | 0.9604 | | | | |
| 149. | 2.3875 | | | | |
| 150. | 1.0284 | | | | |
| 151. | 1.5276 | | | | |
| 152. | 1.4893 | | | | |
| 153. | 1.6956 | | | | |
| 154. | 1.1851 | | | | |
| 155. | 1.1881 | | | | |
| 156. | 1.5433 | | | | |
| 157. | 7.157 | | | | |
| 158. | 5.4655 | | | | |
| 159. | 1.4861 | | 24 | | |
| 160. | 1.7061 | | 30 | | |
| 161. | 2.4094 | | 16.7 | | |
| 162. | 1.3325 | | | | |
| 163. | 3.464 | | | | |
| 164. | 0.6099 | | | | |
| 165. | 1.5767 | | | | |
| 166. | 1.367 | | | | |
| 167. | 0.6427 | | | | |
| 168. | 2.4491 | | | | |
| 169. | 0.2652 | | | | |
| 170. | 0.3465 | | | | |
| 171. | 0.2828 | | | | |
| 172. | 0.0656 | 0.19 | 0.5985 | | |
| 173. | 0.3158 | | 0.508 | | |
| 174. | 0.1148 | | | | |
| 175. | 0.6491 | | | | |
| 176. | 1.1755 | | | | |
| 177. | 0.4724 | | | | |
| 178. | 0.5148 | | | | |
| 179. | 0.2632 | | | | |
| 180. | 0.4902 | | | | |
| 181. | 0.0665 | | | | |
| 182. | 0.6059 | | | | |
| 183. | 1.8767 | | 7.6667 | | |
| 184. | 5.6789 | | 10.3 | | |
| 185. | 1.8998 | | | | |
| 186. | 2.574 | | | | |
| 187. | 0.602 | | 2.3333 | | |
| 188. | 0.583 | | 4 | | |
| 189. | 0.6755 | | 4 | | |
| 190. | 0.8215 | 1.9 | 4.5 | 0.490 | |
| 191. | 1.4012 | | 19.5 | | |
| 192. | 0.1989 | | 3.006 | | |
| 193. | 1.0783 | | | | |
| 194. | 0.8446 | | | | |
| 195. | 0.2889 | | | | |
| 196. | 2.7204 | | | | |
| 197. | 0.3864 | | 22 | | |
| 198. | 1.2199 | | | | |
| 199. | 12.69 | | | | |
| 200. | 4.981 | | | | |
| 201. | 4.9728 | | | | |
| 202. | 22.996 | | | | |
| 203. | 5.8198 | | | | |
| 204. | 8.2342 | | | | |
| 205. | 2.8382 | | | | |
| 206. | 0.4004 | | | | |
| 207. | 1.0727 | | | | |
| 208. | 0.6111 | | | | |
| 209. | 0.5692 | | | | |
| 210. | 0.2908 | | | | |
| 211. | 0.2256 | | | | |
| 212. | 0.2921 | | | | |
| 213. | 0.1562 | | 3.5105 | | |
| 214. | 1.0067 | | | | |
| 215. | 0.6936 | | | | |
| 216. | 0.6365 | | | | |
| 217. | 0.6598 | | | | |

-continued

| | | |
|---|---|---|
| 218. | 0.7793 | |
| 219. | 0.6276 | |
| 220. | 0.3988 | |
| 221. | 0.7134 | |
| 222. | 0.5544 | |
| 223. | 0.1995 | |
| 224. | 0.1553 | |
| 225. | 6.0319 | 4.7715 |
| 226. | 8.564 | |
| 227. | 6.1551 | |
| 228. | 2.3847 | |
| 229. | 2.0568 | |
| 230. | 1.6601 | |
| 231. | 1.937 | |
| 232. | 4.0483 | |
| 233. | 5.2119 | |
| 234. | 4.3655 | |
| 235. | 0.0612 | |
| 236. | 0.0102 | 0.096 |
| 237. | 0.1479 | |
| 238. | 0.1186 | |
| 239. | 0.0866 | |
| 240. | 0.1268 | |
| 241. | | |
| 242. | 0.053 | |
| 243. | 0.129 | |
| 244. | 0.0072 | 0.113 |
| 245. | 0.013 | 0.461 |
| 246. | 0.0085 | 0.069 |
| 247. | 0.0181 | |
| 248. | 0.0067 | |
| 249. | 0.0082 | 0.244 |
| 250. | 0.0158 | 0.573 |
| 251. | 0.0079 | |
| 252. | 0.0122 | 0.627 |
| 253. | 0.0075 | 0.239 |
| 254. | 1.1912 | |
| 255. | 0.7357 | |
| 256. | 0.116 | |
| 257. | 0.2035 | |
| 258. | 0.6529 | |
| 259. | 0.4832 | |
| 260. | 1.1914 | |
| 261. | 0.5531 | |
| 262. | 0.0185 | 0.149 |
| 263. | 0.2115 | |
| 264. | 0.0111 | 0.142 |
| 265. | 7.4467 | |
| 266. | 1.9319 | |
| 267. | 1.7411 | |
| 268. | 2.8038 | |
| 269. | 0.7767 | |
| 270. | 0.4584 | |
| 271. | 1.2612 | |
| 272. | 0.073 | |
| 273. | 0.0583 | |
| 274. | 3.6385 | |
| 275. | 0.0071 | 0.107 |
| 276. | 0.0581 | 0.125 |
| 277. | 0.022 | 0.036 |
| 278. | 0.034 | 0.040 |
| 279. | 0.8739 | |
| 280. | 1.1993 | |
| 281. | 0.3905 | |
| 282. | 0.0067 | 0.044 |
| 283. | 0.1171 | |
| 284. | 0.009 | 0.013 |

| Ex | ERK5 IMAP IC$_{50}$ (µM) | ERK5-MEF2D (HeLa) IC$_{50}$ (µM) |
|---|---|---|
| 285. | 1.56 ± 0.05 | 0.671 + 0.023 |
| 286. | 7.07 ± 0.02 | 2.477 + 0.246 |
| 287. | 7.55 ± 0.30 | 3.203 + 0.534 |

Where more than one data point has been obtained, the table above shows an average (e.g. geometric mean) of these data points (to two significant figures).

Pharmaceutical Formulations (i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and optionally 1% by weight of magnesium stearate and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

(v) Injectable Formulation III

A formulation for i.v. delivery by injection or infusion can be prepared by dissolving the compound of formula (I) (e.g. in a salt form) in water at 20 mg/ml. The vial is then sealed and sterilised by autoclaving.

(vi) Injectable Formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (I) with pharmaceutical grade corn oil to give a concentration of 5 mg/ml. The composition is sterilised and filled into a suitable container.

(viii) Lyophilised formulation

Aliquots of formulated compound of formula (I) or a salt thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(ix) Lyophilised Formulation for Use in i.v. Administration

An aqueous buffered solution is prepared by dissolving compound of formula (I) or a salt thereof as defined herein at a concentration of 10-20 mg/ml in a buffer.

The buffered solution is filled, with filtration to remove particulate matter, into a container (such as class 1 glass vials) which is then partially sealed (e.g. by means of a Florotec stopper). If the compound and formulation are sufficiently stable, the formulation is sterilised by autoclaving at 121° C. for a suitable period of time. If the formulation is not stable to autoclaving, it can be sterilised using a suitable filter and filled under sterile conditions into sterile vials. The solution is freeze dried using a suitable cycle: for example Freezing—freeze to −40° C. over 2 hours and hold at −40° C. for 3 hours.

Primary drying—ramp −40° C. to −30° C. over 8 hours and hold at −30° C. for 7 hours.

Secondary drying—ramp to +30° C. over 4 hours and hold at +30° C. for 8-10 hours On completion of the freeze drying cycle the vials are back filled with nitrogen to atmospheric pressure, stoppered and secured (e.g. with an aluminium crimp). For intravenous administration, the freeze dried solid can be reconstituted into a pharmaceutically acceptable excipient, such as 0.9% saline or 5% dextrose. The solution can be dosed as is, or can be injected into an infusion bag (containing a pharmaceutically acceptable excipient, such as 0.9% saline or 5% dextrose), before administration.

Equivalents

The foregoing examples are presented for the purpose of illustrating the invention and should not be construed as imposing any limitation on the scope of the invention. It will readily be apparent that numerous modifications and alterations may be made to the specific embodiments of the invention described herein and illustrated in the examples without departing from the principles underlying the invention. All such modifications and alterations are intended to be embraced by this application.

The invention claimed is:

1. A compound of formula (I)

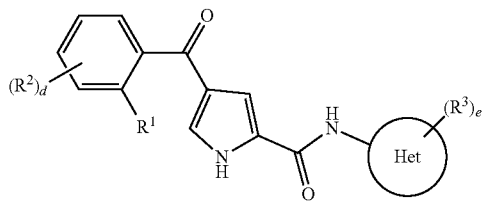

(I)

or a tautomer, stereoisomer, N-oxide, pharmaceutically acceptable salt or solvate thereof, wherein:

$R^1$ is halo;

Het is a monocyclic or bicyclic heterocyclic ring containing from 3 to 12 ring members which contains one or more heteroatoms independently selected from nitrogen, oxygen or sulfur;

d is 0, 1, 2 or 3;

$R^2$ is independently selected from -Q-$R^a$, —Y-carbocyclyl and —Y-heterocyclyl wherein the carbocyclyl and heterocyclyl groups contain 3 to 12 ring members and said carbocyclyl and heterocyclyl groups may be optionally substituted by one or more $R^c$; and wherein Y is independently selected from a bond, —C(=O)— (CR$^x$R$^y$)$_s$—, —(CR$^x$R$^y$)$_s$—C(=O)—, —C(=O)O—, —(CR$^x$R$^y$)$_n$—, —NR$^x$—(CR$^x$R$^y$)$_s$—, —(CR$^x$R$^y$)$_s$—NR$^x$—, —CONR$^x$—, —NR$^x$CO—, —SO$_2$NR$^x$—, —NR$^x$SO$_2$—, —NR$^x$C(=O)NR$^y$—, —NR$^x$CSNR$^y$—, —O—(CR$^x$R$^y$)$_s$—, —(CR$^x$R$^y$)$_s$—O—, —S—, —SO— and —(CR$^x$R$^y$)$_s$—SO$_2$—;

e is 0, 1, 2 or 3;

$R^3$ is independently selected from -Q-$R^b$, —Z-carbocyclyl and —Z-heterocyclyl wherein the carbocyclyl group contains 4 to 12 ring members, the heterocyclyl group contains 3 to 12 ring members and said carbocyclyl and heterocyclyl groups may be optionally substituted by one or more $R^c$; and wherein Z is independently selected from a bond, —C(=O)—(CR$^x$R$^y$)$_s$—, —(CR$^x$R$^y$)$_s$—C(=O)—, —C(=O)O—, —(CR$^x$R$^y$)$_n$—, —NR$^x$—(CR$^x$R$^y$)$_s$—, —(CR$^x$R$^y$)$_s$—NR$^x$—, —CONH—, —NHCO—, —SO$_2$NR$^x$—, —NR$^x$SO$_2$—, —NR$^x$C(=O)NR$^y$—, —NR$^x$CSNR$^y$—, —O—(CR$^x$R$^y$)$_s$—, —(CR$^x$R$^y$)$_s$—O—, —S—, —SO— and —(CR$^x$R$^y$)$_s$—SO$_2$—;

$R^a$ is independently selected from halogen, $C_{1-6}$ alkyl, $C_{2-6}$ alkenyl, $C_{2-6}$ alkynyl, —(CH$_2$)$_s$—$C_{3-8}$ cycloalkyl, —(CH$_2$)$_s$—$C_{3-8}$ cycloalkenyl, —(CH$_2$)$_s$-phenyl, —(CH$_2$)$_s$-(4-7 membered saturated heterocyclyl), —(CR$^x$R$^y$)$_s$—O—$R^z$, —O—(CR$^x$R$^y$)$_n$—OR$^z$, halo$C_{1-6}$ alkyl, halo$C_{1-6}$ alkoxy, $C_{1-6}$ alkanol, nitro, Si(R$^x$)$_4$, —(CH$_2$)$_s$—CN, —(CH$_2$)$_s$—S(O)$_q$—R$^x$, —C(=O)R$^x$, —(CR$^x$R$^y$)$_s$—C(=O)OR$^z$, —(CR$^x$R$^y$)$_s$—O—C(=O)—R$^z$, —(CR$^x$R$^y$)$_s$—C(=O)NR$^x$R$^y$, —(CH$_2$)$_s$—NR$^x$C(=O)R$^y$, —(CH$_2$)$_s$—OC(=O)NR$^x$R$^y$, —(CH$_2$)$_s$—NR$^x$C(=O)OR$^y$, —(CH$_2$)$_s$—NR$^x$R$^y$, —NR$^x$—(CH$_2$)$_s$—R$^z$, —(CH$_2$)$_s$—O—C(=O)—$C_{1-4}$alkyl-NR$^x$R$^y$, —(CH$_2$)$_s$—NR$^x$—(CH$_2$)$_n$—O—C(=O)—R$^z$, —(CH$_2$)$_s$—NR$^x$—(CH$_2$)$_s$—SO$_2$—R$^y$, —(CH$_2$)$_s$—NH—SO$_2$—NR$^x$R$^y$, —(CH$_2$)$_s$—SO$_2$NR$^x$R$^y$ groups and —P(=O)(R$^x$)$_2$, wherein the $C_{1-6}$ alkyl, $C_{2-6}$ alkenyl, $C_{2-6}$ alkynyl, $C_{3-8}$ cycloalkyl, $C_{3-8}$ cycloalkenyl, phenyl and heterocyclyl groups may be optionally substituted by one or more R$^x$;

$R^b$ and $R^c$ are independently selected from halogen, $C_{1-6}$ alkyl, $C_{2-6}$ alkenyl, $C_{2-6}$ alkynyl, —(CH$_2$)$_s$—C$_{4-8}$ cycloalkyl, —(CH$_2$)$_n$-cyclopropyl, —(CH$_2$)$_s$—$C_{3-8}$ cycloalkenyl, —(CH$_2$)$_s$-phenyl, —(CH$_2$)$_s$-(4-7 membered saturated heterocyclyl), —(CR$^x$R$^y$)$_s$—O—R$^z$, —O—(CR$^x$R$^y$)$_n$—OR$^z$, halo$C_{1-6}$ alkyl, halo$C_{1-6}$ alkoxy, $C_{1-6}$ alkanol, =O, =S, nitro, Si(R$^x$)$_4$, —(CH$_2$)$_s$—CN, —(CH$_2$)$_s$—S(O)$_q$—R$^x$, —C(=O)R$^x$, —(CR$^x$R$^y$)$_s$—C(=O)OR$^z$, —(CR$^x$R$^y$)$_s$—O—C(=O)—R$^z$, —(CR$^x$R$^y$)$_s$—C(=O)NR$^x$R$^y$, —(CH$_2$)$_s$—NHC(=O)R$^y$, —(CH$_2$)$_s$—OC(=O)NR$^x$R$^y$, —(CH$_2$)$_s$—NR$^x$C(=O)OR$^y$, —(CH$_2$)$_s$—NR$^x$R$^y$, —NR$^x$—(CH$_2$)$_s$—R$^z$, —(CH$_2$)$_s$—O—C(=O)—$C_{1-4}$alkyl-NR$^x$R$^y$, —(CH$_2$)$_s$—NR$^x$—(CH$_2$)$_n$—O—C(=O)—R$^z$, —(CH$_2$)$_s$—NR$^x$—(CH$_2$)$_s$—SO$_2$—R$^y$, —(CH$_2$)$_s$—NH—SO$_2$—NR$^x$R$^y$, —(CH$_2$)$_s$—SO$_2$NR$^x$R$^y$ groups and —P(=O)(R$^x$)$_2$, wherein the $C_{1-6}$ alkyl, $C_{2-6}$ alkenyl, $C_{2-6}$ alkynyl, $C_{3-8}$ cycloalkyl, $C_{3-8}$ cycloalkenyl, phenyl and heterocyclyl groups may be optionally substituted by one or more R$^x$;

Q is independently selected from NR$^x$ and a bond;

$R^x$, $R^y$ and $R^z$ are independently selected from halogen, hydrogen, $C_{1-6}$ alkyl, $C_{2-6}$ alkenyl, $C_{2-6}$ alkynyl, —(CH$_2$)$_s$—$C_{3-8}$ cycloalkyl, —(CH$_2$)$_s$—$C_{3-8}$ cycloalkenyl, —(CH$_2$)$_n$-phenyl, —(CH$_2$)$_s$-(4-7 membered saturated heterocyclyl), $C_{1-6}$ alkanol optionally substituted with one or more halo, —C(=O)OC$_{1-6}$ alkyl, hydroxy, $C_{1-6}$ alkoxy, halo$C_{1-6}$ alkyl, —(CH$_2$)$_n$—O—$C_{1-6}$alkyl, —C(=O)—(CH$_2$)$_n$—$C_{1-6}$ alkoxy, —C(=O)—$C_{1-6}$alkyl, —(CH$_2$)$_s$—CN, $C_{1-6}$ alkyl-N(H)$_{2-q}$(C$_{1-6}$alkyl)$_q$, —N(H)$_{2-q}$(C$_{1-6}$alkyl)$_q$, —C(=O)—N(H)$_{2-q}$(C$_{1-6}$alkyl)$_q$, —(CH$_2$)$_s$—NH—SO$_2$—N(H)$_{2-q}$(C$_{1-6}$alkyl)$_q$, —(CH$_2$)$_s$—N(C$_{1-4}$alkyl)-SO$_2$—N(H)$_{2-q}$(C$_{1-6}$alkyl)$_q$ and —(CH$_2$)$_s$—O—C(=O)—C$_{1-4}$alkyl-N(H)$_{2-q}$(C$_{1-6}$alkyl)$_q$, and when attached to nitrogen, carbon, silicon or phosphorus atom $R^x$ and $R^y$ may join to form a 3-7 membered ring optionally containing one or two additional heteroatoms selected from nitrogen, oxygen or sulfur;

s is independently selected from 0, 1, 2, 3 and 4;

n is independently selected from 1, 2, 3 and 4; and q is independently selected from 0, 1 and 2.

2. A compound of formula (I) according to claim 1, wherein Het is a monocyclic or bicyclic heterocyclic ring containing from 3 to 12 ring members which contains one or more nitrogen atom and optionally one or more heteroatoms independently selected from oxygen and sulfur.

3. A compound of formula (I) according to claim 1, wherein Het is a monocyclic heterocyclic ring containing 5 or 6 ring members which contains one or two nitrogen atoms and optionally one heteroatom selected from oxygen and sulphur.

4. A compound of formula (I) according to claim 1, wherein Het is pyridyl, pyrazolyl, pyrrolyl, imidazolyl, pyrazinyl, pyrimidinyl, pyridazinyl, triazinyl or tetrazolyl.

5. A compound of formula (I) according to claim 4, wherein Het is pyridyl or pyrazolyl.

6. A compound of formula (I) according to claim 1, wherein $R^1$ is F, Cl, or Br.

7. A compound of formula (I) according to claim 1, wherein $R^1$ is F.

8. A compound of formula (I) according to claim 1, wherein $R^2$ is independently selected from -Q-$R^a$, wherein $R^a$ is independently selected from halogen, $C_{1-6}$ alkyl, $C_{2-6}$ alkenyl, $C_{2-6}$ alkynyl, —$(CH_2)_s$—$C_{3-8}$ cycloalkyl, —$(CH_2)_s$—$C_{3-8}$ cycloalkenyl, —$(CH_2)_s$-phenyl, —$(CH_2)_s$-(4-7 membered saturated heterocyclyl), —$(CR^xR^y)_s$—O—$R^z$, —O—$(CR^xR^y)_n$—$OR^z$, halo$C_{1-6}$ alkyl, halo$C_{1-6}$ alkoxy, $C_{1-6}$ alkanol, nitro, $Si(R^x)_4$, —$(CH_2)_s$—CN, —$(CH_2)_s$—S(O)$_q$—$R^x$, —C(=O)$R^x$, —$(CR^xR^y)_s$—C(=O)$OR^z$, —$(CR^xR^y)_s$—O—C(=O)—$R^z$, —$(CR^xR^y)_s$—C(=O)$NR^xR^y$, —$(CH_2)_s$—$NR^xC$(=O)$R^y$, —$(CH_2)_s$—OC(=O)$NR^xR^y$, —$(CH_2)_s$—$NR^xC$(=O)$OR^y$, —$(CH_2)_s$—$NR^xR^y$, —$NR^x$—$(CH_2)_s$—$R^z$, —$(CH_2)_s$—O—C(=O)—$C_{1-4}$alkyl-$NR^xR^y$, —$(CH_2)_s$—$NR^x$—$(CH_2)_n$—O—C(=O)—$R^z$, —$(CH_2)_s$—$NR^x$—$(CH_2)_s$—$SO_2$—$R^y$, —$(CH_2)_s$—NH—$SO_2$—$NR^xR^y$, —$(CH_2)_s$—$SO_2NR^xR^y$ groups and —P(=O)$(R^x)_2$, wherein the $C_{1-6}$ alkyl, $C_{2-6}$ alkenyl, $C_{2-6}$ alkynyl, $C_{3-8}$ cycloalkyl, $C_{3-8}$ cycloalkenyl, phenyl and heterocyclyl groups may be optionally substituted by one or more $R^x$;
Q is independently selected from $NR^x$ and a bond;
$R^x$, $R^y$ and $R^z$ are independently selected from halogen, hydrogen, $C_{1-6}$ alkyl, $C_{2-6}$ alkenyl, $C_{2-6}$ alkynyl, —$(CH_2)_s$—$C_{3-8}$ cycloalkyl, —$(CH_2)_s$—$C_{3-8}$ cycloalkenyl, —$(CH_2)_n$-phenyl, —$(CH_2)_s$-(4-7 membered saturated heterocyclyl), $C_{1-6}$ alkanol optionally substituted with one or more halo, —C(=O)O$C_{1-6}$ alkyl, hydroxy, $C_{1-6}$ alkoxy and halo$C_{1-6}$ alkyl;
s is independently selected from 0, 1, 2, 3 and 4;
n is independently selected from 1, 2, 3 and 4; and
q is independently selected from 0, 1 and 2.

9. A compound of formula (I) according to claim 1, wherein:
$R^2$ is -Q-$R^a$ and Q is a bond, or $R^2$ is independently selected from halogen, $C_{1-6}$ alkyl, $C_{2-6}$ alkenyl, $C_{2-6}$ alkynyl, hydroxyl, $C_{1-6}$ alkoxy, halo$C_{1-6}$ alkyl, halo$C_{1-6}$ alkoxy and $C_{1-6}$ alkanol, or
$R^2$ is independently selected from halogen, $C_{1-6}$ alkyl, $C_{1-6}$ alkoxy and halo$C_{1-6}$ alkyl, or
$R^2$ is independently selected from halogen, $C_{1-3}$ alkyl, $C_{1-3}$ alkoxy and halo$C_{1-3}$alkyl, or
$R^2$ is independently selected from F, Cl, and —$OCH_3$.

10. A compound of formula (I) according to claim 1, wherein d is 1 or 2.

11. A compound of formula (I) according to claim 1, wherein $R^3$ is independently selected from -Q-$R^b$, —Z-carbocyclyl and —Z-heterocyclyl wherein the carbocyclyl group contains 4 to 12 ring members, the heterocyclyl group contains 3 to 12 ring members and said carbocyclyl and heterocyclyl groups may be optionally substituted by one or more $R^b$; and wherein Z is independently selected from a bond, —$(CR^xR^y)_n$—, —$NR^x$—$(CR^xR^y)_s$—, —$(CR^xR^y)_s$—$NR^x$—, —O—$(CR^xR^y)_s$—, and —$(CR^xR^y)_s$—O—;
$R^b$ is independently selected from halogen, $C_{1-6}$ alkyl, $C_{2-6}$ alkenyl, $C_{2-6}$ alkynyl, —$(CH_2)_s$—$C_{4-8}$ cycloalkyl, —$(CH_2)_n$-cyclopropyl, —$(CH_2)_s$—$C_{3-8}$ cycloalkenyl, —$(CH_2)_s$-phenyl, —$(CH_2)_s$-(4-7 membered saturated heterocyclyl), —$(CR^xR^y)_s$—O—$R^z$, —O—$(CR^xR^y)_n$—$OR^z$, halo$C_{1-6}$ alkyl, halo$C_{1-6}$ alkoxy, $C_{1-6}$ alkanol, —C(=O)$R^x$, —$(CR^xR^y)_s$—C(=O)$OR^z$, —$(CR^xR^y)_s$—O—C(=O)—$R^z$, —$(CR^xR^y)_s$—C(=O)$NR^xR^y$, —$(CH_2)_s$—NHC(=O)$R^y$, —$(CH_2)_s$—OC(=O)$NR^xR^y$, —$(CH_2)_s$—$NR^xC$(=O)$OR^y$, —$(CH_2)_s$—$NR^xR^y$, —$NR^x$—$(CH_2)_s$—$R^z$, —$(CH_2)_s$—O—C(=O)—$C_{1-4}$alkyl-$NR^xR^y$, —$(CH_2)_s$—$NR^x$—$(CH_2)_n$—O—C(=O)—$R^z$, —$(CH_2)_s$—$NR^x$—$(CH_2)_s$—$SO_2$—$R^y$, —$(CH_2)_s$—NH—$SO_2$—$NR^xR^y$, —$(CH_2)_s$—$SO_2NR^xR^y$ groups and —P(=O)$(R^x)_2$, wherein the $C_{1-6}$ alkyl, $C_{2-6}$ alkenyl, $C_{2-6}$ alkynyl, $C_{3-8}$ cycloalkyl, $C_{3-8}$ cycloalkenyl, phenyl and heterocyclyl groups may be optionally substituted by one or more $R^x$;
Q is independent selected from $NR^x$ and a bond;
$R^x$, $R^y$ and $R^z$ are independently selected from halogen, hydrogen, $C_{1-6}$ alkyl, $C_{2-6}$ alkenyl, $C_{2-6}$ alkynyl, —$(CH_2)_s$—$C_{3-8}$ cycloalkyl, —$(CH_2)_s$—$C_{3-8}$ cycloalkenyl, —$(CH_2)_n$-phenyl, —$(CH_2)_s$-(4-7 membered saturated heterocyclyl), $C_{1-6}$ alkanol optionally substituted with one or more halo, —C(=O)O$C_{1-6}$ alkyl, hydroxy, $C_{1-6}$ alkoxy and halo$C_{1-6}$ alkyl;
s is independently selected from 0, 1, 2, 3 and 4; and
n is independently selected from 1, 2, 3 and 4.

12. A compound of formula (I) according to claim 1, wherein $R^3$ is independently selected from halogen, $C_{1-6}$ alkyl, $C_{2-6}$ alkenyl, $C_{2-6}$ alkynyl, hydroxyl, $C_{1-6}$ alkoxy, halo$C_{1-6}$ alkyl, halo$C_{1-6}$ alkoxy, $C_{1-6}$ alkanol or —Z-carbocyclyl and —Z-heterocyclyl wherein the carbocyclyl group contains 4 to 12 ring members, the heterocyclyl group contains 3 to 12 ring members and said carbocyclyl and heterocyclyl groups may be optionally substituted by one or more $R^c$;
and wherein Z is independently selected from a bond, —$(CR^xR^y)_n$—, —$NR^x$—$(CR^xR^y)_s$—, —$(CR^xR^y)_s$—$NR^x$—, —O—$(CR^xR^y)_s$—, and —$(CR^xR^y)_s$—O—;
$R^b$ is independently selected from halogen, $C_{1-6}$ alkyl, $C_{2-6}$ alkenyl, $C_{2-6}$ alkynyl, hydroxyl, $C_{1-6}$ alkoxy, halo$C_{1-6}$ alkyl, and halo$C_{1-6}$ alkoxy;
$R^x$ and $R^y$ are selected from halogen, hydrogen, $C_{1-6}$ alkyl, $C_{2-6}$ alkenyl, $C_{2-6}$ alkynyl, —$(CH_2)_s$—$C_{3-8}$ cycloalkyl, —$(CH_2)_s$—$C_{3-8}$ cycloalkenyl, —$(CH_2)_n$-phenyl, —$(CH_2)_s$-(4-7 membered saturated heterocyclyl), $C_{1-6}$ alkanol optionally substituted with one or more halo, —C(=O)O$C_{1-6}$ alkyl, hydroxy, $C_{1-6}$ alkoxy and halo$C_{1-6}$ alkyl;
s is independently selected from 0, 1, 2, 3 and 4; and
n is independently selected from 1, 2, 3 and 4.

13. A compound of formula (I) according to claim 1, wherein:
$R^3$ is independently selected from $C_{1-6}$ alkyl, $C_{2-6}$ alkenyl, $C_{2-6}$ alkynyl, and —Z-heterocyclyl wherein the heterocyclyl group contains 5 or 6 ring members and contains one or more nitrogen atom and optionally one or more heteroatoms independently selected from oxygen and sulphur, and the heterocyclyl group may be optionally substituted by one or more $R^c$;

and wherein Z is independently selected from a bond, —(CH$_2$)$_n$—, —NR$^x$—(CH$_2$)$_s$—, —(CH$_2$)$_s$—NR$^x$—, —O—(CH$_2$)$_s$—, and —(CH$_2$)$_s$—O—;
R$^b$ is independently selected from C$_{1-6}$ alkyl, C$_{2-6}$ alkenyl, C$_{2-6}$ alkynyl, hydroxyl, C$_{1-6}$ alkoxy, haloC$_{1-6}$ alkyl, and haloC$_{1-6}$ alkoxy;
R$^x$ and R$^y$ are independently selected from C$_{1-6}$ alkyl, C$_{2-6}$ alkenyl, C$_{2-6}$ alkynyl, hydroxyl, C$_{1-6}$ alkoxy, haloC$_{1-6}$ alkyl, and haloC$_{1-6}$ alkoxy;
s is independently selected from 0, 1, 2, 3 and 4; and
n is independently selected from 1, 2, 3 and 4, or
R$^3$ is independently selected from —Z-heterocyclyl wherein the heterocyclyl group is pyridinyl and piperidnyl, and may be substituted by one or more R$^c$;
and wherein Z is independently selected from a bond, —(CH$_2$)$_n$—, —NR$^x$—(CH$_2$)$_s$—, —(CH$_2$)$_s$—NR$^x$—, —O—(CH$_2$)$_s$ and —(CH$_2$)$_s$—O—;
R$^c$ is independently selected from C$_{1-6}$ alkyl, C$_{2-6}$ alkenyl, C$_{2-6}$ alkynyl, hydroxyl, C$_{1-6}$ alkoxy, haloC$_{1-6}$ alkyl, and haloC$_{1-6}$ alkoxy;
R$^x$ and R$^y$ are independently selected from C$_{1-6}$ alkyl, C$_{2-6}$ alkenyl, C$_{2-6}$ alkynyl, hydroxyl, C$_{1-6}$ alkoxy, haloC$_{1-6}$ alkyl, and haloC$_{1-6}$ alkoxy;
s is independently selected from 0, 1, 2, 3 and 4; and
n is independently selected from 1, 2, 3 and 4.

14. A compound of formula (I) according to claim 1, wherein the compound is of the formula (IIIb):

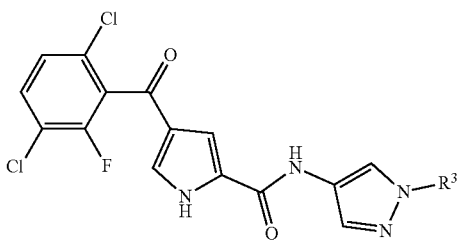

(IIIb)

wherein R$^3$ is C$_{1-6}$ alkyl, or wherein the compound is of the formula (IIc):

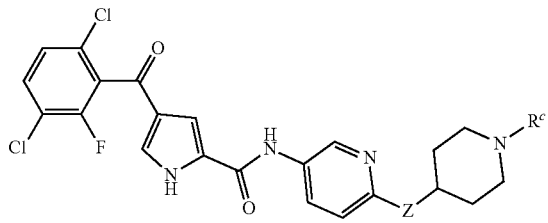

(IIc)

wherein Z is a bond, —(CH$_2$)$_s$—, —NH—(CH$_2$)$_s$— or —O—(CH$_2$)$_s$—, wherein s is 0, 1, 2 or 3, and R$^c$ is H or C$_{1-3}$ alkyl.

15. A compound according to claim 1, or a tautomer, stereoisomer, N-oxide, pharmaceutically acceptable salt or solvate thereof, wherein the compound is selected from:
4-(2-Chloro-6-fluorobenzoyl)-N-(1-isopropylpiperidin-4-yl)-1H-pyrrole-2-carboxamide;
tert-Butyl 4-(4-(3,6-dichloro-2-fluorobenzoyl)-1H-pyrrole-2-carboxamido) piperidine-1-carboxylate;
4-(2-Chloro-6-fluorobenzoyl)-N-(piperidin-4-yl)-1H-pyrrole-2-carboxamide;
4-(3,6-Dichloro-2-fluorobenzoyl)-N-(piperidin-4-yl)-1H-pyrrole-2-carboxamide;
4-(2-Chloro-6-fluorobenzoyl)-N-(1-ethylpiperidin-4-yl)-1H-pyrrole-2-carb oxamide;
N-(1-Acetylpiperidin-4-yl)-4-(2-chloro-6-fluorobenzoyl)-1H-pyrrole-2-carboxamide;
N-(1-Acetylpiperidin-4-yl)-4-(3,6-dichloro-2-fluorobenzoyl)-1H-pyrrole-2-carboxamide;
4-(2-Chloro-6-fluorobenzoyl)-N-(1-(methylsulfonyl)piperidin-4-yl)-1H-pyrrole-2-carboxamide;
4-(3,6-Dichloro-2-fluorobenzoyl)-N-(1-(methylsulfonyl) piperidin-4-yl)-1H-pyrrole-2-carboxamide;
4-(2-Chloro-6-fluorobenzoyl)-N-(1-(pyrimidin-2-yl)piperidin-4-yl)-1H-pyrrole-2-carboxamide;
4-(3,6-Dichloro-2-fluorobenzoyl)-N-(1-(2,2,2-trifluoroacetyl)piperidin-4-yl)-1H-pyrrole-2-carboxamide;
4-(2-Chloro-6-fluorobenzoyl)-N-(2-(methylamino)pyrimidin-5-yl)-1H-pyrrole-2-carboxamide;
4-(2-Chloro-6-fluorobenzoyl)-N-(2-(dimethylamino)pyrimidin-5-yl)-1H-pyrrole-2-carboxamide;
4-(2-Chloro-6-fluorobenzoyl)-N-(2-(pyrrolidin-1-yl)pyrimidin-5-yl)-1H-pyrrole-2-carboxamide;
4-(2-Chloro-6-fluorobenzoyl)-N-(2-(4-methylpiperazin-1-yl)pyrimidin-5-yl)-1H-pyrrole-2-carboxamide;
4-(3,6-Dichloro-2-fluorobenzoyl)-N-(2-(4-methylpiperazin-1-yl)pyrimidin-5-yl)-1H-pyrrole-2-carboxamide;
N-(2-(4-cyclopropylpiperazin-1-yl)pyrimidin-5-yl)-4-(3,6-dichloro-2-fluorobenzoyl)-1H-pyrrole-2-carboxamide;
tert-Butyl 4-(5-(4-(3,6-dichloro-2-fluorobenzoyl)-1H-pyrrole-2-carboxamido)pyrimidin-2-yl)piperazine-1-carboxylate;
4-(2-Chloro-6-fluorobenzoyl)-N-(2-morpholinopyrimidin-5-yl)-1H-pyrrole-2-carboxamide;
4-(3,6-Dichloro-2-fluorobenzoyl)-N-(2-morpholinopyrimidin-5-yl)-1H-pyrrole-2-carboxamide;
1-(5-(4-(2-Chloro-6-fluorobenzoyl)-1H-pyrrole-2-carboxamido)pyrimidin-2-yl)piperidin-4-yl acetate;
1-(5-(4-(3,6-Dichloro-2-fluorobenzoyl)-1H-pyrrole-2-carboxamido) pyrimidin-2-yl)piperidin-4-yl acetate;
4-(2-Chloro-6-fluorobenzoyl)-N-(2-((1-methylpiperidin-4-yl)amino) pyrimidin-5-yl)-1H-pyrrole-2-carboxamide;
4-(3,6-Dichloro-2-fluorobenzoyl)-N-(2-((1-methylpiperidin-4-yl)amino)pyrimidin-5-yl)-1H-pyrrole-2-carboxamide;
N-(2-((1-Cyclopropylpiperidin-4-yl)amino)pyrimidin-5-yl)-4-(3,6-dichloro-2-fluorobenzoyl)-1H-pyrrole-2-carboxamide;
4-(2-Chloro-6-fluorobenzoyl)-N-(2-(piperazin-1-yl)pyrimidin-5-yl)-1H-pyrrole-2-carboxamide;
4-(3,6-Dichloro-2-fluorobenzoyl)-N-(2-(piperazin-1-yl) pyrimidin-5-yl)-1H-pyrrole-2-carboxamide;
4-(2-Chloro-6-fluorobenzoyl)-N-(2-(4-hydroxypiperidin-1-yl)pyrimidin-5-yl)-1H-pyrrole-2-carboxamide;
4-(3,6-Dichloro-2-fluorobenzoyl)-N-(2-(4-hydroxypiperidin-1-yl)pyrimidin-5-yl)-1H-pyrrole-2-carboxamide;
4-(2-Chloro-6-fluorobenzoyl)-N-(2-methoxypyrimidin-5-yl)-1H-pyrrole-2-carboxamide;
4-(2-Chloro-6-fluorobenzoyl)-N-(6-(4-methylpiperazin-1-yl)pyridin-3-yl)-1H-pyrrole-2-carboxamide;
4-(3,6-Dichloro-2-fluorobenzoyl)-N-(6-((1-methylpiperidin-4-yl)amino)pyridin-3-yl)-1H-pyrrole-2-carboxamide;

4-(3,6-Dichloro-2-fluorobenzoyl)-N-(6-(piperazin-1-yl)pyridin-3-yl)-1H-pyrrole-2-carboxamide;
4-(2-Chloro-6-fluorobenzoyl)-N-(2-chloropyridin-4-yl)-1H-pyrrole-2-carb oxamide;
4-(2-Chloro-6-fluorobenzoyl)-N-(2-(pyrrolidin-1-yl)pyridin-4-yl)-1H-pyrrole-2-carboxamide;
4-(2-Chloro-6-fluorobenzoyl)-N-(2-(4-methylpiperazin-1-yl)pyridin-4-yl)-1H-pyrrole-2-carboxamide;
4-(3,6-Dichloro-2-fluorobenzoyl)-N-(2-(4-methylpiperazin-1-yl)pyridin-4-yl)-1H-pyrrole-2-carboxamide;
4-(3,6-Dichloro-2-fluorobenzoyl)-N-(2-morpholinopyridin-4-yl)-1H-pyrrole-2-carboxamide;
4-(2-Chloro-6-fluorobenzoyl)-N-(2-(trifluoromethyl)pyridin-4-yl)-1H-pyrrole-2-carboxamide;
4-(2-Chloro-6-fluorobenzoyl)-N-(2-methoxypyridin-4-yl)-1H-pyrrole-2-carboxamide;
4-(3,6-Dichloro-2-fluorobenzoyl)-N-(1-((1-methylpiperidin-4-yl)methyl)-1H-pyrazol-4-yl)-1H-pyrrole-2-carboxamide;
4-(3,6-Dichloro-2-fluorobenzoyl)-N-(1-(1-(2,2,2-trifluoroethyl)piperidin-4-yl)-1H-pyrazol-4-yl)-1H-pyrrole-2-carboxamide;
4-(3,6-Dichloro-2-fluorobenzoyl)-N-(1-(2-(diethylamino)ethyl)-1H-pyrazol-4-yl)-1H-pyrrole-2-carboxamide;
4-(3,6-Dichloro-2-fluorobenzoyl)-N-(1H-pyrazol-4-yl)-1H-pyrrole-2-carboxamide;
4-(3,6-Dichloro-2-fluorobenzoyl)-N-(1-methyl-1H-pyrazol-4-yl)-1H-pyrrole-2-carboxamide;
4-(3,6-Dichloro-2-fluorobenzoyl)-N-(1-ethyl-1H-pyrazol-4-yl)-1H-pyrrole-2-carboxamide;
4-(3,6-Dichloro-2-fluorobenzoyl)-N-(1-(2-methoxyethyl)-1H-pyrazol-4-yl)-1H-pyrrole-2-carboxamide;
4-(3,6-Dichloro-2-fluorobenzoyl)-N-(1-(pyridin-2-ylmethyl)-1H-pyrazol-4-yl)-1H-pyrrole-2-carboxamide;
4-(3,6-Dichloro-2-fluorobenzoyl)-N-(1-(pyridin-3-ylmethyl)-1H-pyrazol-4-yl)-1H-pyrrole-2-carboxamide;
4-(3,6-Dichloro-2-fluorobenzoyl)-N-(1-(pyridin-4-ylmethyl)-1H-pyrazol-4-yl)-1H-pyrrole-2-carboxamide;
4-(3,6-Dichloro-2-fluorobenzoyl)-N-(1-((1-methyl-1H-imidazol-2-yl)methyl)-1H-pyrazol-4-yl)-1H-pyrrole-2-carboxamide;
4-(2-Chloro-6-fluorobenzoyl)-N-(1-(piperidin-4-yl)-1H-pyrazol-4-yl)-1H-pyrrole-2-carboxamide;
4-(3,6-Dichloro-2-fluorobenzoyl)-N-(1-(piperidin-4-yl)-1H-pyrazol-4-yl)-1H-pyrrole-2-carboxamide;
N-(1-(Azetidin-3-yl)-1H-pyrazol-4-yl)-4-(3,6-dichloro-2-fluorobenzoyl)-1H-pyrrole-2-carboxamide;
4-(3,6-Dichloro-2-fluorobenzoyl)-N-(1-(piperidin-4-ylmethyl)-1H-pyrazol-4-yl)-1H-pyrrole-2-carboxamide;
4-(3,6-Dichloro-2-fluorobenzoyl)-N-(1-(1-methylpiperidin-4-yl)-1H-pyrazol-4-yl)-1H-pyrrole-2-carboxamide;
4-(3,6-Dichloro-2-fluorobenzoyl)-N-(3-methylisoxazol-5-yl)-1H-pyrrole-2-carboxamide;
4-(3,6-Dichloro-2-fluorobenzoyl)-N-(5-methylisoxazol-3-yl)-1H-pyrrole-2-carboxamide;
4-(3,6-Dichloro-2-fluorobenzoyl)-N-(1-methyl-1H-pyrazol-3-yl)-1H-pyrrole-2-carboxamide;
4-(3,6-Dichloro-2-fluorobenzoyl)-N-(1-methyl-1H-imidazol-4-yl)-1H-pyrrole-2-carboxamide;
4-(6-Chloro-2-fluoro-3-methoxybenzoyl)-N-(6-((1-methylpiperidin-4-yl)amino)pyridin-3-yl)-1H-pyrrole-2-carboxamide;
4-(6-Chloro-2-fluoro-3-methoxybenzoyl)-N-(1-methyl-1H-pyrazol-4-yl)-1H-pyrrole-2-carboxamide;
4-(6-Chloro-2-fluoro-3-methoxybenzoyl)-N-(1-(2-methoxyethyl)-1H-pyrazol-4-yl)-1H-pyrrole-2-carboxamide;
4-(6-Chloro-2-fluoro-3-methoxybenzoyl)-N-(1-(1-(2,2,2-trifluoroethyl) piperidin-4-yl)-1H-pyrazol-4-yl)-1H-pyrrole-2-carboxamide;
4-(6-Chloro-2-fluoro-3-methoxybenzoyl)-N-(1-(pyridin-2-ylmethyl)-1H-pyrazol-4-yl)-1H-pyrrole-2-carboxamide;
4-(6-Chloro-2-fluoro-3-methoxybenzoyl)-N-(1-(pyridin-3-ylmethyl)-1H-pyrazol-4-yl)-1H-pyrrole-2-carboxamide;
4-(6-Chloro-2-fluoro-3-methoxybenzoyl)-N-(1-(pyridin-4-ylmethyl)-1H-pyrazol-4-yl)-1H-pyrrole-2-carboxamide;
4-(6-Chloro-2-fluoro-3-methoxybenzoyl)-N-(1-((1-methylpiperidin-4-yl)methyl)-1H-pyrazol-4-yl)-1H-pyrrole-2-carboxamide;
4-(6-Chloro-2-fluoro-3-methoxybenzoyl)-N-(6-(piperazin-1-yl)pyridin-3-yl)-1H-pyrrole-2-carboxamide;
4-(6-chloro-2-fluoro-3-methoxybenzoyl)-N-(1-methylpiperidin-4-yl)-1H-pyrrole-2-carboxamide;
4-(2-chloro-6-fluoro-3-methoxybenzoyl)-N-(1-methylpiperidin-4-yl)-1H-pyrrole-2-carboxamide;
4-(6-chloro-2-fluoro-3-methoxybenzoyl)-N-(pyridin-3-yl)-1H-pyrrole-2-carboxamide;
4-(2-chloro-6-fluoro-3-methoxybenzoyl)-N-(pyridin-3-yl)-1H-pyrrole-2-carboxamide;
4-(6-chloro-2-fluoro-3-methoxybenzoyl)-N-(pyrimidin-5-yl)-1H-pyrrole-2-carboxamide;
4-(2-chloro-6-fluoro-3-methoxybenzoyl)-N-(pyrimidin-5-yl)-1H-pyrrole-2-carboxamide;
4-(2-Chloro-6-fluorobenzoyl)-N-(2-ethylpyridin-3-yl)-1H-pyrrole-2-carboxamide;
4-(2-Chloro-6-fluorobenzoyl)-N-(2-propylpyridin-3-yl)-1H-pyrrole-2-carboxamide;
4-(2-Chloro-6-fluorobenzoyl)-N-(2-methoxypyridin-3-yl)-1H-pyrrole-2-carboxamide;
4-(2-Chloro-6-fluorobenzoyl)-N-(2-ethoxypyridin-3-yl)-1H-pyrrole-2-carb oxamide;
4-(2-Chloro-6-fluorobenzoyl)-N-(2-(pyrrolidin-1-yl)pyridin-3-yl)-1H-pyrrole-2-carboxamide;
4-(3,6-Dichloro-2-fluorobenzoyl)-N-(2-methylpyridin-3-yl)-1H-pyrrole-2-carboxamide;
4-(3,6-Dichloro-2-fluorobenzoyl)-N-(2-ethylpyridin-3-yl)-1H-pyrrole-2-carboxamide;
4-(3,6-Dichloro-2-fluorobenzoyl)-N-(2-propylpyridin-3-yl)-1H-pyrrole-2-carboxamide;
4-(3,6-Dichloro-2-fluorobenzoyl)-N-(2-methoxypyridin-3-yl)-1H-pyrrole-2-carboxamide;
4-(3,6-Dichloro-2-fluorobenzoyl)-N-(2-ethoxypyridin-3-yl)-1H-pyrrole-2-carboxamide;
4-(3,6-Dichloro-2-fluorobenzoyl)-N-(2-(pyrrolidin-1-yl)pyridin-3-yl)-1H-pyrrole-2-carboxamide;
4-(2-Chloro-6-fluorobenzoyl)-N-(4-methylpyridin-3-yl)-1H-pyrrole-2-carb oxamide;
4-(2-Chloro-6-fluorobenzoyl)-N-(4-ethylpyridin-3-yl)-1H-pyrrole-2-carboxamide;
4-(2-Chloro-6-fluorobenzoyl)-N-(4-propylpyridin-3-yl)-1H-pyrrole-2-carboxamide;
4-(2-Chloro-6-fluorobenzoyl)-N-(4-methoxypyridin-3-yl)-1H-pyrrole-2-carboxamide;
4-(2-Chloro-6-fluorobenzoyl)-N-(4-ethoxypyridin-3-yl)-1H-pyrrole-2-carb oxamide;
4-(2-Chloro-6-fluorobenzoyl)-N-(4-(pyrrolidin-1-yl)pyridin-3-yl)-1H-pyrrole-2-carboxamide;

4-(3,6-Dichloro-2-fluorobenzoyl)-N-(4-methylpyridin-3-yl)-1H-pyrrole-2-carboxamide;
4-(3,6-Dichloro-2-fluorobenzoyl)-N-(4-ethylpyridin-3-yl)-1H-pyrrole-2-carboxamide;
4-(3,6-Dichloro-2-fluorobenzoyl)-N-(4-propylpyridin-3-yl)-1H-pyrrole-2-carboxamide;
4-(3,6-Dichloro-2-fluorobenzoyl)-N-(4-methoxypyridin-3-yl)-1H-pyrrole-2-carboxamide;
4-(3,6-Dichloro-2-fluorobenzoyl)-N-(4-ethoxypyridin-3-yl)-1H-pyrrole-2-carboxamide;
4-(3,6-Dichloro-2-fluorobenzoyl)-N-(4-(pyrrolidin-1-yl)pyridin-3-yl)-1H-pyrrole-2-carboxamide;
4-(3,6-Dichloro-2-fluorobenzoyl)-N-(2-((2-(dimethylamino)ethyl)amino)pyrimidin-5-yl)-1H-pyrrole-2-carboxamide;
4-(3,6-Dichloro-2-fluorobenzoyl)-N-(2-((2-(diethylamino)ethyl)amino)pyrimidin-5-yl)-1H-pyrrole-2-carboxamide;
4-(3,6-Dichloro-2-fluorobenzoyl)-N-(2-((2-(methyl sulfonyl)ethyl)amino)pyrimidin-5-yl)-1H-pyrrole-2-carboxamide;
4-(3,6-Dichloro-2-fluorobenzoyl)-N-(2-((2-(pyrrolidin-1-yl)ethyl)amino)pyrimidin-5-yl)-1H-pyrrole-2-carboxamide;
4-(3,6-Dichloro-2-fluorobenzoyl)-N-(2-((2-morpholinoethyl)amino)pyrimidin-5-yl)-1H-pyrrole-2-carboxamide;
4-(3,6-Dichloro-2-fluorobenzoyl)-N-(2-((2-(piperidin-1-yl)ethyl)amino)pyrimidin-5-yl)-1H-pyrrole-2-carboxamide;
4-(3,6-Dichloro-2-fluorobenzoyl)-N-(2-(methyl(1-methylpiperidin-4-yl)amino)pyrimidin-5-yl)-1H-pyrrole-2-carboxamide;
4-(3,6-Dichloro-2-fluorobenzoyl)-N-(2-(methyl(piperidin-4-yl)amino)pyrimidin-5-yl)-1H-pyrrole-2-carboxamide;
4-(3,6-Dichloro-2-fluorobenzoyl)-N-(6-(methyl(piperidin-4-yl)amino)pyridin-3-yl)-1H-pyrrole-2-carboxamide;
4-(3,6-Dichloro-2-fluorobenzoyl)-N-(6-(methyl(1-methylpiperidin-4-yl)amino)pyridin-3-yl)-1H-pyrrole-2-carboxamide;
4-(3,6-Dichloro-2-fluorobenzoyl)-N-(6-(piperidin-4-yloxy)pyridin-3-yl)-1H-pyrrole-2-carboxamide;
4-(3,6-Dichloro-2-fluorobenzoyl)-N-(6-((1-methylpiperidin-4-yl)oxy)pyridin-3-yl)-1H-pyrrole-2-carboxamide;
4-(3,6-Dichloro-2-fluorobenzoyl)-N-(6-(piperidin-4-ylmethyl)pyridin-3-yl)-1H-pyrrole-2-carboxamide;
4-(3,6-Dichloro-2-fluorobenzoyl)-N-(6-((1-methylpiperidin-4-yl)methyl)pyridin-3-yl)-1H-pyrrole-2-carboxamide;
4-(3,6-Dichloro-2-fluorobenzoyl)-N-(6-(piperazin-1-ylmethyl)pyridin-3-yl)-1H-pyrrole-2-carboxamide;
4-(3,6-Dichloro-2-fluorobenzoyl)-N-(6-((4-methylpiperazin-1-yl)methyl)pyridin-3-yl)-1H-pyrrole-2-carboxamide;
4-(3,6-Dichloro-2-fluorobenzoyl)-N-(6-(morpholinomethyl)pyridin-3-yl)-1H-pyrrole-2-carboxamide;
4-(6-Chloro-2-fluoro-3-methoxybenzoyl)-N-(6-(morpholinomethyl)pyridin-3-yl)-1H-pyrrole-2-carboxamide;
4-(6-Chloro-2-fluoro-3-methoxybenzoyl)-N-(6-(piperidin-4-ylmethyl)pyridin-3-yl)-1H-pyrrole-2-carboxamide;
4-(2-Bromo-6-fluorobenzoyl)-N-(pyridin-4-yl)-1H-pyrrole-2-carboxamide;
4-(2-Fluoro-6-methylbenzoyl)-N-(pyridin-4-yl)-1H-pyrrole-2-carboxamide;
4-(2-Fluoro-6-methylbenzoyl)-N-(pyridin-3-yl)-1H-pyrrole-2-carboxamide;
4-(2-Chloro-6-fluorobenzoyl)-N-(pyridin-4-yl)-1H-pyrrole-2-carboxamide;
4-(2-Chloro-6-fluorobenzoyl)-N-(pyridin-3-yl)-1H-pyrrole-2-carboxamide;
4-(2-Bromo-6-fluorobenzoyl)-N-(pyridin-3-yl)-1H-pyrrole-2-carboxamide;
4-(2-Chloro-6-fluorobenzoyl)-N-(1-methylpiperidin-4-yl)-1H-pyrrole-2-carboxamide;
tert-Butyl 4-(4-(2-chloro-6-fluorobenzoyl)-1H-pyrrole-2-carboxamido)piperidine-1-carboxylate;
4-(2-Chloro-6-fluorobenzoyl)-N-(tetrahydro-2H-pyran-4-yl)-1H-pyrrole-2-carboxamide;
4-(2-Bromo-6-fluorobenzoyl)-N-(1-methylpiperidin-4-yl)-1H-pyrrole-2-carboxamide;
tert-Butyl 4-(4-(2-bromo-6-fluorobenzoyl)-1H-pyrrole-2-carboxamido)piperidine-1-carboxylate;
4-(2-Bromo-6-fluorobenzoyl)-N-(tetrahydro-2H-pyran-4-yl)-1H-pyrrole-2-carboxamide;
4-(2-Fluoro-6-methylbenzoyl)-N-(piperidin-4-yl)-1H-pyrrole-2-carboxamide;
4-(2-Bromo-6-fluorobenzoyl)-N-(piperidin-4-yl)-1H-pyrrole-2-carboxamide;
4-(2-Ethyl-6-fluorobenzoyl)-N-(pyridin-3-yl)-1H-pyrrole-2-carboxamide;
4-(2-Ethyl-6-fluorobenzoyl)-N-(piperidin-4-yl)-1H-pyrrole-2-carboxamide
4-(2-Ethyl-6-fluorobenzoyl)-N-(1-methylpiperidin-4-yl)-1H-pyrrole-2-carboxamide;
4-(2-Cyclopropyl-6-fluorobenzoyl)-N-(pyridin-3-yl)-1H-pyrrole-2-carboxamide;
4-(2-Cyclopropyl-6-fluorobenzoyl)-N-(piperidin-4-yl)-1H-pyrrole-2-carboxamide,
4-(2-Cyclopropyl-6-fluorobenzoyl)-N-(1-methylpiperidin-4-yl)-1H-pyrrole-2-carboxamide;
4-(2-Ethynyl-6-fluorobenzoyl)-N-(1-methylpiperidin-4-yl)-1H-pyrrole-2-carboxamide;
N-(Pyridin-3-yl)-4-(2,3,6-trifluorobenzoyl)-1H-pyrrole-2-carboxamide;
N-(Pyrimidin-5-yl)-4-(2,3,6-trifluorobenzoyl)-1H-pyrrole-2-carboxamide;
N-(1-Methylpiperidin-4-yl)-4-(2,3,6-trifluorobenzoyl)-1H-pyrrole-2-carboxamide;
4-(3-Chloro-2,6-difluorobenzoyl)-N-(pyridin-3-yl)-1H-pyrrole-2-carboxamide;
4-(3-Chloro-2,6-difluorobenzoyl)-N-(pyrimidin-5-yl)-1H-pyrrole-2-carboxamide;
4-(3-Chloro-2,6-difluorobenzoyl)-N-(1-methylpiperidin-4-yl)-1H-pyrrole-2-carboxamide
4-(2-Chloro-3,6-difluorobenzoyl)-N-(pyridin-3-yl)-1H-pyrrole-2-carboxamide;
4-(2-Chloro-3,6-difluorobenzoyl)-N-(1-methylpiperidin-4-yl)-1H-pyrrole-2-carboxamide;
4-(2,6-Difluoro-3-methylbenzoyl)-N-(pyridin-3-yl)-1H-pyrrole-2-carboxamide;
4-(2,6-Difluoro-3-methylbenzoyl)-N-(pyrimidin-5-yl)-1H-pyrrole-2-carboxamide;
4-(2,6-Difluoro-3-methylbenzoyl)-N-(1-methylpiperidin-4-yl)-1H-pyrrole-2-carboxamide;
4-(6-Chloro-2,3-difluorobenzoyl)-N-(pyridin-3-yl)-1H-pyrrole-2-carboxamide;
4-(6-Chloro-2,3-difluorobenzoyl)-N-(pyrimidin-5-yl)-1H-pyrrole-2-carboxamide;

4-(6-Chloro-2,3-difluorobenzoyl)-N-(1-methylpiperidin-4-yl)-1H-pyrrole-2-carboxamide;
4-(2,5-Difluorobenzoyl)-N-(1-methylpiperidin-4-yl)-1H-pyrrole-2-carboxamide;
4-(2,5-Difluorobenzoyl)-N-(pyridin-3-yl)-1H-pyrrole-2-carboxamide;
4-(5-Chloro-2-fluorobenzoyl)-N-(pyridin-3-yl)-1H-pyrrole-2-carboxamide;
4-(5-Chloro-2-fluorobenzoyl)-N-(pyrimidin-5-yl)-1H-pyrrole-2-carboxamide;
4-(5-Chloro-2-fluorobenzoyl)-N-(1-methylpiperidin-4-yl)-1H-pyrrole-2-carboxamide;
4-(2-Fluoro-5-methylbenzoyl)-N-(pyridin-3-yl)-1H-pyrrole-2-carboxamide;
4-(2-Fluoro-5-methylbenzoyl)-N-(pyrimidin-5-yl)-1H-pyrrole-2-carboxamide;
4-(2-Fluoro-5-methylbenzoyl)-N-(1-methylpiperidin-4-yl)-1H-pyrrole-2-carboxamide;
N-(Piperidin-4-yl)-4-(2,3,6-trifluorobenzoyl)-1H-pyrrole-2-carboxamide;
4-(3-Chloro-2,6-difluorobenzoyl)-N-(piperidin-4-yl)-1H-pyrrole-2-carboxamide;
4-(2-Chloro-3,6-difluorobenzoyl)-N-(piperidin-4-yl)-1H-pyrrole-2-carboxamide;
4-(2,6-Difluoro-3-methylbenzoyl)-N-(piperidin-4-yl)-1H-pyrrole-2-carboxamide;
4-(6-Chloro-2,3-difluorobenzoyl)-N-(piperidin-4-yl)-1H-pyrrole-2-carboxamide;
4-(2,5-Difluorobenzoyl)-N-(piperidin-4-yl)-1H-pyrrole-2-carboxamide;
4-(5-Chloro-2-fluorobenzoyl)-N-(piperidin-4-yl)-1H-pyrrole-2-carboxamide;
4-(2,6-Difluorobenzoyl)-N-(pyridin-4-yl)-1H-pyrrole-2-carboxamide;
4-(2,6-Difluorobenzoyl)-N-(pyridin-3-yl)-1H-pyrrole-2-carboxamide;
tert-Butyl 4-(4-(2,6-difluorobenzoyl)-1H-pyrrole-2-carboxamido)piperidine-1-carboxylate;
4-(2,6-Difluorobenzoyl)-N-(tetrahydro-2H-pyran-4-yl)-1H-pyrrole-2-carboxamide;
4-(2,6-Difluorobenzoyl)-N-(pyrrolidin-3-yl)-1H-pyrrole-2-carboxamide;
4-(2,6-Difluorobenzoyl)-N-(piperidin-4-yl)-1H-pyrrole-2-carboxamide;
4-(4-(2,6-Difluorobenzoyl)-1H-pyrrole-2-carboxamido)pyridine 1-oxide;
3-(4-(2,6-Difluorobenzoyl)-1H-pyrrole-2-carboxamido)pyridine 1-oxide;
4-(2,6-Difluorobenzoyl)-N-(1-methylpiperidin-4-yl)-1H-pyrrole-2-carboxamide;
4-(2,6-Difluorobenzoyl)-N-(pyrimidin-4-yl)-1H-pyrrole-2-carboxamide;
4-(2,3-Dichlorobenzoyl)-N-(pyrimidin-4-yl)-1H-pyrrole-2-carboxamide;
4-(2-Chloro-6-fluorobenzoyl)-N-(pyrimidin-4-yl)-1H-pyrrole-2-carboxamide;
4-(2-Bromo-6-fluorobenzoyl)-N-(pyrimidin-4-yl)-1H-pyrrole-2-carboxamide;
4-(2-Chloro-6-fluorobenzoyl)-N-(2,6-dimethylpyridin-4-yl)-1H-pyrrole-2-carboxamide;
4-(2-Bromo-6-fluorobenzoyl)-N-(2,6-dimethylpyridin-4-yl)-1H-pyrrole-2-carboxamide;
4-(2-Chloro-6-fluorobenzoyl)-N-(2-methylpyridin-4-yl)-1H-pyrrole-2-carboxamide;
4-(2-Bromo-6-fluorobenzoyl)-N-(2-methylpyridin-4-yl)-1H-pyrrole-2-carboxamide;
4-(2-Chloro-6-fluorobenzoyl)-N-(2-methylpyridin-3-yl)-1H-pyrrole-2-carboxamide;
4-(2-Bromo-6-fluorobenzoyl)-N-(2-methylpyridin-3-yl)-1H-pyrrole-2-carboxamide;
4-(2-Chloro-6-fluorobenzoyl)-N-(6-methylpyridin-3-yl)-1H-pyrrole-2-carboxamide;
4-(2-Bromo-6-fluorobenzoyl)-N-(6-methylpyridin-3-yl)-1H-pyrrole-2-carboxamide;
4-(2-Chloro-6-fluorobenzoyl)-N-(6-fluoropyridin-3-yl)-1H-pyrrole-2-carboxamide;
4-(2-Bromo-6-fluorobenzoyl)-N-(6-fluoropyridin-3-yl)-1H-pyrrole-2-carboxamide;
4-(2-Chloro-6-fluorobenzoyl)-N-(pyridazin-4-yl)-1H-pyrrole-2-carboxamide;
4-(2-Bromo-6-fluorobenzoyl)-N-(pyridazin-4-yl)-1H-pyrrole-2-carboxamide;
4-(2-Chloro-6-fluorobenzoyl)-N-(2-chloropyrimidin-4-yl)-1H-pyrrole-2-carboxamide;
4-(2-Bromo-6-fluorobenzoyl)-N-(2-chloropyrimidin-4-yl)-1H-pyrrole-2-carboxamide;
4-(2-Chloro-6-fluorobenzoyl)-N-(2,6-dimethylpyrimidin-4-yl)-1H-pyrrole-2-carboxamide;
4-(2-Bromo-6-fluorobenzoyl)-N-(2,6-dimethylpyrimidin-4-yl)-1H-pyrrole-2-carboxamide;
4-(2-Chloro-6-fluorobenzoyl)-N-(pyrimidin-5-yl)-1H-pyrrole-2-carboxamide;
4-(2-Chloro-6-fluorobenzoyl)-N-(2-methylpyrimidin-5-yl)-1H-pyrrole-2-carboxamide;
4-(2-Bromo-6-fluorobenzoyl)-N-(pyrimidin-5-yl)-1H-pyrrole-2-carboxamide;
4-(2-Bromo-6-fluorobenzoyl)-N-(2-methylpyrimidin-5-yl)-1H-pyrrole-2-carboxamide;
4-(2-Chloro-6-fluorobenzoyl)-N-(2-oxo-1,2-dihydropyrimidin-4-yl)-1H-pyrrole-2-carboxamide;
4-(2-Bromo-6-fluorobenzoyl)-N-(2-oxo-1,2-dihydropyrimidin-4-yl)-1H-pyrrole-2-carboxamide;
4-(2-Chloro-6-fluorobenzoyl)-N-(1H-indazol-6-yl)-1H-pyrrole-2-carboxamide;
4-(2-Bromo-6-fluorobenzoyl)-N-(1H-indazol-6-yl)-1H-pyrrole-2-carboxamide;
4-(2,3-Dichlorobenzoyl)-N-(pyridin-3-yl)-1H-pyrrole-2-carboxamide;
4-(2,3-Dichlorobenzoyl)-N-(pyridin-4-yl)-1H-pyrrole-2-carboxamide;
4-(2-Fluoro-6-(trifluoromethyl)benzoyl)-N-(piperidin-4-yl)-1H-pyrrole-2-carboxamide;
4-(2,3-Dichlorobenzoyl)-N-(piperidin-4-yl)-1H-pyrrole-2-carboxamide;
(3-Ethyl-2,6-difluorophenyl)(5-((pyridin-3-ylamino)methyl)-1H-pyrrol-3-yl)methanone;
4-(3-Ethyl-2,6-difluorobenzoyl)-N-(pyrimidin-5-yl)-1H-pyrrole-2-carboxamide;
4-(3-Ethyl-2,6-difluorobenzoyl)-N-(1-methylpiperidin-4-yl)-1H-pyrrole-2-carboxamide;
4-(2,6-Difluoro-3-vinylbenzoyl)-N-(pyridin-3-yl)-1H-pyrrole-2-carboxamide;
4-(2,6-Difluoro-3-vinylbenzoyl)-N-(pyrimidin-5-yl)-1H-pyrrole-2-carboxamide;
4-(2,6-Difluoro-3-vinylbenzoyl)-N-(1-methylpiperidin-4-yl)-1H-pyrrole-2-carboxamide;
4-(2,6-Difluoro-3-(prop-1-en-2-yl)benzoyl)-N-(pyridin-3-yl)-1H-pyrrole-2-carboxamide;
4-(2,3-Dichloro-6-fluorobenzoyl)-N-(pyridin-3-yl)-1H-pyrrole-2-carboxamide;
4-(3,6-Dichloro-2-fluorobenzoyl)-N-(pyridin-3-yl)-1H-pyrrole-2-carboxamide;

4-(2-Chloro-6-fluoro-3-methylbenzoyl)-N-(pyridin-3-yl)-1H-pyrrole-2-carboxamide;
4-(6-Chloro-2-fluoro-3-methylbenzoyl)-N-(pyridin-3-yl)-1H-pyrrole-2-carboxamide;
4-(2,3-Dichloro-6-fluorobenzoyl)-N-(pyrimidin-5-yl)-1H-pyrrole-2-carboxamide;
4-(3,6-Dichloro-2-fluorobenzoyl)-N-(pyrimidin-5-yl)-1H-pyrrole-2-carboxamide;
4-(2-Chloro-6-fluoro-3-methylbenzoyl)-N-(pyrimidin-5-yl)-1H-pyrrole-2-carboxamide;
4-(6-Chloro-2-fluoro-3-methylbenzoyl)-N-(pyrimidin-5-yl)-1H-pyrrole-2-carboxamide;
4-(2,3-Dichloro-6-fluorobenzoyl)-N-(1-methylpiperidin-4-yl)-1H-pyrrole-2-carboxamide;
4-(3,6-dichloro-2-fluorobenzoyl)-N-(1-methylpiperidin-4-yl)-1H-pyrrole-2-carboxamide;
4-(2-Chloro-6-fluoro-3-methylbenzoyl)-N-(1-methylpiperidin-4-yl)-1H-pyrrole-2-carboxamide;
4-(6-Chloro-2-fluoro-3-methylbenzoyl)-N-(1-methylpiperidin-4-yl)-1H-pyrrole-2-carboxamide;
4-(3-Bromo-6-chloro-2-fluorobenzoyl)-N-(pyridin-3-yl)-1H-pyrrole-2-carboxamide;
4-(3-Bromo-6-chloro-2-fluorobenzoyl)-N-(pyrimidin-5-yl)-1H-pyrrole-2-carboxamide;
4-(2-Fluoro-6-(trifluoromethyl)benzoyl)-N-(pyridin-4-yl)-1H-pyrrole-2-carboxamide;
4-(2-Fluoro-6-(trifluoromethyl)benzoyl)-N-(pyridin-3-yl)-1H-pyrrole-2-carboxamide;
4-(3,6-Dichloro-2-fluorobenzoyl)-N-(1-(2-hydroxyethyl)-1H-pyrazol-4-yl)-1H-pyrrole-2-carboxamide;
4-(6-Chloro-2-fluoro-3-methoxybenzoyl)-N-(6-((1-methylpiperidin-4-yl)methyl)pyridin-3-yl)-1H-pyrrole-2-carboxamide;
4-(3,6-Dichloro-2-fluorobenzoyl)-N-(1-(tetrahydro-2H-pyran-4-yl)-1H-pyrazol-4-yl)-1H-pyrrole-2-carboxamide;
4-(3,6-Dichloro-2-fluorobenzoyl)-N-(1-(2-(methylsulfonyl)ethyl)-1H-pyrazol-4-yl)-1H-pyrrole-2-carboxamide;
4-(3,6-Dichloro-2-fluorobenzoyl)-N-(1-(oxetan-3-yl)-1H-pyrazol-4-yl)-1H-pyrrole-2-carboxamide;
4-(3,6-Dichloro-2-fluorobenzoyl)-N-(1-(tetrahydrofuran-3-yl)-1H-pyrazol-4-yl)-1H-pyrrole-2-carboxamide;
(S)-4-(3,6-Dichloro-2-fluorobenzoyl)-N-(pyrrolidin-3-yl)-1H-pyrrole-2-carboxamide;
4-(3,6-Dichloro-2-fluorobenzoyl)-N-(2-(morpholinomethyl)pyrimidin-5-yl)-1H-pyrrole-2-carboxamide;
4-(6-Chloro-2-fluoro-3-methoxybenzoyl)-N-(2-(morpholinomethyl)pyrimidin-5-yl)-1H-pyrrole-2-carboxamide;
4-(3,6-Dichloro-2-fluorobenzoyl)-N-(2-((4-methylpiperazin-1-yl)methyl)pyrimidin-5-yl)-1H-pyrrole-2-carboxamide;
4-(6-Chloro-2-fluoro-3-methoxybenzoyl)-N-(2-((4-methylpiperazin-1-yl)methyl) pyrimidin-5-yl)-1H-pyrrole-2-carboxamide;
4-(6-Chloro-2-fluoro-3-methoxybenzoyl)-N-(6-((4-methylpiperazin-1-yl)methyl) pyridin-3-yl)-1H-pyrrole-2-carboxamide;
4-(6-Chloro-2-fluoro-3-methoxybenzoyl)-N-(2-((1-methylpiperidin-4-yl)methyl) pyrimidin-5-yl)-1H-pyrrole-2-carboxamide;
4-(3,6-Dichloro-2-fluorobenzoyl)-N-(2-((1-methylpiperidin-4-yl)methyl)pyrimidin-5-yl)-1H-pyrrole-2-carboxamide;
4-(3,6-Dichloro-2-fluorobenzoyl)-N-(2-(piperazin-1-ylmethyl)pyrimidin-5-yl)-1H-pyrrole-2-carboxamide;
4-(6-Chloro-2-fluoro-3-methoxybenzoyl)-N-(2-(piperazin-1-ylmethyl)pyrimidin-5-yl)-1H-pyrrole-2-carboxamide;
4-(6-Chloro-2-fluoro-3-methoxybenzoyl)-N-(6-(piperazin-1-ylmethyl)pyridin-3-yl)-1H-pyrrole-2-carboxamide;
4-(6-Chloro-2-fluoro-3-methoxybenzoyl)-N-(2-(piperidin-4-ylmethyl)pyrimidin-5-yl)-1H-pyrrole-2-carboxamide;
4-(3,6-Dichloro-2-fluorobenzoyl)-N-(2-(piperidin-4-ylmethyl)pyrimidin-5-yl)-1H-pyrrole-2-carboxamide;
4-(6-Chloro-2-fluoro-3-hydroxybenzoyl)-N-(pyridin-3-yl)-1H-pyrrole-2-carboxamide;
4-(6-Chloro-2-fluoro-3-hydroxybenzoyl)-N-(1-methyl-1H-pyrazol-4-yl)-1H-pyrrole-2-carboxamide;
4-(6-Chloro-3-ethoxy-2-fluorobenzoyl)-N-(pyridin-3-yl)-1H-pyrrole-2-carboxamide;
4-(6-Chloro-3-ethoxy-2-fluorobenzoyl)-N-(1-methyl-1H-pyrazol-4-yl)-1H-pyrrole-2-carboxamide;
4-(6-Chloro-2-fluoro-3-(2-methoxyethoxy)benzoyl)-N-(pyridin-3-yl)-1H-pyrrole-2-carboxamide;
4-(6-Chloro-2-fluoro-3-((tetrahydrofuran-3-yl)oxy)benzoyl)-N-(pyridin-3-yl)-1H-pyrrole-2-carboxamide;
4-(6-Chloro-2-fluoro-3-(2-methoxyethoxy)benzoyl)-N-(1-methyl-1H-pyrazol-4-yl)-1H-pyrrole-2-carboxamide;
4-(6-Chloro-2-fluoro-3-((tetrahydrofuran-3-yl)oxy)benzoyl)-N-(1-methyl-1H-pyrazol-4-yl)-1H-pyrrole-2-carboxamide;
4-(3,6-Dichloro-2-fluorobenzoyl)-N-(6-((2-(diethylamino)ethyl)amino)pyridin-3-yl)-1H-pyrrole-2-carboxamide;
4-(3,6-Dichloro-2-fluorobenzoyl)-N-(6-((2-(methyl sulfonyl)ethyl)amino)pyridin-3-yl)-1H-pyrrole-2-carboxamide;
4-(3,6-Dichloro-2-fluorobenzoyl)-N-(6-((2-(piperidin-1-yl)ethyl)amino)pyridin-3-yl)-1H-pyrrole-2-carboxamide;
4-(2,6-difluoro-3-formylbenzoyl)-N-(pyridin-3-yl)-1H-pyrrole-2-carboxamide;
2,4-difluoro-3-(5-(pyridin-3-ylcarbamoyl)-1H-pyrrole-3-carbonyl) benzoic acid;
4-(6-Chloro-2-fluoro-3-((tetrahydro-2H-pyran-4-yl)oxy)benzoyl)-N-(pyridin-3-yl)-1H-pyrrole-2-carboxamide;
4-(6-Chloro-2-fluoro-3-((tetrahydro-2H-pyran-4-yl)oxy)benzoyl)-N-(1-methyl-1H-pyrazol-4-yl)-1H-pyrrole-2-carboxamide;
4-(2-Chloro-6-fluorobenzoyl)-N-(1-methyl-1H-pyrazol-4-yl)-1H-pyrrole-2-carboxamide;
4-(6-Chloro-3-((1-chloro-3-hydroxypropan-2-yl)oxy)-2-fluorobenzoyl)-N-(pyridin-3-yl)-1H-pyrrole-2-carboxamide;
4-(6-Chloro-3-((1,3-dichloropropan-2-yl)oxy)-2-fluorobenzoyl)-N-(pyridin-3-yl)-H-pyrrole-2-carboxamide;
4-(6-Chloro-2-fluoro-3-(oxetan-3-yloxy)benzoyl)-N-(pyridin-3-yl)-1H-pyrrole-2-carboxamide;
4-(6-Chloro-2-fluoro-3-(oxetan-3-yloxy)benzoyl)-N-(1-methyl-1H-pyrazol-4-yl)-1H-pyrrole-2-carboxamide;
4-(2,6-difluoro-3-((methylamino) methyl) benzoyl)-N-(pyridin-3-yl)-1H-pyrrole-2-carboxamide;
4-(3,6-Dichloro-2-fluorobenzoyl)-N-(6-((2-(pyrrolidin-1-yl)ethyl)amino)pyridin-3-yl)-1H-pyrrole-2-carboxamide;
4-(3,6-Dichloro-2-fluorobenzoyl)-N-(6-((2-morpholinoethyl)amino)pyridin-3-yl)-1H-pyrrole-2-carboxamide;

4-(3,6-Dichloro-2-fluorobenzoyl)-N-(6-((dimethylamino)methyl)pyridin-3-yl)-1H-pyrrole-2-carboxamide;
4-(3,6-Dichloro-2-fluorobenzoyl)-N-(6-(((2-methoxyethyl)(methyl)amino)methyl) pyridin-3-yl)-1H-pyrrole-2-carboxamide;
4-(3,6-Dichloro-2-fluorobenzoyl)-N-(6-(oxetan-3-yloxy)pyridin-3-yl)-1H-pyrrole-2-carboxamide;
4-(3,6-Dichloro-2-fluorobenzoyl)-N-(6-(2-hydroxyethoxy)pyridin-3-yl)-1H-pyrrole-2-carboxamide;
4-(3,6-Dichloro-2-fluorobenzoyl)-N-(6-(2-hydroxyethoxy)pyridin-3-yl)-1H-pyrrole-2-carboxamide;
4-(3,6-Dichloro-2-fluorobenzoyl)-N-(6-((4-hydroxypiperidin-1-yl)methyl)pyridin-3-yl)-1H-pyrrole-2-carboxamide;
N-(6-((bis(2-methoxyethyl)amino)methyl)pyridin-3-yl)-4-(3,6-dichloro-2-fluorobenzoyl)-1H-pyrrole-2-carboxamide;
4-(3,6-Dichloro-2-fluorobenzoyl)-N-(6-(piperidin-1-ylmethyl)pyridin-3-yl)-1H-pyrrole-2-carboxamide;
4-(2,6-Difluorobenzoyl)-N-(1-methyl-1H-pyrazol-4-yl)-1H-pyrrole-2-carboxamide;
4-(2-Fluoro-6-methylbenzoyl)-N-(1-methyl-1H-pyrazol-4-yl)-1H-pyrrole-2-carboxamide; and
4-(2-Fluorobenzoyl)-N-(1-methyl-1H-pyrazol-4-yl)-1H-pyrrole-2-carboxamide.

16. A compound according to claim 1, or a tautomeric form, stereochemically isomeric form, N-oxide, pharmaceutically acceptable salt or solvate thereof, wherein the compound is selected from:
4-(3,6-Dichloro-2-fluorobenzoyl)-N-(1-(piperidin-4-ylmethyl)-1H-pyrazol-4-yl)-1H-pyrrole-2-carboxamide,
4-(3,6-Dichloro-2-fluorobenzoyl)-N-(6-(piperidin-4-ylmethyl)pyridin-3-yl)-1H-pyrrole-2-carboxamide;
4-(3,6-Dichloro-2-fluorobenzoyl)-N-(6-((1-methylpiperidin-4-yl)methyl)pyridin-3-yl)-1H-pyrrole-2-carboxamide;
4-(3,6-Dichloro-2-fluorobenzoyl)-N-(6-((1-methylpiperidin-4-yl)oxy)pyridin-3-yl)-1H-pyrrole-2-carboxamide;
4-(3,6-Dichloro-2-fluorobenzoyl)-N-(1-(piperidin-4-yl)-1H-pyrazol-4-yl)-1H-pyrrole-2-carboxamide;
4-(3,6-Dichloro-2-fluorobenzoyl)-N-(1-methyl-1H-pyrazol-4-yl)-1H-pyrrole-2-carboxamide; and
4-(3,6-Dichloro-2-fluorobenzoyl)-N-(pyridin-3-yl)-1H-pyrrole-2-carboxamide.

17. A combination comprising a compound of formula (I) as defined in claim 1 with one or more other therapeutic agents.

18. A pharmaceutical composition comprising a compound of formula (I) as defined in claim 1, and a pharmaceutically acceptable carrier.

19. A method for the treatment of a disease state or condition mediated by ERK5, the method comprising administering to a patient a compound as defined in claim 1, wherein the disease state or condition mediated by ERK5 is selected from prostate cancer, breast cancer, liver cancer, oral cancer, and osteosarcoma.

20. A process for the preparation of a compound of formula (I) as defined in claim 1, or a tautomer, stereoisomer, N-oxide, pharmaceutically acceptable salt, or solvate thereof which comprises:
(a) reacting a compound of formula (A) with a compound of formula (B):

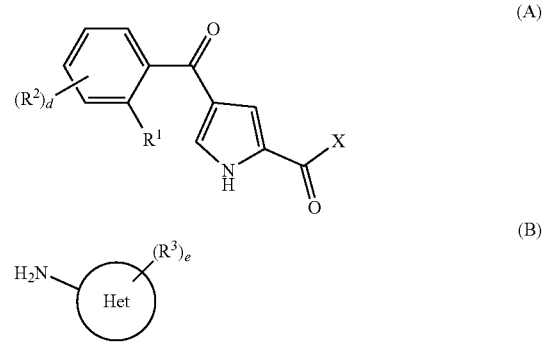

where $R^1$, $R^2$, d, $R^3$, e, and Het are as defined in claim 1, and X is a leaving group and/or
(b) interconversion of a compound of formula (I) or protected derivative thereof to a further compound of formula (I) or protected derivative thereof; and/or
(c) deprotection of a protected derivative of a compound of formula (I); and/or
(d) providing a compound of formula (I) and forming a pharmaceutically acceptable salt of the compound.

* * * * *

UNITED STATES PATENT AND TRADEMARK OFFICE
CERTIFICATE OF CORRECTION

PATENT NO. : 10,344,017 B2
APPLICATION NO. : 15/512661
DATED : July 9, 2019
INVENTOR(S) : Reuillon et al.

It is certified that error appears in the above-identified patent and that said Letters Patent is hereby corrected as shown below:

In the Claims

Column 230, Line 4: Claim 1, Delete "-NR$^x$SO$_2$-," and insert -- -NR$^x$SO$_2$-, --

Column 234, Line 6: Claim 15, Delete "1$H$-pyrrole-2-carb oxamide;" and insert -- 1$H$-pyrrole-2-carboxamide; --

Column 235, Line 4: Claim 15, Delete "1$H$-pyrrole-2-carb oxamide;" and insert -- 1$H$-pyrrole-2-carboxamide; --

Column 236, Line 41: Claim 15, Delete "1$H$-pyrrole-2-carb oxamide;" and insert -- 1$H$-pyrrole-2-carboxamide; --

Column 236, Line 57: Claim 15, Delete "1$H$-pyrrole-2-carb oxamide;" and insert -- 1$H$-pyrrole-2-carboxamide; --

Column 236, Line 65: Claim 15, Delete "1$H$-pyrrole-2-carb oxamide;" and insert -- 1$H$-pyrrole-2-carboxamide; --

Column 237, Line 20: Claim 15, Delete "-(methyl sulfonyl)" and insert -- -(methylsulfonyl) --

Column 239, Line 65: Claim 15, Delete "1$H$-pyrrole-2-carb oxamide;" and insert -- 1$H$-pyrrole-2-carboxamide; --

Column 239, Line 67: Claim 15, Delete "1$H$-pyrrole-2-carb oxamide;" and insert -- 1$H$-pyrrole-2-carboxamide; --

Column 240, Line 2: Claim 15, Delete "1$H$-pyrrole-2-carb oxamide;" and insert -- 1$H$-pyrrole-2-carboxamide; --

Signed and Sealed this
Tenth Day of September, 2019

Andrei Iancu
*Director of the United States Patent and Trademark Office*

CERTIFICATE OF CORRECTION (continued)
U.S. Pat. No. 10,344,017 B2

Column 240, Line 4: Claim 15, Delete "1*H*-pyrrole-2-carb oxamide;" and insert
-- 1*H*-pyrrole-2-carboxamide; --

Column 240, Line 6: Claim 15, Delete "1*H*-pyrrole-2-carb oxamide;" and insert
-- 1*H*-pyrrole-2-carboxamide; --

Column 240, Line 8: Claim 15, Delete "1*H*-pyrrole-2-carb oxamide;" and insert
-- 1*H*-pyrrole-2-carboxamide; --

Column 242, Line 34: Claim 15, Delete "-(methyl sulfonyl)" and insert -- -(methylsulfonyl) --